(12) United States Patent
Garrick et al.

(10) Patent No.: US 7,696,210 B2
(45) Date of Patent: *Apr. 13, 2010

(54) GONADOTROPIN RELEASING HORMONE RECEPTOR ANTAGONISTS

(75) Inventors: Lloyd Michael Garrick, Arvada, CO (US); Daniel Michael Green, Ambler, PA (US); Diane Barbara Hauze, St. Davids, PA (US); Kenneth Lewis Kees, Glenmoore, PA (US); Joseph Theodore Lundquist, IV, Collegeville, PA (US); Charles William Mann, Philadelphia, PA (US); John Francis Mehlmann, King of Prussia, PA (US); Jeffrey Claude Pelletier, Lafayette Hill, PA (US); John Francis Rogers, Jr., Bryn Mawr, PA (US); Jay Edward Wrobel, Lawrenceville, NJ (US)

(73) Assignee: Wyeth, Madison, NJ (US)

( * ) Notice: Subject to any disclaimer, the term of this patent is extended or adjusted under 35 U.S.C. 154(b) by 763 days.

This patent is subject to a terminal disclaimer.

(21) Appl. No.: 11/154,795

(22) Filed: Jun. 16, 2005

(65) Prior Publication Data

US 2006/0019965 A1    Jan. 26, 2006

Related U.S. Application Data

(60) Provisional application No. 60/580,640, filed on Jun. 17, 2004.

(51) Int. Cl.
*A61K 31/497* (2006.01)
*C07D 403/00* (2006.01)

(52) U.S. Cl. .................. 514/254.06; 544/370

(58) Field of Classification Search .......... None
See application file for complete search history.

(56) References Cited

U.S. PATENT DOCUMENTS

| | | | |
|---|---|---|---|
| 3,325,506 A | 6/1967 | Jones et al. |
| 3,996,233 A | 12/1976 | Denzel et al. |
| 4,459,296 A | 7/1984 | Ancher et al. |
| 4,833,142 A | 5/1989 | Hartog et al. |
| 5,057,517 A | 10/1991 | Johnston et al. |
| 5,338,740 A | 8/1994 | Carpino et al. |
| 5,424,313 A | 6/1995 | Hartog et al. |
| 5,502,187 A | 3/1996 | Ayer et al. |
| 5,576,460 A | 11/1996 | Buchwald et al. |
| 5,643,944 A | 7/1997 | Garfield et al. |
| 5,716,964 A | 2/1998 | Hansen, Jr. et al. |
| 6,277,989 B1 | 8/2001 | Chakravarty et al. |
| 6,306,859 B1 | 10/2001 | Childers et al. |
| 6,307,087 B1 | 10/2001 | Buchwald et al. |
| 6,310,066 B1 | 10/2001 | Kelly et al. |
| 6,313,126 B1 | 11/2001 | Mewshaw et al. |
| 6,376,141 B1 | 4/2002 | Mishra et al. |
| 6,399,629 B1 | 6/2002 | Chamberland et al. |
| 6,476,031 B1 | 11/2002 | Chakravarty et al. |
| 6,492,517 B1 | 12/2002 | Burdeniuc |
| 6,548,505 B1 | 4/2003 | Martin et al. |
| 6,559,167 B1 | 5/2003 | Garst et al. |
| 6,620,529 B1 | 9/2003 | Ise et al. |
| 6,696,469 B2 | 2/2004 | Peglion et al. |
| 6,723,724 B2 | 4/2004 | Koh et al. |
| 6,821,967 B2 | 11/2004 | Lehmann-Lintz et al. |
| 6,841,549 B1 | 1/2005 | Asano et al. |
| 2001/0020030 A1 | 9/2001 | Stewart et al. |
| 2002/0013324 A1 | 1/2002 | Childers et al. |
| 2002/0055133 A1 | 5/2002 | Hahn et al. |
| 2002/0072053 A1 | 6/2002 | McNally et al. |
| 2002/0147197 A1 | 10/2002 | Newman et al. |
| 2002/0161010 A1 | 10/2002 | Chakravarty et al. |
| 2002/0168630 A1 | 11/2002 | Fleming et al. |
| 2002/0182623 A1 | 12/2002 | Lefevre et al. |
| 2003/0021851 A1 | 1/2003 | Goswami et al. |
| 2003/0028018 A1 | 2/2003 | Renhowe et al. |
| 2003/0051260 A1 | 3/2003 | Chada et al. |
| 2003/0055057 A1 | 3/2003 | Blume et al. |
| 2003/0069248 A1 | 4/2003 | Chakravarty et al. |
| 2003/0165920 A1 | 9/2003 | Chou et al. |
| 2003/0220365 A1 | 11/2003 | Stewart et al. |
| 2004/0018240 A1 | 1/2004 | Ohmachi et al. |
| 2004/0036868 A1 | 2/2004 | Jones et al. |
| 2004/0082635 A1 | 4/2004 | Hashimoto et al. |

(Continued)

FOREIGN PATENT DOCUMENTS

DE    39 26 770 A1    2/1991

(Continued)

OTHER PUBLICATIONS

Dorwald F. A. Side Reactions in Organic Synthesis, 2005, Wiley: VCH, Weinheim p. IX of Preface.*

(Continued)

*Primary Examiner*—James O Wilson
*Assistant Examiner*—Jeffrey H Murray
(74) *Attorney, Agent, or Firm*—Wilmer Cutler Pickering Hale and Dorr LLP

(57) ABSTRACT

Compounds of Formula I, useful as Gonadotropin Releasing Hormone ("GnRH") (also known as Leutinizing Hormone Releasing Hormone) receptor antagonists, are disclosed.

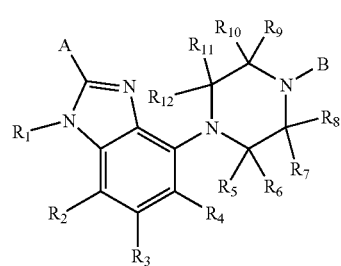

23 Claims, No Drawings

U.S. PATENT DOCUMENTS

| | | |
|---|---|---|
| 2004/0082798 A1 | 4/2004 | Alonso-Alija et al. |
| 2004/0102502 A1 | 5/2004 | Watanabe et al. |
| 2004/0121008 A1 | 6/2004 | Shiraishi et al. |
| 2004/0122001 A1 | 6/2004 | Agejas-Chicharro et al. |
| 2004/0219208 A1 | 11/2004 | Kawamura et al. |
| 2005/0009894 A1 | 1/2005 | Babin et al. |
| 2005/0065196 A1 | 3/2005 | Inaba et al. |
| 2005/0101647 A1 | 5/2005 | Oda et al. |
| 2005/0282820 A1* | 12/2005 | Gontcharov et al. ... 514/254.06 |
| 2006/0019965 A1 | 1/2006 | Garrick et al. |
| 2006/0111355 A1 | 5/2006 | Garrick et al. |
| 2006/0189616 A1* | 8/2006 | Pelletier et al. ............. 514/248 |
| 2006/0189617 A1* | 8/2006 | Pelletier et al. ............. 514/248 |
| 2006/0189618 A1* | 8/2006 | Pelletier ..................... 514/249 |
| 2006/0189619 A1 | 8/2006 | Tadayon et al. |
| 2006/0264631 A1 | 11/2006 | Green et al. |
| 2006/0270848 A1 | 11/2006 | Lundquist et al. |

FOREIGN PATENT DOCUMENTS

| | | |
|---|---|---|
| DE | 10030376 | 1/2002 |
| DE | 10110750 | 9/2002 |
| DE | 20217340 | 2/2003 |
| EP | 0138280 | 4/1985 |
| EP | 0300726 | 1/1989 |
| EP | 0400974 | 12/1990 |
| EP | 0434038 | 6/1991 |
| EP | 0 471 236 B1 | 2/1992 |
| EP | 1136483 | 9/2001 |
| EP | 1197485 | 4/2002 |
| EP | 1239283 | 9/2002 |
| GB | 1009807 | 11/1965 |
| GB | 1049330 | 11/1966 |
| GB | 2097790 | * 11/1982 |
| GB | 2097790 | 11/1983 |
| GB | 2369616 | 6/2002 |
| GB | 2370270 | 6/2002 |
| IT | 1298727 | 2/2000 |
| JP | 2003083968 | 4/1991 |
| JP | 2003231687 | 10/1991 |
| JP | 2002161084 | 6/2002 |
| JP | 2002193946 | 7/2002 |
| JP | 2002212101 | 7/2002 |
| JP | 2003040890 | 2/2003 |
| JP | 2003083968 | 3/2003 |
| JP | 2003231687 | 8/2003 |
| NL | 6409237 | 4/1965 |
| NL | 6413475 | 5/1965 |
| RU | 2182708 | 5/2002 |
| WO | WO-9320078 | 10/1993 |
| WO | WO-9907703 | 2/1999 |
| WO | WO-9916755 | 4/1999 |
| WO | WO 99/55672 | 11/1999 |
| WO | WO-9955672 | 11/1999 |
| WO | WO-9962908 | 12/1999 |
| WO | WO-0002887 | 1/2000 |
| WO | WO-0012089 | 3/2000 |
| WO | WO 00/40554 | 7/2000 |
| WO | WO-0040554 | 7/2000 |
| WO | WO 01/02369 | 1/2001 |
| WO | WO-0102369 | 1/2001 |
| WO | WO 01/47898 | 7/2001 |
| WO | WO-0147898 | 7/2001 |
| WO | WO-0149688 | 7/2001 |
| WO | WO-0157038 | 8/2001 |
| WO | WO-0170728 | 9/2001 |
| WO | WO-0170743 | 9/2001 |
| WO | WO-0174786 | 10/2001 |
| WO | WO 02/008221 | 1/2002 |
| WO | WO 02/08245 | 1/2002 |
| WO | WO-0208221 | 1/2002 |
| WO | WO-0208245 | 1/2002 |
| WO | WO 02/14859 | 2/2002 |
| WO | WO-0214859 | 2/2002 |
| WO | WO 02/18383 | 3/2002 |
| WO | WO 02/21135 | 3/2002 |
| WO | WO 02/22598 | 3/2002 |
| WO | WO-0208221 | 3/2002 |
| WO | WO-0218383 | 3/2002 |
| WO | WO-0221135 | 3/2002 |
| WO | WO-0222598 | 3/2002 |
| WO | WO-0222600 | 3/2002 |
| WO | WO 02/28839 | 4/2002 |
| WO | WO 02/30935 | 4/2002 |
| WO | WO-0228839 | 4/2002 |
| WO | WO-0230935 | 4/2002 |
| WO | WO-0232422 | 4/2002 |
| WO | WO 02/34263 | 5/2002 |
| WO | WO 02/36562 | 5/2002 |
| WO | WO 02/40019 | 5/2002 |
| WO | WO 02/40653 | 5/2002 |
| WO | WO 02/41906 | 5/2002 |
| WO | WO 02/42292 | 5/2002 |
| WO | WO-0234263 | 5/2002 |
| WO | WO-0235474 | 5/2002 |
| WO | WO-0236562 | 5/2002 |
| WO | WO-0240019 A1 | 5/2002 |
| WO | WO-0240653 | 5/2002 |
| WO | WO-0241906 | 5/2002 |
| WO | WO-0242292 | 5/2002 |
| WO | WO 02/43709 | 6/2002 |
| WO | WO 02/44168 | 6/2002 |
| WO | WO 02/44170 | 6/2002 |
| WO | WO 02/45707 | 6/2002 |
| WO | WO 02/48152 | 6/2002 |
| WO | WO 02/50062 | 6/2002 |
| WO | WO-0243709 | 6/2002 |
| WO | WO-0244168 | 6/2002 |
| WO | WO-0244170 | 6/2002 |
| WO | WO-0245707 | 6/2002 |
| WO | WO-0248152 | 6/2002 |
| WO | WO-0250062 | 6/2002 |
| WO | WO 02/055012 | 7/2002 |
| WO | WO 02/055013 | 7/2002 |
| WO | WO-02051409 | 7/2002 |
| WO | WO-02055012 | 7/2002 |
| WO | WO-02055013 | 7/2002 |
| WO | WO-02059088 | 7/2002 |
| WO | WO-02062949 | 7/2002 |
| WO | WO 02/059088 | 8/2002 |
| WO | WO 02/062949 | 8/2002 |
| WO | WO 02/064590 | 8/2002 |
| WO | WO-02064590 | 8/2002 |
| WO | WO 02/068399 | 9/2002 |
| WO | WO 02/069901 | 9/2002 |
| WO | WO 02/071073 | 9/2002 |
| WO | WO 02/072549 | 9/2002 |
| WO | WO 02/074340 | 9/2002 |
| WO | WO-02068399 | 9/2002 |
| WO | WO-02069901 | 9/2002 |
| WO | WO-02071073 | 9/2002 |
| WO | WO-02072549 | 9/2002 |
| WO | WO-02074340 | 9/2002 |
| WO | WO-02083952 | 9/2002 |
| WO | WO 02/076439 | 10/2002 |
| WO | WO 02/076926 | 10/2002 |
| WO | WO 02/076947 | 10/2002 |
| WO | WO 02/076960 | 10/2002 |
| WO | WO 02/076976 | 10/2002 |
| WO | WO 02/079192 | 10/2002 |
| WO | WO 02/079690 | 10/2002 |
| WO | WO 02/081463 | 10/2002 |
| WO | WO 02/083143 | 10/2002 |
| WO | WO 02/083608 | 10/2002 |

| | | |
|---|---|---|
| WO | WO 02/083952 | 10/2002 |
| WO | WO-02076439 | 10/2002 |
| WO | WO-02076926 | 10/2002 |
| WO | WO-02076947 | 10/2002 |
| WO | WO-02076960 | 10/2002 |
| WO | WO-02076976 | 10/2002 |
| WO | WO-02079192 | 10/2002 |
| WO | WO-02079690 | 10/2002 |
| WO | WO-02081463 | 10/2002 |
| WO | WO-02083143 | 10/2002 |
| WO | WO-02083608 | 10/2002 |
| WO | WO 02/089738 | 11/2002 |
| WO | WO-02089738 | 11/2002 |
| WO | WO-02101087 | 11/2002 |
| WO | WO 02/101087 | 12/2002 |
| WO | WO 02/102774 | 12/2002 |
| WO | WO 02/102978 | 12/2002 |
| WO | WO-02102774 | 12/2002 |
| WO | WO-02102978 | 12/2002 |
| WO | WO 03/004023 | 1/2003 |
| WO | WO 03/004488 | 1/2003 |
| WO | WO 03/007945 | 1/2003 |
| WO | WO-03004023 | 1/2003 |
| WO | WO-03004488 | 1/2003 |
| WO | WO-03007945 | 1/2003 |
| WO | WO 03/013488 | 2/2003 |
| WO | WO 03/013609 | 2/2003 |
| WO | WO-03013488 | 2/2003 |
| WO | WO-03013609 | 2/2003 |
| WO | WO 03/018835 | 3/2003 |
| WO | WO 03/021851 | 3/2003 |
| WO | WO 03/022214 | 3/2003 |
| WO | WO 03/024401 | 3/2003 |
| WO | WO 03/025563 | 3/2003 |
| WO | WO-03018835 | 3/2003 |
| WO | WO-03021851 | 3/2003 |
| WO | WO-03022214 | 3/2003 |
| WO | WO-03024401 | 3/2003 |
| WO | WO-03025563 | 3/2003 |
| WO | WO 03/026664 | 4/2003 |
| WO | WO 03/026665 | 4/2003 |
| WO | WO 03/026666 | 4/2003 |
| WO | WO 03/027223 | 4/2003 |
| WO | WO 03/031436 | 4/2003 |
| WO | WO 03/032984 | 4/2003 |
| WO | WO-03026664 | 4/2003 |
| WO | WO-03026665 | 4/2003 |
| WO | WO-03026666 | 4/2003 |
| WO | WO-03027223 | 4/2003 |
| WO | WO-03031436 | 4/2003 |
| WO | WO-03032984 | 4/2003 |
| WO | WO 03/035065 | 5/2003 |
| WO | WO 03/035644 | 5/2003 |
| WO | WO 03/037871 | 5/2003 |
| WO | WO 03/037872 | 5/2003 |
| WO | WO 03/038401 | 5/2003 |
| WO | WO-03035065 | 5/2003 |
| WO | WO-03035644 | 5/2003 |
| WO | WO-03037871 | 5/2003 |
| WO | WO-03037872 | 5/2003 |
| WO | WO-03038401 | 5/2003 |
| WO | WO 03/048140 | 6/2003 |
| WO | WO-03048140 | 6/2003 |
| WO | WO-03-053939 A1 | 7/2003 |
| WO | WO 03/053948 | 7/2003 |
| WO | WO-03053948 | 7/2003 |
| WO | WO 03/068754 | 8/2003 |
| WO | WO 03/070943 | 8/2003 |
| WO | WO-03068754 | 8/2003 |
| WO | WO-03070943 | 8/2003 |
| WO | WO 03/082272 | 10/2003 |
| WO | WO-03082272 | 10/2003 |
| WO | WO 03/091408 | 11/2003 |
| WO | WO 03/095432 | 11/2003 |
| WO | WO 03/095995 | 11/2003 |
| WO | WO-03091408 | 11/2003 |
| WO | WO-03095432 | 11/2003 |
| WO | WO-03095995 | 11/2003 |
| WO | WO-2004016611 | 2/2004 |
| WO | WO-2004035549 | 4/2004 |

OTHER PUBLICATIONS

López-Rodriguez, et al., "Synthesis of New (Benzimidazolyl) Piperazines with Affinity for the 5-$HT_{1A}$ Receptor Via Pd(0) Amination of Bromobenzimidazoles", Bioorg. & Med. Chem. Letters (1999) vol. 9, 2339-42.

López-Rodriguez, et al., "Pd(0) Amination of Benzimidazoles as an Efficient Method towards New (Benzimidazolyl) piperazines with High Affinity for the 5-$HT_{1A}$ Receptor", Tetrahedron 56 (2000) 3245-53.

López-Rodriguez, et al., "Design and Synthesis of New Benzimidazole-Arylpiperazine Derivatives Acting as Mixed 5-$HT_{1A}$/5-$HT_3$ Ligands", Bioorg. & Med. Chem. Letters (2003) vol. 13, 3177-80.

López-Rodriguez, et al., "Design and Synthesis of S-(-)-2-[[4-(napht-1-yl)piperazin-1-yl]-methyl]-1,4-dioxoperhydropyr-rolo[1,2-a]pyrazine (CSP-2503) Using Computational Simulation. A 5-$HT_{1A}$ Receptor Agonist", Bioorg. & Med. Chem. Letters (2003) vol. 13, 1429-32.

Mewshaw, et al., "New Generation Dopaminergic Agents. 5. Heterocyclic Bioisosteres That Exploit the 3-OH-$N^1$-Phenylpiperazine Dopaminergic Template", Bioorg. & Med. Chem. Letters (1998) vol. 8, 2675-80.

Armer and Smelt, "Non_peptidic GnRh Receptor Antagonists," Current Medicinal Chemistry, vol. 11, pp. 3017-3028 (2004).

Artamonova, et al., "Preparation of 1,5-Disubstituted Tetrazoles Under Phase-Transfer Conditions", Synthesis (1996) 12, 1428-30.

Barraclough et al. "Inotropic 'A' Ring Substituted Sulmazole and Isomazole Analogues," J. Med. Chem., 1999, 33, 2231-2239.

Buchwald, et al., "Long-term, Continuous Intravenous Heparin Administration by an Implantable Infusion Pump in Ambulatory Patients with Recurrent Venous Thrombosis", Surgery, 88(4):507-516 (1980).

Bundgaard, "Design and Application of Prodrugs", in Textbook of Drug Design and Development, Kgrogsgaard-Larsen, et al., eds., Harwood Academic Publishers, Chapter 5, pp. 113-191 (1991).

Chengalvala, M.V. et al., "GnRH Agonists and Antagonists in Cancer Therapy," Curr. Med. Chem.—Anti-Cancer Agents, 2003, 3, 399-410.

Clayton, et al., "Receptor-binding Affinity of Gonadotropin-releasing Hormone Analogs: Analysis by Radioligand-receptor Assay", Endocrinology, 106(4):1154-1159 (1980).

Controlled Drug Bioavailability, Drug Product Design and Performance, Smolen, et al., eds., John Wiley & Sons (1984).

Dandegaonker, et al., "Brom-hydroxychalkone", Monatshefte fuer Chemie 96(2), (1965) 450-60.

Decroix, et al., "Synthese de Composes Polyazotes a Partir de Nitrile ou D'iminoether Furannique, Thiophenique et Selenophenique", Bulletin de la Societe Chimique de France (1976) (3-4, Pt. 2) 621-7.

Design of Prodrugs, Bundgaard, ed., Elsevier (1985).

Dox, A.W. "Acetamidine Hydrochloride," Organic Syntheses, 1932, pp. 5-7.

During, et al., "Controlled Release of Dopamine from a Polymeric Brain Implant: In Vivo Characterization", Ann. Neural., 25(4):351-356 (1989).

Edlin, et al., "Selective Solvent Extraction of Tetrahedrally-Coordinating Transition Metal Ions From Acidic Aqueous Media Using Benzimidazole-Phosphinate Ligands: Specificity for Zinc(II) Over Copper(II)", New Journal of Chemistry 23(8) (1999) 819-26.

Enuguehard, et al., Ipso- or Cine-Substitutions of 6-Haloimidazo[1,2-a]pyridine Derivatives with Different Azoles Depending on the Reaction Conditions, J. Org. Chem, 68:5614-5617 (2003).

Finkelstein, "Regioselective Lithiation and Reaction of [1,2,4]Triazolo[1,5-a]pyridine and Pyrazolo[1,5-a]pyridine", J. Org. Chem., 57:5538-5540 (1992).

Gilchrist, et al., "Cyclisations of Ortho-Substituted N-Arylbenzimidoyl Nitrenes. Part 1. Cyclisations With Ortho-Alkyl Substituents: Skeletal Rearrangements and [1,9]Alkyl Migrations", J. Chem. Soc. Perkin Trans. I (1979) 1871-73.

Goodson, "Dental Applications", *Medical Applications of Controlled Release*, vol. 2, Langer, et al,. eds., CRC Press, Boca Raton, FL, pp. 115-138 (1984).

Grenda, et al., "Novel Preparation of Benzimidazoles From N-Arylamidines. New Synthesis of Thiabendazole", J. Org. Chem. (1965) 30(1) 259-61.

Grundker, C. et al., "Gonadotropin-releasing hormone receptor-targeted gene therapy of gynecologic cancers," Molecular Cancer Therapeutics 2005; 4(2). Feb. 2005, 225-231.

Gudmundsson, et al., "Synthesis of Novel Imidazo[1,2-a]pyridines with Potent Activity Against Herpesviruses", Org. Lett, 5(8):1369-1372 (2003).

Harris, et al., "Improved Functional Group Compatibility in the Palladium-Catalyzed Synthesis of Aryl Amines", Org. Lett. (2002) 4, 2885-8.

Haruki et al., "The Preparation of 2-Substituted Benzimidazoles and 2-Phenylnaphtho-[1, 2-d]imidazole From N-Arylamidines", Bull. Chem. Soc. Japan (1965) 38(10), 1805.

Haruki, et al., "Some Reactions of N-Haloamidines", Bull. Chem. Soc. Japan (1968) 41, 1361-67.

Hirsch, L. et al., "Birth Control: Birth Control Pill," TeensHealth, Nemours Foundation, http://kidshealth.org/teen/sexual_health/contraception/contraception_birth.html, Jul. 2, 2008.

Hisano, et al., "Synthesis of Benzoxazoles, Benzothiazoles and Benzimidazoles and Evaluation of Their Antifungal, Insecticidal and Herbicidal Activities", Chem. Pharm. Bull. (1982) 30(8), 2996-3004.

Howard III, et al., "Intracerebral Drug Delivery in Rats with Lesion-Induced Memory Deficits", J. Neurosurg., 71:105-112 (1989).

Ichikawa, et al., "Acidic Properties of Benzimidazoles and Substituent Effects. III: The Substituent Effect on the Imidazole Cyclization From N-(m-Substituted-Phenyl) Picolylamidines", Organic Preparations and Procedures International (1979) 10(5), 205-9.

Ichikawa, et al., "Acidic Properties of Benzimidazoles and Substituent Effects. IV. Relationship Between the Acidities of N'-(Substituted Phenyl) Arylamidines and Ring Closures to Imidazole", Chem. Pharm. Bull. (1979) 27(5), 1255-64.

Katritzky, et al., "Pyrazolo(1,5-c)Pyrimidines From Pyrylium Salts and Amidrazones and Pyridine Imidoyl-N-Imides From Imidoyl Chlorides", Heterocycles (1982) 18, 21-28.

Langer, "New Methods of Drug Delivery", Science, 249:1527-1533 (1990).

Langer, et al., "Chemical and Physical Structure of Polymers as Carriers for Controlled Release of Bioactive Agents: A Review", J. Macromol. Sci. Rev. Macromol. Chem., C23(1):61-126 (1983).

Levy, et al., "Inhibition of Calcification of Bioprosthetic Heart Valves by Local Controlled-Release Diphosphonate", Science, 228:190-192 (1985).

Liu, et al., "A Particularly Convenient Preparation of Benzohydroximinoyl Chlorides (Nitrile Oxide Precursors)", J. Org. Chem. (1980) 45, 3916-18.

Lopez-Berestein, "Treatment of Systemic Fungal Infections with Liposomal-Amphotericin B", Liposomes in the Therapy of Infectious Diseases and Cancer, Lopez-Berstein, et al., eds., Alan R. Liss, Inc., New York, pp. 317-327 (1989).

March, Advanced Organic Chemistry: Reactions, Mechanisms and Structures, Fourth Edition, John Wiley & Sons, pp. 69-74 (1992).

Medical Applications of Controlled Release, vols. I and II, Langer and Wise, eds., CRC Press, Inc., Boca Raton, FL (1984).

Methods in Enzymology, vol. 112, Widder, et al., eds., Academic Press (1985).

Nielsen, et al., "Glycolamide Esters as Biolabile Prodrugs of Carboxylic Acid Agents: Synthesis, Stability, Bioconversion, and Physiochemical Properties", Journal of Pharmaceutical Sciences, 77(4):285-298 (1988).

Partridge, et al., "Cyclic Amidines. Part VII. Preparation of Benziminazoles From N'-Aryl-N-Hydroxyamidines", J. Chem. Soc. (1958) 2086-92.

Prodrugs as Novel Drug Delivery Systems, Higuchi, et al., eds., American Chemical Society, Washington, Dc (1975).

Radebaugh, et al., "Preformulation", Remington: The Science and Practice of Pharmacy, 19th Edition, Gennaro, Ed., pp. 1447-1462 (1995).

Ramsden, et al., "Rearrangement and Cyclo-alpha-Elimination of N-Substituted Amidines Using (Diacetoxyiodo) Benzene", J. Chem. Soc. Perkin Trans. I (1995) 615-17.

Saudek, et al., "A Prelminiary Trial of the Programmable Implantable Medication System for Insulin Delivery", New England Journal of Med., 321(9):574-579 (1989).

Sefton, "Implantable Pumps", CRC Crit. Ref. Biomed. Eng., 14(3):201-240 (1987).

Smith, et al., "Amidrazones III. The Synthesis and Properties of 1,1,1-Trimethyl-2-(N-Phenlbenzimidoyl)Hydrazinium Hydroxide Inner Salt—A Novel Ylid", Tetrahedron Lett. (1973) 3941-42.

Smith, et al., "The Thermal Breakdown of Diaryltetrazoles", J. Am. Chem. Soc. (1958) 80, 4647-54.

Treat, et al., "Liposome Encapsulated Doxorubicin Preliminary Results of Phase I and Phase II Trials", Liposomes in the Therapy of Infectious Diseases and Cancer, Lopez-Berestein, et al., eds., Alan R. Liss, Inc., New York, pp. 353-365 (1989).

Wolfe, et al., "Simple, Efficient Catalyst System for the Palladium-Catalyzed Amination of Aryl Chlorides, Bromides, and Triflates", J. Org. Chem. (2000) 65, 1158-74.

\* cited by examiner

GONADOTROPIN RELEASING HORMONE RECEPTOR ANTAGONISTS

This application claims the benefit of provisional application U.S. Ser. No. 60/580,640, filed Jun. 17, 2004, which is hereby incorporated by reference into the subject application in its entirety.

Throughout this application, various publications are referenced. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights whatsoever.

FIELD OF INVENTION

The present invention relates to Gonadotropin Releasing Hormone ("GnRH") (also known as Leutinizing Hormone Releasing Hormone) receptor antagonists, processes for preparing them and to pharmaceutical compositions containing them.

BACKGROUND

GnRH is a decameric peptide released from the hypothalamus. In the anterior pituitary gland, GnRH activates the GnRH receptor. Activation of the GnRH receptor triggers the release of follicle stimulating hormone (FSH) and leuteinizing hormone (LH). FSH and LH stimulate the biosynthesis and release of sex steroids in the gonads of both genders.

Typically, this is desirable, but certain sex hormone dependent pathological conditions exist where it would be beneficial to prevent activation of the GnRH receptor. For example, inhibition of the GnRH receptor can lead to a large drop in sex steroid production, which in turn can alleviate sex hormone dependent pathological conditions such as prostate cancer, endometriosis, uterine fibroids, uterine cancer, breast cancer, ovarian cancer, testicular cancer, or primary hirsutism. Moreover, there are other situations where it would be beneficial to prevent activation of the GnRH receptor, such as during some points of the in vitro fertilization process, such as to prevent LH surge.

All currently marketed GnRH therapeutics are peptides that exhibit receptor antagonism in one of two ways. The first is through GnRH receptor superagonism. The GnRH receptor, when stimulated in bursts, causes normal release of the gonadotropins, FSH and LH. Under constant stimulation, the receptor becomes desensitized and the overall effect is GnRH receptor inhibition. The superagonism process is somewhat undesirable, as inhibition via this process can take up to two weeks to arise in human patients. During this delay there is often an increase in disease symptoms due to the initial hormone stimulation phase. This phenomenon is referred to as flare.

The second method for receptor inhibition is through direct antagonism of the GnRH receptor with peptide antagonists. This causes an immediate drop in plasma LH levels. However, as mentioned above, current pharmaceuticals that cause blockade of the GnRH receptor are all peptides. As such they are not orally bioavailable and must be administered via parenteral means such as intravenous, subcutaneous or intramuscular injection. Thus, an orally effective GnRH antagonist would be of significant benefit.

Therefore, based upon the foregoing, it is clear that GnRH receptor antagonists are useful, and development of new GnRH receptor antagonists is highly desirable.

SUMMARY

In one embodiment, the present invention relates to compounds, and methods of use for compounds, of the formula I:

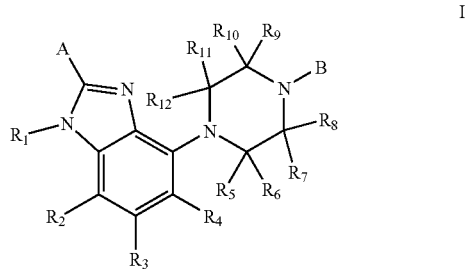

and pharmaceutically acceptable salts thereof, wherein:

A is aryl or heteroaryl, each optionally substituted;

B is $(CR_{13}R_{14})_k$-D;

D is H, alkyl, cycloalkyl, heterocycloalkyl, aryl, or heteroaryl, each alkyl, cycloalkyl, heterocycloalkyl, aryl, or heteroaryl being optionally substituted;

k is 0, 1, 2, or 3;

$R_1$ is H, the tautomeric form, or optionally substituted alkyl;

$R_2$, $R_3$, and $R_4$ are, independently, H, optionally substituted alkyl, halogen, or $OR_1$;

$R_5$, $R_6$, $R_7$, $R_8$, $R_9$, $R_{10}$, $R_{11}$, and $R_{12}$, are, independently, H, alkyl, alkenyl, or alkynyl, each alkyl, alkenyl, or alkynyl being optionally substituted;

$R_{13}$ and $R_{14}$ are, independently at each occurrence, H or optionally substituted alkyl.

In some embodiments, the compounds of Formula I find use as GnRH receptor antagonists.

In some embodiments, the compounds of Formula I find use in pharmaceutical compositions comprising compounds of Formula I and an additional active agent.

DETAILED DESCRIPTION

In one embodiment, the present invention comprises a compound of the formula I:

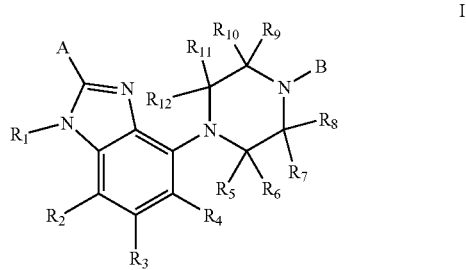

and pharmaceutically acceptable salts thereof, wherein:

A is aryl or heteroaryl, each optionally substituted;

B is $(CR_{13}R_{14})_k$-D;

D is H, alkyl, cycloalkyl, heterocycloalkyl, aryl, or heteroaryl, each alkyl, cycloalklyl, heterocycloalkyl, aryl, or heteroaryl being optionally substituted;

k is 0, 1, 2, or 3;

$R_1$ is H, the tautomeric form, or optionally substituted alkyl;

$R_2$, $R_3$, and $R_4$ are, independently, H, optionally substituted alkyl, halogen, or $OR_1$;

$R_5$, $R_6$, $R_7$, $R_8$, $R_9$, $R_{10}$, $R_{11}$, and $R_{12}$, are, independently, H, alkyl, alkenyl, or alkynyl, each alkyl, alkenyl, or alkynyl being optionally substituted;

$R_{13}$ and $R_{14}$ are, independently at each occurrence, H or optionally substituted alkyl.

In one embodiment, $R_1$, $R_2$, $R_3$, and $R_4$ are, independently, H or $C_1$-$C_3$ alkyl.

In another embodiment, $R_5$, $R_6$, $R_7$, $R_8$, $R_9$, $R_{10}$, $R_{11}$, and $R_{12}$, are, independently, H, $C_1$-$C_4$ alkyl, $C_2$-$C_6$ alkenyl, or $C_2$-$C_6$ alkynyl.

In another embodiment, $R_{13}$ and $R_{14}$ are, independently at each occurrence, H or $C_1$-$C_3$ alkyl.

In one embodiment, A is phenyl or thiophenyl, each optionally substituted.

In one embodiment, A is phenyl substituted with $C_1$-$C_4$ alkyl. In another embodiment, A is phenyl substituted with an ethyl or t-butyl group. In still another embodiment, A is phenyl substituted with a t-butyl group.

In one embodiment, D is:

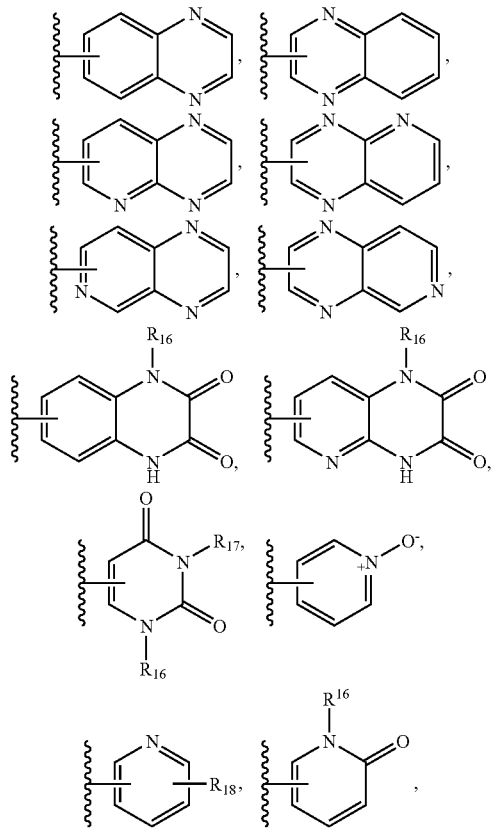

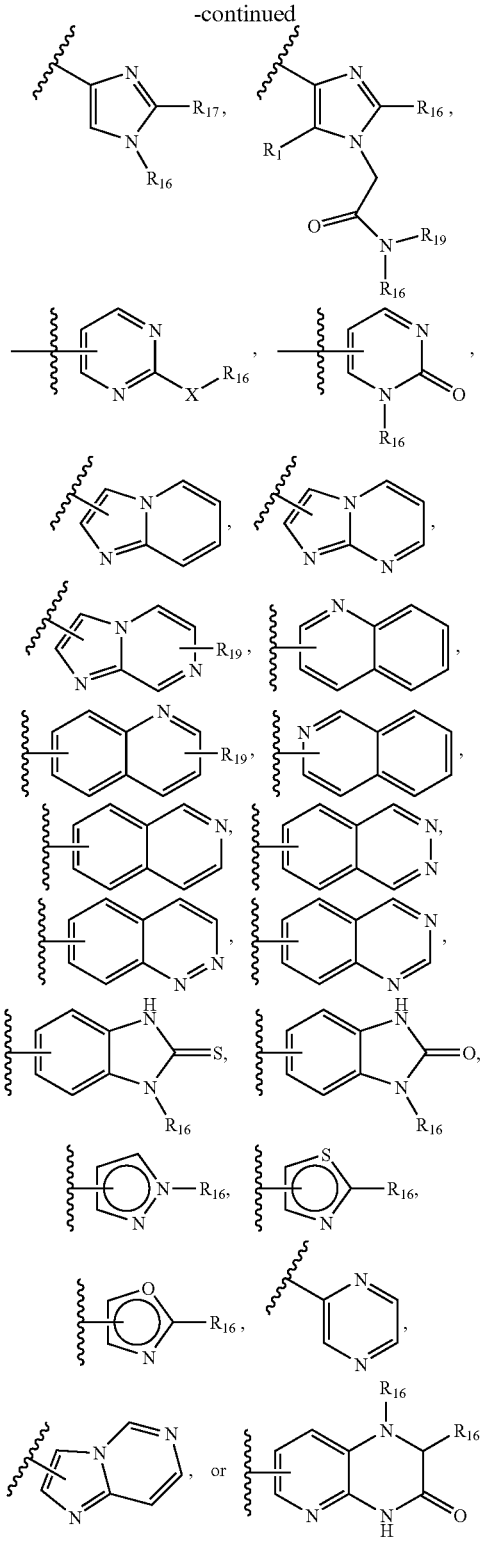

each D also having up to three $R_{19}$ substituents attached to the ring of D containing at least one N;

wherein:

$R_{16}$ is hydrogen, $C_1$-$C_{10}$ alkyl, $C_2$-$C_{10}$ alkenyl, $C_2$-$C_{10}$alkynyl, $R_{20}$-E-$R_{21}$, C(=O)E$R_{20}$, E$R_{20}$, N$R_{20}R_{21}$, or $(CH_2)_nG$, optionally substituted alkyl, optionally substituted aryl, aryl substituted with optionally substituted alkyl, alkyl substituted with optionally substituted aryl, alkyl substituted with imidazole, alkyl substituted with optionally substituted imidazole, or alkyl substituted with indole;

$R_{17}$ is hydrogen, $C_1$-$C_6$ alkyl, $C_2$-$C_6$ alkenyl, $C_2$-$C_6$ alkynyl, $(CH_2)_mCO_2R_{20}$, $(CH_2)_mC(=O)NR_{20}R_{21}$;

$R_{18}$ is $CO_2R_{20}$, $C(=O)NR_{20}R_{21}$, or $SO_mR_{20}$;

$R_{19}$ is H, $C_1$-$C_3$ alkyl, $C_2$-$C_6$ alkenyl, or $C_2$-$C_6$ alkynyl; or alternatively, $R_{16}$ and $R_{19}$, taken together with the atoms to which they are attached, form a cyclic or heterocyclic group, e.g., of 3-8 ring members and the heteroatoms are selected from O, N and S;

$R_{20}$ and $R_{21}$ are, independently, H, $C_1$-$C_3$ alkyl, or heteroalkyl, or alternatively, $R_{20}$ and $R_{21}$, taken together with the atoms to which they are attached, form a cyclic or heterocyclic group, e.g., of 3-8 ring members and the heteroatoms are selected from O, N and S;

m is 0, 1, or 2;

n is 0, 1, 2, 3, or 4;

X is O, $NR_{21}$, or $SO_m$;

E is O, N, $NR_{21}$, or $SO_m$; and

G is phenyl, 2-pyridyl, 3-pyridyl or 4-pyridyl.

In another embodiment, D is $C_1$-$C_6$ alkyl.

In one embodiment, k is 1, $R_{13}$ is H, and $R_{14}$ is H or methyl.

In one embodiment, D is quinoxalin-6-yl, pyridopyrazin-3-yl, or 1-(4-methylbenzyl)pyridin-3-yl-6-one.

In one embodiment, $R_1$, $R_2$, $R_3$, $R_4$, $R_5$, $R_6$, $R_7$, $R_{10}$, $R_{11}$, and $R_{12}$ are H.

In one embodiment, $R_{13}$ and $R_{14}$ are H.

In one embodiment, $R_9$ is H, methyl, or ethyl. In another embodiment, $R_9$ is H. In another embodiment, $R_9$ is methyl or ethyl.

In one embodiment, A is phenyl substituted with $C_1$-$C_6$ alkyl, alkenyl, alkynyl, $NR_{22}R_{23}$, $CR_{24}(CF_3)_2$, $JR_{22}$, or $C(=O)R_{22}$, wherein J is O or $SO_m$, wherein m is 0, 1, or 2; $R_{22}$ and $R_{23}$ are, independently, H, $C_1$-$C_7$ alkyl, alkenyl, alkynyl, aryl, or heteroalkyl, each alkyl, alkenyl, alkynyl, aryl, or heteroaryl being optionally substituted; alternatively, $R_{22}$ and $R_{23}$, taken together with the atoms to which they are attached, form an optionally substituted cyclic or optionally substituted heterocyclic group, e.g., of 3-8 ring members and the heteroatoms are selected from O, N and S; and $R_{24}$ is H, or OH. In one embodiment, $R_{22}$ and $R_{23}$ form a cyclic or heterocyclic group, and said cyclic or heterocyclic group is substituted with $R_{20}ER_{21}$, wherein $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, e.g., of 3-8 ring members and the heteroatoms are selected from O, N and S, and E is O, N, $NR_{21}$, or $SO_m$, wherein m is 0, 1, or 2. In another embodiment, $R_{22}$ and $R_{23}$ are ethyl. In another embodiment, $R_{22}$ and $R_{23}$ taken together with the atoms to which they are attached form pyrrolidine, piperidine, hexamethyleneimine, piperazine, homopiperazine, aziridine, or azetidine, each optionally substituted. In one embodiment, said pyrrolidine, piperidine, hexamethyleneimine, piperazine, homopiperazine, aziridine, or azetidine is substituted with $R_{20}ER_{21}$, wherein $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, and E is O, N, $NR_{21}$, or $SO_m$, wherein m is 0, 1, or 2.

In one embodiment, $R_{22}$ is aryl, and is substituted with halogen, $R_{25}$, $OR_{25}$, or $NR_{26}R_{27}$, wherein $R_{25}$ is H, $C_1$-$C_3$ alkyl, or heteroalkyl; $R_{26}$ and $R_{27}$ are, independently, H, $C_1$-$C_3$ alkyl, or heteroalkyl, alternatively, $R_{26}$ and $R_{27}$, taken together with the atoms to which they are attached, form a cyclic or heterocyclic group, e.g., of 3-8 ring members and the heteroatoms are selected from O, N and S. In another embodiment, $R_{26}$ and $R_{27}$ form pyrrolidine, piperidine, hexamethyleneimine, piperazine, homopiperazine, aziridine, or azetidine.

In another embodiment of the present invention, a method for modulating the activity of a Gonadotropin Releasing Hormone (GnRH) receptor, comprising contacting said receptor with an effective amount of a compound according to Formula I is provided.

In one embodiment, the method further comprises determining the activity of said receptor.

Further, in one embodiment, the determination is made before said contacting step. In another embodiment, the determination is made after said contacting step.

In another embodiment of the present invention, a method for treating a patient suspected of suffering from a condition associated with excessive Gonadotropin Releasing Hormone (GnRH) receptor activity, comprising the step of administering to the patient a therapeutically effective amount of a compound according to Formula I is provided.

In one embodiment, the condition is prostate cancer, endometriosis, uterine fibroids, uterine cancer, breast cancer, ovarian cancer, testicular cancer, primary hirsutism, or LH surge.

In one embodiment, the compound of Formula I is 6-({(2S)-4-[2-(4-tert-butylphenyl)-1H-benzimidazol-4-yl]-2-methylpiperazin-1-yl}methyl)quinoxaline; 6-({4-[2-(4-ethylphenyl)-1H-benzimidazol-4-yl]piperazin-1-yl}methyl)quinoxaline; 3-(4-{4-[4-(quinoxalin-6-ylmethyl)piperazin-1-yl]-1H-benzimidazol-2-yl}phenoxy)phenol; 6-({4-[2-(4-tert-butylphenyl)-1H-benzimidazol-4-yl]piperazin-1-yl}methyl)quinoxaline; phenyl(4-{4-[4-(quinoxalin-6-ylmethyl)piperazin-1-yl]-1H-benzimidazol-2-yl}phenyl)methanone; 6-({4-[2-(4-tert-butylphenyl)-1H-benzimidazol-4-yl]-2-methylpiperazin-1-yl}methyl)quinoxaline; 6-[(4-{2-[4-(methylsulfonyl)phenyl]-1H-benzimidazol-4-yl}piperazin-1-yl)methyl]quinoxaline; 6-[(4-{2-[4-(ethylsulfonyl)phenyl]-1H-benzimidazol-4-yl}piperazin-1-yl)methyl]quinoxaline; 6-({4-[2-(4-isopropylphenyl)-1H-benzimidazol-4-yl]piperazin-1-yl}methyl)quinoxaline; 6-({(2R)-4-[2-(4-tert-butylphenyl)-1H-benzimidazol-4-yl]-2-methylpiperazin-1-yl}methyl)quinoxaline; 6-({(2S)-4-[2-(4-tert-butylphenyl)-1H-benzimidazol-4-yl]-2-methylpiperazin-1-yl}methyl)quinoxaline; N,N-diethyl-N-(4-{4-[4-(quinoxalin-6-ylmethyl)piperazin-1-yl]-1H-benzimidazol-2-yl}phenyl)amine; 6-({(2S)-4-[2-(4-tert-butylphenyl)-1H-benzimidazol-7-yl]-2-ethylpiperazin-1-yl}methyl)quinoxaline; 6-[(4-{2-[5-(methylthio)thien-2-yl]-1H-benzimidazol-4-yl}piperazin-1-yl)methyl]quinoxaline; 6-[(4-{2-[4-(methylthio)phenyl]-1H-benzimidazol-4-yl}piperazin-1-yl)methyl]quinoxaline; 6-({4-[2-(4-methoxyphenyl)-1H-benzimidazol-4-yl]piperazin-1-yl}methyl)quinoxaline; 6-{[4-(2-thien-2-yl-1H-benzimidazol-4-yl)piperazin-1-yl]methyl}quinoxaline; 6-{[4-(2-thien-3-yl-1H-benzimidazol-4-yl)piperazin-1-yl]methyl}quinoxaline; 4-{4-[4-(quinoxalin-6-ylmethyl)piperazin-1-yl]-1H-benzimidazol-2-yl}benzenesulfonamide; 2-methoxy-5-{4-[4-(quinoxalin-6-ylmethyl)piperazin-1-yl]-1H-benzimidazol-2-yl}phenol; 6-[(4-{2-[4-(1H-pyrrol-1-yl)phenyl]-1H-benzimidazol-4-yl}piperazin-1-yl)methyl]quinoxaline; 6-({4-[2-(3,3-dimethyl-1,1-dioxido-2,3-dihydro-1-benzothien-6-yl)-1H-benzimidazol-4-yl]piperazin-1-yl}methyl)quinoxaline; 6-({(2R,6S)-4-[2-(4-tert-butylphenyl)-1H-benzimidazol-4-yl]-2,6-dimethylpiperazin-1-yl}methyl)quinoxaline; 6-[(4-{2-[4-(phenylsulfonyl)

phenyl]-1H-benzimidazol-4-yl}piperazin-1-yl)methyl]quinoxaline; 6-[(4-{2-[5-(methylsulfonyl)thien-2-yl]-1H-benzimidazol-4-yl}piperazin-1-yl)methyl]quinoxaline; N,N-diethyl-N-(4-{7-[(3S)-3-ethyl-4-(quinoxalin-6-ylmethyl)piperazin-1-yl]-1H-benzimidazol-2-yl}phenyl)amine; 6-({4-[2-(4-pyrrolidin-1-ylphenyl)-1H-benzimidazol-4-yl]piperazin-1-yl}methyl)quinoxaline; 1-(4-{4-[4-(quinoxalin-6-ylmethyl)piperazin-1-yl]-1H-benzimidazol-2-yl}phenyl)ethanone; 6-({4-[2-(5-tert-butylthien-2-yl)-1H-benzimidazol-4-yl]piperazin-1-yl}methyl)quinoxaline; 2,2,2-trifluoro-1-(4-{4-[4-(quinoxalin-6-ylmethyl)piperazin-1yl]-1H-benzimidazol-2-yl}phenyl)ethane-1,1-diol; 1,1,1,3,3,3-hexafluoro-2-(4-{7-[4-(quinoxalin-6-ylmethyl)piperazin-1-yl]-1H-benzimidazol-2-yl}phenyl)propan-2-ol; 6-{[4-(2-{4-[2,2,2-trifluoro-1-(trifluoromethyl)ethyl]phenyl}-1H-benzimidazol-7-yl)piperazin-1-yl]methyl}quinoxaline; 2-({4-[2-(4-tert-butylphenyl)-1H-benzimidazol-7-yl]piperazin-1-yl}methyl)imidazo[1,2-a]pyrimidine; 2-({(2S)-4-[2-(4-tert-butylphenyl)-1H-benzimidazol-7-yl]-2-methylpiperazin-1-yl}methyl)imidazo[1,2-a]pyrimidine; 2-({4-[2-(4-tert-butylphenyl)-1H-benzimidazol-7-yl]piperazin-1-yl}methyl)-3-nitroimidazo[1,2-a]pyrimidine; 2-(4-tert-butylphenyl)-4-[4-(imidazo[1,2-a]pyridin-2-ylmethyl)piperazin-1-yl]-1H-benzimidazole; 2-(4-tert-butylphenyl)-7-{4-[(5,7-dimethylimidazo[1,2-a]pyridin-2-yl)methyl]piperazin-1-yl}-1H-benzimidazole; 2-(4-tert-butylphenyl)-7-{(3S)-4-[(5,7-dimethylimidazo[1,2-a]pyridin-2-yl)methyl]-3-methylpiperazin-1-yl}-1H-benzimidazole; 2-(4-tert-butylphenyl)-7-{4-[(7-methylimidazo[1,2-a]pyridin-2-yl)methyl]piperazin-1-yl}-1H-benzimidazole; 2-(4-tert-butylphenyl)-7-{(3S)-3-methyl-4-[(7-methylimidazo[1,2-a]pyridin-2-yl)methyl]piperazin-1-yl}-1H-benzimidazole; 2-({4-[2-(4-tert-butylphenyl)-1H-benzimidazol-7-yl]piperazin-1-yl}methyl)imidazo[1,2-a]pyridine-6-carboxamide; 2-(4-tert-butylphenyl)-7-{4-[(5-methylimidazo[1,2-a]pyridin-2-yl)methyl]piperazin-1-yl}-1H-benzimidazole; 2-({4-[2-(4-tert-butylphenyl)-1H-benzimidazol-7-yl]piperazin-1-yl}methyl)-5,7-dimethylimidazo[1,2-c]pyrimidine; 2-({4-[2-(4-tert-butylphenyl)-1H-benzimidazol-7-yl]piperazin-1-yl}methyl)imidazo[1,2-a]pyrazine; 3-{4-[2-(4-tert-butylphenyl)-1H-benzimidazol-4-yl]piperazin-1-yl}propane-1-sulfonamide; 5-[(4-{2-[4-(diethylamino)phenyl]-1H-benzimidazol-4-yl}piperazin-1-yl)methyl]-1-ethylpyrimidine-2,4(1H,3H)-dione; 2-(4-tert-butylphenyl)-4-[4-(1H-imidazol-5-ylmethyl)piperazin-1-yl]-1H-benzimidazole; 2-(4-tert-butylphenyl)-4-{4-[(4-methyl-1H-imidazol-5-yl)methyl]piperazin-1-yl}-1H-benzimidazole; 2-(4-tert-butylphenyl)-4-{4-[(2-phenyl-1H-imidazol-4-yl)methyl]piperazin-1-yl}-1H-benzimidazole; 2-(4-tert-butylphenyl)-4-{4-[(2-methyl-1H-imidazol-4-yl)methyl]piperazin-1-yl}-1H-benzimidazole; 2-(4-tert-butylphenyl)-4-{4-[(2-ethyl-4-methyl-1H-imidazol-5-yl)methyl]piperazin-1-yl}-1H-benzimidazole; 2-(4-tert-butylphenyl)-4-{(3R)-4-[(2-ethyl-5-methyl-1H-imidazol-4-yl)methyl]-3-methylpiperazin-1-yl}-1H-benzimidazole; 2-(4-tert-butylphenyl)-4-{(3S)-4-[(2-ethyl-5-methyl-1H-imidazol-4-yl)methyl]-3-methylpiperazin-1-yl}-1H-benzimidazole; 4-{4-[(2-ethyl-5-methyl-1H-imidazol-4-yl)methyl]piperazin-1-yl}-2-(4-isopropylphenyl)-1H-benzimidazole; 4-{4-[(2-ethyl-4-methyl-1H-imidazol-5-yl)methyl]piperazin-1-yl}-2-[4-(ethylsulfonyl)phenyl]-1H-benzimidazole; 4-{4-[(2-ethyl-4-methyl-1H-imidazol-5-yl)methyl]piperazin-1-yl}-2-[4-(isopropylsulfonyl)phenyl]-1H-benzimidazole; 4-{4-[(2-ethyl-4-methyl-1H-imidazol-5-yl)methyl]piperazin-1-yl}-2-[4-(methylsulfonyl)phenyl]-1H-benzimidazole; N,N-diethyl-N-[4-(4-{4-[(2-ethyl-5-methyl-1H-imidazol-4-yl)methyl]piperazin-1-yl}-1H-benzimidazol-2-yl)phenyl]amine; 4-{4-[(2-butyl-1H-imidazol-4-yl)methyl]piperazin-1-yl}-2-(4-tert-butylphenyl)-1H-benzimidazole; 4-{4-[(2-butyl-5-chloro-1H-imidazol-4-yl)methyl]piperazin-1-yl}-2-(4-tert-butylphenyl)-1H-benzimidazole; 2-(4-tert-butylphenyl)-4-{4-[(2-ethyl-1,5-dimethyl-1H-imidazol-4-yl)methyl]piperazin-1-yl}-1H-benzimidazole; 2-(4-tert-butylphenyl)-4-{4-[(1,5-dimethyl-1H-imidazol-4-yl)methyl]piperazin-1-yl}-1H-benzimidazole; 2-(4-tert-butylphenyl)-4-{4-[(1-methyl-1H-imidazol-4-yl)methyl]piperazin-1-yl}-1H-benzimidazole; 2-(4-tert-butylphenyl)-4-{4-[(1,2-dimethyl-1H-imidazol-4-yl)methyl]piperazin-1-yl}-1H-benzimidazole; 2-(4-tert-butylphenyl)-4-{4-[(2-ethyl-1H-imidazol-4-yl)methyl]piperazin-1-yl}-1H-benzimidazole; 2-(4-tert-butylphenyl)-4-{4-[(1,2-diethyl-5-methyl-1H-imidazol-4-yl)methyl]piperazin-1-yl}-1H-benzimidazole; 2-(4-tert-butylphenyl)-4-{4-[(1-ethyl-2-methyl-1H-imidazol-4-yl)methyl]piperazin-1-yl}-1H-benzimidazole; 2-(4-tert-butylphenyl)-4-{4-[(1-ethyl-1H-imidazol-4-yl)methyl]piperazin-1-yl}-1H-benzimidazole; 2-(4-tert-butylphenyl)-4-{4-[(1-ethyl-5-methyl-1H-imidazol-4-yl)methyl]piperazin-1-yl}-1H-benzimidazole; 4-{4-[(1-ethyl-5-methyl-1H-imidazol-4-yl)methyl]piperazin-1-yl}-2-[4-(methylsulfonyl)phenyl]-1H-benzimidazole; 2-(4-tert-butylphenyl)-7-{(3S)-3-ethyl-4-[(1-ethyl-5-methyl-1H-imidazol-4-yl)methyl]piperazin-1-yl}-1H-benzimidazole; 2-(4-tert-butylphenyl)-4-{4-[(2-ethyl-1-methyl-1H-imidazol-4-yl)methyl]piperazin-1-yl}-1H-benzimidazole; 4-({4-[2-(4-tert-butylphenyl)-1H-benzimidazol-4-yl]piperazin-1-yl}methyl)-N,N-dimethyl-1H-imidazole-1-sulfonamide; 2-(4-tert-butylphenyl)-4-{4-[(1,2-diethyl-1H-imidazol-4-yl)methyl]piperazin-1-yl}-1H-benzimidazole; 4-{4-[(2-butyl-1-methyl-1H-imidazol-4-yl)methyl]piperazin-1-yl}-2-(4-tert-butylphenyl)-1H-benzimidazole; 2-(4-tert-butylphenyl)-4-{4-[(5-methyl-1-propyl-1H-imidazol-4-yl)methyl]piperazin-1-yl}-1H-benzimidazole; 2-(4-tert-butylphenyl)-4-{4-[(1-isopropyl-5-methyl-1H-imidazol-4-yl)methyl]piperazin-1-yl}-1H-benzimidazole; 2-[4-({4-[2-(4-tert-butylphenyl)-1H-benzimidazol-4-yl]piperazin-1-yl}methyl)-1H-imidazol-1-yl]acetamide; 2-{4-[(4-{2-[4-(methylsulfonyl)phenyl]-1H-benzimidazol-4-yl}piperazin-1-yl)methyl]-1H-imidazol-1-yl}acetamide; 2-{4-[((2S)-2-methyl-4-{2-[4-(methylsulfonyl)phenyl]-1H-benzimidazol-4-yl}piperazin-1-yl)methyl]-1H-imidazol-1-yl}acetamide; 2-[4-({4-[2-(4-tert-butylphenyl)-1H-benzimidazol-4-yl]piperazin-1-yl}methyl)-5-methyl-1H-imidazol-1-yl]acetamide; 2-[4-({4-[2-(4-tert-butylphenyl)-1H-benzimidazol-4-yl]piperazin-1-yl}methyl)-2-methyl-1H-imidazol-1-yl]acetamide; 2-[4-({(2S)-4-[2-(4-tert-butylphenyl)-1H-benzimidazol-4-yl]-2-methylpiperazin-1-yl}methyl)-2-methyl-1H-imidazol-1-yl]acetamide; 2-{2-methyl-4-[(4-{2-[4-(methylsulfonyl)phenyl]-1H-benzimidazol-4-yl}piperazin-1-yl)methyl]-1H-imidazol-1-yl}acetamide; 2-{2-methyl-4-[((2S)-2-methyl-{2-[4-(methylsulfonyl)phenyl]-1H-benzimidazol-4-yl}piperazin-1-yl)methyl]-1H-imidazol-1-yl}acetamide; 2-[4-({4-[2-(4-tert-butylphenyl)-1H-benzimidazol-4-yl]piperazin-1-yl}methyl)-2-ethyl-1H-imidazol-1-yl]acetamide; 2-[4-({(2S)-4-[2-(4-tert-butylphenyl)-1H-benzimidazol-7-yl]-2-ethylpiperazin-1-yl}methyl)-2-methyl-1H-imidazol-1-yl]acetamide; [4-({4-[2-(4-tert-butylphenyl)-1H-benzimidazol-4-yl]piperazin-1-yl}methyl)-2-ethyl-1H-imidazol-1-yl]acetic acid; [4-({4-[2-(4-tert-butylphenyl)-1H-benzimidazol-4-yl]piperazin-1-yl}methyl)-2-methyl-1H-imidazol-1-yl]acetic acid; tert-butyl [4-({4-[2-(4-tert-butylphenyl)-1H-benzimidazol-4-yl]piperazin-1-yl}methyl)-2-methyl-1H-imidazol-1-yl]acetate; 2-[4-({4-[2-(4-tert-butylphenyl)-1H-benzimidazol-4-yl]piperazin-1- yl}methyl)-2-methyl-1H-imidazol-1-yl]-N-methylacetamide; 2-(4-{4-[2-(4-tert-Butyl-phenyl)-1H-benzoimidazol-4-yl]-piperazin-1-ylmethyl}-2-methyl-imidazol-1-yl)-N-ethyl-acetamide; 2-(4-{4-[2-(4-tert-Butyl-phenyl)-1H-benzoimidazol-4-yl]-piperazin-1-ylmethyl}-2-methyl-imidazol-1-yl)-N,N-dimethyl-acetamide; 2-(4-{4-[2-(4-tert-Butyl-phenyl)-1H-benzoimidazol-4-yl]-piperazin-1-ylmethyl}-2-methyl-imidazol-1-yl)-N,N-diethyl-acetamide; 2-(4-{4-[2-(4-tert-Butyl-phenyl)-1H-benzoimidazol-4-yl]-piperazin-1-ylmethyl}-2-methyl-imidazol-1-yl)-N-ethyl-N-methyl-acetamide; 2-(4-{4-[2-(4-tert-Butyl-phenyl)-1H-benzoimidazol-4-yl]-piperazin-1-ylmethyl}-2-methyl-imidazol-1-yl)-N-isopropyl-N-methyl-acetamide; 2-(4-{4-[2-(4-tert-Butyl-phenyl)-1H-benzoimidazol-4-yl]-piperazin-1-ylmethyl}-2-methyl-imidazol-1-yl)-N-methyl-N-propyl-acetamide; 2-(4-{4-[2-(4-tert-Butyl-phenyl)-1H-benzoimidazol-4-yl]-piperazin-1-ylmethyl}-2-methyl-imidazol-1-yl)-N-isopropyl-acetamide; 2-(4-{4-[2-(4-tert-Butyl-phenyl)-1H-benzoimidazol-4-yl]-piperazin-1-ylmethyl}-2-methyl-imidazol-1-yl)-N-(1-ethyl-propyl)-acetamide; 2-(4-{4-[2-(4-tert-Butyl-phenyl)-1H-benzoimidazol-4-yl]-piperazin-1-ylmethyl}-2-methyl-imidazol-1-yl)-N-(2,2-dimethyl-propyl)-acetamide; N-Butyl-2-(4-{4-[2-(4-tert-butyl-phenyl)-1H-benzoimidazol-4-yl]-piperazin-1-ylmethyl}-2-methyl-imidazol-1-yl)-acetamide; N-sec-Butyl-2-(4-{4-[2-(4-tert-butyl-phenyl)-1H-benzoimidazol-4-yl]-piperazin-1-ylmethyl}-2-methyl-imidazol-1-yl)-acetamide; N-sec-Butyl-2-(4-{4-[2-(4-tert-butyl-phenyl)-1H-benzoimidazol-4-yl]-piperazin-1-ylmethyl}-2-methyl-imidazol-1-yl)-acetamide; 2-(4-{4-[2-(4-tert-Butyl-phenyl)-1H-benzoimidazol-4-yl]-piperazin-1-ylmethyl}-2-methyl-imidazol-1-yl)-N-cyclobutyl-acetamide; 2-(4-{4-[2-(4-tert-Butyl-phenyl)-1H-benzoimidazol-4-yl]-piperazin-1-ylmethyl}-2-methyl-imidazol-1-yl)-N-cyclopentyl-acetamide; 2-(4-{4-[2-(4-tert-Butyl-phenyl)-1H-benzoimidazol-4-yl]-piperazin-1-ylmethyl}-2-methyl-imidazol-1-yl)-N-cyclohexyl-acetamide; 2-(4-{4-[2-(4-tert-Butyl-phenyl)-1H-benzoimidazol-4-yl]-piperazin-1-ylmethyl}-2-methyl-imidazol-1-yl)-N-cyclopropylmethyl-acetamide; 2-(4-{4-[2-(4-tert-Butyl-phenyl)-1H-benzoimidazol-4-yl]-piperazin-1-ylmethyl}-2-methyl-imidazol-1-yl)-N-cyclohexylmethyl-acetamide; 2-(4-{4-[2-(4-tert-Butyl-phenyl)-1H-benzoimidazol-4-yl]-piperazin-1-ylmethyl}-2-methyl-imidazol-1-yl)-N-(tetrahydro-furan-2-ylmethyl)-acetamide; 2-(4-{4-[2-(4-tert-Butyl-phenyl)-1H-benzoimidazol-4-yl]-piperazin-1-ylmethyl}-2-methyl-imidazol-1-yl)-1-pyrrolidin-1-yl-ethanone; 2-(4-{4-[2-(4-tert-Butyl-phenyl)-1H-benzoimidazol-4-yl]-piperazin-1-ylmethyl}-2-methyl-imidazol-1-yl)-1-(4-methyl-piperidin-1-yl)-ethanone; 2-(4-{4-[2-(4-tert-Butyl-phenyl)-1H-benzoimidazol-4-yl]-piperazin-1-ylmethyl}-2-methyl-imidazol-1-yl)-N-phenyl-acetamide; 2-(4-{4-[2-(4-tert-Butyl-phenyl)-1H-benzoimidazol-4-yl]-piperazin-1-ylmethyl}-2-methyl-imidazol-1-yl)-N-pyridin-4-yl-acetamide; 2-(4-{4-[2-(4-tert-Butyl-phenyl)-1H-benzoimidazol-4-yl]-piperazin-1-ylmethyl}-2-methyl-imidazol-1-yl)-N-(1-phenyl-ethyl)-acetamide; 2-[4-({4-[2-(4-tert-butylphenyl)-1H-benzimidazol-4-yl]piperazin-1-yl}methyl)-2-methyl-1H-imidazol-1-yl]-N-[(1R)-1-phenylethyl]acetamide; 2-(4-{4-[2-(4-tert-Butyl-phenyl)-1H-benzoimidazol-4-yl]-piperazin-1-ylmethyl}-2-methyl-imidazol-1-yl)-N-phenethyl-acetamide; N-benzyl-2-[4-({4-[2-(4-tert-butylphenyl)-1H-benzimidazol-7-yl]piperazin-1-yl}methyl)-2-methyl-1H-imidazol-1-yl]-N-methylacetamide; benzyl {2-[4-({4-[2-(4-tert-butylphenyl)-1H-benzimidazol-4-yl]piperazin-1-yl}methyl)-2-methyl-1H-imidazol-1-yl]ethyl}carbamate; 4-{4-[(1-butyl-4-methyl-1H-imidazol-5-yl)methyl]piperazin-1-yl}-2-(4-tert-butylphenyl)-1H-benzimidazole; 4-{4-[(1-butyl-5-methyl-1H-imidazol-4-yl)methyl]piperazin-1-yl}-2-(4-tert-butylphenyl)-1H-benzimidazole; {2-[4-({4-[2-(4-tert-butylphenyl)-1H-benzimidazol-4-yl]piperazin-1-yl}methyl)-2-methyl-1H-imidazol-1-yl]ethyl}amine; N-[2-(4-{4-[2-(4-tert-Butyl-phenyl)-1H-benzoimidazol-4-yl]-piperazin-1-ylmethyl}-2-methyl-imidazol-1-yl)-ethyl]-acetamide; N-[2-(4-{4-[2-(4-tert-Butyl-phenyl)-1H-benzoimidazol-4-yl]-piperazin-1-ylmethyl}-2-methyl-imidazol-1-yl)-ethyl]-propionamide; N-[2-(4-{4-[2-(4-tert-Butyl-phenyl)-1H-benzoimidazol-4-yl]-piperazin-1-ylmethyl}-2-methyl-imidazol-1-yl)-ethyl]-benzamide; 3-[2-(4-{4-[2-(4-tert-Butyl-phenyl)-1H-benzoimidazol-4-yl]-piperazin-1-ylmethyl}-2-methyl-imidazol-1-yl)-ethyl]-1,1-dimethyl-urea; 3-[2-(4-{4-[2-(4-tert-Butyl-phenyl)-1H-benzoimidazol-4-yl]-piperazin-1-ylmethyl}-2-methyl-imidazol-1-yl)-ethyl]-1,1-diethyl-urea; Morpholine-4-carboxylic acid [2-(4-{4-[2-(4-tert-butyl-phenyl)-1H-benzoimidazol-4-yl]-piperazin-1-ylmethyl}-2-methyl-imidazol-1-yl)-ethyl]-amide; Pyrrolidine-1-carboxylic acid [2-(4-{4-[2-(4-tert-butyl-phenyl)-1H-benzoimidazol-4-yl]-piperazin-1-ylmethyl}-2-methyl-imidazol-1-yl)-ethyl]-amide; 3-[2-(4-{4-[2-(4-tert-Butyl-phenyl)-1H-benzoimidazol-4-yl]-piperazin-1-ylmethyl}-2-methyl-imidazol-1-yl)-ethyl]-1,1-dimethyl-sulfamate; N-[2-(4-{4-[2-(4-tert-Butyl-phenyl)-1H-benzoimidazol-4-yl]-piperazin-1-ylmethyl}-2-methyl-imidazol-1-yl)-ethyl]-benzenesulfonamide; [2-(4-{4-[2-(4-tert-Butyl-phenyl)-1H-benzoimidazol-4-yl]-piperazin-1-ylmethyl}-2-methyl-imidazol-1-yl)-ethyl]-carbamic acid ethyl ester; Benzyl-[2-(4-{4-[2-(4-tert-butyl-phenyl)-1H-benzoimidazol-4-yl]-piperazin-1-ylmethyl}-2-methyl-imidazol-1-yl)-ethyl]-amine; 2-(4-tert-butylphenyl)-4-{4-[(2-ethyl-4-methyl-1-propyl-1H-imidazol-5-yl)methyl]piperazin-1-yl}-1H-benzimidazole; 2-(4-tert-butylphenyl)-4-{4-[(2-ethyl-5-methyl-1-propyl-1H-imidazol-4-yl)methyl]piperazin-1-yl}-1H-benzimidazole; 2-(4-tert-butylphenyl)-4-{4-[(2-methyl-1-propyl-1H-imidazol-4-yl)methyl]piperazin-1-yl}-1H-benzimidazole; 2-(4-tert-butylphenyl)-4-{4-[(2-methyl-1-propyl-1H-imidazol-5-yl)methyl]piperazin-1-yl}-1H-benzimidazole; 5-({4-[2-(4-tert-butylphenyl)-1H-benzimidazol-4-yl]piperazin-1-yl}methyl)-1-hexylpyrimidine-2,4(1H,3H)-dione; 1-butyl-5-({4-[2-(4-tert-butylphenyl)-1H-benzimidazol-4-yl]piperazin-1-yl}methyl)pyrimidine-2,4(1H,3H)-dione; 5-({4-[2-(4-tert-butylphenyl)-1H-benzimidazol-4-yl]piperazin-1-yl}methyl)-1-(2,6-difluorobenzyl)pyrimidine-2,4(1H,3H)-dione; 1-benzyl-5-({4-[2-(4-tert-butylphenyl)-1H-benzimidazol-4-yl]piperazin-1-yl}methyl)pyrimidine-2,4(1H,3H)-dione; 5-({4-[2-(4-tert-butylphenyl)-1H-benzimidazol-4-yl]piperazin-1-yl}methyl)-1-(2-fluorobenzyl)pyrimidine-2,4(1H,3H)-dione; 5-({4-[2-(4-tert-butylphenyl)-1H-benzimidazol-4-yl]piperazin-1-yl}methyl)-1-pentylpyrimidine-2,4(1H,3H)-dione; 5-({4-[2-(4-tert-butylphenyl)-1H-benzimidazol-4-yl]piperazin-1-yl}methyl)-1-[(2-methoxyethoxy)methyl]pyrimidine-2,4(1H,3H)-dione; 5-({4-[2-(4-tert-butylphenyl)-1H-benzimidazol-4-yl]piperazin-1-yl}methyl)pyrimidine-2,4(1H,3H)-dione; 5-({(2S)-4-[2-(4-tert-butylphenyl)-1H-benzimidazol-4-yl]-2-methylpiperazin-1-yl}methyl)pyrimidine-2,4(1H,3H)-dione; 5-({(2S)-4-[2-(4-tert-butylphenyl)-1H-benzimidazol-7-yl]-2-ethylpiperazin-1-yl}methyl)pyrimidine-2,4(1H,3H)-dione; 5-[(4-{2-[4-(methylsulfonyl)phenyl]-1H-benzimidazol-4-yl}piperazin-1-yl)methyl]pyrimidine-2,4(1H,3H)-dione; 5-[((2S)-2-methyl-4-{2-[4-(methylsulfonyl)phenyl]-1H-benzimidazol- 4-yl}piperazin-1-yl)methyl]pyrimidine-2,4(1H,3H)-dione; 5-[(4-{2-[4-(ethylsulfonyl)phenyl]-1H-benzimidazol-4-yl}piperazin-1-yl)methyl]pyrimidine-2,4(1H,3H)-dione; 5-[(4-{2-[4-(isopropylsulfonyl)phenyl]-1H-benzimidazol-4-yl}piperazin-1-yl)methyl]pyrimidine-2,4(1H,3H)-dione; 5-[(4-{2-[4-(diethylamino)phenyl]-1H-benzimidazol-4-yl}piperazin-1-yl)methyl]pyrimidine-2,4(1H,3H)-dione; 5-({4-[2-(4-tert-butylphenyl)-1H-benzimidazol-4-yl]piperazin-1-yl}methyl)-1,3-dimethylpyrimidine-2,4(1H,3H)-dione; 5-({4-[2-(4-tert-butylphenyl)-1H-benzimidazol-4-yl]piperazin-1-yl}methyl)-1,3-diethylpyrimidine-2,4(1H,3H)-dione; 5-({4-[2-(4-tert-butylphenyl)-1H-benzimidazol-4-yl]piperazin-1-yl}methyl)-1-ethylpyrimidine-2,4(1H,3H)-dione; 5-({(2S)-4-[2-(4-tert-butylphenyl)-1H-benzimidazol-4-yl]-2-methylpiperazin-1-yl}methyl)-1-ethylpyrimidine-2,4(1H,3H)-dione; 5-({(2S)-4-[2-(4-tert-butylphenyl)-1H-benzimidazol-7-yl]-2-ethylpiperazin-1-yl}methyl)-1-ethylpyrimidine-2,4(1H,3H)-dione; 1-ethyl-5-[(4-{2-[4-(methylsulfonyl)phenyl]-1H-benzimidazol-4-yl}piperazin-1-yl)methyl]pyrimidine-2,4(1H,3H)-dione; 5-[((2S)-4-{2-[4-(diethylamino)phenyl]-1H-benzimidazol-7-yl}-2-ethylpiperazin-1-yl)methyl]-1-ethylpyrimidine-2,4(1H,3H)-dione; 1-ethyl-5-{[4-(2-{4-[2,2,2-trifluoro-1-hydroxy-1-(trifluoromethyl)ethyl]phenyl}-1H-benzimidazol-7-yl)piperazin-1-yl]methyl}pyrimidine-2,4(1H,3H)-dione; 1-ethyl-5-[(4-{2-[4-(2,2,2-trifluoro-1-hydroxyethyl)phenyl]-1H-benzimidazol-4-yl}piperazin-1-yl)methyl]pyrimidine-2,4(1H,3H)-dione; 5-({4-[2-(4-tert-butylphenyl)-1H-benzimidazol-4-yl]piperazin-1-yl}methyl)-1-propylpyrimidine-2,4(1H,3H)-dione; 5-({4-[2-(4-tert-butylphenyl)-1H-benzimidazol-4-yl]piperazin-1-yl}methyl)-1-isopropylpyrimidine-2,4(1H,3H)-dione; 1-allyl-5-({4-tert-butylphenyl)-1H-benzimidazol-4-yl}piperazin-1-yl}methyl)pyrimidine-2,4(1H,3H)-dione; 5-({4-[2-(4-tert-butylphenyl)-1H-benzimidazol-4-yl]piperazin-1-yl}methyl)-1-prop-2-ynylpyrimidine-2,4(1H,3H)-dione; 5-({4-[2-(4-tert-butylphenyl)-1H-benzimidazol-4-yl]piperazin-1-yl}methyl)-1-methylpyrimidine-2,4(1H,3H)-dione; 2-[5-({4-[2-(4-tert-butylphenyl)-1H-benzimidazol-4-yl]piperazin-1-yl}methyl)-2,4-dioxo-3,4-dihydropyrimidin-1(2H)-yl]acetamide; 2-[5-({(2S)-4-[2-(4-tert-butylphenyl)-1H-benzimidazol-4-yl]-2-methylpiperazin-1-yl}methyl)-2,4-dioxo-3,4-dihydropyrimidin-1(2H)-yl]acetamide; 5-({4-[2-(4-tert-butylphenyl)-1H-benzimidazol-4-yl]piperazin-1-yl}methyl)-3-ethylpyrimidine-2,4(1H,3H)-dione; 2-[5-({4-[2-(4-tert-butylphenyl)-1H-benzimidazol-4-yl]piperazin-1-yl}methyl)-2,6-dioxo-3,6-dihydropyrimidin-1(2H)-yl]acetamide; 2-(4-tert-butylphenyl)-7-(4-{[2-(methylthio)pyrimidin-4-yl]methyl}piperazin-1-yl)-1H-benzimidazole; 2-(4-tert-butylphenyl)-7-(4-{[2-(methylsulfonyl)pyrimidin-4-yl]methyl}piperazin-1-yl)-1H-benzimidazole; 2-(4-tert-butylphenyl)-4-(4-{[2-(methylthio)pyrimidin-5-yl]methyl}piperazin-1-yl)-1H-benzimidazole; 2-(4-tert-butylphenyl)-4-((3S)-3-methyl-4-{[2-(methylthio)pyrimidin-5-yl]methyl}piperazin-1-yl)-1H-benzimidazole; N,N-diethyl-N-{4-[4-(4-{[2-(methylthio)pyrimidin-5-yl]methyl}piperazin-1-yl)-1H-benzimidazol-2-yl]phenyl}amine; 3-({4-[2-(4-tert-butylphenyl)-1H-benzimidazol-7-yl]piperazin-1-yl}methyl)imidazo[1,2-a]pyrimidine; 2-(4-tert-butylphenyl)-4-[4-(pyridin-2-ylmethyl)piperazin-1-yl]-1H-benzimidazole; 3-(4-{4-[4-(pyridin-2-ylmethyl)piperazin-1-yl]-1H-benzimidazol-2-yl}phenoxy)phenol; 2-[4-(methylsulfonyl)phenyl]-4-[4-(pyridin-2-ylmethyl)piperazin-1-yl]-1H-benzimidazole; 2-ethyl-5-{4-[4-(pyridin-2-ylmethyl)piperazin-1-yl]-1H-benzimidazol-2-yl}phenol; 2-(4-tert-Butyl-phenyl)-4-[4-(6-methyl-pyridin-2-ylmethyl)-piperazin-1-yl]-1H-benzoimidazole; methyl 6-({4-[2-(4-tert-butylphenyl)-1H-benzimidazol-7-yl]piperazin-1-yl}methyl)pyridine-2-carboxylate; 6-({4-[2-(4-tert-butylphenyl)-1H-benzimidazol-7-yl]piperazin-1-yl}methyl)pyridine-2-carboxamide; methyl 6-({4-[2-(4-tert-butylphenyl)-1H-benzimidazol-7-yl]piperazin-1-yl}methyl)nicotinate; 6-({4-[2-(4-tert-butylphenyl)-1H-benzimidazol-7-yl]piperazin-1-yl}methyl)nicotinamide; methyl 2-({4-[2-(4-tert-butylphenyl)-1H-benzimidazol-7-yl]piperazin-1-yl}methyl)isonicotinate; 2-({4-[2-(4-tert-butylphenyl)-1H-benzimidazol-7-yl]piperazin-1-yl}methyl)isonicotinamide; 2-(4-tert-butylphenyl)-4-{4-[(1-oxidopyridin-2-yl)methyl]piperazin-1-yl}-1H-benzimidazole; 6-({4-[2-(4-tert-butylphenyl)-1H-benzimidazol-4-yl]piperazin-1-yl}methyl)pyridin-2-ol; 2-(4-tert-butylphenyl)-4-[4-(pyridin-3-ylmethyl)piperazin-1-yl]-1H-benzimidazole; 3-({4-[2-(4-tert-butylphenyl)-1H-benzimidazol-4-yl]piperazin-1-yl}methyl)pyridin-2-amine; 5-({4-[2-(4-tert-butylphenyl)-1H-benzimidazol-7-yl]piperazin-1-yl}methyl)pyridine-2-carboxamide; methyl 5-({4-[2-(4-tert-butylphenyl)-1H-benzimidazol-7-yl]piperazin-1-yl}methyl)nicotinate; 5-({4-[2-(4-tert-butylphenyl)-1H-benzimidazol-7-yl]piperazin-1-yl}methyl)nicotinamide; 5-({4-[2-(4-tert-butylphenyl)-1H-benzimidazol-7-yl]piperazin-1-yl}methyl)nicotinic acid; 5-({4-[2-(4-tert-butylphenyl)-1H-benzimidazol-7-yl]piperazin-1-yl}methyl)-N-methylnicotinamide; 5-({4-[2-(4-tert-butylphenyl)-1H-benzimidazol-7-yl]piperazin-1-yl}methyl)-N,N-dimethylnicotinamide; 2-(4-tert-butylphenyl)-4-{4-[(6-methoxypyridin-3-yl)methyl]piperazin-1-yl}-1H-benzimidazole; 2-(4-tert-butylphenyl)-4-[4-(pyridin-4-ylmethyl)piperazin-1-yl]-1H-benzimidazole; 2-(4-tert-Butyl-phenyl)-4-[4-(1-oxy-pyridin-4-ylmethyl)-piperazin-1-yl]-1H-benzoimidazole; 4-{4-[2-(4-tert-Butyl-phenyl)-1H-benzoimidazol-4-yl]-piperazin-1-ylmethyl}-5-hydroxymethyl-2-methyl-pyridin-3-ol; 7-({4-[2-(4-tert-butylphenyl)-1H-benzimidazol-4-yl]piperazin-1-yl}methyl)-1,4-dihydropyrido[2,3-b]pyrazine-2,3-dione; 7-({(2S)-4-[2-(4-tert-butylphenyl)-1H-benzimidazol-4-yl]-2-methylpiperazin-1-yl}methyl)-1,4-dihydropyrido[2,3-b]pyrazine-2,3-dione; 7-[(4-{2-[4-(methylsulfonyl)phenyl]-1H-benzimidazol-4-yl}piperazin-1-yl)methyl]-1,4-dihydropyrido[2,3-b]pyrazine-2,3-dione; 7-[((2S)-2-methyl-4-{2-[4-(methylsulfonyl)phenyl]-1H-benzimidazol-4-yl}piperazin-1-yl)methyl]-1,4-dihydropyrido[2,3-b]pyrazine-2,3-dione; 3-({4-[2-(4-tert-butylphenyl)-1H-benzimidazol-4-yl]piperazin-1-yl}methyl)pyrido[3,4-b]pyrazine; 3-({4-[2-(4-tert-butylphenyl)-1H-benzimidazol-4-yl]piperazin-1-yl}methyl)pyrido[2,3-b]pyrazine; 2-({4-[2-(4-tert-butylphenyl)-1H-benzimidazol-4-yl]piperazin-1-yl}methyl)quinoxaline; 2-({(2S)-4-[2-(4-tert-butylphenyl)-1H-benzimidazol-4-yl]-2-methylpiperazin-1-yl}methyl)quinoxaline; N,N-diethyl-N-(4-{4-[4-(quinoxalin-2-ylmethyl)piperazin-1-yl]-1H-benzimidazol-2-yl}phenyl)amine; 2-({(2S)-4-[2-(4-tert-butylphenyl)-1H-benzimidazol-4-yl]-2-ethylpiperazin-1-yl}methyl)quinoxaline; 2-{[4-(2-{4-[2,2,2-trifluoro-1-(trifluoromethyl)ethyl]phenyl}-1H-benzimidazol-7-yl)piperazin-1-yl]methyl}quinoxaline; 6-({4-[2-(4-tert-butylphenyl)-1H-benzimidazol-4-yl]piperazin-1-yl}methyl)pyrido[2,3-b]pyrazine; 6-({(2S)-4-[2-(4-tert-butylphenyl)-1H-benzimidazol-4-yl]-2-methylpiperazin-1-yl}methyl)pyrido[2,3-b]pyrazine; 7-({4-[2-(4-tert-butylphenyl)-1H-benzimidazol-4-yl]piperazin-1-yl}methyl)pyrido[2,3-b]pyrazine; 7-[(4-{2-[4-(methylsulfonyl)phenyl]-1H-benzimidazol-4-yl}piperazin-1-yl)methyl]pyrido[2,3-b]pyrazine; 7-({4-[2-(4-tert-butylphenyl)-1H-benzimidazol-7-yl]-2-methylpiperazin-1-yl}methyl)pyrido[2,3-b]pyrazine; 1,1,1,3,3,3-hexafluoro-2-(4-{7-[4-(pyrido[2,3-b]pyrazin-7- ylmethyl)piperazin-1-yl]-1H-benzimidazol-2-yl}phenyl) propan-2-ol; 7-{[4-(2-{4-[2,2,2-trifluoro-1-(trifluoromethyl)ethyl]phenyl}-1H-benzimidazol-7-yl)piperazin-1-yl] methyl}pyrido[2,3-b]pyrazine; 6-({4-[2-(4-tert-butylphenyl)-1H-benzimidazol-4-yl]piperazin-1-yl}methyl) quinoline; 7-({4-[2-(4-tert-butylphenyl)-1H-benzimidazol-4-yl]piperazin-1-yl}methyl)quinoline; 5-({4-[2-(4-tert-butylphenyl)-1H-benzimidazol-4-yl]piperazin-1-yl}methyl) pyridin-2(1H)-one; 5-{4-[2-(4-tert-Butyl-phenyl)-1H-benzoimidazol-4-yl]-piperazin-1-ylmethyl}-1-methyl-1H-pyridin-2-one; 5-{4-[2-(4-tert-Butyl-phenyl)-1H-benzoimidazol-4-yl]-piperazin-1-ylmethyl}-1-ethyl-1H-pyridin-2-one; 5-{4-[2-(4-tert-Butyl-phenyl)-1H-benzoimidazol-4-yl]-piperazin-1-ylmethyl}-1-propyl-1H-pyridin-2-one; 5-{4-[2-(4-tert-Butyl-phenyl)-1H-benzoimidazol-4-yl]-piperazin-1-ylmethyl}-1-isopropyl-1H-pyridin-2-one; 1-Butyl-5-{4-[2-(4-tert-butyl-phenyl)-1H-benzoimidazol-4-yl]-piperazin-1-ylmethyl}-1H-pyridin-2-one; 5-{4-[2-(4-tert-Butyl-phenyl)-1H-benzoimidazol-4-yl]-piperazin-1-ylmethyl}-1-pentyl-1H-pyridin-2-one; 5-{4-[2-(4-tert-Butyl-phenyl)-1H-benzoimidazol-4-yl]-piperazin-1-ylmethyl}-1-hexyl-1H-pyridin-2-one; 5-{4-[2-(4-tert-Butyl-phenyl)-1H-benzoimidazol-4-yl]-piperazin-1-ylmethyl}-1-cyclopentyl-1H-pyridin-2-one; 5-{4-[2-(4-tert-Butyl-phenyl)-1H-benzoimidazol-4-yl]-piperazin-1-ylmethyl}-1-(3,3,3-trifluoro-propyl)-1H-pyridin-2-one; 1-Benzyl-5-{4-[2-(4-tert-butyl-phenyl)-1H-benzoimidazol-4-yl]-piperazin-1-ylmethyl}-1H-pyridin-2-one; 5-{4-[2-(4-tert-Butyl-phenyl)-1H-benzoimidazol-4-yl]-piperazin-1-ylmethyl}-1-(4-methyl-benzyl)-1H-pyridin-2-one; 5-{4-[2-(4-tert-Butyl-phenyl)-1H-benzoimidazol-4-yl]-piperazin-1-ylmethyl}-1-(4-nitro-benzyl)-1H-pyridin-2-one; 5-{4-[2-(4-tert-Butyl-phenyl)-1H-benzoimidazol-4-yl]-piperazin-1-ylmethyl}-1-(3-trifluoromethyl-benzyl)-1H-pyridin-2-one; 2-(4-tert-Butyl-phenyl)-7-[4-(2-methoxy-pyrimidin-4-ylmethyl)-piperazin-1-yl]-1H-benzoimidazole; 4-{4-[2-(4-tert-Butyl-phenyl)-3H-benzoimidazol-4-yl]-piperazin-1-ylmethyl}-pyrimidin-2-ol; 7-[4-(2-Allyloxy-pyrimidin-4-ylmethyl)-piperazin-1-yl]-2-(4-tert-butyl-phenyl)-1H-benzoimidazole; 2-(4-tert-Butyl-phenyl)-7-[4-(2-cyclobutoxy-pyrimidin-4-ylmethyl)-piperazin-1-yl]-1H-benzoimidazole; 2-(4-tert-Butyl-phenyl)-7-[4-(2-phenoxy-pyrimidin-4-ylmethyl)-piperazin-1-yl]-1H-benzoimidazole; 7-[4-(2-Benzyloxy-pyrimidin-4-ylmethyl)-piperazin-1-yl]-2-(4-tert-butyl-phenyl)-1H-benzoimidazole; 2-(4-tert-Butyl-phenyl)-7-{4-[2-(pyridin-2-ylmethoxy)-pyrimidin-4-ylmethyl]-piperazin-1-yl}-1H-benzoimidazole; (4-{4-[2-(4-tert-Butyl-phenyl)-3H-benzoimidazol-4-yl]-piperazin-1-ylmethyl}-pyrimidin-2-yl)-diethyl-amine; (4-{4-[2-(4-tert-Butyl-phenyl)-3H-benzoimidazol-4-yl]-piperazin-1-ylmethyl}-pyrimidin-2-yl)-ethyl-amine; (4-{4-[2-(4-tert-Butyl-phenyl)-3H-benzoimidazol-4-yl]-piperazin-1-ylmethyl}-pyrimidin-2-yl)-methyl-amine; (4-{4-[2-(4-tert-Butyl-phenyl)-3H-benzoimidazol-4-yl]-piperazin-1-ylmethyl}-pyrimidin-2-yl)-ethyl-methyl-amine; (4-{4-[2-(4-tert-Butyl-phenyl)-3H-benzoimidazol-4-yl]-piperazin-1-ylmethyl}-pyrimidin-2-yl)-cyclopropylmethyl-amine; 2-(4-tert-Butyl-phenyl)-7-[4-(2-pyrrolidin-1-yl-pyrimidin-4-ylmethyl)-piperazin-1-yl]-1H-benzoimidazole; (4-{4-[2-(4-tert-Butyl-phenyl)-3H-benzoimidazol-4-yl]-piperazin-1-ylmethyl}-pyrimidin-2-yl)-isopropyl-methyl-amine; (4-{4-[2-(4-tert-Butyl-phenyl)-3H-benzoimidazol-4-yl]-piperazin-1-ylmethyl}-pyrimidin-2-yl)-isobutyl-amine; (4-{4-[2-(4-tert-Butyl-phenyl)-3H-benzoimidazol-4-yl]-piperazin-1-ylmethyl}-pyrimidin-2-yl)-cyclopentyl-amine; 2-(4-tert-Butyl-phenyl)-7-{4-[2-(2-methyl-piperidin-1-yl)-pyrimidin-4-ylmethyl]-piperazin-1-yl}-1H-benzoimidazole; 2-(4-tert-Butyl-phenyl)-7-{4-[2-(3-methyl-piperidin-1-yl)-pyrimidin-4-ylmethyl]-piperazin-1-yl}-1H-benzoimidazole; 2-(4-tert-Butyl-phenyl)-7-{4-[2-(4-methyl-piperidin-1-yl)-pyrimidin-4-ylmethyl]-piperazin-1-yl}-1H-benzoimidazole; (4-{4-[2-(4-tert-Butyl-phenyl)-3H-benzoimidazol-4-yl]-piperazin-1-ylmethyl}-pyrimidin-2-yl)-cyclohexylmethyl-amine; (4-{4-[2-(4-tert-Butyl-phenyl)-3H-benzoimidazol-4-yl]-piperazin-1-ylmethyl}-pyrimidin-2-yl)-phenethyl-amine; (4-{4-[2-(4-tert-Butyl-phenyl)-3H-benzoimidazol-4-yl]-piperazin-1-ylmethyl}-pyrimidin-2-yl)-(4-methyl-benzyl)-amine; 2-(4-tert-butylphenyl)-7-{4-[(2-piperidin-1-ylpyrimidin-4-yl)methyl]piperazin-1-yl}-1H-benzimidazole; N-butyl-4-({4-[2-(4-tert-butylphenyl)-1H-benzimidazol-7-yl]piperazin-1-yl}methyl)pyrimidin-2-amine; 4-({4-[2-(4-tert-butylphenyl)-1H-benzimidazol-7-yl]piperazin-1-yl}methyl)-N,N-dipropylpyrimidin-2-amine; 2-(4-tert-butylphenyl)-4-{4-[(1S)-1-(2-ethyl-5-methyl-1H-imidazol-4-yl)ethyl]piperazin-1-yl}-1H-benzimidazole; 5-((1S)-1-{4-[2-(4-tert-butylphenyl)-1H-benzimidazol-4-yl]piperazin-1-yl}ethyl)-1-ethylpyrimidine-2,4(1H,3H)-dione; 6-((1S)-1-{4-[2-(4-tert-butylphenyl)-1H-benzimidazol-4-yl]piperazin-1-yl}ethyl)quinoxaline; 6-({4-[2-(4-tert-butylphenyl)-1H-benzimidazol-4-yl]piperazin-1-yl}methyl)-1,4-dihydroquinoxaline-2,3-dione; 7-({4-[2-(4-tert-butylphenyl)-1H-benzimidazol-4-yl]piperazin-1-yl}methyl)-1-(pyridin-3-ylmethyl)-1,4-dihydroquinoxaline-2,3-dione; 6-({4-[2-(4-ethylphenyl)-1H-benzimidazol-4-yl]piperazin-1-yl}methyl)-1,4-dihydroquinoxaline-2,3-dione; 6-({4-[2-(4-tert-butylphenyl)-1H-benzimidazol-4-yl]piperazin-1-yl}methyl)-1,4-dihydroquinoxaline-2,3-dione; 6-({(2R)-4-[2-(4-tert-butylphenyl)-1H-benzimidazol-4-yl]-2-methylpiperazin-1-yl}methyl)-1,4-dihydroquinoxaline-2,3-dione; 6-({(2S)-4-[2-(4-tert-butylphenyl)-1H-benzimidazol-4-yl]-2-methylpiperazin-1-yl}methyl)-1,4-dihydroquinoxaline-2,3-dione; 6-({(2S)-4-[2-(4-tert-butylphenyl)-1H-benzimidazol-7-yl]-2-ethylpiperazin-1-yl}methyl)-1,4-dihydroquinoxaline-2,3-dione; 6-({4-[2-(4-isopropylphenyl)-1H-benzimidazol-4-yl]piperazin-1-yl}methyl)-1,4-dihydroquinoxaline-2,3-dione; 6-[(4-{2-[4-(methylsulfonyl)phenyl]-1H-benzimidazol-4-yl}piperazin-1-yl)methyl]-1,4-dihydroquinoxaline-2,3-dione; 6-[(4-{2-[4-(ethylsulfonyl)phenyl]-1H-benzimidazol-4-yl}piperazin-1-yl)methyl]-1,4-dihydroquinoxaline-2,3-dione; 7-({4-[2-(4-ethylphenyl)-1H-benzimidazol-4-yl]piperazin-1-yl}methyl)-1-methyl-1,4-dihydroquinoxaline-2,3-dione; 1-Ethyl-7-{4-[2-(4-ethyl-phenyl)-1H-benzoimidazol-4-yl]-piperazin-1-ylmethyl}-1,4-dihydro-quinoxaline-2,3-dione; 7-{4-[2-(4-Ethyl-phenyl)-1H-benzoimidazol-4-yl]-piperazin-1-ylmethyl}-1-isopropyl-1,4-dihydro-quinoxaline-2,3-dione; 1-Cyclobutyl-7-{4-[2-(4-ethyl-phenyl)-1H-benzoimidazol-4-yl]-piperazin-1-ylmethyl}-1,4-dihydro-quinoxaline-2,3-dione; 1-Cyclopropylmethyl-7-{4-[2-(4-ethyl-phenyl)-1H-benzoimidazol-4-yl]-piperazin-1-ylmethyl}-1,4-dihydro-quinoxaline-2,3-dione; 7-{4-[2-(4-Ethyl-phenyl)-1H-benzoimidazol-4-yl]-piperazin-1-ylmethyl}-1-isobutyl-1,4-dihydro-quinoxaline-2,3-dione; 1-Cyclopentyl-7-{4-[2-(4-ethyl-phenyl)-1H-benzoimidazol-4-yl]-piperazin-1-ylmethyl}-1,4-dihydro-quinoxaline-2,3-dione; 1-Cyclohexyl-7-{4-[2-(4-ethyl-phenyl)-1H-benzoimidazol-4-yl]-piperazin-1-ylmethyl}-1,4-dihydro-quinoxaline-2,3-dione; 1-Benzyl-7-{4-[2-(4-ethyl-phenyl)-1H-benzoimidazol-4-yl]-piperazin-1-ylmethyl}-1,4-dihydro-quinoxaline-2,3-dione; 7-{4-[2-(4-Ethyl-phenyl)-1H-benzoimidazol-4-yl]-piperazin-1-ylmethyl}-1-pyridin-3-ylmethyl-1,4-dihydro-quinoxaline-2,3-dione; 7-{4-[2-(4-Ethyl-phenyl)-1H-benzoimidazol-4-yl]-piperazin-1- ylmethyl}-1-phenethyl-1,4-dihydro-quinoxaline-2,3-dione; 7-{4-[2-(4-Ethyl-phenyl)-1H-benzoimidazol-4-yl]-piperazin-1-ylmethyl}-1-(2-pyridin-3-yl-ethyl)-1,4-dihydro-quinoxaline-2,3-dione; 7-({4-[2-(4-tert-butylphenyl)-1H-benzimidazol-4-yl]piperazin-1-yl}methyl)-1-methyl-1,4-dihydroquinoxaline-2,3-dione; 7-({4-[2-(4-tert-butylphenyl)-1H-benzimidazol-4-yl]piperazin-1-yl}methyl)-1-(2-pyridin-3-ylethyl)-1,4-dihydroquinoxaline-2,3-dione; 7-({4-[2-(4-tert-butylphenyl)-1H-benzimidazol-4-yl]piperazin-1-yl}methyl)-1-(3-pyridin-3-ylpropyl)-1,4-dihydroquinoxaline-2,3-dione; 7-({4-[2-(4-tert-butylphenyl)-1H-benzimidazol-4-yl]piperazin-1-yl}methyl)-1-(2-pyridin-2-ylethyl)-1,4-dihydroquinoxaline-2,3-dione; 7-({4-[2-(4-tert-butylphenyl)-1H-benzimidazol-4-yl]piperazin-1-yl}methyl)-1-(2-pyridin-4-ylethyl)-1,4-dihydroquinoxaline-2,3-dione; 7-{4-[2-(4-tert-Butyl-phenyl)-1H-benzoimidazol-4-yl]-piperazin-1-ylmethyl}-1-(3-morpholin-4-yl-propyl)-1,4-dihydro-quinoxaline-2,3-dione; 7-{4-[2-(4-tert-Butyl-phenyl)-1H-benzoimidazol-4-yl]-piperazin-1-ylmethyl}-1-(2-morpholin-4-yl-ethyl)-1,4-dihydro-quinoxaline-2,3-dione; 7-{4-[2-(4-tert-Butyl-phenyl)-1H-benzoimidazol-4-yl]-piperazin-1-ylmethyl}-1-(2-piperidin-1-yl-ethyl)-1,4-dihydro-quinoxaline-2,3-dione; 6-({4-[2-(4-ethylphenyl)-1H-benzimidazol-4-yl]piperazin-1-yl}methyl)-1-methyl-1,4-dihydroquinoxaline-2,3-dione; 1-Cyclobutyl-6-{4-[2-(4-ethyl-phenyl)-3H-benzoimidazol-4-yl]-piperazin-1-ylmethyl}-1,4-dihydro-quinoxaline-2,3-dione; 1-Cyclopropylmethyl-6-{4-[2-(4-ethyl-phenyl)-3H-benzoimidazol-4-yl]-piperazin-1-ylmethyl}-1,4-dihydro-quinoxaline-2,3-dione; 6-{4-[2-(4-Ethyl-phenyl)-3H-benzoimidazol-4-yl]-piperazin-1-ylmethyl}-1-isobutyl-1,4-dihydro-quinoxaline-2,3-dione; 1-Cyclopentyl-6-{4-[2-(4-ethyl-phenyl)-3H-benzoimidazol-4-yl]-piperazin-1-ylmethyl}-1,4-dihydro-quinoxaline-2,3-dione; 1-Cyclohexyl-6-{4-[2-(4-ethyl-phenyl)-3H-benzoimidazol-4-yl]-piperazin-1-ylmethyl}-1,4-dihydro-quinoxaline-2,3-dione; 1-Benzyl-6-{4-[2-(4-ethyl-phenyl)-3H-benzoimidazol-4-yl]-piperazin-1-ylmethyl}-1,4-dihydro-quinoxaline-2,3-dione; 6-{4-[2-(4-Ethyl-phenyl)-3H-benzoimidazol-4-yl]-piperazin-1-ylmethyl}-1-pyridin-4-ylmethyl-1,4-dihydro-quinoxaline-2,3-dione; 6-{4-[2-(4-Ethyl-phenyl)-3H-benzoimidazol-4-yl]-piperazin-1-ylmethyl}-1-pyridin-3-ylmethyl-1,4-dihydro-quinoxaline-2,3-dione; 6-{4-[2-(4-Ethyl-phenyl)-3H-benzoimidazol-4-yl]-piperazin-1-ylmethyl}-1-phenethyl-1,4-dihydro-quinoxaline-2,3-dione; 6-{4-[2-(4-Ethyl-phenyl)-3H-benzoimidazol-4-yl]-piperazin-1-ylmethyl}-1-(2-pyridin-3-yl-ethyl)-1,4-dihydro-quinoxaline-2,3-dione; 1-ethyl-6-({4-[2-(4-ethylphenyl)-1H-benzimidazol-4-yl]piperazin-1-yl}methyl)-1,4-dihydroquinoxaline-2,3-dione; 6-({4-[2-(4-tert-butylphenyl)-1H-benzimidazol-4-yl]piperazin-1-yl}methyl)-3,4-dihydroquinoxalin-2(1H)-one; 6-{4-[2-(4-Ethyl-phenyl)-1H-benzoimidazol-4-yl]-piperazin-1-ylmethyl}-3,4-dihydro-1H-quinoxalin-2-one; 6-{4-[2-(4-Ethyl-phenyl)-1H-benzoimidazol-4-yl]-piperazin-1-ylmethyl}-3-methyl-3,4-dihydro-1H-quinoxalin-2-one; 6-{4-[2-(4-Ethyl-phenyl)-1H-benzoimidazol-4-yl]-piperazin-1-ylmethyl}-3-hydroxymethyl-3,4-dihydro-1H-quinoxalin-2-one; 6-{4-[2-(4-Ethyl-phenyl)-1H-benzoimidazol-4-yl]-piperazin-1-ylmethyl}-3-isopropyl-3,4-dihydro-1H-quinoxalin-2-one; 6-{4-[2-(4-Ethyl-phenyl)-1H-benzoimidazol-4-yl]-piperazin-1-ylmethyl}-3-isobutyl-3,4-dihydro-1H-quinoxalin-2-one; 3-Benzyl-6-{4-[2-(4-ethyl-phenyl)-1H-benzoimidazol-4-yl]-piperazin-1-ylmethyl}-3,4-dihydro-1H-quinoxalin-2-one; 6-{4-[2-(4-Ethyl-phenyl)-1H-benzoimidazol-4-yl]-piperazin-1-ylmethyl}-3-(3H-imidazol-4-ylmethyl)-3,4-dihydro-1H-quinoxalin-2-one; 6-{4-[2-(4-Ethyl-phenyl)-1H-benzoimidazol-4-yl]-piperazin-1-ylmethyl}-3-(3-methyl-3H-imidazol-4-ylmethyl)-3,4-dihydro-1H-quinoxalin-2-one; 6-{4-[2-(4-Ethyl-phenyl)-1H-benzoimidazol-4-yl]-piperazin-1-ylmethyl}-3-(1H-indol-3-ylmethyl)-3,4-dihydro-1H-quinoxalin-2-one; 6-{4-[2-(4-Ethyl-phenyl)-1H-benzoimidazol-4-yl]-piperazin-1-ylmethyl}-3-methyl-3,4-dihydro-1H-quinoxalin-2-one; 6-{4-[2-(4-Ethyl-phenyl)-1H-benzoimidazol-4-yl]-piperazin-1-ylmethyl}-3-hydroxymethyl-3,4-dihydro-1H-quinoxalin-2-one; 6-{4-[2-(4-Ethyl-phenyl)-1H-benzoimidazol-4-yl]-piperazin-1-ylmethyl}-3-isopropyl-3,4-dihydro-1H-quinoxalin-2-one; 6-{4-[2-(4-Ethyl-phenyl)-1H-benzoimidazol-4-yl]-piperazin-1-ylmethyl}-3-isobutyl-3,4-dihydro-1H-quinoxalin-2-one; 2-(7-{4-[2-(4-Ethyl-phenyl)-1H-benzoimidazol-4-yl]-piperazin-1-ylmethyl}-3-oxo-1,2,3,4-tetrahydro-quinoxalin-2-yl)-acetamide; 3-Benzyl-6-{4-[2-(4-ethyl-phenyl)-1H-benzoimidazol-4-yl]-piperazin-1-ylmethyl}-3,4-dihydro-1H-quinoxalin-2-one; 6-{4-[2-(4-Ethyl-phenyl)-1H-benzoimidazol-4-yl]-piperazin-1-ylmethyl}-3-(3H-imidazol-4-ylmethyl)-3,4-dihydro-1H-quinoxalin-2-one; 6-{4-[2-(4-Ethyl-phenyl)-1H-benzoimidazol-4-yl]-piperazin-1-ylmethyl}-3-(1H-indol-3-ylmethyl)-3,4-dihydro-1H-quinoxalin-2-one; 6-{4-[2-(4-Ethyl-phenyl)-1H-benzoimidazol-4-yl]-piperazin-1-ylmethyl}-3-(4-hydroxy-benzyl)-3,4-dihydro-1H-quinoxalin-2-one; 2-(4-tert-butylphenyl)-4-{4-[(2,4-dimethyl-1,3-oxazol-5-yl)methyl]piperazin-1-'yl}-1H-benzimidazole; 2-(4-tert-butylphenyl)-4-{4-[(2-ethyl-4-methyl-1,3-oxazol-5-yl)methyl]piperazin-1-yl}-1H-benzimidazole; 2-(4-tert-butylphenyl)-4-(4-{[2-(methoxymethyl)-5-methyl-1,3-oxazol-4-yl]methyl}piperazin-1-yl)-1H-benzimidazole; 2-(4-tert-butylphenyl)-4-[4-(1,3-thiazol-2-ylmethyl)piperazin-1-yl]-1H-benzimidazole; 2-(4-tert-butylphenyl)-4-{4-[(2,5-dimethyl-1,3-thiazol-4-yl)methyl]piperazin-1-yl}-1H-benzimidazole; 2-(4-tert-butylphenyl)-4-{(3S)-4-[(2,5-dimethyl-1,3-thiazol-4-yl)methyl]-3-methylpiperazin-1-yl}-1H-benzimidazole; ethyl 4-({4-[2-(4-tert-butylphenyl)-1H-benzimidazol-7-yl]piperazin-1-yl}methyl)-1,3-thiazole-2-carboxylate; 4-({4-[2-(4-tert-butylphenyl)-1H-benzimidazol-7-yl]piperazin-1-yl}methyl)-N-methyl-1,3-thiazol-2-amine; 2-(4-tert-butylphenyl)-4-{4-[(2,4-dimethyl-1,3-thiazol-5-yl)methyl]piperazin-1-yl}-1H-benzimidazole; 2-(4-tert-butylphenyl)-4-{4-[(4-ethyl-2-methyl-1,3-thiazol-5-yl)methyl]piperazin-1-yl}-1H-benzimidazole; 2-(4-tert-butylphenyl)-4-{4-[(2-ethyl-4-methyl-1,3-thiazol-5-yl)methyl]piperazin-1-yl}-1H-benzimidazole; 4-{4-[(2-but-3-enyl-4-methyl-1,3-thiazol-5-yl)methyl]piperazin-1-yl}-2-(4-tert-butylphenyl)-1H-benzimidazole; 4-{4-[(2-butyl-4-methyl-1,3-thiazol-5-yl)methyl]piperazin-1-yl}-2-(4-tert-butylphenyl)-1H-benzimidazole; 1-[5-({4-[2-(4-tert-butylphenyl)-1H-benzimidazol-4-yl]piperazin-1-yl}methyl)-4-methyl-1,3-thiazol-2-yl]propan-2-ol; 2-(4-tert-butylphenyl)-4-(4-{[2-(methoxymethyl)-4-methyl-1,3-thiazol-5-yl]methyl}piperazin-1-yl)-1H-benzimidazole; 2-(4-tert-butylphenyl)-4-{4-[(2-ethyl-5-methyl-1,3-oxazol-4-yl)methyl]piperazin-1-yl}-1H-benzimidazole; 2-(4-tert-butylphenyl)-4-(4-{[2-(methoxymethyl)-5-methyl-1,3-oxazol-4-yl]methyl}piperazin-1-yl)-1H-benzimidazole; 2-(4-tert-butylphenyl)-4-{4-[(3-ethyl-1-methyl-1H-pyrazol-5-yl)methyl]piperazin-1-yl}-1H-benzimidazole; 2-(4-tert-butylphenyl)-4-{4-[(5-ethyl-1-methyl-1H-pyrazol-3-yl)methyl]piperazin-1-yl}-1H-benzimidazole; 2-(4-tert-butylphenyl)-4-{4-[(1,3-dimethyl-1H-pyrazol-5-yl)methyl]piperazin-1-yl}-1H-benzimidazole; 2-(4-tert-butylphenyl)-4-{(3S)-4-[(1,3-dimethyl-1H-pyrazol-5-yl)methyl]-3- methylpiperazin-1-yl}-1H-benzimidazole; 2-(4-tert-butylphenyl)-4-{4-[(1,3,5-trimethyl-1H-pyrazol-4-yl)methyl]piperazin-1-yl}-1H-benzimidazole; 2-(4-tert-butylphenyl)-4-{4-[(3-ethyl-1-methyl-1H-pyrazol-5-yl)methyl]piperazin-1-yl}-1H-benzimidazole; 2-(4-tert-butylphenyl)-4-{4-[(5-ethyl-1-methyl-1H-pyrazol-3-yl)methyl]piperazin-1-yl}-1H-benzimidazole; 2-(4-tert-butylphenyl)-4-{4-[(3,5-dimethyl-1H-pyrazol-4-yl)methyl]piperazin-1-yl}-1H-benzimidazole; 2-(4-tert-butylphenyl)-4-{4-[(1,5-dimethyl-1H-pyrazol-3-yl)methyl]piperazin-1-yl}-1H-benzimidazole; 2-(4-tert-butylphenyl)-4-{4-[(3-methyl-1H-pyrazol-5-yl)methyl]piperazin-1-yl}-1H-benzimidazole; 2-(4-tert-butylphenyl)-4-{4-[(1,3-dimethyl-1H-pyrazol-4-yl)methyl]piperazin-1-yl}-1H-benzimidazole; 2-(4-tert-butylphenyl)-4-{4-[(1-ethyl-5-methyl-1H-pyrazol-3-yl)methyl]piperazin-1-yl}-1H-benzimidazole; 2-(4-tert-butylphenyl)-4-{4-[(1-methyl-1H-pyrazol-5-yl)methyl]piperazin-1-yl}-1H-benzimidazole; 6-({(2S,6S)-4-[2-(4-tert-butylphenyl)-1H-benzimidazol-4-yl]-2,6-dimethylpiperazin-1-yl}methyl)quinoxaline; 4-({4-[2-(4-tert-butylphenyl)-1H-benzimidazol-4-yl]piperazin-1-yl}methyl)-1,3-dihydro-2H-benzimidazole-2-thione; 4-({4-[2-(4-tert-butylphenyl)-1H-benzimidazol-4-yl]piperazin-1-yl}methyl)-1,3-dihydro-2H-benzimidazol-2-one; 5-({4-[2-(4-tert-butylphenyl)-1H-benzimidazol-4-yl]piperazin-1-yl}methyl)quinoxaline; or 2E)-4-({4-[2-(4-tert-butylphenyl)-1H-benzimidazol-4-yl]piperazin-1-yl}methyl)-1,3-dihydro-2H-benzimidazol-2-ylidenecyanamide.

In one embodiment, the compounds of the present invention are administered in combination with an additional active agent.

In one embodiment, the additional active agent is selected from the group consisting of at least one of androgens, estrogens, progesterones, antiestrogens, antiprogestogens, testosterone, antiprogestogens, angiotensin-converting enzyme inhibitor (such as ENALAPRIL or CAPTOPRIL), angiotensin II-receptor antagonist (such as LOSARTAN), renin inhibitor, bisphosphonates (bisphosphonic acids), growth hormone secretagogues (such as MK-0677), 5a-reductase 2 inhibitor (such as finasteride or episteride), a 5a-reductase 1 inhibitor (such as 4,7b-dimethyl-4-aza-5a-cholestan-3-one, 3-oxo-4-aza-4,7b-dimethyl-16b-(4-chlorophenoxy)-5a-androstane, and 3-oxo-4-aza-4,7b-dimethyl-16b-(phenoxy)-5a-androstane), dual inhibitors of 5a-reductase 1 and 5a-reductase 2 (such as 3-oxo-4-aza-17b-(2,5-trifluoromethylphenyl-carbamoyl)-5a-androstan), antiandrogens (such as flutamide, casodex and cyproterone acetate), alpha-1 blockers (such as prazosin, terazosin, doxazosin, tamsulosin, and alfuzosin), growth hormone, and luteinizing hormone releasing compounds (such as a peptide (including leuprorelin, gonadorelin, buserelin, triptorelin, goserelin, nafarelin, histrelin, deslorelin, meterlin and recirelin) or natural hormone or analog thereof).

For example, when used with compounds of the present invention: androgens, estrogens, progesterones, antiestrogens and antiprogestogens find use in the treatment of endometriosis, fibroids and in contraception; testosterone or other androgens or antiprogestogens find use in men as a contraceptive; angiotensin-converting enzyme inhibitors, angiotensin II-receptor antagonists, and renin inhibitor find use in the treatment of uterine fibroids; bisphosphonates (bisphosphonic acids) and growth hormone secretagogues find use in the treatment and prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GnRH antagonist; 5a-reductase 2 inhibitor, 5a-reductase 1 inhibitor, dual inhibitors of 5a-reductase 1 and 5a-reductase 2, antiandrogens, and alpha-1 blockers are useful as well; growth hormone, growth hormone releasing hormone or growth hormone secretagogues, to delay puberty in growth hormone deficient children; a compound having luteinizing hormone releasing activity is useful as well.

Definitions

All recitations of a group, such as alkyl, are understood for the purposes of this specification to encompass both substituted and unsubstituted forms.

The term "alkyl", as used herein, whether used alone or as part of another group, refers to a substituted or unsubstituted aliphatic hydrocarbon chain and includes, but is not limited to, straight and branched chains containing from 1 to 12 carbon atoms, or in some instances, from 1 to 6 carbon atoms, unless explicitly specified otherwise. For example, methyl, ethyl, propyl, isopropyl, butyl, i-butyl and t-butyl are encompassed by the term "alkyl." $C_1$-$C_6$ alkyl includes straight and branched chain aliphatic groups having from 1 to 6 carbons. Specifically included within the definition of "alkyl" are those aliphatic hydrocarbon chains that are optionally substituted. In one embodiment, an alkyl is substituted with one or more of the following groups: —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

Likewise, the term "heteroalkyl" as used herein refers to an alkyl group (e.g., of 2-7 carbon atoms) in which 1-3 carbon atoms within the carbon backbone are independently replaced by O, S or N heteroatoms. For example, methoxy, ethoxy, methylthio, ethylthio, methylamine, ethylamine, dimethylamine, diethylamine, methoxy methyl, ethoxymethyl, aminomethyl, and hydroxymethyl are encompassed by the term "heteroalkyl." In one embodiment, a heteroalkyl is substituted with one or more of the following groups: —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted hydrocarbon chain and includes, but is not limited to, straight and branched chains having 2 to 8 carbon atoms and containing at least one double bond. In one embodiment, the alkenyl moiety has 1 or 2 double bonds. Such alkenyl moieties may exist in the E or Z conformations and the compounds of this invention include both conformations. $C_2$-$C_6$ alkenyl includes a 2 to 6 carbon straight or branched chain having at least one carbon-carbon double bond. Specifically included within the definition of "alkenyl" are those aliphatic hydrocarbon chains that are optionally substituted. In one embodiment, a heteroatom, such as O, S or N, attached to an alkenyl is not attached to a carbon atom that is bonded to a double bond. In one embodiment, an alkenyl is substituted with one or more of the following groups: —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

The term "alkynyl" refers to a hydrocarbon moiety containing at least one carbon-carbon triple bond. $C_2$-$C_6$ alkynyl includes a 2 to 6 carbon straight or branched chain having at least one carbon-carbon triple bond. In one embodiment, an alkynyl is substituted with one or more of the following groups: —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

The term "cycloalkyl" refers to a monocyclic, bicyclic, tricyclic, fused, bridged, or spiro monovalent saturated hydrocarbon moiety, wherein the carbon atoms are located inside or outside of the ring system, e.g., of 3-15 carbon atoms. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro [4.5]decanyl, and homologs, isomers, and the like. $C_3$-$C_6$ cycloalkyl includes monocyclic, saturated rings of 3 to 6 carbons. In one embodiment, a cycloalkyl is substituted with one or more of the following groups: —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

"Heteroaryl" refers to a 5 to 6 membered aromatic heterocyclic ring which contains from 1 to 4 heteroatoms selected from the group consisting of oxygen, nitrogen, and sulfur atoms in the ring and may be fused with a carbocyclic or heterocyclic ring at any possible position (e.g. of 5-8 ring atoms, the fused heterocyclic ring containing from 1 to 4 heteroatoms selected from the group consisting of oxygen, nitrogen, and sulfur atoms in the ring). In one embodiment, a heteroaryl is substituted with one or more of the following groups: —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

"Heterocycloalkyl" refers to a 5 to 7-membered saturated ring containing carbon atoms and from 1 to 2 heteroatoms selected from N, O, and S. In one embodiment, a heterocycloalkyl is substituted with one or more of the following: =O, —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

The term "aryl" as used herein as a group or part of a group refers to an aromatic carbocyclic ring, e.g., of from 6 to 14 carbon atoms such as phenyl, which may be optionally substituted."Phenyl", as used herein, whether used alone or as part of another group, refers to a substituted or unsubstituted phenyl group. In one embodiment, an aryl group such as phenyl is substituted with one or more of the following: —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl. Additional substituents on aryl are illustrated above in connection with A when phenyl in paragraph [0026].

An optionally substituted moiety may be substituted with one or more substituents, examples of which are as illustrated herein. In one embodiment, an "optionally substituted" moiety is substituted with one or more of the following: =O, —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl or phenyl; and wherein each V is independently a bond or ($C_1$-$C_6$)-alkyl.

When such moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, $CF_2CF_3$, $CF_2CF_2CF_3$, and the like.

The term halogen includes bromine, chlorine, fluorine, and iodine.

For the sake of simplicity, connection points ("-") are not depicted. When an atom or compound is described to define a variable, it is understood that it is intended to replace the variable in a manner to satisfy the valency of the atom or compound. For example, if "X*" was C(R*)=C(R*), both carbon atoms form a part of the ring in order to satisfy their respective valences. Likewise, when divalent substituents are presented, it is understood that they are not limited to the order listed, for example, as used in this specification "OCH$_2$" encompasses CH$_2$O and OCH$_2$.

As used herein, a compound of the present invention also includes a pharmaceutically acceptable salt of a compound of the present invention. The term "pharmaceutically acceptable salt" as used herein refers to a salt of an acid and a basic nitrogen atom of a compound of the present invention. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes a hydrate of a compound of the present invention.

The term "patient", as used herein, refers to a mammal, in one embodiment, a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The term "carrier", as used herein, shall encompass carriers, excipients, and diluents.

The term "tautomer" as used herein refers to compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992).

The compounds of this invention may contain an asymmetric carbon atom and some of the compounds of this invention may contain one or more asymmetric centers and may thus give rise to optical isomers and diastereomers. While shown without respect to stereochemistry in formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is provided, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one stereoisomer, in one embodiment, less than about 50% of the other, in another embodiment, less than about 75%, and in yet another embodiment, less than about 90%, in one embodiment, less than about 95%, in another embodiment, less than about 98%, and in yet another embodiment, less than about 99%.

The terms "effective amount", "therapeutically effective amount" and "effective dosage" as used herein, refer to the amount of a compound, that, when administered to a patient, is effective to at least partially ameliorate (and, in other embodiments, cure) a condition form which the patient is suspected to suffer.

Compounds of the present invention have been found to act as GnRH receptor antagonists. They are therefore useful in the treatment of prostate cancer, endometriosis, uterine fibroids, uterine cancer, breast cancer, ovarian cancer, testicular cancer, primary hirsutism, or LH surge. In addition, they are useful as oral contraceptives. The present invention thus provides pharmaceutical compositions comprising at least one compound of the present invention and one or more pharmaceutically acceptable carriers, excipients, or diluents.

Examples of such carriers are well known to those skilled in the art and are prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets in one embodiment contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Exemplary surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulisifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, including sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

In one embodiment, the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs of compounds of the present invention. Various forms of prodrugs are known in the art, for example, as discussed in, for example, Bundgaard, (ed.), *Design of Prodrugs*, Elsevier (1985); Widder, et al. (ed.), *Methods in Enzymology*, vol. 4, Academic Press (1985); Krogsgaard-Larsen, et al. (ed.), "*Design and Application of Prodrugs*", *Textbook of Drug Design and Development*, Chapter 5, 113-191 (1991), Bundgaard, et al., *Journal of Drug Delivery* reviews, 8:1-38 (1992), Bundgaard, J. of Pharmaceutical Sciences, 77:285 et seq. (1988); and Higuchi and Stella (eds.) *Prodrugs as Novel Drug Delivery Systems*, American Chemical Society (1975), each of which is incorporated by reference in its entirety.

It is understood that the dosage, regimen and mode of administration of these compounds can vary according to the malady and the individual being treated and, in some embodiments, is subject to the judgment of the medical practitioner involved. In one embodiment, the administration of one or more of the compounds herein begins at a low dose and is increased until the desired effects are achieved.

The compounds of the invention can be prepared using a variety of methods starting from commercially available compounds, known compounds, or compounds prepared by known methods. General synthetic routes to many of the compounds of the invention are included in the following schemes. It is understood by those skilled in the art that protection and deprotection steps not shown in the Schemes may be required for these syntheses, and that the order of steps may be changed to accommodate functionality in the target molecules.

Methods of Making

As used in the schemes, $R_1$ and $R_2$ are each independently hydrogen or optionally substituted alkyl;

$R_3$ is

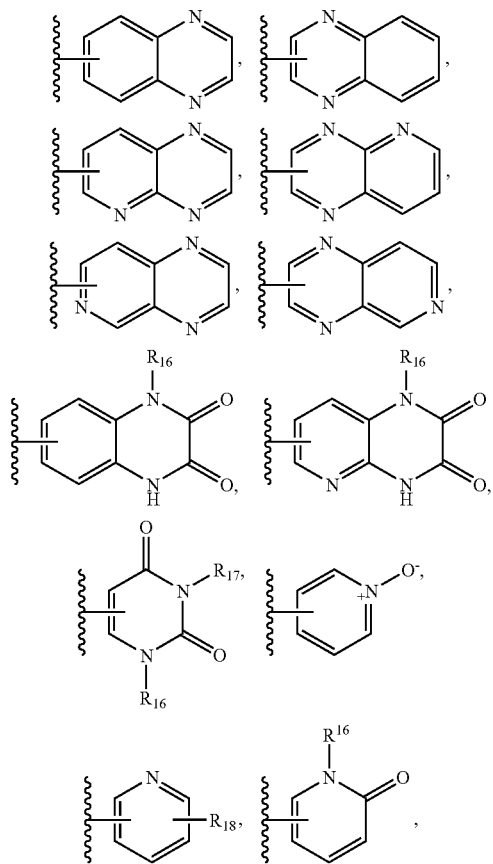

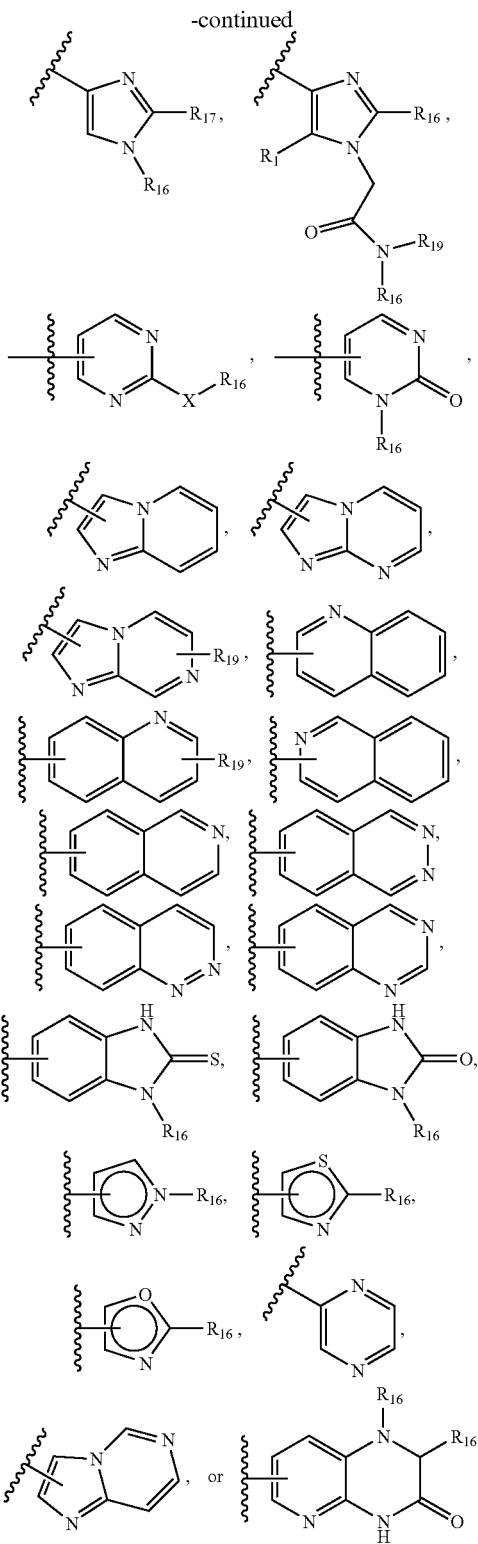

each $R_3$ also having up to three $R_{19}$ substituents attached to the ring of $R_3$ containing at least one N;

$R_4$ and $R_5$ are each independently hydrogen, alkyl, alkenyl, or alkynyl, wherein each alkyl, alkenyl, or alkynyl is optionally substituted;

Ar is aryl, such as phenyl or thiophenyl;

$R_6$ is $C_1$-$C_6$ alkyl, alkenyl, alkynyl, $NR_{22}R_{23}$, $CR_{24}(CF_3)_2$, $JR_{22}$, or $C(=O)R_{22}$, wherein J is O or $SO_m$, wherein m is 0, 1, or 2;

$R_{16}$ is hydrogen, $C_1$-$C_{10}$ alkyl, $C_2$-$C_{10}$ alkenyl, $C_2$-$C_{10}$alkynyl, $R_{20}$-E-$R_{21}$, $C(=O)ER_{20}$, $ER_{20}$, $NR_{20}R_{21}$, or $(CH_2)_nG$, optionally substituted alkyl, optionally substituted aryl, aryl substituted with optionally substituted alkyl, alkyl substituted with optionally substituted aryl, alkyl substituted with imidazole, alkyl substituted with optionally substituted imidazole, or alkyl substituted with indole;

$R_{17}$ is hydrogen, $C_1$-$C_6$ alkyl, $C_2$-$C_6$ alkenyl, $C_2$-$C_6$ alkynyl, $(CH_2)_mCO_2R_{20}$, $(CH_2)_mC(=O)NR_{20}R_{21}$;

$R_{18}$ is $CO_2R_{20}$, $C(=O)NR_{20}R_{21}$, or $SO_mR_{20}$;

$R_{19}$ is H, $C_1$-$C_3$ alkyl, $C_2$-$C_6$ alkenyl, or $C_2$-$C_6$ alkynyl; or alternatively, $R_{16}$ and $R_{19}$, taken together with the atoms to which they are attached, form a cyclic or heterocyclic group, e.g., of 3-8 ring members and the heteroatoms are selected from O, N and S;

$R_{20}$ and $R_2$, are, independently, H, $C_1$-$C_3$ alkyl, or heteroalkyl, or alternatively, $R_{20}$ and $R_{21}$, taken together with the atoms to which they are attached, form a cyclic or heterocyclic group, e.g., of 3-8 ring members and the heteroatoms are selected from O, N and S;

m is 0, 1, or 2;

n is 0, 1, 2, 3, or 4;

X is O, $NR_{21}$, or $SO_m$;

E is O, N, $NR_{21}$, or $SO_m$; and

G is phenyl, 2-pyridyl, 3-pyridyl or 4-pyridyl;

$R_{22}$ and $R_{23}$ are, independently, H, $C_1$-$C_7$ alkyl, alkenyl, alkynyl, aryl, or heteroalkyl, each alkyl, alkenyl, alkynyl, aryl, or heteroaryl being optionally substituted; alternatively, $R_{22}$ and $R_{23}$, taken together with the atoms to which they are attached, form an optionally substituted cyclic or optionally substituted heterocyclic group; and $R_{24}$ is H, or OH.

The key intermediate 4 can be prepared in two ways (Schemes 1 and 2). In scheme 1, 2,6-difluoronitrobenzene 1 is treated with a slight excess of sodium azide for 2 hours then the reaction mixture is treated with a 50% excess of piperazine, 2-substituted piperazine or 2,6-disubstituted piperazine in unprotected form or protected at the more hindered nitrogen as a Boc or Cbz function. Intermediate 2 is obtained in yields ranging from 50-90%. The nitro and azide functions are reduced under standard catalytic conditions ($H_2$, Pt/C, MeOH) and the product phenylenediamine is treated with a substituted benzaldehyde and Pd/C to promote oxidation. The product benzimidazole is deprotected if necessary ($H_2$, Pd/C if PG=Cbz; TFA-DCM if PG=Boc) and the product, in most cases, can be crystallized from acetonitrile.

Scheme 1

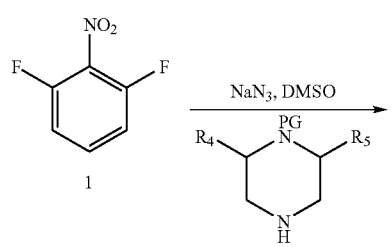

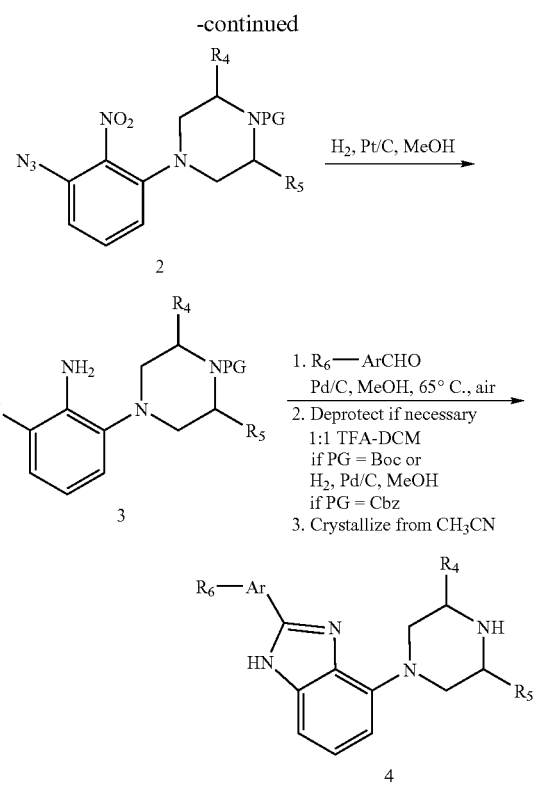

PG = H, Boc or Cbz

Scheme 2 indicates that the phenylenediamine intermediate 3 can be condensed with an acid and the product amide can be reacted with weak acid to cyclize and provide the intermediate 4 after deprotection.

Scheme 2

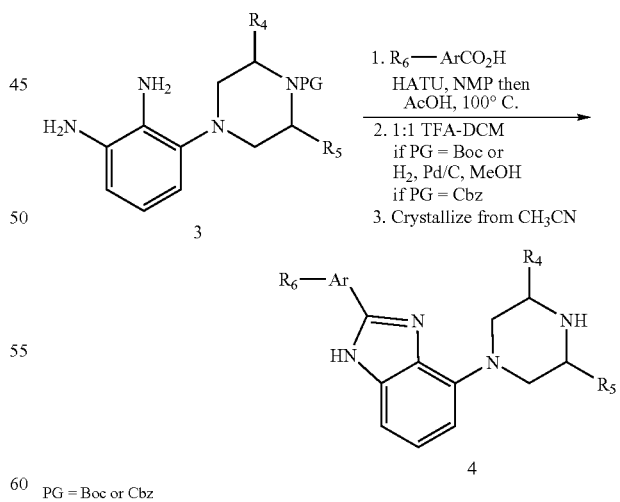

PG = Boc or Cbz

Substitution on the secondary nitrogen of the piperazine ring is achieved in three ways: Scheme 3 shows substitution occurring through nucleophilic substitution of an alkyl halide to provide the target products (I).

Scheme 3

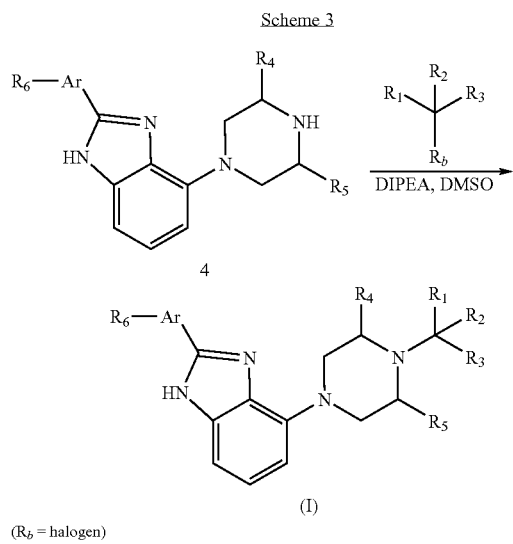

(R$_b$ = halogen)

Scheme 4 indicates products (I) are prepared via reductive amination between aldehydes/ketones and the intermediate 4.

Scheme 4

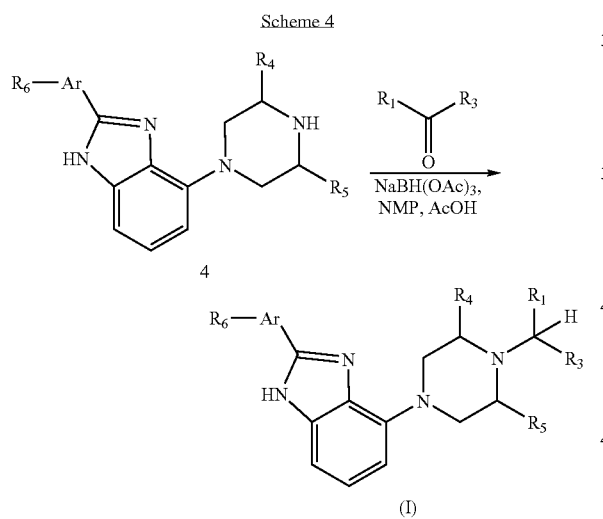

Scheme 5 indicates products (I) can also be obtained by condensing intermediate 4 with an activated acid to form and amide. The amide can be reduced under certain conditions to provide (I).

Scheme 5

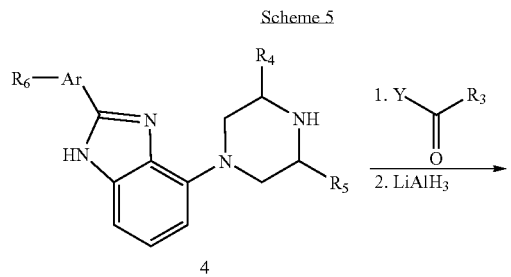

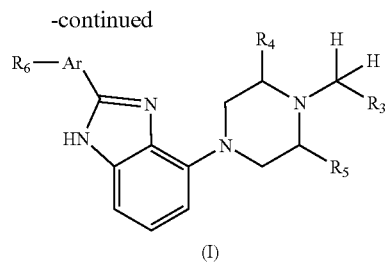

Y = Cl, other leaving group

One of skill in the art will recognize that Schemes 1-5 can be adapted to produce the other compounds and pharmaceutically acceptable salts of compounds according to the present invention.

EXAMPLES

Example 1A

Activity

COS cell membranes containing human GnRH receptors were incubated with radioactively labeled D-trp6 GnRH in the presence of increasing concentrations of test compound. Membrane bound radioactivity was measured after separating the free radioactivity by filtration method, and IC50 values were calculated using SAS analysis system (Receptor-binding affinity of gonadotropin-releasing hormone analogs: analysis by radioligand-receptor assay. *Endocrinology*, 1980, 106:1154-1159). All compounds have hGnRH binding IC$_{50}$'s between 1 and 10,000 nM.

Abbreviations: HPLC and LC/MS Methods for the Following Examples and Intermediates Method A: Column; Xterra MS C18, 5 µm, 50×2.1 mm. Mobile phase: 90/10-5/95 water (0.1% formic acid)/acetonitrile (0.1% formic acid), 2 min, hold 1.5 min, 0.8 mL/min., 210-400 nm.

Method B: LC/MS: YMC CombiScreen ProC18 50×4.6 mm I.D. column, S-5 µm, 12 nm. Flow rate 1.0 mL/min. Gradient: 10/90 Acetonitrile/Water (0.1 % TFA in both solvents) to 100% acetonitrile over 10 minutes. Hold 100% acetonitrile for 3 mins then back to 10/90 over 2 mins. MS detection using a ThermoFinnigan AQA mass spectrometer in ESI positive mode.

Method C: Column; Xterra RP18, 3.5u, 150×4.6 mm. Mobile phase: 85/15-5/95 Ammonium formate buffer (pH=3.5)/ACN+MeOH (1:1) for 10 min, hold 4min, 1.2 mL/min., 210-370 nm.

Method D: Column; Xterra RP18, 3.5u, 150 x 4.6 mm. Mobile phase: 85/15-5/95 Phosphate buffer (pH=2.1)/ACN+MeOH (1:1) for 10 min, hold 4 min, 1.2 mL/min., 210-370 nm.

Method E: Method E-YMC CombiPrep ProC18 50×20 mm I.D. column, S-5 µm, 12 nm. Flow rate 20 mL/min. Gradient: 10/90 Acetonitrile/Water (0.1% TFA in both solvents) to 100 % acetonitrile over 10 minutes then hold for three minutes at 100% acetonitrile and ramp back to 10/90 acetonitrile/water over two minutes.

Example 1B

Preparation of Intermediate Aldehydes 2-(4-Dimethoxymethyl-phenyl)-1,1,1,3,3,3-hexafluoro-propan-2-ol

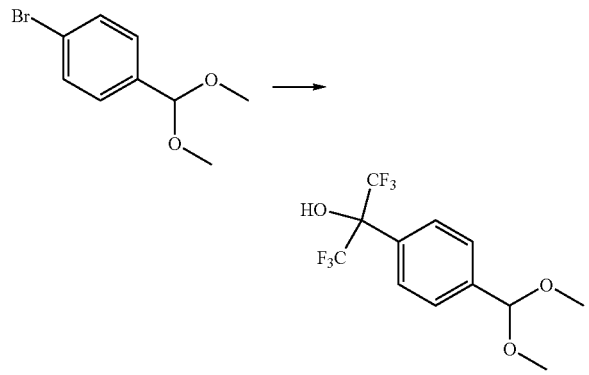

Commercially-available 1-Bromo-4-dimethoxymethyl-benzene (5.0 g, 22 mmol) was dissolved in THF (10 ml) and cooled to −78° C. under a nitrogen atmosphere. (A hexane solution of nBuLi (31 mmol, 12.3 ml of 2.5 M solution) was added dropwise over 5 min. Hexafluoroacetone was bubbled through this solution for approximately 10 m, and the solution was allowed to warm to RT. The reaction mixture was quenched with 1 ml of MeOH and the solvents were removed under vacuum. The crude was purified by silica gel column chromatography with 5% ethyl acetate/hexane to give the title product as a yellow oil (3.12 g (45%), 9.4 mmol). $^1$H NMR (DMSO-d$_6$) δ=8.78 (s, 1H), 7.71 (d, J=8.2 Hz, 2H), 7.53 (d, J=8.5 Hz, 2H), 5.48 (s, 1H), 3.25 (s, 6H).

4-(2,2,2-Trifluoro-1-hydroxy-1-trifluoromethyl-ethyl)-benzaldehyde

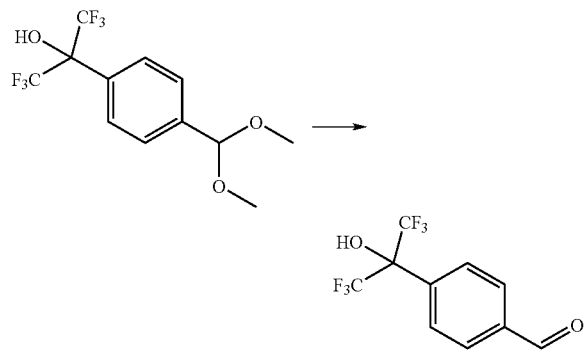

2-(4-Dimethoxymethyl-phenyl)-1,1,1,3,3,3-hexafluoro-propan-2-ol (350 mg, 1.1 mmol) was dissolved in DCM (5 ml). A 50% aqueous TFA (5 ml) was added and the solution was allowed to stir for 2h. The solvent was removed under vacuum, and the reaction mixture was partitioned between ethyl acetate and a 1M sodium carbonate solution. The organic layer was washed with carbonate two additional times, and then it was washed with brine. It was dried over MgSO$_4$, and the solvent was removed to yield the title product (300 mg (100%), 1.1 mmol) as a white solid. $^1$H NMR (DMSO-d$_6$) δ=10.1 (s, 1H), 9.05 (s, 1H), 8.12 (d, J=8.5 Hz, 2H), 7.96 (d, J=8.2 Hz, 2H).

1-Bromo-4-(2,2,2-trifluoro-1-trifluoromethyl-ethyl)-benzene

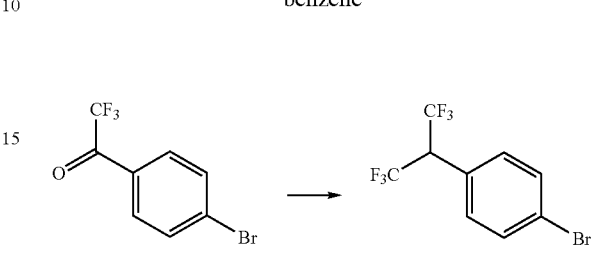

1-(4-Bromo-phenyl)-2,2,2-trifluoro-ethanone (500 mg, 2 mmol) and triphenylphosphine (1.05 g, 4 mmol) were dissolved in diglyme (25 ml) and heated to 150° C. in a three-neck flask fitted with both an addition funnel and a reflux condenser under nitrogen. A solution of sodium chlorodifluoroacetate, dissolved in diglyme (13 ml), was slowly added via the addition funnel. The addition took about one hour. After it was complete, the reaction mixture was allowed to stir for an additional hour. It was then cooled to below 100° C., and potassium fluoride (476 mg, 8.2 mmol) and water (0.3 ml) were added. The mixture was allowed to stir for 18 h at 95° C. The reaction mixture was heated to 130° C., water was added and the title product was steam distilled into a collection flask (with a large amount of diglyme, complicating yield calculations). $^1$H NMR (CDCl$_3$) δ=7.61 (d, J=8.4 Hz, 2H), 7.32 (d, J=8.4 Hz, 2H), 4.06 (septet, J$_{H,F}$=8.2 Hz, 1H).

1-(2,2,2-Trifluoro-1-trifluoromethyl-ethyl)-4-vinyl-benzene

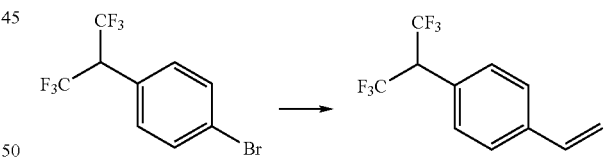

Crude 1-bromo-4-(2,2,2-trifluoro-1-trifluoromethyl-ethyl)-benzene, (approximately 100 mg of starting material, contaminated with diglyme) was dissolved in toluene (3 ml) in a sealed tub under a nitrogen atmosphere. Tetrakispalladium (15 mg, 0.013 mmol) and LiCl (42 mg, 1 mmol) were added, followed by the addition of tributylvinyltin (155 mg, 0.49 mmol). The reaction mixture was heated to 80° C. for 18 h, and then purified by silica gel column chromatography (100% hexane -2% ethyl acetate/hexane) to yield the title product, whose volatility made yield calculations impossible. $^1$H NMR (CDCl$_3$) δ=7.49 (d, J=8.4 Hz, 2H), 7.40 (d, J=8.4 Hz, 2H), 6.71 (dd, J=10.9, 17.6 Hz, 1H), 5.82 (d, J=17.7, 1H), 5.33 (d, J=10.9 Hz, 1H), 4.06 (septet, J$_{H,F}$=8.3 Hz, 1H).

4-(2,2,2-Trifluoro-1-trifluoromethyl-ethyl)-benzaldehyde

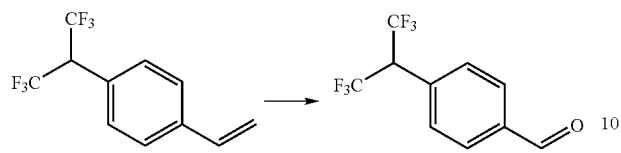

1-(2,2,2-Trifluoro-1-trifluoromethyl-ethyl)-4-vinyl-benzene (80 mg, 0.3 mmol) was dissolved in dioxane (6 ml) and water (5 ml). NaIO$_4$ (181 mg, 0.84 mmol) and OsO$_4$ (0.18 ml of a 2.5 % t-BuOH solution) were added. The mixture was allowed to stir at room temperature for 2 h, and then it was partitioned between ethyl acetate and brine. The ethyl acetate was washed with three additional times with brine, dried over MgSO$_4$, and the solvent was removed under vacuum to give the title product (47 mg (61%), 0.18 mmol). $^1$H NMR (CDCl$_3$): δ=10.08 (s, 1H), 8.04 (d, J=8.3 Hz, 2H), 7.76 (d, J=8.3 Hz, 2H), 5.82 (m, 1H).

Example 1C

Preparation of Intermediate benzimidazolylpiperazines

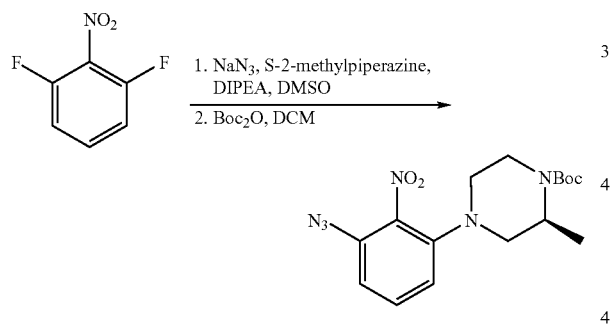

To a solution of 2,6-difluoronitrobenzene (1.0 g, 6.3 mMol) in dimethylsulfoxide (7 mL) was added sodium azide (0.45 g, 6.9 mMol). After stirring for 2 h at 20° C. diisopropylethylamine (0.81 g, 6.3 mMol, 1.1 mL) was added to the reaction mixture followed by S-2-methylpiperazine (0.95 g, 9.5 mMol). The reaction mixture stirred at 60° C. for 10 h then 20° C. for an additional 12 h at which point it was diluted with ethyl acetate (50 mL), washed with 1N sodium hydroxide solution (20 mL) and water (2×20 mL). The organic layer was dried (MgSO$_4$), evaporated and the residue dissolved in dichloromethane (25 mL) and treated with di-t-butyldicarbonate (1.5 g, 7.1 mMol). After stirring for 16 h at 20° C. the solvent was evaporated and the residue was chromatographed on silica gel eluted with 75% hexanes in ethyl acetate to provide the product as a yellow gum (2.2 g, 96%). $^1$H-NMR (CDCl$_3$), δ=7.42 (dd, 1H, J=8.2 Hz, J=8.2 Hz), 7.0 (d, 1H, J=8.2 Hz), 6.95 (d, 1H, J=8.2 Hz), 4.28 (bm, 1H), 3.88 (bd, 1H, J=13.3 Hz), 3.00 (m, 5H), 1.48 (s, 9H), 1.22 (d, 3H, J=6.8 Hz). LC/MS (Method A), rt=2.05 mins., purity=89.8%, calculated mass=362, [M+H—C$_5$H$_9$O$_2$]+=263.

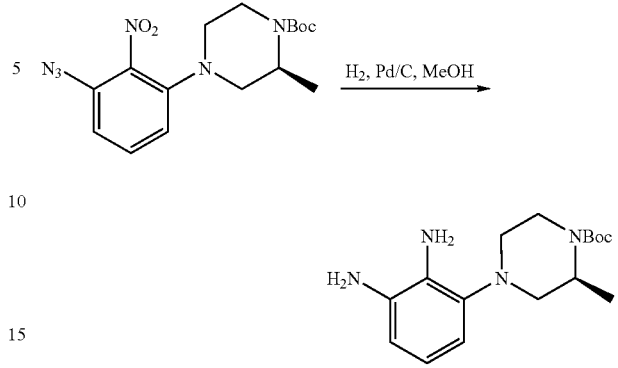

A mixture of the piperazinylnitroazide (2.2 g, 6.1 mMol) in methanol (50 mL) was hydrogenated (1 atmosphere hydrogen pressure, ballon) over 10% palladium on carbon (0.20 g) for 5 h. During this time the reaction mixture was purged with hydrogen three times. The catalyst was filtered with the aid of diatomaceous earth, washed with several portions of methanol and the combined filtrates were evaporated under reduced pressure to leave the phenylenediamine product as a brown, foamy solid (1.8 g, 96%). $^1$H-NMR (CDCl$_3$), δ=6.68 (dd, 1H, J=7.9 Hz, J=7.7 Hz), 6.57 (d, 1H, J=8.3 Hz), 6.54 (d, 1H, J=7.6 Hz), 4.35 (bs, 1H), 3.97 (bd, 1H, J=12.5 Hz), 3.80 (bs, 2H), 3.37 (bs, 2H), 3.27 (td, 1H, J=13.0 Hz, J=4.7 Hz), 2.99 (bd, 1H, J=11.7 Hz), 2.90 (bd, 1H, J=10.9 Hz), 2.81 (dd, 1H, J=10.9 Hz, J=3.1 Hz), 2.70 (td, 1H, J=12.5 Hz, J=3.9 Hz), 1.51 (s, 9H), 1.40 (d, 3H, J=7.8 Hz). LC/MS (Method A), rt=1.22 mins., purity=98.0 %, calculated mass=306, [M+H]+=307.

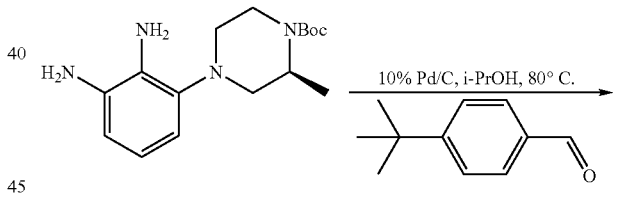

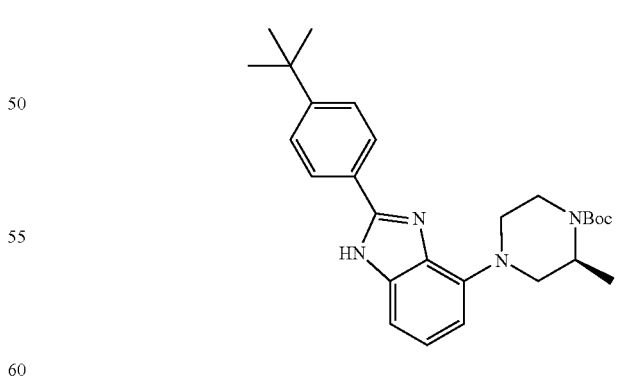

A mixture of the phenylenediamine (1.8 g, 5.9 mMol), 4-t-butylbenzaldehyde (1.1 g, 7.1 mMol, 1.2 mL) and 10% palladium on carbon (0.60 g) in isopropanol (40 mL) was stirred rapidly and heated to 80° C. for 2 h. After cooling to room temperature the catalyst was filtered with the aid of diatomaceous earth, washed with isopropanol and the combined filtrates were evaporated under reduced pressure. The crude product was chromatographed on silica gel eluted with 75% hexanes in ethyl acetate to leave the product as a foamy solid (2.5 g, 95%). ¹H-NMR (acetone-d₆), δ=11.63 (bs, 1H), 8.00 (d, 2H, J=8.5 Hz), 7.45 (d, 2H, J=8.5 Hz), 6.91 (m, 2H), 6.42 (dd, 1H, J=7.2 Hz, J=1.4 Hz), 4.47 (bd, 1H, J=9.4 Hz), 4.28 (bs, 1H), 4.02 (bd, 1H, J=12.5 Hz), 3.88 (bd, 1H, J=12.5 Hz), 3.22 (td, 1H, J=13.3 Hz, J=3.9 Hz), 2.87 (dd, 1H, J=11.7 hz, J=3.9 Hz), 2.65 (m, 1H), 1.38 (s, 9H), 1.35 (d, 3H, J=6.3 Hz), 1.25 (s, 9H). LC/MS (Method A), rt=1.91 mins., purity=89.9 %, calculated mass=448, [M+H]⁺=449, [M−H]⁻=447.

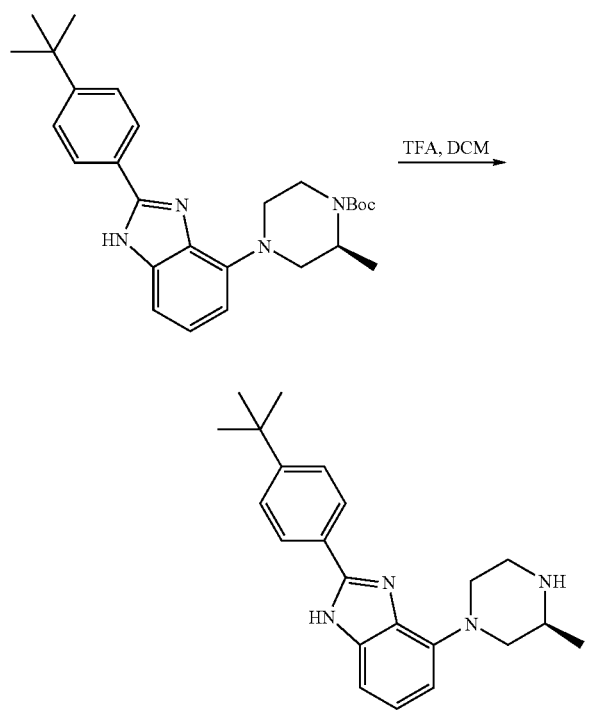

A solution of the Boc protected piperazinylbenzimidazole (2.4 g, 5.3 mMol) in trifluoroacetic acid (20 mL) and dichloromethane (20 mL) was stirred for 2 h. The solvents were evaporated and the crude product was purified by reversed phase HPLC (method E). The product containing fractions were combined, neutralized with 1M sodium carbonate solution and extracted with ethyl acetate (2×50 mL). The extracts were combined, dried (MgSO₄) and evaporated under reduced pressure to provide the product as a white, foamy solid (1.0 g, 54%). ¹H-NMR (acetone-d₆), δ=11.72 (bs, 1H), 8.12 (d, 2H, J=8.7 Hz), 7.57 (d, 2H, J=8.7 Hz), 7.05 (dd, 1H, J=7.8 Hz, J=7.7 Hz), 6.99 (d, 1H, J=7.8 Hz), 6.53 (d, 1H, J=7.7 Hz), 4.40 (d, 1H, J=11.1 Hz), 4.33 (d, 1H, J=11.0 Hz), 3.07 (m, 3H), 2.72 (m, 2H), 2.40 (t, 1H, J=10.6 Hz), 1.37 (s, 9H), 1.11 (d, 3H, J=6.3 Hz). HPLC (method D), rt=5.5 mins. (100% @ 254 and 300 nms). MS, calculated MW=348.2, [M+H]⁺=349, [M−H]⁻=347.

Table 1 indicates other intermediates prepared using the above method:

TABLE 1

| No. | $R_A$ | $R_B$ | $R_C$ | [M + H]⁺ |
|---|---|---|---|---|
| 1 | t-Butyl | H | H | 335 |
| 2 | t-Butyl | H | {R}-Methyl | 349 |
| 3 | t-Butyl | H | {S}-Ethyl | 363 |
| 4 | t-Butyl | {S}-Methyl | {R}-Methyl | 363 |
| 5 | n-Propyl | H | H | 321 |
| 6 | i-Propyl | H | H | 321 |
| 7 | Ethyl | H | H | 314 |
| 8 | Methanesulfonyl | H | H | 357 |
| 9 | Methanesulfonyl | H | {S}-Methyl | 371 |
| 10 | Ethanesulfonyl | H | H | 371 |
| 11 | 2-Propanesulfonyl | H | H | 385 |
| 12 | Benzenesulfonyl | H | H | 418 |
| 13 | N,N-Diethylamino | H | H | 350 |
| 14 | N,N-Diethylamino | H | {S}-Methyl | 364 |
| 15 | N,N-Diethylamino | H | {S}-Ethyl | 378 |
| 16 | 3-(hydroxy)phenoxy | H | H | 387 |
| 17 | Benzoyl | H | H | 383 |
| 18 | 1-Pyrrolidinyl | H | H | 348 |
| 19 | 1',1',1',3',3',3'-hexafluoroisopropane | H | H | 429 |
| 20 | 1',1',1',3',3',3'-hexafluoroisopropane-2-ol | H | H | 445 |
| 21 | 2',2',2'-trifluoroacetyl | H | H | 374, 392 |
| 22 | Acetyl | H | H | 321 |
| 23 | Dimethylphosphonyl | H | H | 355 |
| 24 | 1-Pyrrolyl | H | H | 344 |
| 25 | Aminosulfonyl | H | H | 358 |
| 26 | Methoxy | H | H | 309 |
| 27 | Methanethio | H | H | 325 |
| 28 | Acetamido | H | H | 336 |

Example 1D

Preparation of Substituted Imidazole Intermediates

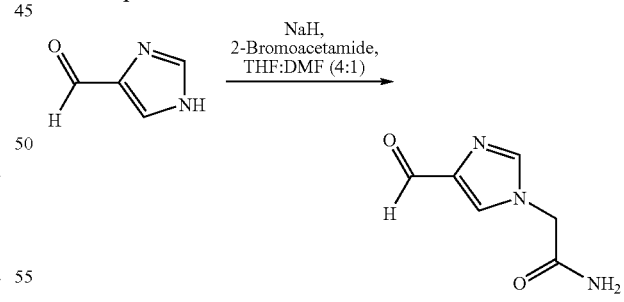

A solution of 1H-imidazole-4-carbaldehyde (1.92 g, 20 mMol) in anhydrous THF (32 mL) and DMF (8 mL) was treated with sodium hydride (60% dispersion in mineral oil, 880 mg, 22 mMol) for 5 mins. 2-Bromoacetamide (3.59 g, 26 mMol) was added and the reaction was stirred continuously overnight. The THF was concentrated, loaded on a silica column, and eluted with 20% methanol in dichloromehane. The solvent was filtered and evaporated to yield 2.70 of the product as a white solid (88.2%). ¹H NMR (400 MHz, CD₃OD) δ=9.75 (s, 1H), 7.95 (d, 1H, J=1.0 Hz), 7.82 (s, 1H), 4.89 (s, 2H); $^{13}$C NMR (75.5 MHz, CD$_3$OD) δ 186.0, 170.8, 142.7, 142.3, 130.7, 50.0; HPLC (Method D) rt=1.5 min, 96.4% purity at 256 nm. LC/MS calculated mass=153.14, [M−H]$^−$=152, [M+H]$^+$=154.

Table 2 indicates other intermediates prepared using the above method:

TABLE 2

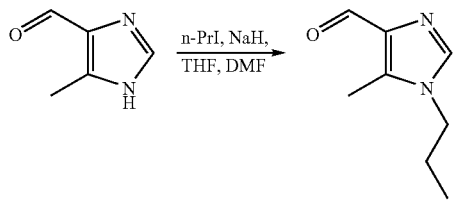

| No. | R$_D$ | R$_E$ | R$_F$ | R$_G$ | [M + H]$^+$ |
|---|---|---|---|---|---|
| 1 | Methyl | H | H | H | 168 |
| 2 | Ethyl | H | H | H | 182 |
| 3 | H | Methyl | H | H | 168 |
| 4 | H | Methyl | Methyl | Benzyl | 272 |
| 5 | H | Methyl | H | (R)-2-phenylethyl | 272 |
| 6 | H | Methyl | H | (S)-2-phenylethyl | 272 |
| 7 | H | Methyl | H | H | 182 |

Example 1E

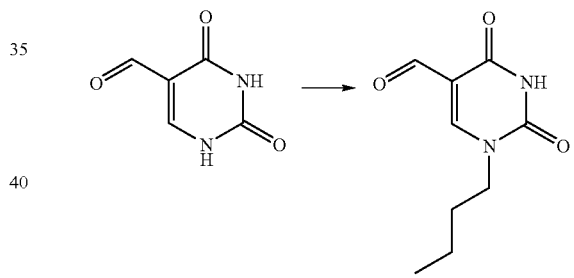

2-Methyl-1-propyl-1H-imidazole-4-carbaldehyde: 2-Methyl-1H-imidazole-4-carbaldehyde (940 mg, 8.5 mmol) was dissolved in THF (40 ml) with DMF (5 ml). NaH (380 mg of a 60% dispersion in mineral oil) was added carefully and the reaction mixture was allowed to stir 5 minutes under nitrogen. Propyl iodide (1.65 g, 9.7 mmol) was added and it was allowed to stir for 1 h, at which time the reaction was judged complete. The solvent was removed under vacuum, and the crude was purified on silica eluted with 100% ethyl acetate −1% MeOH/ethyl acetate to yield the title product as the main isomer (390 mg (30%), 2.6 mmol). $^1$H NMR (DMSO-d$_6$): δ=9.68 (s, 1H), 8.02 (s, 1H), 3.97 (t, J=7.3 Hz, 2H), 2.31 (s, 3H), 1.71 (sextet, J=7.3 Hz, 2H), 0.85 (t, J=7.3 Hz, 3H).

Table 3 indicates other intermediates prepared using the above method:

TABLE 3

| No. | R$_H$ | R$_I$ | R$_J$ | [M + H]$^+$ |
|---|---|---|---|---|
| 1 | Me | Me | Et | |
| 2 | Me | Me | H | 125 |
| 3 | H | Me | H | |
| 4 | H | Me | Me | |
| 5 | Me | Et | Et | |
| 6 | H | Et | Me | |
| 7 | H | Et | H | |
| 8 | Me | Et | H | |
| 9 | H | Me | Et | |
| 10 | H | Et | Et | |
| 11 | Me | i-Pr | H | |
| 12 | Me | Et | H | 149 |
| 13 | Me | n-Bu | H | |
| 14 | Me | n-Pr | Et | |
| 15 | Me | n-Pr | Et | |
| 16 | H | n-Pr | Me | |

Example 1F

Preparation of Substituted Uracil Intermediates

A suspension of 5-formyluracil (0.84 g, 6.0 mMol) in anhydrous dimethylformamide (12 mL) under a nitrogen atmosphere was cooled to −40° C. The reaction mixture was treated with sodium hydride (60% mineral oil dispersion, 0.26 g, 6.6 mMol), stirred 30 mins., then treated with 1-bromobutane (0.91 g, 6.6 mMol). The mixture warmed to 20° C. over 3 h., then was brought to 40° C. for 48 h. At this time the reaction mixture was cooled to room temperature, treated with methanol (5 mL) and evaporated to dryness under reduced pressure. The residue was purified by chromatography on silica gel eluted with a gradient of ethyl acetate in hexanes (1:3 to 1:2 to 1:1) to leave the product as a white powder (0.25 g, 21%). 300 MHz $^1$H-NMR (DMSO-d$_6$) δ=11.72 (bs, 1H), 9.77 (s, 1H), 8.48 (s, 1H), 3.80 (t, 2H, J=7.3 Hz), 1.59 (m, 2H), 1.28 (m, 2H), 0.89 (t, 3H, J=7.4 Hz). HPLC (method D), rt=4.41, purity=98.4% @ 210-370 nm and 98.9% @ 288 rn. ESMS [M+H]$^+$ calculated=196.2, found=197.

Table 4 indicates other intermediates prepared using the above method:

TABLE 4

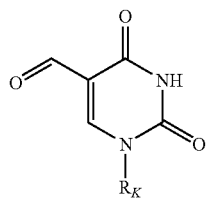

| No. | $R_K$ | $[M + H]^+$ |
|---|---|---|
| 1 | Me | 155 |
| 2 | Et | 169 |
| 3 | n-Pr | 183 |
| 4 | i-Pr | 183 |
| 5 | Allyl | 181 |
| 6 | Propargyl | 179 |
| 7 | n-Pentyl | 211 |
| 8 | n-Hexyl | 225 |
| 9 | 1-Methoxyethoxy-methyl | 229 |
| 10 | Benzyl | 231 |
| 11 | 2-Fluorobenzyl | 249 |
| 12 | 2,6-Difluoro-benzyl | 267 |
| 13 | 1-Acetamido | 198 |

Example 1G

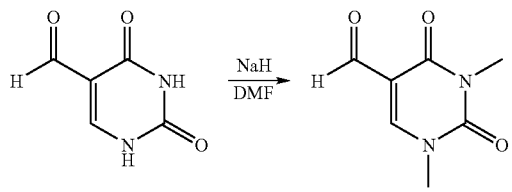

To a slurry of 400mg of 5-formyluracil (2.8 mM) in DMF (10 mL) at room temperature was added sodium hydride (280 mg, 7 mM, 60% in oil). After stirring for 30 min., MeI (1.013 g, 7.2 mM) was added. When the turbid reaction mixture became a homogeneous yellow solution tlc revealed the absence of starting uracil. The reaction mixture was treated with MeOH and water, concentrated on the rotovap and the residue partitioned between MeOH and hexane. The MeOH fraction was concentrated and the residue partitioned between chloroform and water. The organic phase dried ($MgSO_4$), filtered and concentrated to give 420 mg (89% yield) of 1,3-dimethyl-5-formyluracil as an off-white waxy solid. $^1$H-NMR (DMSO-$d_6$), δ=9.82 (s, 1H), 8.52 (s, 1H), 3.43 (s, 3H), 3.2 (s, 3H). LC/MS; rt=0.34 mins. m/z=169, $[M+H]^+$.

Example 1H

Preparation of Oxazole and Thiazole Intermediates

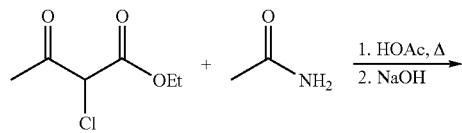

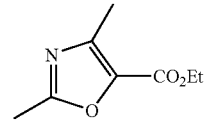

2,4-Dimethyl-oxazole-5-carboxylic acid ethyl ester. Prepared as in *J. Heterocyclic Chem.* 1998, 35, 859. A solution of chloroacetoacetate (20 g, 121 mmol) and acetamide (14.4 g, 240 mmol) in glacial acetic acid (40 mL) was heated to reflux for 72 h. The mixture was cooled to rt and concentrated under vacuum. The resulting material was cooled in an ice bath and made basic (pH 9-10) with 6 N NaOH solution. The aqueous solution was extracted with $Et_2O$ (3×100 mL). The combined $Et_2O$ layers were dried ($Na_2SO_4$), filtered, and concentrated to afford a light brown oil. The crude material was purified by silica gel chromatography, eluting with a gradient of 20 % EtOAc/hexanes to 25 % EtOAc/hexanes to provide the ester (1.8 g, 9 %) as a pale yellow solid. $^1$H NMR 300 MHz ($CDCl_3$): δ=4.37 (q, J=7.1 Hz, 2 H), 2.49 (s, 3H), 2.43 (s, 3H), 1.38 (t, J=7.1 Hz, 3H). MS (ESI-POS): $[M+H]^+$=191.

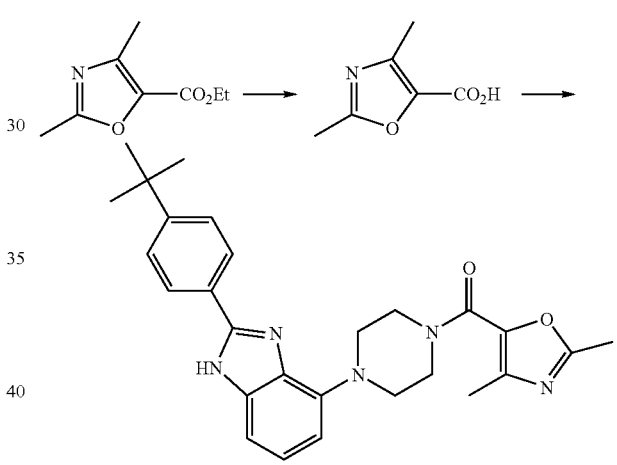

2-(4-tert-butylphenyl)-4-{4-[(2,4-dimethyl-1,3-oxazol-5-yl)carbonyl]piperazin-1-yl}-1H-benzimidazole. To a solution of 2,4-dimethyl-oxazole-5-carboxylic acid ethyl ester (1.8 g, 10.6 mmol) in THF (20 mL) cooled in an ice bath was added a solution of $LiOH \cdot H_2O$ (0.98 g, 23 mmol) in $H_2O$ (20 mL), followed by MeOH (10 mL). The reaction was stirred in the ice bath and allowed to come to rt overnight. The solution was concentrated in vacuuo. The aqueous solution was cooled in an ice bath and brought to pH 3 with the addition of 2 N HCl. The white precipitate was collected by filtration and dried in vacuuo to afford the acid as a white powder (0.67 g, 45%). MS (ESI-POS): $[M+H]^+$=142. The crude acid (49 mg, 0.35 mmol) was combined with the piperazinylbenzimidazole (101 mg, 0.30 mmol), HATU (133 mg, 0.35 mmol), and DIEA (60 μL, 0.36 mmol) in NMP (6 mL) and the solution was stirred at rt for 48 h. To the solution was added EtOAc (50 mL) and $H_2O$ (15 mL) and the layers were separated. The organic layer was washed with $H_2O$ (8×15 mL) and brine (20 mL), dried ($Na_2SO_4$), filtered, and concentrated. The residue was purified using silica gel chromatography, eluting with a gradient of 2% MeOH/$CH_2Cl_2$ to 3% MeOH/$CH_2Cl_2$ to afford the amide (90 mg, 65%) as a white powder. $^1$H NMR 300 MHz ($CDCl_3$): δ=9.38 (s, 1 H), 7.97 (d, J=8.4 Hz, 2H), 7.52 (d, J=8.4 Hz, 2H), 7.17 (t, J=7.8 Hz, 1H), 7.11 (d, J=7.9 Hz, 1H), 6.65 (d, J=7.8 Hz, 1H), 4.01 (bs, 4H), 3.67 (bs, 4H), 2.49 (s, 3H), 2.39 (s, 3H), 1.37 (s, 9H). MS (ESI-POS): [M+H]$^+$=4.59. Anal. Calc. for $C_{27}H_{31}N_5O_2$ 0.2 $CH_2Cl_2$: C, 68.84; H, 6.67; N, 14.67. Found: C, 68.99; H, 6.87; N, 14.56.

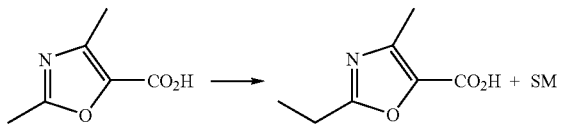

2-Ethyl-4-methyl-oxazole-5-carboxylic acid Prepared as in *J. Chem. Soc. Perkin* 1 1991, 10, 2417. To a solution of 2,4-dimethyl-oxazole-5-carboxylic acid (0.25 g, 1.7 mmol, prepared as in example 1) in THF (30 mL) cooled in a dry ice acetone bath was added LDA (2.0 M in THF, 2.2 mL, 4.4 mmol). The green solution was stirred in the bath for an additional 10 min., then methyl iodide (330 □L, 5.2 mmol) was added. The solution was stirred and allowed to warm slowly to rt overnight. To the solution was added H$_2$O (10 mL), and the THF was removed in vacuuo. To the residue was added EtOAc (75 mL), and sat. NaHCO$_3$ solution (2×25 mL) was used to wash the organic layer. The combined aqueous layers were acidified (pH 4) with 2 N HCl. The acidified aqueous layer was extracted with EtOAc (3×40 mL). The combined EtOAc layers were washed with brine, dried (Na$_2$SO$_4$), filtered, and concentrated under reduced pressure. The crude reaction showed product [MS (ESI-POS) [M+H]$^+$=156] to starting material in a 1:2 ratio by $^1$H NMR. The crude mixture was used as is for the next step below.

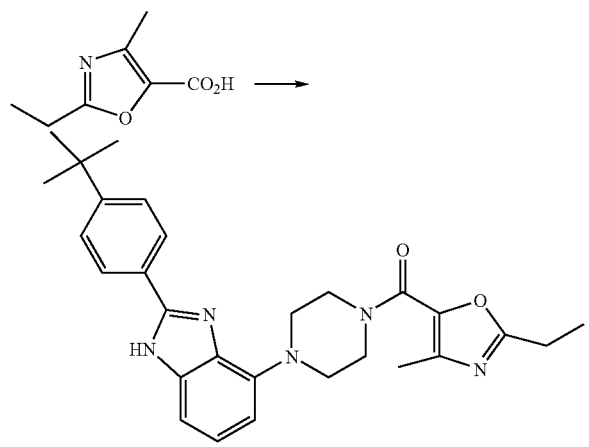

{4-[2-(4-tert-Butyl-phenyl-1H-benzimidazol-4-yl]-piper-azin-1-yl}-(2-ethyl-4-methyl-oxazol-5-yl)-methanone. To a solution of the mixture of carboxylic acids prepared in the previous reaction (0.13 g) in NMP (8 mL) was added the piperazinylbenzimidazole (0.26 g, 0.77 mmol), HATU (0.35 g, 0.92 mmol), and DIEA (170 μL, 0.96 mmol). The solution was stirred at rt overnight. To the solution was added EtOAc (125 mL) and sat. NaHCO$_3$ solution (25 mL). The layers were separated and the organic layer was washed with NaHCO$_3$ (25 mL), H$_2$O (6×25 mL), and brine (25 mL). The organic layer was dried (Na$_2$SO$_4$), filtered, and concentrated under reduced pressure. The crude mixture was purified using reversed-phase HPLC (30% 0.1% TFA/acetonitrile /H$_2$O, isocratic). The product fractions were combined and concentrated under reduced pressure. The aqueous residue was brought to pH 8 with the addition of solid K$_2$CO$_3$. The aqueous mixture was extracted with EtOAc (3×30 mL). The EtOAc layers were washed with brine (10 mL). The organic layer was dried (Na$_2$SO$_4$), filtered, and concentrated under reduced pressure to afford the title compound (38 mg, 5% over 2 steps) as an ivory powder. $^1$H NMR 400 MHz (DMSO-d$_6$): δ=8.08 (d, J=8.1 Hz, 2H), 7.57 (d, J=8.5 Hz, 2H), 7.08 (d, J=3.1 Hz, 2H), 6.56 (bs, 1H), 3.86 (bs, 2H), 3.60 (bs, 2H), 3.32 (s, 4H), 2.79 (q, J=7.5 Hz, 2H), 2.26 (s, 3H), 1.34 (s, 9H), 1.26 (t, J=7.5 Hz, 3H). MS (ESI-POS) [M+H]$^+$=4.72. HPLC (column: Xterra MS, C18, 3.5 mm, 4.6×50 mm; 5/95-95/5, 10 mins., hold for 2.5 mins., A=0.1% TFA in H$_2$O, B=acetonitrile) rt=6.4 mins. (97.1% (210 nm; 97.8% @ 254 nm).

Methoxyacetamide Prepared as in *J. Org. Chem.* 1990, 55, 3330. To a solution of methoxy acetic acid (15.3 g, 0.17 mol) in CHCl$_3$ (50 mL) cooled in an ice bath was added dropwise thionyl chloride (15.5 mL, 0.21 mol). The solution was stirred in an ice bath for 15 mins., then at rt for 1 h. The reaction was heated in a 40° C. bath overnight. The resulting solution was cooled to rt and concentrated under reduced pressure, keeping the bath below 40° C. The residual solution was carefully added to an aqueous solution of ammonia (50 mL) cooled in an ice bath. The reaction was stirred in the ice bath for 1 h. The mixture was filtered to collect a white solid. The filtrate was extracted with EtOAc (3×125 mL). The EtOAc layers were washed with brine (50 mL), dried (Na$_2$SO$_4$), filtered, and concentrated to provide the amide as white needles (3.2 g, 21%). $^1$H NMR 300 MHz (CDCl$_3$): δ=3.91 (s, 2H), 3.44 (s, 3H). mp=92-93° C.

2-Methoxy-thioacetamide Prepared as in WO 94/19332. To a suspension of 2-methoxyacetamide (3.2 g, 36 mmol) in Et$_2$O (100 mL) was added P$_4$S$_{10}$ (1.6 g, 3.6 mmol) in portions over 10 mins. The reaction was stirred at rt overnight. The mixture was filtered to collect a yellow solid. The filtrate was concentrated. A 2:3 mixture of amide to thioamide was seen by $^1$H NMR. The mixture was redissolved in Et$_2$O (80 mL) and P$_4$S$_{10}$ (1.6 g, 3.6 mmol) was added in portions. The reaction was stirred at rt for 2 h. The mixture was filtered. The filtrate was concentrated under reduced pressure to afford the thioamide (2.7 g, 72%) as a golden oil. $^1$H NMR 300 MHz (CDCl$_3$): δ=4.28 (s, 2H), 3.45 (s, 3H). MS (ESI-POS) [M+H]$^+$=106.

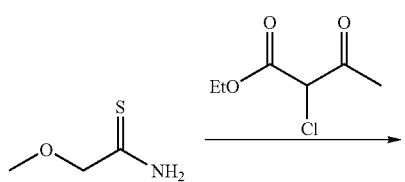

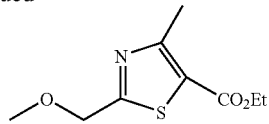

2-Methoxymethyl-4-methyl-thiazole-5-carboxylic acid ethyl ester Prepared as in EP (1991) 434,620. To a solution of 2-methoxy-thioacetamide (2.7 g, 26 mmol) in EtOH (anhydrous, 35 mL) was added chloroethyl acetoacetate (3.6 mL, 26 mmol) and the solution was heated in a 70° C. bath overnight. The mixture was cooled and concentrated under reduced pressure. The residue was dissolved in EtOAc (250 mL) and sat. NaHCO$_3$ (50 mL) and the layers were separated. The organic layer was washed with H$_2$O (40 mL) and brine (40 mL). The EtOAc solution was dried (Na$_2$SO$_4$), filtered, and concentrated to afford an orange oil. Purification by column chromatography, eluting with a gradient of 10% EtOAc/hexanes and 20% EtOAc/hexanes afforded the thiazole as a white solid (2.9 g, 52%). $^1$H NMR 400 MHz (CDCl$_3$): δ=4.68 (s, 2H), 4.33 (q, J=7.2 Hz, 2H), 3.87 (s, 3H), 2.72 (s, 3H), 1.37 (t, J=7.2 Hz, 3H). MS (ESI-POS) [M+H]$^+$=216. Anal. Calc. for C$_9$H$_{13}$NO$_3$S: C, 50.21; H, 6.09; N, 6.51. Found: C, 50.01; H, 5.88; N, 6.30.

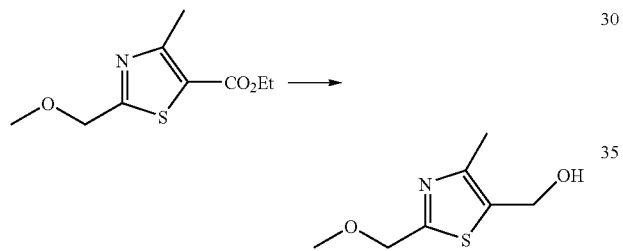

(2-Methoxymethyl-4-methyl-thiazol-5-yl)-methanol To a solution of 2-methoxymethyl-4-methyl-thiazole-5-carboxylic acid ethyl ester (0.50 g, 2.3 mmol) in EtOH (anhydrous, 15 mL) cooled in an ice bath was added NaBH$_4$ (0.09 g, 2.3 mmol) in three portions over 5 min. The reaction was stirred in the bath for 15 mins., then at rt for 2 h. The reaction was heated in a 45° C. bath for 2 h. The reaction was cooled to rt and additional NaBH4 (0.09 g, 2.3 mmol) was added. The reaction was returned to the bath and heated overnight. The reaction was cooled to rt and quenched by the addition of H$_2$O (5 mL) to the solution cooled in an ice bath. The mixture was concentrated. The residue was dissolved in EtOAc (150 mL) and washed with brine (2×50 mL). The organic layer was dried (Na$_2$SO$_4$), filtered, and concentrated. The crude material was purified using silica gel chromatography, eluting with a gradient of 40% EtOAc/hexanes to 100% EtOAc, to afford the alcohol (0.26 g, 65%). $^1$H NMR 300 MHz (CDCl$_3$): δ=4.78 (bs, 2H), 4.66 (s, 2H), 3.47 (s, 3H), 2.38 (s, 3H). MS (ESI-NEG) [M−H]$^-$=172.

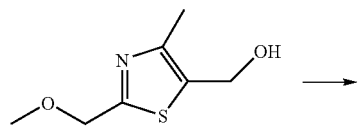

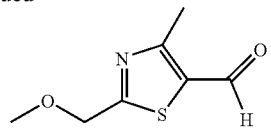

2-Methoxymethyl-4-methyl-thiazole-5-carbaldehyde To a solution of (2-methoxymethyl-4-methyl-thiazol-5-yl)-methanol (0.26 g, 1.5 mmol) in CHCl$_3$ (35 mL) was added activated MnO$_2$ (1.9 g, 23 mmol) and the reaction was stirred vigorously at rt for 4.5 h. The mixture was filtered through diatomaceous earth. The filtrate was concentrated under reduced pressure to afford a mixture (0.26 g) of aldehyde and alcohol (4:1). The crude mixture was taken on without purification. $^1$H NMR 300 MHz (CDCl$_3$): δ=10.08 (s, 1H), 4.71 (s, 2H), 3.53 (s, 3H), 2.73 (s, 3H).

Example 1I

Preparation of Pyridine Intermediates

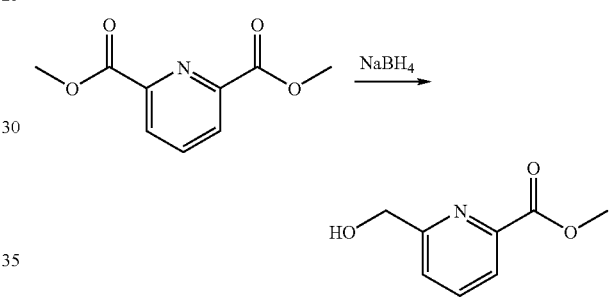

To a stirring solution of dimethyl-2,6-pyridinedicarboxylate (1.45 g, 7.44 mmol) in MeOH (36 mL) and DCM (7.2 mL) at 0° C. was added sodium borohydride (563 mg, 14.87 mmol). The reaction was stirred at 0° C. for 30 minutes, treated with 1 N HCl, and concentrated to dryness. The resulting solid was partitioned between saturated NaHCO$_3$ and DCM, and extracted with DCM (3×). The combined organic extracts were dried with MgSO$_4$ and concentrated to yield pure product (972 mg, 5.80 mmol, 78%). $^1$H NMR (DMSO-d$_6$): δ=8.00 (dd, J=8 Hz+7 Hz, 1H), 7.92 (d, J=8 Hz, 1H), 7.72 (d, J=7 Hz 1H), 5.56 (t, J=5 Hz, 1H), 4.62 (d, J=5 Hz, 2H), 3.92 (s, 3H). Calculated mass=167.2, [M+H]$^+$=168. Anal. Calcd. for C$_8$H$_9$NO$_3$ (167.16): C, 57.48; H, 5.43; N, 8.38. Found C, 57.31; H, 5.28; N, 8.25.

Table 5 indicates other intermediates prepared using the above method:

TABLE 5

| No. | R$_L$ | [M + H]$^+$ |
|---|---|---|
| 1 | 5-CO$_2$Me | 168 |
| 2 | 4-CO$_2$Me | 168 |

Example 1J

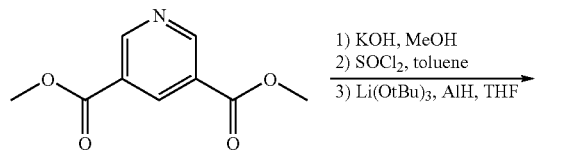

A solution of potassium hydroxide (1.30 g, 23.2 mmol.) in MeOH (25 mL) was added carefully to a solution of pyridine-3,5-dicarboxylic acid dimethyl ester (4.53 g, 23.2 mmol.) in MeOH (50 mL). The reaction mixture was stirred at room temperature for 16 h. Diethyl ether (600 mL) was added, the reaction was filtered, and the precipitate was suspended in MeOH (20 mL). Concentrated HCl (75 mL) was added followed by ditheyl ether (120 mL). Filtration of the resulting mixture yielded the ester/acid as the hydrochloride salt (3.23 g, 14.9 mmol., 64%) which was used without further purification. The ester/acid (1.0 g, 4.61 mmol.) was suspended in toluene and thionyl chloride (1.33 mL, 18.44 mmol.) was added. The reaction was heated to reflux for 4 h, then concentrated without heating the reaction flask above 50° C. The crude acid chloride was dried in vacuo and used directly in the next step. Lithium tri-tertbutoxyaluminum hydride (1M, 3.58 mL, 3.58 mmol.) was added to a solution of acid chloride (841 mg, 3.58 mmol.) in THF (10 mL) at −78° C. The reaction was allowed to warm to room temperature, was stirred for 16 h, and was quenched with 1N HCl. The resulting solution was concentrated, was partitioned between ethyl acetate and saturated sodium bicarbonate was extracted with ethyl acetate (3×). The combined organic extracts were dried with MgSO$_4$ and concentrated. The crude alcohol was purified by column chromatography (70% ethyl acetate/hexane) to yield pure product (200 mg, 1.20 mmol., 26%). $^1$H NMR (DMSO-d$_6$): δ=8.97 (s, 1H), 8.75 (s, 1H), 8.24 (s, 1H), 5.48 (t, J=6 Hz, 1H), 4.62 (d, J=6 Hz, 3H), 3.89 (s, 3H). Calculated mass=165.1, [M+H]$^+$=168. HPLC (method D) rt=3.4 min (98%).

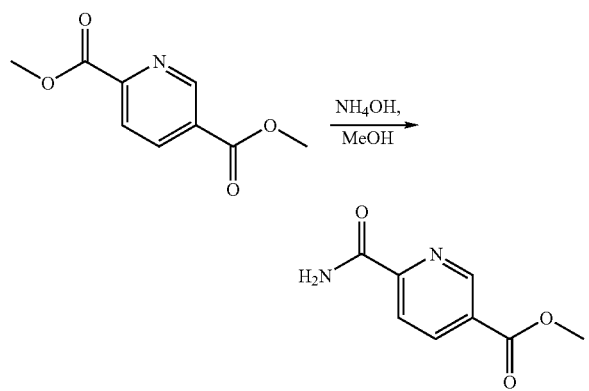

To a solution of pyridine-2,5-dicarboxylic acid dimethyl ester (3.55 g, 18.2 mmol.) in MeOH (100 mL) was added ammonium hydroxide (30%, 100 mL). The reaction was stirred at room temperature for 15 min., concentrated to dryness, and purified by column chromatography (70% ethyl acetate/hexane) to yield the product amide (1.57 g, 8.74 mmol., 48%). $^1$H NMR (DMSO-d$_6$): δ 9.10 (s, 1H), 8.48 (d, J=8 Hz, 1H), 8.27 (s, 1H), 8.18 (d, J=8 Hz, 1H), 7.83 (s, 1H), 3.92 (s, 3H). Calculated mass=180.2, [M+H]$^+$=181. HPLC (method D) rt=4.2mins. (85.1%).

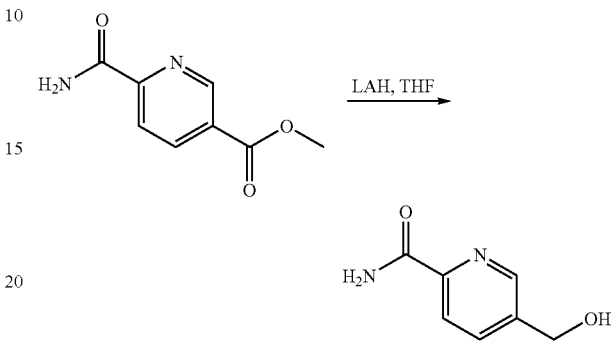

To a solution of the amide prepared above (1.57 g, 8.72 mmol) in THF (90 mL) at 0° C. was added lithium aluminum hydride (1M in THF, 17.44 mL, 17.44 mmol.). The reaction mixture was stirred 20 minutes, then carefully quenched using 1 N potassium hydroxide. Brine was added and the resulting solution was extracted with ethyl acetate (4×). The combined organic extracts were dried with MgSO$_4$, concentrated, and purified by column chromatography (100% ethyl acetate) to yield pure alcohol (539 mg, 3.58 mmol., 41%). $^1$H NMR (DMSO-d$_6$): δ 8.56 (s, 1H), 8.08 (s, 1H), 8.00 (d, J=8 Hz, IH), 7.89 (d, J=8 Hz, 1H), 7.58 (s, 1H), 5.44 (t, J=6 Hz, 1H), 4.62 (d, J=6 Hz, 2H). Calculated mass=152.2, [M+H]$^+$=153. HPLC (method D) rt=9.0 mins (>99.9%).

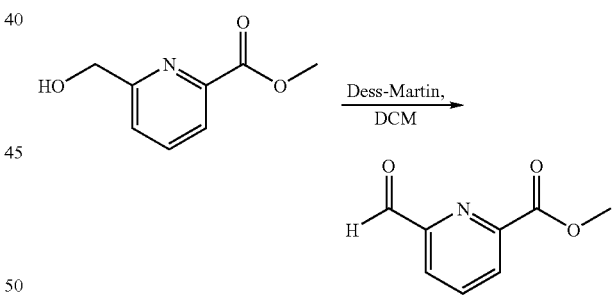

To a solution of the alcohol (655 mg, 3.92 mmol.) in DCM (7 mL) was added Dess-Martin periodinane (3.3 g, 7.84 mmol.). Stirred for 16h, then diethyl ether was added. The reaction was concentrated, and then partitioned between diethyl ether and a solution of sodium thiosulfate (6.8 g, 43.12 mmol.) in saturated NaHCO$_3$ (50 mL). The aqueous layer was extracted using diethyl ether (2×). The combined organic extracts were dried with MgSO$_4$ and concentrated. The crude product was purified by column chromatography to yield 6 (460 mg, 2.78 mmol, 71%). $^1$H-NMR (DMSO-d$_6$): δ=10.03 (s, 1H), 8.33 (d, J=8Hz, 1H), 8.25 (dd, J=8 Hz+8 Hz, 1H), 8.15 (d, J=8 Hz, 1H), 3.95 (s, 3H). Calculated mass=165.1, [M]$^+$=165.

Table 6 indicates other intermediates prepared using the above method:

TABLE 6

| No. | $R_M$ | $R_N$ | $[M + H]^+$ |
| --- | --- | --- | --- |
| 1 | 2-CHO | 5-CO$_2$Me | 166 |
| 2 | 2-CHO | 4-CO$_2$Me | 166 |
| 3 | 5-CHO | 2-CONH$_2$ | 151 |
| 4 | 3-CHO | 5-CO$_2$Me | 166 |

Example 1K

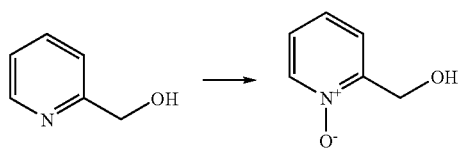

2-Pyridinemethanol 1-oxide Prepared as in WO (2002) 22,600. To a solution of the alcohol (2.6 mL, 27 mmol) in glacial HOAc (18 mL) was added dropwise H$_2$O$_2$ (30% aq., 2.8 mL, 24 mmol). The solution was heated in a 70° C. bath for 2h. The solution was cooled to rt and additional (2.8 mL, 24 mmol) H$_2$O$_2$ solution was added. The reaction was heated overnight. The solution was cooled and concentrated under reduced pressure. The resulting yellow oil was dissolved in CHCl$_3$ (40 mL). Solid NaHCO$_3$ (3.12 g) was added portionwise. The mixture was stirred for 1 h at rt. The mixture was filtered to collect a solid. The solid was heated in a 60° C. bath in CHCl$_3$ (40 mL) for 10 mins. The mixture was filtered. The filtrates were combined. This extraction process was repeated five times. The combined filtrates were concentrated to afford a yellow solid. The solid was purified using silica gel chromatography, eluting with a gradient of 5% MeOH/CHCl$_3$ to 8% MeOH/CHCl$_3$ to afford the product (3.0 g, 90%) as a white solid. $^1$H NMR 400 MHz (CDCl$_3$): δ 8.27 (d, J=6.2 Hz, 1H), 7.46-7.26 (m, 3H), 4.83 (s, 2H). MS (ESI-POS): [M+H]$^+$=126.

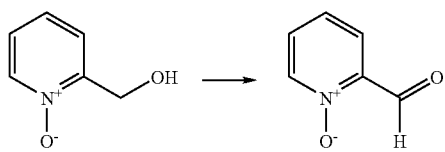

1-Oxy-pyridine-2-carbaldehyde prepared as in WO (2002) 22,600. To a solution of 2-pyridinemethanol 1-oxide (1.50 g, 11.98 mmol) in CHCl$_3$ (90 mL) was added activated MnO$_2$ (4.17 g, 47.85 mmol) and the suspension was stirred vigorously at rt overnight. The solution was filtered through diatomaceous earth. The filtrate was concentrated. The resulting yellow oil was purified using silica gel chromatography, eluting with a gradient of 3% MeOH/CH$_2$Cl$_2$ to 10% MeOH/CH$_2$Cl$_2$ to afford the product (0.73 g, 49%) as a white solid, along with recovered alcohol (0.47 g, 31%). $^1$H NMR 400 MHz (CDCl$_3$): δ 10.64 (s, 1H), 8.23 -8.21 (m, 1H), 7.83 (dd, J=7.8, 2.2 Hz, 1H), 7.49-7.45 (m, 1H), 7.35-7.31 (m, 1H). MS (ESI-POS): [M+H]$^+$=123.

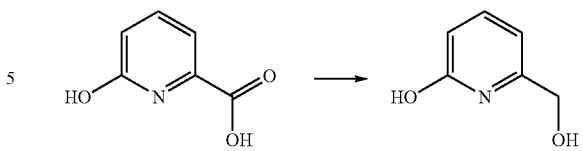

6-Hydroxymethyl-pyridin-2-ol Prepared as in WO (2002) 22,600. To a stirred suspension of acid (1.04 g, 7.47 mmol) in THF (35 mL) was added dropwise a 1.0 M solution of BH$_3$ in THF (37 mL, 37.38 mmol). The mixture was heated in a 65° C. bath overnight. The reaction was cooled to rt and quenched in an ice bath with the addition of MeOH (anhydrous, 30 mL). The reaction was heated in a 62° C. bath overnight. The reaction was cooled to rt and concentrated in vacuuo. To the residue was added MeOH (anhydrous, 20 mL) and the solution was concentrated. A portion (125 mg) of the crude material was purified using silica gel chromatography, eluting with 10% MeOH/CH$_2$Cl$_2$ to afford an analytical sample of the product as a white powder. $^1$H NMR 300 MHz (DMSO-d$_6$): δ 11.34 (bs, 1H), 7.38 (dd, J=9.1, 6.8 Hz, 1H), 6.18-6.14 (m, 2H), 5.40 (t, J=5.9 Hz, 1H), 4.26 (d, J=5.9 Hz, 2H). MS (ESI-POS) [M+H]$^+$=126.

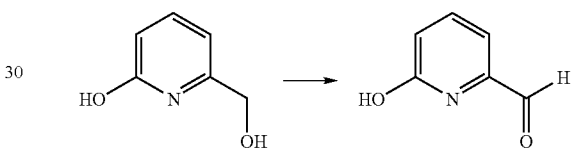

6-Hydroxy-pyridine-2-carbaldehyde Prepared as in WO (2002) 22,600. To a suspension of crude 6-hydroxymethyl-pyridin-2-ol from the previous step in pyridine (50 mL) was added activated MnO$_2$ (6.4 g, 73.6 mmol). The mixture was stirred vigorously at rt for 72 h. The suspension was filtered through diatomaceous earth. The filtrate was concentrated. The crude material was purified using silica gel chromatography, eluting with a gradient of 3% MeOH/CH$_2$Cl$_2$ to 5% MeOH/CH$_2$Cl$_2$ to afford the product (172 mg, 22%) as a solid. $^1$H NMR 300 MHz (CDCl$_3$): δ 9.55 (s, 1H), 9.46 (bs, 1H), 7.55 (dd, J=9.3, 6.4 Hz, 1H), 6.90 (dd, J=9.3, 0.8 Hz, 1H), 6.79 (dd, J=6.4, 0.8 Hz, 1H). MS (ESI-POS) [M+H]$^+$=122.

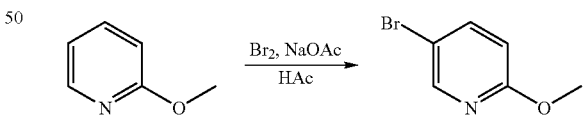

A solution of bromine (13.1mL, 256.6 mMol) in glacial acetic acid (45 mL) was added drop wise into a mechanically stirred suspension of 2-Methoxy-pyridine (19 mL, 183 mMol) in glacial acetic acid (88 mL) with the temperature kept at ten degrees. After complete addition the solution was allowed to stir overnight while gradually warming to room temperature. Upon arrival the reaction mixture was poured over ice and the pH adjusted to eight with solid sodium hydroxide. The material was then diluted with diethyl ether (150 mL) and filtered thru Celite. The aqueous layer was extracted with diethyl ether (2×100 mL) and ethyl acetate (2×100 mL) and all the organics combined. The solution was dried with magnesium sulfate, filtered, and concentrated on a rotary evaporator to a dark brown oil. The oil was eluted thru a plug of silica gel with hexanes and concentrated to yield 22.6 g (66% yield) of 5-Bromo-2-methoxy-pyridine as a clear oil. ¹H NMR (DMSO-d₆): δ=8.29 (dd,1H,J=2.6,0.5 Hz), 7.89 (dd, 1H, J=8.8, 2,6 Hz), 6.84 (dd, 1H, J=8.8, 0.5 Hz), 3.84 (s, 3H). LC/MS (Method A), rt=1.35 mins., purity=76.5%, calculated mass=187,[M+H]⁺=188/190, [M−H]⁻ 187/189. HPLC (Method C): rt=8.1 mins., purity=88.0% @ 210-370 nm and 88.3% @ 286 nm.

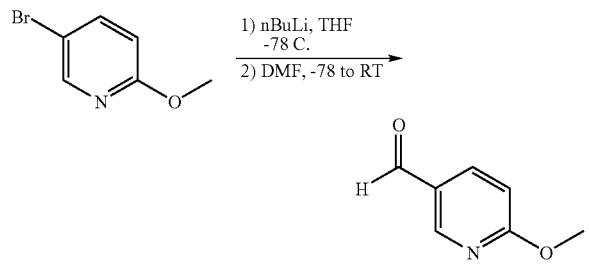

N-Butyl lithium (50 mL, 2.5M in hexane) was added drop wise to a solution of 5-Bromo-2-methoxy-pyridine (22.4 g, 119.1 mMol) in dry tetrahydrofuran (240 mL) at −78 degrees. After complete addition the solution was stirred at −78 for an additional ninety minutes at which time dimethylformamide (18.5 mL, 238.3 mMol) was added drop wise and the solution stirred for ninety more minutes at −78 and then allowed to warm to room temperature. The mixture was then poured into saturated sodium bicarbonate solution (1000 mL) and extracted with diethyl ether (3×250mL). The combined organics were dried with magnesium sulfate, filtered, and concentrated to dryness to yield 15.4 g (94% yield) of 6-Methoxy-pyridine-3-carbaldehyde as a pale yellow solid. ¹H NMR (DMSO-d₆): δ=9.97 (s,1H), 8.77 (m, 1H), 8.12 (dd, 1H, J=8.6, 2.3 Hz), 6.99 (d, 1H, J=8.7 Hz), 3.97 (s, 3H). LC/MS (Method A), rt=0.25 mins., purity=92.8%, calculated mass=137, [M+H]⁺=138. HPLC (Method C): rt=4.9 mins., purity=95.9% @ 210-370 nm and 98.7% @ 256 nm.

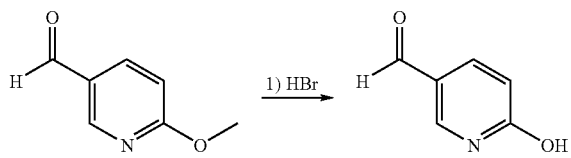

6-Methoxy-pyridine-3-carbaldehyde (1.0 g, 7.29 mMol) was dissolved in hydrobromic acid (14 mL, 48% in water) and the resulting solution heated to 150 degrees gradually over one hour. The solution was then cooled to room temperature and concentrated to dryness on a rotary evaporator. Methanol (4 mL) and acetone (2 mL) were added and the solution washed with diethyl ether (3×15 mL). Water (10 mL) was added and the pH adjusted to neutral with sodium bicarbonate. The solution was then filtered and concentrated to dryness on a rotary evaporator to yield a tan solid. Purification by flash column chromatography on silica gel using 30% methanol in chloroform as eluant yielded 1.09 g (73% yield ) of 6-Oxo-1,6-dihydro-pyridine-3-carbaldehyde as a hydrobromide salt. ¹H NMR (DMSO-d₆): δ=12.30 (br s, 1H), 9.60 (s, 1H), 8.26 (m, 1H), 7.75 (dd, 1H, J=9.5, 2.6Hz), 6.41 (d, 1H, J=9.5 Hz). LC/MS (Method A), rt=0.25 mins., purity=98%, calculated mass=123,[M−H]⁻=122. HPLC (Method C): rt=1.76 mins., purity=91.2% @ 210-370nm and 91.5% (286 nm.

Example 1L

Preparation of pyrazine, quinoline, quinoxaline and pyridopyrazine intermediates

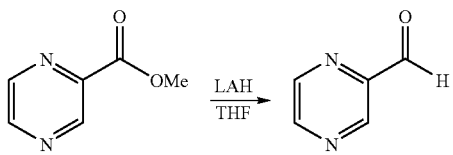

Pyrazine-2-carbaldehyde: Prepared as in *J. Org. Chem.* 1963,28, 1898. Pyrazine-2-carboxylic acid methyl ester (5.00 g, 36.2 mmol) was stirred in anhydrous THF (100 mL) and cooled in a dry ice-acetone bath. Under a positive stream of nitrogen lithium aluminum hydride (1 molar, 18.1 mL, 18.1 mmol) was added dropwise, via syringe, over a 30 min. period. The reaction was stirred in the dry ice-acetone bath, under nitrogen, for an additional 15 min. Glacial acetic acid (5 mL) was added to quench the reaction. The solvent was removed, in vacuo, to give a black oil. The oil was dissolved in chloroform (100 mL) and washed with 2.5 M HCl solution (50 mL). The organic layer was separated off and the aqueous phase was extracted with chloroform (10×50 mL). The organic extracts were combined and washed with saturated sodium bicarbonate solution (3×100 mL), dried (Na₂SO₄), filtered and the solvent removed, in vacuo, to give a black oil (1.8 g). This material was adsorbed onto silica gel and purified by column chromatography, eluting with a 99:1 solution of chloroform:methanol to afford the product (608 mg, 16% Yield) as an amber colored liquid. Low molecular weight LC-MS revealed one peak, retention time=0.32 min., total peak area=98%,[M+H]⁺=108. ¹H NMR (DMSO): δ10.10 (s, 1H), 9.15 (s, 1H), 8.95 (d, 2H).

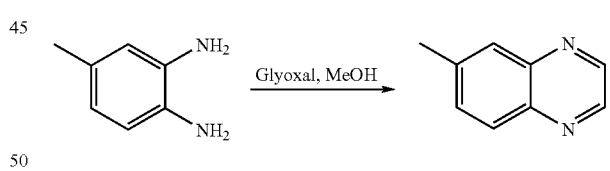

A solution of 4-methyl-1,2-phenylenediamine (5.0 g, 41 mMol) in methanol (250 mL) was treated with a solution of 40% aqueous glyoxal and stirred for 16 h. The solvent was evaporated and the residue was distilled under vacuum (2 mmHg, 85-88° C.) to leave a colorless oil (1.5 g, 25%). ¹H-NMR (CDCl₃), δ=8.82 (d, 1H, J=1.8 Hz), 8.80 (d, 1H, J=1.8 Hz), 8.01 (d, 1H, J=8.6 Hz), 7.89 (d, 1H, J=1.8 Hz), 7.63 (dd, 1H, J=8.6 Hz, J=1.8 Hz), 2.63 (s, 3H). LC/MS (Method A), rt=1.02 mins., purity=99.5%.

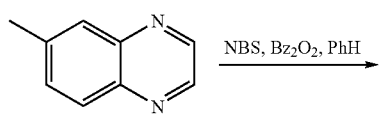

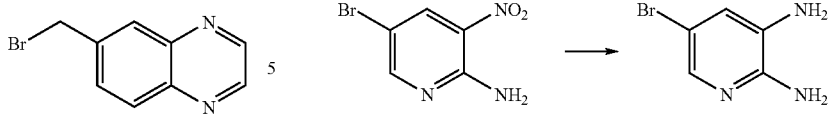

A mixture of 6-methylquinoxaline (1.5 g, 10.4 mMol), N-bromosuccinimide (2.2 g, 12.5 mMol) and benzoylperoxide (0.30 g, 1.25 mMol) in benzene (35 mL) was stirred rapidly and heated to reflux for 5 h. Upon cooling the mixture was diluted with ethyl acetate (25 mL), washed with 1N sodium hydroxide solution (50 mL) and saturated sodium chloride solution (50 mL). The organic layer was dried (MgSO$_4$) and evaporated to a crystalline solid (2.5 g, 77% desired product, 23% α,α-dibrominated product). $^1$H-NMR (CDCl$_3$), δ=8.89 (d, 1H, J=1.8 Hz), 8.87 (d, 1H, J=1.8 Hz), 8.13 (m, 2H), 7.83 (dd, 1H, J=8.7 Hz, J=2.1 Hz), 4.70 (s, 2H).

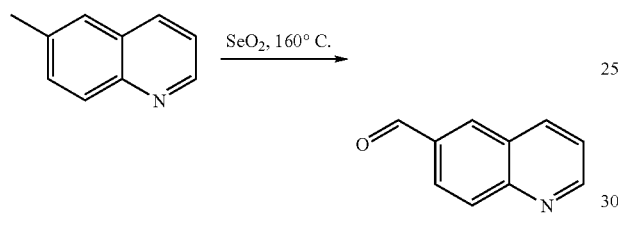

Prepared as in *J. Med. Chem.* 2000, 43, 3878. 6-Methylquinoline (1.0 g, 7.0 mMol) was heated to 160° C. with stirring. Selenium dioxide (0.50 g, 4.5 mMol) was added and heating continued for 12 h. After cooling to room temperature heptane (5 mL) was added and the solid residue was broken up and shaken for an hour. The solvent was decanted and the solid residue was treated again with heptane and decanted. To the combined heptane layers was added trimethylorthoformate (2 mL), aminomethylpolystyrene (1% DVB cross linked, 2.4 mMol/g, 2.0 g, 4.8 mMol) and acetic acid (50 μL). The mixture was shaken for 4 h then the resin was removed by filtration, washed with dichloromethane (3×20 mL) and methanol (2×20 mL) and dried under vacuum. The resin was shaken in a mixture of tetrahydrofuran-water-trifluoroacetic acid (8:1:1, 12 mL) for 12 h then filtered, washed (methanol, 3×20 mL) and the combined filtrates were evaporated. The residue was dissolved in dichloromethane (25 mL), washed with 1M sodium carbonate solution (20 mL), dried (MgSO$_4$) and evaporated to leave a solid (49 mg, 5%). Used as is for next reaction.

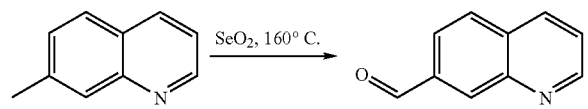

Quinoline-7-carboxaldehyde was prepared as above for quinoline-6-carboxaldehyde. Yield=5%. Used as is for the next reaction.

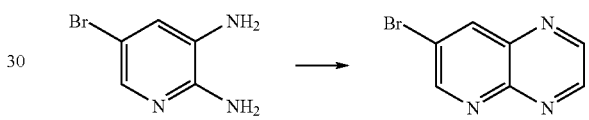

5-Bromo-pyridine-2,3-diamine: Commercially-available 5-bromo-3-nitro-pyridin-2-ylamine (20.0g, 92 mmol) was suspended in a 9:1 ethyl acetate:t-BuOH solution (470 ml). Tin chloride dihydrate (104 g, 460 mmol) was added, and the suspension was stirred under nitrogen for 2 h at 60° C. NaBH$_4$ (1.75 g, 46 mmol) was added slowly, and the suspension was allowed to stir for another 3 hours. The reaction mixture was then cooled and filtered. The filtrate was extracted with 3 N HCl three times, and the collected acid washes were washed with ethyl acetate. The acidic solution was made basic by the careful addition of solid sodium carbonate. This aqueous solution was extracted with ethyl acetate three times, and the organic fractions were combined. The ethyl acetate solution was washed with brine, dried over MgSO$_4$ and concentrated to yield the title product (6.5 g (38%), 35 mmol). $^1$H NMR (DMSO-d$_6$): δ=11.99 (bs, 2H), 7.31 (d,1H, J=2.1 Hz), 6.84 (d, 1H, J=2.1 Hz), 5.90 (bs, 2H). Calculated mass=188.03, [M+H]$^+$=189.

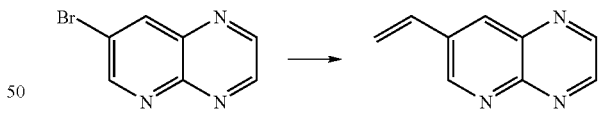

7-Bromo-pyrido[2,3-b]pyrazine: 5-Bromo-pyridine-2,3-diamine (6.5 g, 35 mmol) was dissolved in MeOH (100 ml). Glyoxal (15 ml of a 40% solution). The solution was stirred for 18 h at room temperature. The solvent was removed, and the crude material was partitioned between ethyl acetate and brine. The ethyl acetate was washed two additional times with brine, the organic layer was dried using MgSO$_4$, and the solvent as removed to yield the title product (6.9 g (95%),33 mmol). $^1$H NMR (DMSO-d$_6$): δ=9.28 (d, 1H, J=2.5 Hz), 9.19 (d, 1H, J=1.7 Hz), 9.10 (d,1H, J=1.7 Hz), 8.94(d,1H, J=2.5 Hz). Calculated mass=210.03, [M+H]$^+$=212.

7-Vinyl-pyrido[2,3-b]pyrazine: 7-Bromo-pyrido[2,3-b]pyrazine (560 mg, 2.7 mmol) was suspended in toluene (25 ml) with tributylvinyltin (2.30 ml, 8.1 mmol), tetrakis(triphenylphosphine) palladium (106 mg, 106 mmol) and LiCl (336 mg, 8.06 mmol). The mixture was heated to 100° C. under a nitrogen atmosphere. After 2 h, the reaction was complete and the toluene was removed under vacuum. The crude was taken up in ethyl acetate and washed three times with a 1 N HCl solution. The combined acid washings were washed twice with ethyl acetate. The acidic water was made basic with the addition of solid sodium carbonate, and extracted three times with ethyl acetate. The combined ethyl acetate extracts were washed with brine, dried using MgSO$_4$, and concentrated under vacuum to yield the title product (250 mg, 59%) as a tan solid.$^1$H NMR (DMSO-d$_6$): δ=9.40 (d, 1H, J=2.5Hz), 9.08

(dd, 2H, J=12.3 Hz, 1.8 Hz), 8.60 (d, 1H, J=2.5 Hz), 7.11 (m, 1H), 6.40 (d, 1H, J=17.8 Hz,), 5.64 (d, 1H, J=11.3 Hz). Calculated mass=157.18, [M+H]⁺=158. HPLC Method D: 99.3% @ 210-370 nm; 99.7% @ 240 nm; RT=4.5 min.

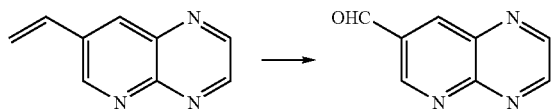

Pyrido[2,3-b]pyrazine-7-carbaldehyde: 7-Vinyl-pyrido[2,3-b]pyrazine (68 mg, 0.43 mmol) was dissolved in dioxane (4 ml) and water (5 ml). OsO₄ (0.227 ml of a 2.5% t-BuOH solution, 0.024 mmol) was added, followed by sodium periodate (276 mg, 1.3 mmol). The reaction mixture was allowed to stir at room temperature. After 2 h, the reaction was judged complete by TLC, and the reaction mixture was partitioned between ethyl acetate and brine. The brine was removed and washed one additional time with ethyl acetate. The combined ethyl acetate extracts were washed again with brine, dried using MgSO₄, and concentrated under vacuum to yield the title product (65 mg, 95%) as a dark, nearly black, solid. ¹H NMR (DMSO-d₆): δ=10.37 (s, 1H), 9.55 (d, 1H, J=2.2 Hz,), 9.28 (d, 1H, J=1.7 Hz), 9.21 (d, 1H, J=1.7 Hz), 9.10 (d, 1H, J=2.2 Hz). Calculated mass=159.15, [M+H]⁺=160. HPLC Method D: 97.5% @ 210-370 nm; 97.9% @ 318 rm; RT=2.4 min.

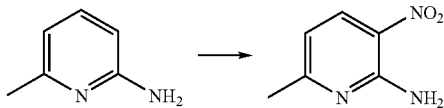

6-Methyl-3-nitro-pyridin-2-ylamine: 6-Amino picoline (5.0 g, 46 mmol) was cautiously suspended in H₂SO₄ (25 ml) and cooled in an ice bath. Fuming nitric acid (5 ml) was added slowly, and care was taken to keep the temperature of the reaction as low as possible. The reaction mixture was allowed to stir 3 h after the addition of the nitric acid was complete. The mixture was added to sodium carbonate (65 g), suspended in about ice water (500 ml). Once the neutralization was complete, the aqueous mixture was extracted four times with ethyl acetate. The combined ethyl acetate washings were washed with brine, dried using MgSO₄, and concentrated under vacuum to yield the title product (1.3 g, 19%) as a red oil. ¹H NMR (DMSO-d₆): δ=8.27 (d, 1H, J=8.5 Hz), 7.88 (bs, 2H), 6.63 (1H, d, J=8.5), 2.39 (s, 3H).

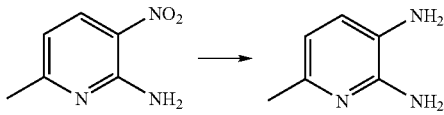

6-Methyl-pyridine-2,3-diamine: 6-Methyl-3-nitro-pyridin-2-ylamine (1.3 g, 8.5 mmol) was dissolved in methanol (40 ml). The flask was purged of all oxygen, placed under a nitrogen atmosphere, and charged with Pd/C (150 mg of 10% palladium on carbon). The reaction mixture was purged, and placed under a hydrogen atmosphere, maintained with a balloon. It was allowed to stir for 18 h until the reduction was judged complete. It was then filtered through Celite™ to remove the palladium. The solvent was removed under vacuum to yield the title compound (1.01 g, 96%). ¹H NMR (DMSO-d₆): δ=6.59 (d, 1H, J=7.5 Hz), 6.19 (d, 1H, J=7.5 Hz), 5.23 (bs, 2H), 4.39 (bs, 2H), 2.11 (s, 3H).

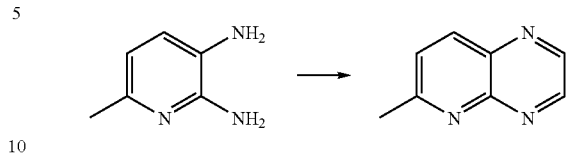

6-Methyl-pyrido[2,3-b]pyrazine: 6-Methyl-pyridine-2,3-diamine (1.01 g, 8.2 mmol) was dissolved in MeOH (40 ml) and glyoxal (14 ml of a 40% aqueous glyoxal solution). Allowed to stir 18 h. The MeOH was removed, and the crude was taken up in ethyl acetate. It was washed three times with a 1 N HCl solution. The combined acid washings were washed twice with ethyl acetate. The acidic water was made basic with the addition of solid sodium carbonate, and it was extracted three times with ethyl acetate. The combined ethyl acetate extracts were washed with brine, dried using MgSO₄, and concentrated under vacuum to yield the title product (980 mg, 80%) as a brown solid. ¹H NMR (DMSO-d₆): δ=9.09 (d, 1H, J=1.8 Hz), 8.99 (d, 1H, J=1.8 Hz), 8.47 (d, 1H, J=8.5 Hz), 7.82 (d, 1H, J=8.5 Hz), 2.78 (s, 3H). Calculated mass=145, [M+H]⁺=146.

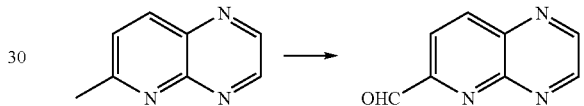

Pyrido[2,3-b]pyrazine-6-carbaldehyde: 6-Methyl-pyrido[2,3-b]pyrazine (100 mg, 0.69 mmol) was dissolved in dioxane. Selenium dioxide (269 mg, 2.4 mmol) was added, and the suspension was refluxed at 110° C. for 3 minutes. The reaction mixture was partitioned between ethyl acetate and water. The ethyl acetate was washed with brine, dried using magnesium sulfate, and concentrated to yield the title product (55 mg, 50%) as a pink solid. ¹H NMR (DMSO-d₆): δ=8 s, 1H), 9.31 (d, 1H, J=1.6 Hz), 9.21 (d, 1H, J=1.6 Hz), 8.81 (d, 1H, J=8.5 Hz), 8.42 (d, 1H, J=8.5 Hz). Calculated mass=159, [M+H]⁺=160.

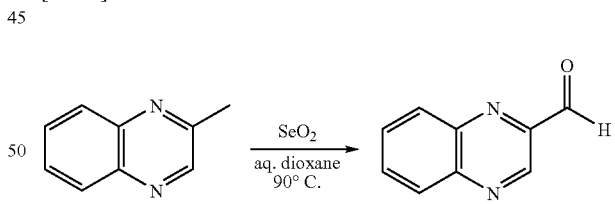

Quinoxaline-2-carbaldehyde: 2-Methyl-quinoxaline (1.00 mL, 7.75 mmol) and selenium dioxane (946 mg, 8.53 mmol) were heated to 90° C. (oil bath temperature) in 1,4-dioxane (6 mL) and distilled water (4 mL), under nitrogen, for 18 h. The solvent was removed, in vacuo, and the material dissolved in ethyl acetate (100 mL) and solid selenium precipitate formed and was filtered out of solution. The organic phase was washed with saturated sodium bicarbonate solution (3×100 mL). The bicarbonate washings were combined and extracted with ethyl acetate (2×100 mL). The organic extracts were combined and washed with brine (150 mL), dried (MgSO₄), filtered and the solvent removed, in vacuo, to give a red solid (440 mg). This material was adsorbed onto silica gel and purified by column chromatography, eluting with a solution of 4:1 hexane:ethyl acetate to afford a tan solid (180 mg, 15% Yield). $^1$H NMR 300 MHz (DMSO): δ=10.20 (s, 1H), 9.40 (s, 1H), 8.35 (dd, 1H, J=7.9 Hz, J=1.5 Hz), 8.25 (dd, 1H, J=7.7 Hz, J=1.1 Hz), 8.08 (m, 2H).

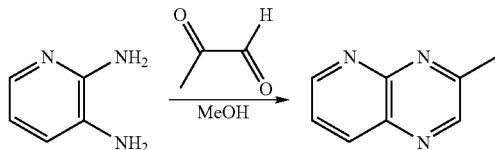

3-Methyl-pyrido[2,3-b]pyrazine: Pyridine-2,3-diamine (2.50 g, 22.9 mmol) was stirred in methanol (100 mL) and cooled in an ice bath and pyruvic aldehyde (40% wt., 4.20 mL, 27.5 mmol) was added, dropwise, and the solution was allowed to warm to room temperature and stirred, under nitrogen for 18 h. The solvent was removed, in vacuo, to give a black oil (4.23 g). This material was adsorbed onto silica gel and purified by column chromatography, eluting with a solution of 95:5 chloroform:acetone to afford a dark red solid (2.96 g, 89% Yield). $^1$H NMR 300 MHz (DMSO): δ=9.13 (dd, 1H, J=4.2 Hz, J=1.9Hz), 8.97 (s, 1H), 8.50 (dd, 1H, J=8.3 Hz, J=1.9 Hz), 7.82 (dd, 1H, J=8.3 Hz, J=4.2 Hz), 2.79 (s, 3H). HPLC (Column; Xterra RP18, 3.5 μm, 4.6×150 mm, Column temp.=40° C.), Flow=1.2 mL/min., 85/15-5/95, 10 min., 5/95, 5.0 min., (25 mM HCO$_2$NH$_4$ buffer, pH=3.5/AcN/MeOH), 99.2% purity @ 210-370 nM, 99.8% @ 238 nM, retention time=3.2 min. Calculated mass =145.06, [M +H]$^+$=146.

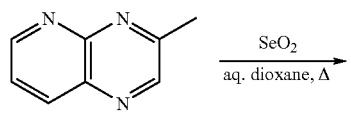

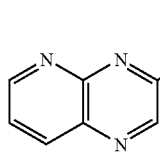

Pyrido[2,3-b]pyrazine-3-carbaldehyde: 3-Methyl-pyrido[2,3-b]pyrazine (1.00 g, 6.89 mmol) and selenium dioxane (800 mg, 7.2 mmol) was heated to reflux in 1,4-dioxane (70 mL) and distilled water (2 mL), under nitrogen, for 4 h. The reaction mixture was cooled to room temperature, allowed to stand for 16 h, filtered through diatomaceous earth, washed with ethyl acetate (50 mL) and the filtrate concentrated under reduced pressure. The residue was treated with dichloromethane (75 mL) and stirred for 30 mins. The DCM soluble portion was added to a column of silica gel and eluted with ethyl acetate to leave the product aldehyde as a light brown solid (254 mg, 23%). 1H-NMR (CDCl$_3$) δ=10.40 (s, 1H), 9.55 (s, 1H), 9.35 (dd, 1H, J=4.1 Hz, J=1.8 Hz), 8.60 (dd, 1H, J=8.5 Hz, J=1.8 Hz), 7.90 (dd, 1H, J=8.5 Hz, J=4.1 Hz). LC/MS (Method A), rt=0.37 mins., purity=97.8%, calculated mass=159, [M+H]$^+$=160.

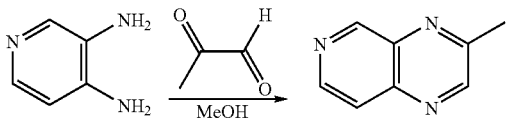

3-Methyl-pyrido[3,4-b]pyrazine: Pyridine-3,4-diamine (2.00 g, 18.3 mmol) was dissolved in methanol (100 mL) and cooled in an ice bath. Pyruvic aldehyde (40% wt., 3.36 mL, 22.0 mmol) was added, dropwise, and the solution was allowed to warm to ambient temperature where it was stirred, under nitrogen, for 18 h. The reaction was monitored by LC-MS and pyruvic aldehyde (2.5 mL, 16.4 mmol) was added and the solution stirred at room temperature, under nitrogen for an additional 5 h. The solvent was removed, in vacuo, to give a black liquid which solidified to a black solid (3.58 g) upon standing. This material was adsorbed onto silica gel and purified by column chromatography, eluting with a solution of 1:1 hexane:ethyl acetate to give a brown solid (2.18 g, 82% Yield). $^1$H NMR 400 MHz (DMSO): δ=9.43 (s, 1H), 9.00 (s, 1H), 8.81 (d, 1H, J=5.9 Hz), 7.91 (dd, 1H, J=5.7 Hz, J=0.8 Hz), 2.79 (s, 3H). HPLC (Column; Xterra RP18, 3.5 μm, 4.6×150 mm, Column temp.=40° C.), Flow=1.2 mL/min., 85/15-5/95, 10 min., 5/95, 5.0 min., (25 mM HCO$_2$NH$_4$ buffer, pH=3.5/AcN/MeOH), No impurities @ 210-370 nM, and no impurities @ 306 nM, retention time =3.5 min. Calculated mass=145.06, [M+H]$^+$=146.

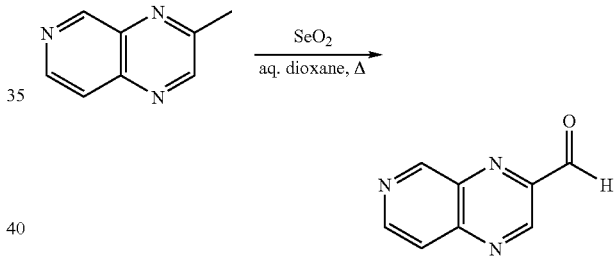

Pyrido[3,4-b]pyrazine-3-carbaldehyde: 3-Methyl-pyrido[3,4-b]pyrazine (1.00 g, 6.89 mmol) and selenium dioxide (1.15 g, 10.3 mmol) were dissolved in 1,4-dioxane (60 mL) and distilled water (1.5 mL)and heated to reflux, under nitrogen, for 1.5 h. The hot mixture was filtered through celite and the filtrate concentrated to give a brownish black solid (1.15 g). This material was adsorbed onto silica gel and purified by column chromatography, eluting with a solution of 97:3 chloroform:methanol to give a reddish brown oily solid (200 mg). Material was impure but used, as is, in the next reaction.

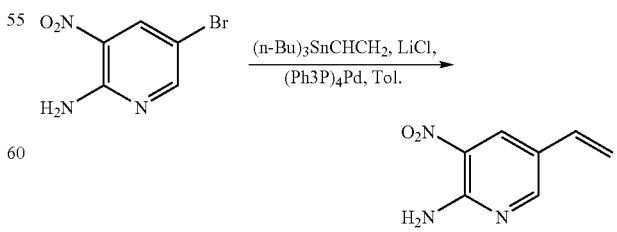

A mixture of 2-amino-5-bromo-3-nitropyridine (1.9 g, 8.7 mMol), lithium chloride (0.46 g, 11 mMol), tri-n-butylvinyltin (3.6 g, 11 mMol, 3.3 mL) and tetrakis(triphenylphosphine)palladium (0.40 g, 0.35 mMol) in toluene (75 mL) was purged with nitrogen, heated to 100° C. and stirred for 18 h. After cooling to room temperature the mixture was added to a silica gel column and eluted with 25% ethyl acetate in hexanes. The product was isolated as a yellow solid (1.1 g, 77%). $^1$H-NMR (CDCl$_3$), δ=8.45 (d, 1H, J=2.2 Hz), 8.42 (d, 1H, J=2.2 Hz), 6.80 (bs, 2H), 6.62 (dd, 1H, J=17.7 Hz, J=11.0 Hz), 5.74 (d, 1H, J=17.7 Hz), 5.32 (d, 1H, J=11.0 Hz). [M+H]$^+$=166. HPLC (method D), rt=6.72 mins., purity=96.6% @ 210-370 nm, 98.3% @ 418 nm.

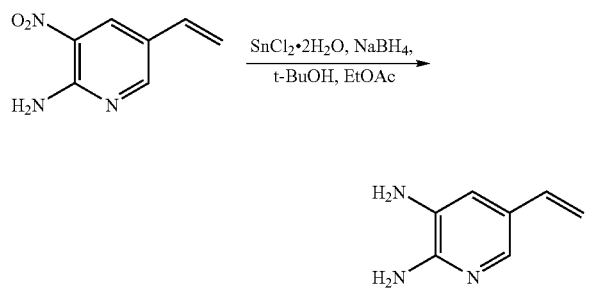

Prepared according to the method of Cai et. al., *J. Med. Chem.* 1997, 40, 3679-3686. A mixture of 2-amino-3-nitro-5-vinylpyridine (0.30 g, 1.8 mMol) and tin (II) chloride dihydrtate (2.0 g, 9.0 mMol) in 9:1 ethyl acetate-t-butanol was stirred and cautiously treated with sodium borohydride (34 mg. 0.90 mMol). The reaction mixture was heated to 60° C. for 3 h, cooled to room temperature and diluted with ethyl acetate (30 mL) and 1N sodium hydroxide solution (30 mL). After separation of the organic layer it was washed again with 1N sodium hydroxide solution (30 mL), dried (MgSO$_4$) and evaporated to leave a tan solid (0.20 g, 82%). $^1$H-NMR (CDCl$_3$), δ=7.66 (d, 1H, J=1.9 Hz), 7.04 (d, 1H, J=1.9 Hz), 6.59 (dd, 1H, J=17.6 Hz, J=11.0 Hz), 5.55 (d, 1H, J=17.6 Hz), 5.11 (d, 1H, J=11.0 Hz), 4.29 (bs, 2H), 3.30 (bs, 2H).

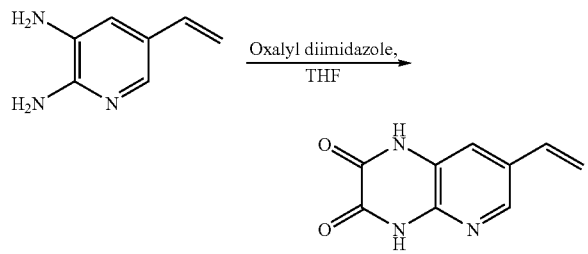

A mixture of 2,3-diamino-5-vinylpyridine (0.19 g, 1.4 mMol) and oxalyldiimidazole (0.40 g, 2.1 mMol) in Tetrahydrofuran (10 mL) was stirred and refluxed under nitrogen for 3 h. After cooling to room temperature the reaction mixture was diluted with water (10 mL), stirred for 1 h and the precipitate was filtered, washed with water and air-dried to leave the product as a solid (0.21 g, 79%) which was collected in two crops. $^1$H-NMR (DMSO-d$_6$), δ=12.40 (bs, 1H), 11.99 (bs, 1H), 8.29 (d, 1H, J=1.8 Hz), 7.50 (d, 1H, J=1.8 Hz), 6.77 (dd, 1H, J=17.7 Hz, 11.0 Hz), 5.80 (d, 1H, J=17.7 Hz), 5.33 (d, 1H, J=11.0 Hz). LC/MS (method A), rt=0.53 mins., purity>99.8%, [M +H]$^+$=190, [M–H]$^-$=188.

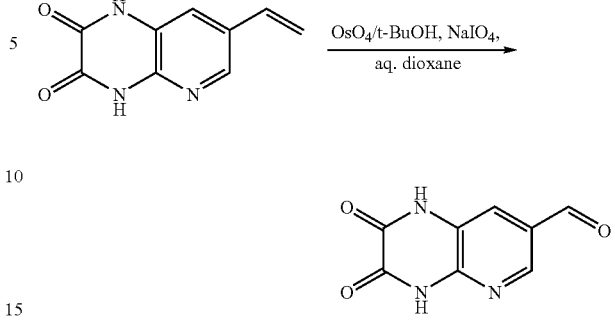

A suspension of the vinylpyridopyrazinedione above (0.14 g, 0.74 mMol) in dioxane (6 mL) and water (3 mL) was treated with 2.5% osmium tetroxide solution in t-butanol (0.38 mL, 37 μMol) and sodium periodate (0.48 g, 2.2 nMol). After stirring for 3 h the reaction mixture was diluted with water (20 mL) and the product was purified by reversed phase HPLC (method F) using nonbuffered mobile phase. The pure product was isolated as a solid (56 mg, 40%). $^1$H-NMR (DMSO-d$_6$), δ=12.80 (bs, 1H), 12.20 (bs, 1H), 10.01 (s, 1H), 8.62 (d, 1H, J=1.8 Hz), 7.78 (d, 1H, J=1.8 Hz).

Example 1M

Preparation of imidazopyridine, imidazopyrimidine and imidazopyrazine intermediates

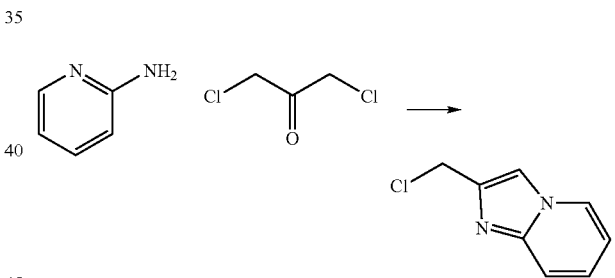

Dichloroacetone (945 mg, 7.5 mMol) and 2-aminopyridine (470 mg, 5 mMol) were dissolved in ethanol and molecular sieves (3 beads, 3 Å, 4-8 mesh) were added. The mixture was heated at 77° C. for three hours at which time the solvent was evaporated. The crude material was partitioned between saturated butanol (25 mL) and saturated sodium bicarbonate (25 mL). The butanol phase was washed with once with water and concentrated. The crude material was purified using flash chromatography eluting with 5% methanol in ethyl acetate. The product was lyopholized to yield 400 mg of white solid (48%). $^1$H NMR (400 MHz, DMSO-d$_6$) δ=8.52 (ddd, 1H, J=6.9 Hz, J=2.4 Hz, J=1.2 Hz), 8.00 (s, 1H), 7.52 (ddd, 1H, J=9.1 Hz, J=1.8 Hz, J=1.0 Hz), 7.26 (ddd, 1H, J=9.1 Hz, J=6.8 Hz, J=1.3 Hz), 6.90 (ddd, 1H, J=6.8 Hz, J=6.8 Hz, 1.2 Hz), 4.85 (s, 2H); $^{13}$C NMR (75.5 MHz, DMSO-d$_6$) δ=144.3, 142.0, 127.0, 125.2, 116.6, 112.2, 111.8 CH$_2$-eclipsed by DMSO-d$_6$ 40.3-38.6; HPLC (Method D) rt=2.4 min, 98.8% purity at 278 nm. LC/MS calculated mass=166, 168; [M +H]$^+$=167, 169.

Example 1N

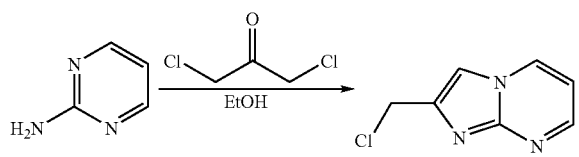

To a solution of 2-aminopyrimidine (500 mg, 5.30 mmol) in ethanol (25 mL), was added 1,3-dichloroacetone (1.0 g, 8.00 mmol) and 3A molecular sieves. The reaction was heated 16 h at 70° C., concentrated to dryness, and partitioned between saturated sodium bicarbonate and saturated (w/water) butanol). The organic layer was concentrated and the crude product was purified by column chromatography (5% methanol/ethyl acetate) to yield pure 26 (176 mg, 1.27 mmol, 24%). $^1$H NMR (DMSO-$d_6$): δ=8.96 (dd, 1H, J=7 Hz, J=2 Hz,), 8.56 (dd, 1H, J=4 Hz, J=2 Hz,), 7.98 (s, 1H), 7.07 (dd, 1H J=7 Hz, J=4 Hz,), 4.88 (s, 2H). Calculated mass=167.6, [M+H]$^+$=168/170. HPLC (method D) rt=5.6 min. (98.8% @ 222 nm).

Table 7 indicates other intermediates prepared using the above method:

TABLE 7

| No. | Structure | [M + H]$^+$ |
|---|---|---|
| 1 | 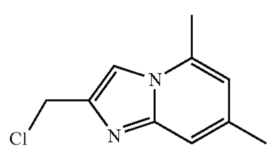 | 195, 197 |
| 2 | 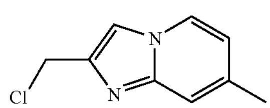 | 181, 183 |
| 3 | 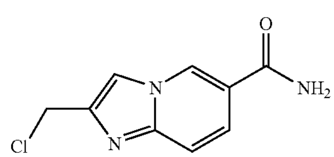 | 210, 212 |
| 4 | 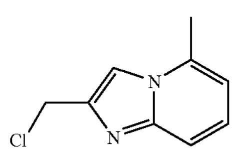 | 181, 183 |
| 5 | 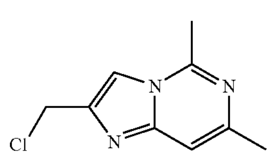 | 196, 198 |
| 6 | 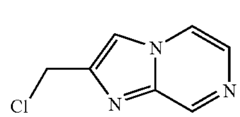 | 168, 170 |

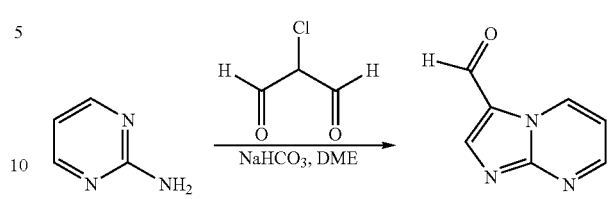

To a stirring mixture of 2-aminopyridine (100 mg, 1.05 mmol), DME (3 mL), and sodium bicarbonate (90 mg, 1.07 mmol) was added 2-chloromalonaldehyde (152 mg, 1.43 mmol). The reaction was heated at 88° C. for 16 h, concentrated to dryness, and partitioned between DCM and water. Extracted with DCM (1×), dried the combined organic extracts with MgSO$_4$ and concentrated. The crude product was purified by column chromatography (5% methanol/ethyl acetate) to yield pure aldehyde 42 (50 mg, 0.336 mmol, 32%). $^1$H NMR (DMSO-$d_6$): δ=9.96 (s, 1H), 9.67 (dd, 1H J=7 Hz, J=2 Hz,), 8.88 (dd, 1H, J=4 Hz, J=2 Hz,), 8.71 (s, 1H), 7.44 (dd, 1H J=7 Hz, J=2 Hz,). Calculated mass=147.1, [M+H]$^+$=148. HPLC (method D), rt=2.1 mins. (>99.9% @ 210-370 nm).

Example 1O

Preparation of pyrimidine intermediates

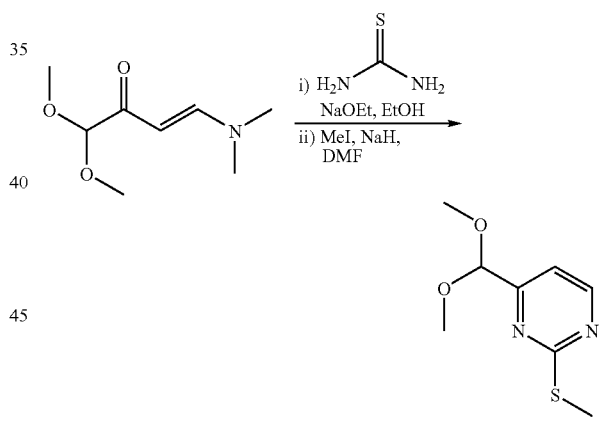

A solution of thiourea (1.32 g, 17.3 mmol) and sodium ethoxide (21% wt in EtOH, 6.5 mL, 17.3 mmol) in ethanol (45 mL) was stirred at room temperature for 15 min, and then was added to a solution of 1,1-dimethoxy-4-dimethylaminobut-3-en-one (3.0 g, 17.3 mmol) in ethanol (20 mL). The reaction was heated to 80° C. for 16 h, and concentrated to dryness to yield 4-dimethoxymethyl-pyrimidine-2-thiol that was used crude in the methylation step. Methylation: To a solution of 4-dimethoxymethyl-pyrimidine-2-thol (4.3 g, 23.1 mmol) in DMF (55 mL) at 0° C. was added sodium hydride (60% dispersion in mineral oil, 1.4 g, 35.0 mmol). The reaction was stirred for 15 min at 0° C. and iodomethane (1.44 mL, 23.1 mmol) was added. After stirring for 16 h, the reaction was partitioned between ethyl acetate and water and extracted with ethyl acetate (2×). The combined organic extracts were dried with MgSO$_4$, concentrated and purified by column chromatography (15% ethyl acetate/hexane) to yield pure acetal 46 (1.94g, 9.7 mmol, 42% for 2 steps). ¹H NMR (chloroform-d₁): δ=8.56 (d, 1H, J=5 Hz,), 7.19 (d, 1H, J=5 Hz,), 5.19 (s, 1H), 3.42 (s, 6H), 2.58 (s, 3H). Calculated mass=200.2, [M+H]⁺=201. HPLC (method C) rt=6.1 min (95.2% @ 210-370 nm).

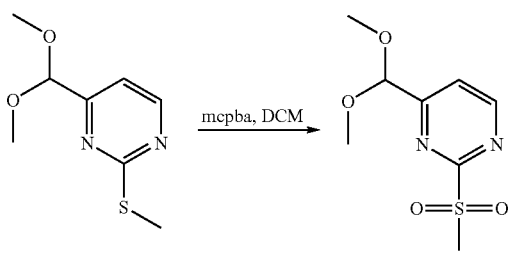

To a solution of the thiomethylpyrimidine (1.3 g, 6.47 mmol) in DCM (86 mL) at 0° C. was added mcpba (2.24 g, 12.9 mmol). The reaction was stirred at room temperature for 3 h, partitioned between DCM and saturated sodium bicarbonate, and extracted with DCM (2×). The combined organic extracts were dried with MgSO₄, concentrated and purified by column chromatography (60% ethyl acetate/hexane) to yield pure sulfonyl compound (1.4 g, 6.01 mmol, 93%). ¹H NMR (chloroform-d₁): δ=8.97 (d, 1H, J=5 Hz), 7.79 (d, 1H, J=5 Hz), 5.35 (s, 1H), 3.48 (s, 6H), 3.39 (s, 3H). Calculated mass=232.3, [M+H]⁺=233. HPLC (method C) rt=3.4. min (87.6% @ 210-370 nm).

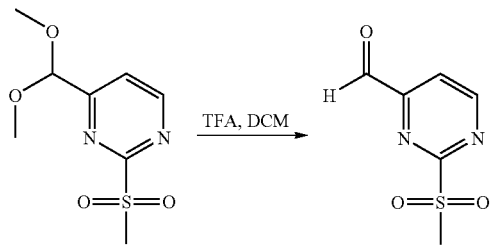

The acetal (4 g, 17.2 mmol) was stirred in a 1:1 mixture of dichloromethane (65 mL) and trifluoroacetic acid (65 mL) at room temperature for 16 h. The reaction was concentrated to dryness, and the crude product was purified by column chromatography (85% ethyl acetate/hexane) to yield pure aldehyde (2.95 g, 15.8 mmol, 92%). ¹H NMR (chloroform-d₁): δ=10.15 (s, 1H), 9.22 (d, 1H, J=5 Hz), 8.06 (d, 1H, J=5Hz), 3.47 (s, 3H). Calculated mass=186.2, [M+H]⁺=187.

Example 1P

Preparation of alkylsulfonamide intermediate

3-Chloro-propane-1-sulfonic acid amide: 3-Chloro-propane-1-sulfonyl chloride (1.96 g, 11.1 mmol) was dissolved in DCM (20 ml) and under a balloon inflated with ammonia gas. The mixture was allowed to stir for 18 h. The ammonium chloride precipitate was removed by filtration, and the solution was concentrated yielding the title product (1.69 g, (97%) 10.7 mmol). ¹H NMR (CDCl₃): δ=4.94 (bs, 2H), 3.73 (t, 2H, J=6Hz), 3.32 (t, 2H, J=7.1 Hz), 2.34 (m, 2H).

Example 1Q

Preparation of (2S)-ethylpiperazine intermediate

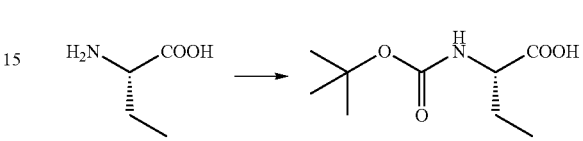

S-2-tert-Butoxycarbonylamino-butyric acid: S-2-Aminobutyric acid (5.0 g, 49 mmol) was suspended in THF (50 ml) with BOC-anhydride (12.8 g, 59 mmol). Potassium carbonate (13.5 g, 98 mmol), dissolved in water (50 ml), was added. The reaction mixture was allowed to stir for 15 h under a nitrogen atmosphere at room temperature. The reaction mixture was made acidic with the careful addition of 1 N HCl. This mixture was extracted three times with ethyl acetate. The combined ethyl acetate extracts were washed with brine, dried using MgSO₄, and concentrated under vacuum to yield the title product (8.3 g, 83%) as a yellow oil. ¹H NMR (DMSO-d₆): δ=7.05 (d, 1H, J=8.2 Hz), 3.82 (m, 1H), 1.62 (m, 2H), 1.37 (s, 9H), 0.87 (t, 3H, J=7.4 Hz,).

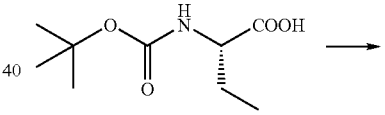

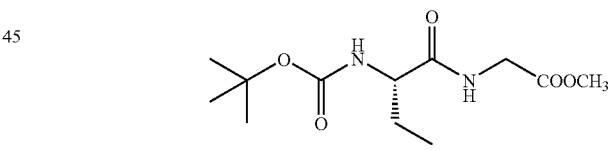

S-(2-tert-Butoxycarbonylamino-butyrylamino)-acetic acid methyl ester: S-2-tert-Butoxycarbonylamino-butyric acid (1.4 g, 16.7 mmol) was dissolved in DCM (50 ml) with DIEA (12.4 ml, 70 mmol). Glycine methyl ester HCl (3.14 g, 25 mmol), EDC (4.8 g, 25 mmol), and DMAP (310 mg, 2.5 mmol) were added, and the reaction was allowed to stir under a nitrogen atmosphere for 18 h. The solvent was removed under vacuum, and the crude was taken up in ethyl acetate. This ethyl acetate mixture was washed with brine, dried using MgSO₄, and concentrated under vacuum to yield the title product (2.7 g, 52%) as a yellow oil. ¹H NMR (DMSO-d₆): δ=8.24 (bt, 1H, J=5.8 Hz), 6.84 (bd, 1H, J=8.1 Hz), 3.91 (m, 3H), 3.65 (s, 3H), 1.64 (m, 2H), 1.38 (s, 9H), 0.87 (t, 3H, J=7.4 Hz).

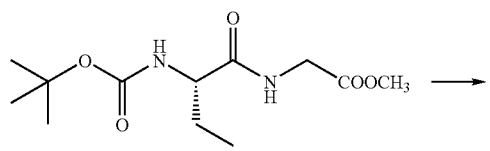

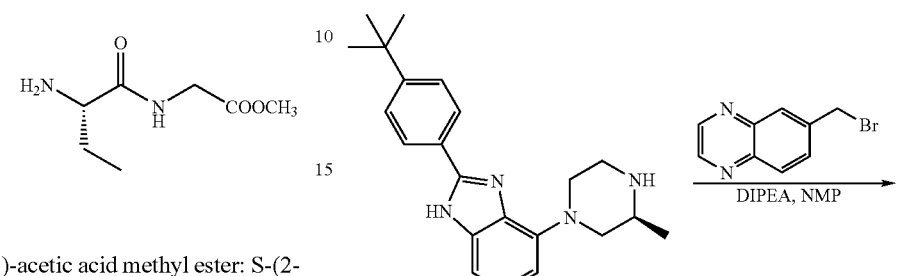

(S-2-Amino-butyrylamino)-acetic acid methyl ester: S-(2-tert-Butoxycarbonylamino-butyrylamino)-acetic acid methyl ester (12.2 g, 39 mmol) was dissolved in ethyl acetate (40 ml) with concentrated HCl (10 ml). The reaction mixture was allowed to stir for 2 h, and the solvent was removed under vacuum. The crude was taken up in 10% MeOH/DCM and stirred with morpholine resin (33 g, 117 molar equivalents). After 14 h, the resin was filtered and the solvent was removed, yielding the title product as a clear oil (7.9 g, 95%). $^1$H NMR (DMSO-$d_6$): δ=8.92 (bt, 1H, J=5.7 Hz), 8.19 (s, 3H), 3.92 (m, 2H), 3.81 (t, 1H, J=6.0 Hz), 3.69 (s, 3H), 1.72 (m, 2H), 1.38 (s, 9H), 0.90 (t, J=7.4 Hz, 3H).

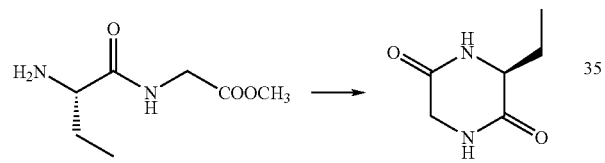

S-3-Ethyl-piperazine-2,5-dione: (S-2-Amino-butyrylamino)-acetic acid methyl ester (7 g, 33 mmol) was suspended in toluene (40 ml) and refluxed for 72 h. This reaction mixture was filtered to yield the title product (1.3 g, 28%), as a sticky white solid. $^1$H NMR (DMSO-$d_6$): δ=8.17 (bs, 1H), 8.01 (bs, 1H), 3.84 (m, 3H), 1.69 (m, 2h), 0.87 (t, J=7.4 Hz, 3H). Calculated mass=142.16, [M+H]$^+$143.

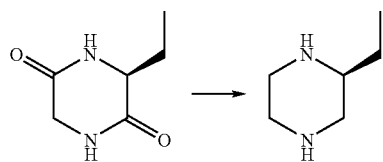

S-2-Ethyl-piperazine: S-3-Ethyl-piperazine-2,5-dione (1.25 g, 8.8 mmol) was suspended in THF and cooled to 0° C. LAH solution (44 ml of a 1M THF solution, 44 mmol) was added dropwise, and when the addition was complete, the solution was refluxed for 18 h. 2.5 N NaOH was added slowly to the reaction mixture until bubbling ceased. The precipitated solid was filtered, and washed with hot ethyl acetate. The solid was filtered away, and the ethyl acetate was removed under vacuum to yield the title product (800mg, 98%). $^1$H NMR (DMSO-$d_6$): δ=2.72 (m, 2H), 2.51 (m, 3H), 2.32 (m, 1H), 2.12 (m, 1H), 1.15 (m, 2H), 0.85 (t, J=7.5 Hz, 3H).

Examples 1-45

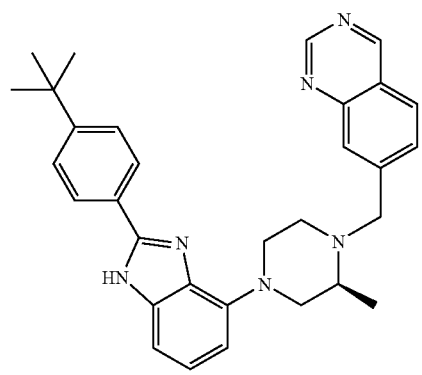

Example 1

(6-({(2S)-4-[2-(4-tert-butylphenyl)-1H-benzimidazol-4-yl]-2-methylpiperazin-1-yl}methyl)quinoxaline): To a solution of the S-2-methylarylpiperazine (2.1 g, 6.0 mMol) in N-methylpyrrolidinone (30 mL) was added the bromomethylquinoxaline (80% pure, 1.84 g, 6.6 mMol) and diisopropylethylamine. The reaction mixture was stirred for 5 h then diluted with ethyl acetate (1500 mL), washed with saturated sodium chloride solution (5×100 mL), dried (MgSO$_4$) and evaporated. The crude product was purified by chromatography on silica gel eluted with a gradient of methanol in dichloromethane (1% to 2.5% to 4%) to provide the product as a pale yellow foamy solid (2.2 g, 75%). $^1$H-NMR (acetone-$d_6$), δ=12.68 (bs, 1H), 8.95 (d, 1H, J=1.8 Hz), 8.92 (d, 1H, J=1.8 Hz), 8.09 (d, 1H, J=8.6 Hz), 8.06 (dd, 1H, J=8.6 Hz, J=5.0 Hz), 8.04 (d, 2H, J=8.6 Hz), 7.92 (dd, 1H, J=8.6 Hz, J=1.8 Hz), 7.55 (d, 2H, J=8.6 Hz), 7.02 (m, 2H), 6.49 (dd, 1H, J=7.3 Hz, J=1.3 Hz), 4.28 (d, 1H, J=14.0 Hz), 4.13 (d, 1H, J=10.6 Hz), 4.02 (d, 1H, J=11.4 Hz), 3.56 (d, 1H, J=14.1 Hz), 3.30 (dd, 1H, J=7.1 Hz, J=4.5 Hz), 2.98 (m, 2H), 2.82 (m, 2H), 1.32 (s, 9H), 1.28 (d, 3H, J=6.2 Hz). HPLC (method D), rt=7.31 mins., 99.3% (210-370 nm, 98.7% @ 302 nm. HRMS calculated=491.2918, found=491.2912.

Table 8 indicates other examples prepared using the above method for example 1:

TABLE 8
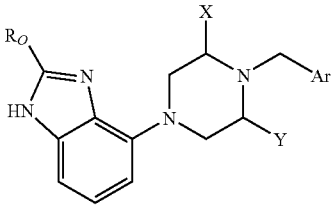
| Example | R_O | X | Y | Ar | [M + H]⁺ |
|---|---|---|---|---|---|
| 2 | 4-EtPh | H | H | (6-quinoxalinyl) | 449 |
| 3 | 4-(3-hydroxyphenoxy)phenyl | H | H | " | 529 |
| 4 | 4-t-BuPh | H | H | " | 477 |
| 5 | 4-benzoylphenyl | H | H | " | 525 |
| 6 | 4-t-BuPh | H | Me | " | 491 |
| 7 | 4-PhSO₂Me | H | H | " | 499 |
| 8 | 4-PhSO₂Et | H | H | " | 513 |
| 9 | 4-i-PrPh | H | H | " | 463 |
| 10 | 4-t-BuPh | H | {R}-Me | " | 491 |
| 11 | 4-t-BuPh | H | {S}-Me | " | 491 |
| 12 | 4-PhNEt₂ | H | H | " | 492 |
| 13 | 4-t-BuPh | H | {S}-Et | " | 505 |
| 14 | 5-(methylthio)thien-2-yl | H | H | " | 549 |
| 15 | 4-PhSMe | H | H | " | 467 |
| 16 | 4-PhOMe | H | H | " | 451 |
| 17 | thien-2-yl | H | H | " | 421 |
| 18 | thien-3-yl | H | H | " | 421 |
| 19 | 4-H₂NSO₂Ph | H | H | " | 500 |
| 20 | 4-methoxy-3-hydroxyphenyl | H | H | " | 467 |

TABLE 8-continued

| Example | R_O | X | Y | Ar | [M + H]+ |
|---|---|---|---|---|---|
| 21 | pyrrol-1-yl | H | H | " | 486 |
| 22 | 3,3-dimethyl-2,3-dihydrobenzo[b]thiophene-1,1-dioxide-6-yl | H | H | " | 539 |
| 23 | 4-t-BuPh | {R}-Me | {S}-Me | " | 505 |
| 24 | 4-(phenylsulfonyl)phenyl | H | H | " | 561 |
| 25 | 5-(methylsulfonyl)thiophen-2-yl | H | H | " | 505 |
| 26 | 4-PhNEt$_2$ | H | {S}-Et | " | 520 |
| 27 | 4-(pyrrolidin-1-yl)phenyl | H | H | " | 490 |
| 28 | 4-acetylphenyl | H | H | " | 463 |
| 29 | 5-t-butylthiophen-2-yl | H | H | " | 483 |
| 30 | 4-(trifluoroacetyl)phenyl | H | H | " | 535 |

TABLE 8-continued
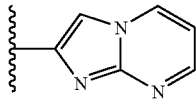
| Example | R$_O$ | X | Y | Ar | [M + H]$^+$ |
|---|---|---|---|---|---|
| 31 | 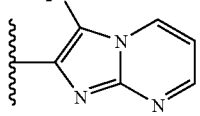 | H | H | " | 587 |
| 32 | 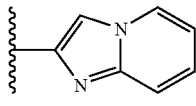 | H | H | " | 571 |
| 33 | 4-t-BuPh | H | H | 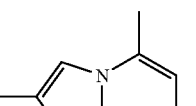 | 466 |
| 34 | 4-t-BuPh | H | {S}-Me | " | 480 |
| 35 | 4-t-BuPh | H | H | 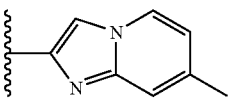 | 511 |
| 36 | 4-t-BuPh | H | H |  | 465 |
| 37 | 4-t-BuPh | H | H |  | 493 |
| 38 | 4-t-BuPh | H | {S}-Me | " | 507 |
| 39 | 4-t-BuPh | H | H |  | 479 |
| 40 | 4-t-BuPh | H | {S}-Me | " | 493 |

TABLE 8-continued
| Example | $R_O$ | X | Y | Ar | $[M + H]^+$ |
|---|---|---|---|---|---|
| 41 | 4-t-BuPh | H | H | imidazo[1,2-a]pyridine-6-carboxamide | 508 |
| 42 | 4-t-BuPh | H | H | 5-methylimidazo[1,2-a]pyridine | 479 |
| 43 | 4-t-BuPh | H | H | 5,7-dimethylimidazo[1,2-c]pyrimidine | 494 |
| 44 | 4-t-BuPh | H | H | imidazo[1,2-a]pyrazine | 466 |
| 45 | 4-t-BuPh | H | H | -CH₂CH₂SO₂NH₂ | 456 |
Examples 46-234
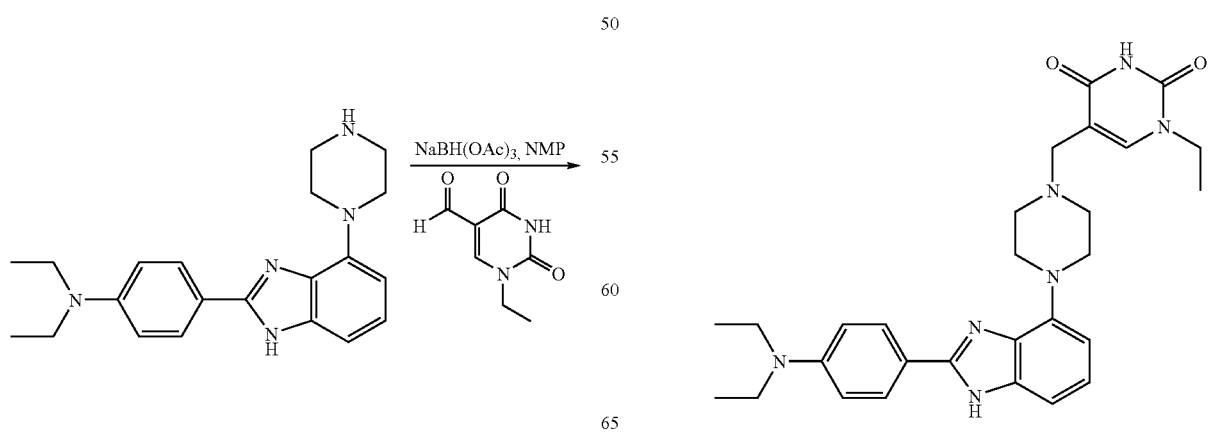

To a solution of Diethyl-[4-(4-piperazin-1-yl-1H-benzoimidazol-2-yl)-phenyl]-amine (1.0 g, 2.0 mMol) in N-methylpyrrolidinone (10 mL) was added 1-Ethyl-2,4-dioxo-1,2,3,4-tetrahydro-pyrimidine-5-carbaldehyde (0.404 g, 2.40 mMol) followed by sodium triacetoxyborohydride (0.849 g, 4.01 mMol) and the mixture stirred at room temperature overnight. Upon arrival the crude reaction mixture was diluted with water (2 mL), filtered, and purified by RP-HPLC (Method E) to yield 168 mg (17% yield) of 5-{4-[2-(4-Diethylamino-phenyl)-1H-benzoimidazol-4-yl]-piperazin-1-ylmethyl}-1-ethyl-1H-pyrimidine-2,4-dione as a very light yellow solid. $^1$H NMR (DMSO-d$_6$): δ=12.33 (s,1H), 11.25 (s,1H), 7.91 (d, 2H, J=9 Hz), 7.66 (s, 1H), 6.96 (m, 2H), 6.77 (d,2H, J=9 Hz), 6.45 (dd, 1H, J=6.0, 2.8 Hz), 3.74 (q, 2H, J=7.1 Hz), 3.53 (br s, 4 h), 3.40 (q, 4H, J=7.1 Hz), 3.23 (s, 2H), 2.62 (m, 4H), 1.18 (t, 3H, J=7.1 Hz), 1.13 (t, 6H, J=7.1 Hz). LC/MS (Method A), rt=0.85 mins., purity=99.2%, calculated mass=501, [M+H]$^+$=502, [M–H]=500. HPLC (Method D): rt=5.5 mins., purity=99.3% @ 210-370 nm and 98.6% @ 372 nm.

Table 9 indicates other examples prepared using the above method for example 46:

TABLE 9

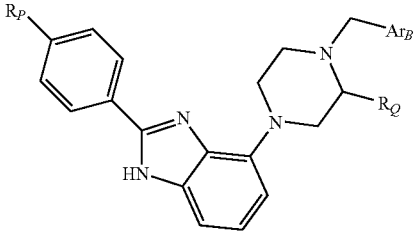

| Example | R$_P$ | R$_Q$ | Ar$_B$ | [M + H]$^+$ |
|---|---|---|---|---|
| 47 | t-Bu | H | 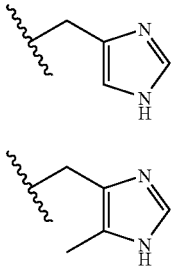 | 415 |
| 48 | t-Bu | H | 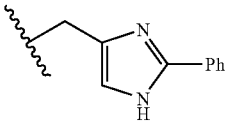 | 429 |
| 49 | t-Bu | H | 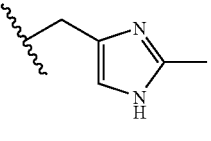 | 491 |
| 50 | t-Bu | H | 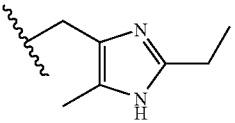 | 429 |
| 51 | t-Bu | H | 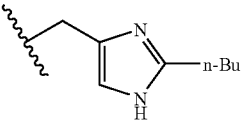 | 457 |
| 52 | " | {R}-Me | " | 471 |
| 53 | " | {S}-Me | " | 471 |
| 54 | i-Pr | H | " | 443 |
| 55 | EtSO$_2$ | H | " | 493 |
| 56 | i-PrSO$_2$ | H | " | 507 |
| 57 | MeSO$_2$ | H | " | 479 |
| 58 | NEt$_2$ | H | " | 472 |
| 59 | t-Bu | H | | 471 |

TABLE 9-continued
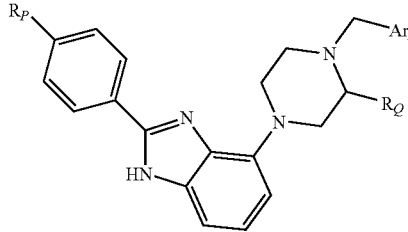
| Example | $R_P$ | $R_Q$ | $Ar_B$ | $[M + H]^+$ |
|---|---|---|---|---|
| 60 | t-Bu | H | 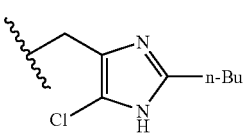 | 505 |
| 61 | t-Bu | H | 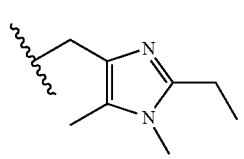 | 471 |
| 62 | t-Bu | H | 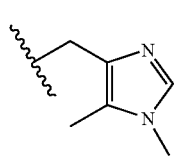 | 443 |
| 63 | t-Bu | H | 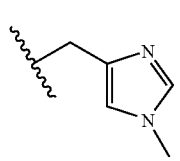 | 429 |
| 64 | t-Bu | H | 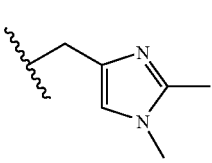 | 443 |
| 65 | t-Bu | H | 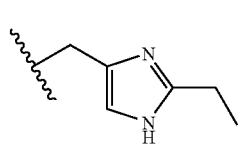 | 443 |
| 66 | t-Bu | H | 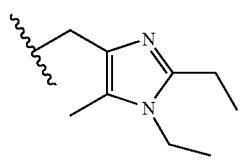 | 485 |
| 67 | t-Bu | H | 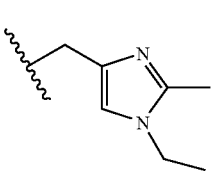 | 457 |

TABLE 9-continued

| Example | R_P | R_Q | Ar_B | [M + H]+ |
|---|---|---|---|---|
| 68 | t-Bu | H | 1-ethyl-1H-imidazol-4-ylmethyl | 443 |
| 69 | t-Bu | H | 1-ethyl-5-methyl-1H-imidazol-4-ylmethyl | 457 |
| 70 | MeSO_2 | H | " | 479 |
| 71 | t-Bu | {S}-Et | " | 485 |
| 72 | t-Bu | H | 2-ethyl-1-methyl-1H-imidazol-4-ylmethyl | 457 |
| 73 | t-Bu | H | 1-(dimethylsulfamoyl)-1H-imidazol-4-ylmethyl | 522 |
| 74 | t-Bu | H | 1,2-diethyl-1H-imidazol-4-ylmethyl | 471 |
| 75 | t-Bu | H | 2-n-butyl-1-methyl-1H-imidazol-4-ylmethyl | 486 |
| 76 | t-Bu | H | 1-methyl-2-n-propyl-1H-imidazol-4-ylmethyl | 471 |

TABLE 9-continued

| Example | R$_P$ | R$_Q$ | Ar$_B$ | [M + H]$^+$ |
|---|---|---|---|---|
| 77 | t-Bu | H | imidazole with methyl and isopropyl | 471 |
| 78 | t-Bu | H | imidazole-CH$_2$CONH$_2$ | 472 |
| 79 | MeSO$_2$ | H | " | 494 |
| 80 | " | {S}-Me | " | 508 |
| 81 | t-Bu | H | methyl imidazole-CH$_2$CONH$_2$ | 486 |
| 82 | t-Bu | H | 2-methyl imidazole-CH$_2$CONH$_2$ | 486 |
| 83 | " | {S}-Me | " | 500 |
| 84 | MeSO$_2$ | H | " | 508 |
| 85 | " | H | " | 522 |
| 86 | t-Bu | H | 2-ethyl imidazole-CH$_2$CONH$_2$ | 500 |
| 87 | " | {S}-Et | " | 514 |
| 88 | t-Bu | H | 2-ethyl imidazole-CH$_2$CO$_2$H | 501 |

TABLE 9-continued
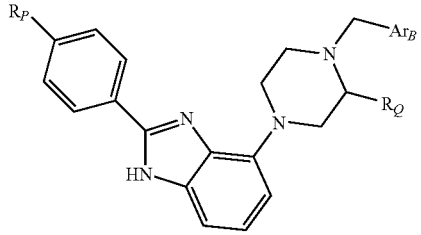
| Example | $R_P$ | $R_Q$ | $Ar_B$ | $[M + H]^+$ |
|---|---|---|---|---|
| 89 | t-Bu | H | 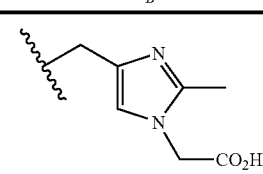 | 487 |
| 90 | t-Bu | H | 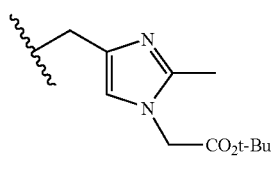 | 543 |
| 91 | t-Bu | H | 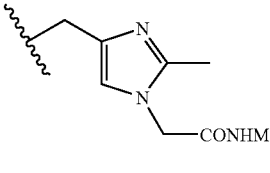 | 500 |
| 92 | t-Bu | H | 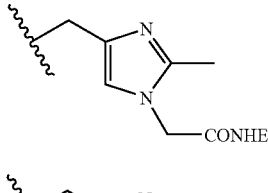 | 514 |
| 93 | t-Bu | H | 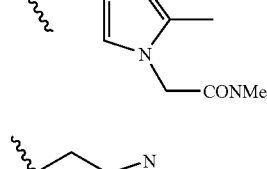 | 514 |
| 94 | t-Bu | H | 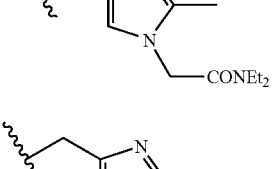 | 542 |
| 95 | t-Bu | H | 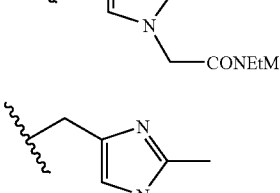 | 528 |
| 96 | t-Bu | H | 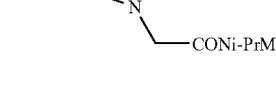 | 542 |

TABLE 9-continued
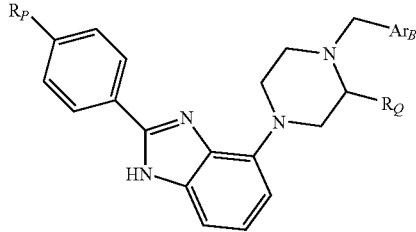
| Example | $R_P$ | $R_Q$ | $Ar_B$ | [M + H]⁺ |
|---|---|---|---|---|
| 97 | t-Bu | H | 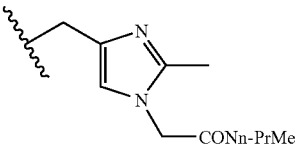 | 542 |
| 98 | t-Bu | H | 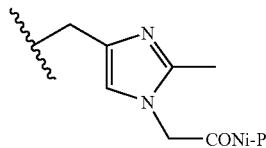 | 528 |
| 99 | t-Bu | H | 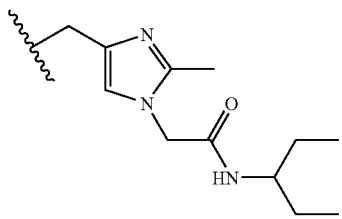 | 556 |
| 100 | t-Bu | H | 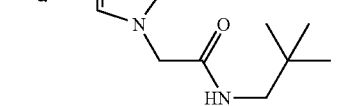 | 556 |
| 101 | t-Bu | H | 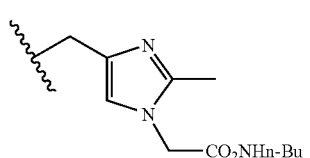 | 542 |
| 102 | t-Bu | H | 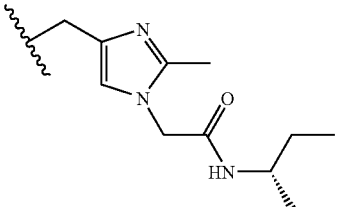 | 542 |

TABLE 9-continued
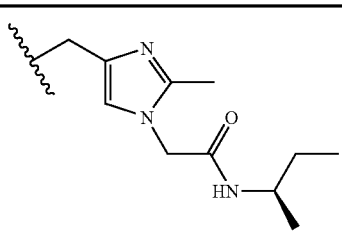
| Example | R_P | R_Q | Ar_B | [M + H]+ |
|---|---|---|---|---|
| 103 | t-Bu | H | 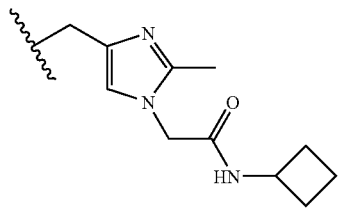 | 542 |
| 104 | t-Bu | H | 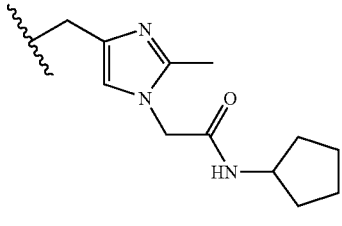 | 540 |
| 105 | t-Bu | H | 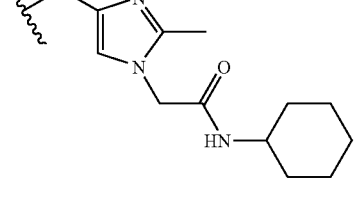 | 554 |
| 106 | t-Bu | H | 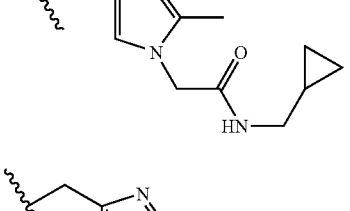 | 568 |
| 107 | t-Bu | H | 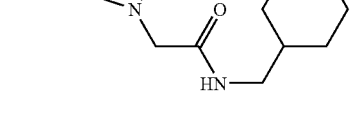 | 540 |
| 108 | t-Bu | H |  | 582 |

TABLE 9-continued
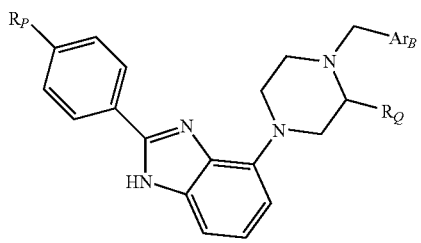
| Example | $R_P$ | $R_Q$ | $Ar_B$ | $[M + H]^+$ |
|---|---|---|---|---|
| 109 | t-Bu | H | 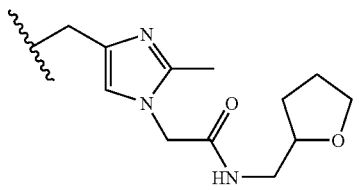 | 570 |
| 110 | t-Bu | H | 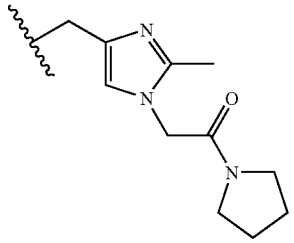 | 540 |
| 111 | t-Bu | H | 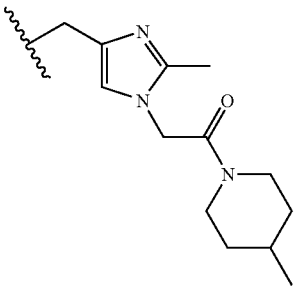 | 568 |
| 112 | t-Bu | H | 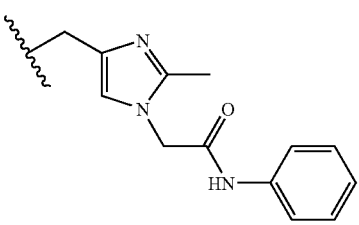 | 562 |
| 113 | t-Bu | H | 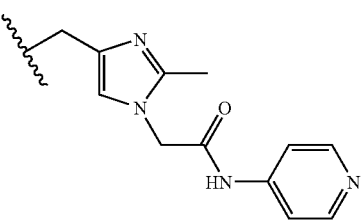 | 563 |

TABLE 9-continued

| Example | R_P | R_Q | Ar_B | [M + H]+ |
|---|---|---|---|---|
| 114 | t-Bu | H | (4-(2-methylimidazol-1-yl)methyl; N-CH(CH3)Ph acetamide) | 590 |
| 115 | t-Bu | H | (4-(2-methylimidazol-1-yl)methyl; N-CH(CH3)Ph acetamide, other enantiomer) | 590 |
| 116 | t-Bu | H | (4-(2-methylimidazol-1-yl)methyl; N-CH2CH2Ph acetamide) | 590 |
| 117 | t-Bu | H | (4-(2-methylimidazol-1-yl)methyl; N-Me, N-Bn acetamide) | 590 |
| 118 | t-Bu | H | (4-(2-methylimidazol-1-yl)methyl; N-CH2CH2-NHCbz) | 606 |
| 119 | t-Bu | H | (4-methyl-1-n-butyl imidazol-5-yl)methyl | 485 |

TABLE 9-continued
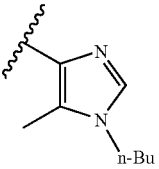
| Example | R$_P$ | R$_Q$ | Ar$_B$ | [M + H]$^+$ |
|---|---|---|---|---|
| 120 | t-Bu | H | 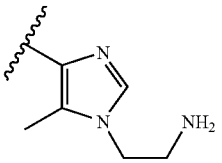 | 485 |
| 121 | t-Bu | H | 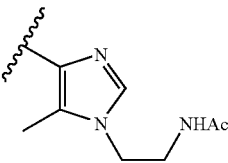 | 472 |
| 122 | t-Bu | H | 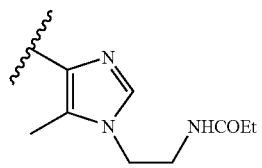 | 514 |
| 123 | t-Bu | H | 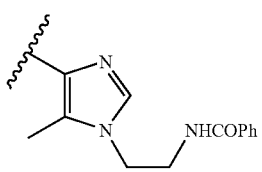 | 528 |
| 124 | t-Bu | H | 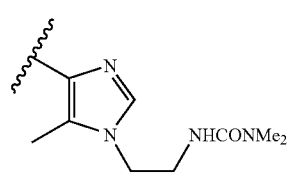 | 576 |
| 125 | t-Bu | H | 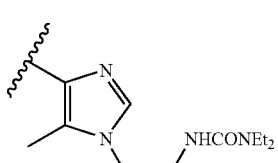 | 543 |
| 126 | t-Bu | H | | 571 |

TABLE 9-continued
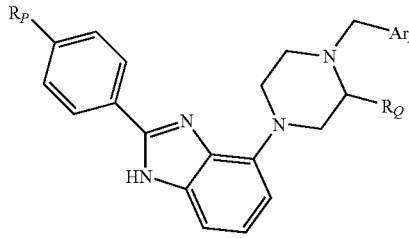
| Example | $R_P$ | $R_Q$ | $Ar_B$ | $[M + H]^+$ |
|---|---|---|---|---|
| 127 | t-Bu | H | 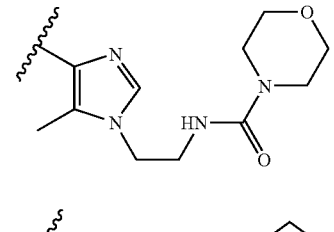 | 585 |
| 128 | t-Bu | H | 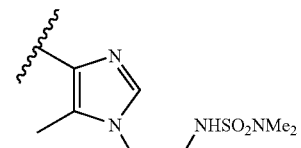 | 569 |
| 129 | t-Bu | H | 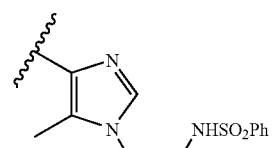 | 579 |
| 130 | t-Bu | H | 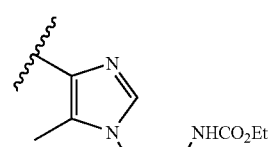 | 612 |
| 131 | t-Bu | H | 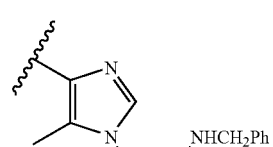 | 544 |
| 132 | t-Bu | H | 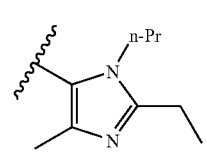 | 562 |
| 133 | t-Bu | H | | 499 |

TABLE 9-continued

| Example | R$_P$ | R$_Q$ | Ar$_B$ | [M + H]$^+$ |
|---|---|---|---|---|
| 134 | t-Bu | H | 4-(2-ethyl-5-methyl-1-n-propyl-imidazolyl) | 499 |
| 135 | t-Bu | H | 4-(2-methyl-1-n-propyl-imidazolyl) | 471 |
| 136 | t-Bu | H | 5-(2-methyl-1-n-propyl-imidazolyl) | 471 |
| 137 | t-Bu | H | 5-(1-n-hexyl-uracilyl) | 543 |
| 138 | t-Bu | H | 5-(1-n-butyl-uracilyl) | 515 |
| 139 | t-Bu | H | 5-(1-(2,6-difluorobenzyl)-uracilyl) | 585 |

TABLE 9-continued
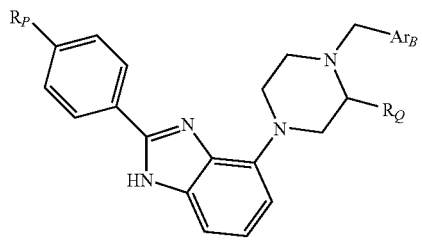
| Example | $R_P$ | $R_Q$ | $Ar_B$ | [M + H]⁺ |
|---|---|---|---|---|
| 140 | t-Bu | H | 5-(1-benzyl-2,4-dioxo-pyrimidinyl) | 549 |
| 141 | t-Bu | H | 5-[1-(2-fluorobenzyl)-2,4-dioxo-pyrimidinyl] | 567 |
| 142 | t-Bu | H | 5-(1-n-pentyl-2,4-dioxo-pyrimidinyl) | 529 |
| 143 | t-Bu | H | 5-{1-[(2-methoxyethoxy)methyl]-2,4-dioxo-pyrimidinyl} | 547 |
| 144 | t-Bu | H | 5-(2,4-dioxo-pyrimidinyl) | 459 |
| 145 | t-Bu | {S}-Me | " | 473 |

TABLE 9-continued

| Example | $R_P$ | $R_Q$ | $Ar_B$ | $[M + H]^+$ |
|---|---|---|---|---|
| 146 | t-Bu | {S}-Et | " | 487 |
| 147 | MeSO$_2$ | H | " | 481 |
| 148 | " | {S}-Me | " | 495 |
| 149 | EtSO$_2$ | H | " | 495 |
| 150 | i-PrSO$_2$ | H | " | 509 |
| 151 | Et$_2$N | H | " | 474 |
| 152 | t-Bu | H | (1,3-dimethyluracil-5-yl) | 487 |
| 153 | t-Bu | H | (1,3-diethyluracil-5-yl) | 515 |
| 154 | t-Bu | H | (1-ethyluracil-5-yl) | 487 |
| 155 | t-Bu | {S}-Me | " | 501 |
| 156 | t-Bu | {S}-Et | " | 515 |
| 157 | MeSO$_2$ | H | " | 509 |
| 158 | Et$_2$N | {S}-Et | " | 530 |
| 159 | ((CF$_3$)$_2$)COH | H | " | 597 |
| 160 | CF$_3$CHOH | H | " | 529 |
| 161 | t-Bu | H | (1-n-propyluracil-5-yl) | 501 |
| 162 | t-Bu | H | (1-i-propyluracil-5-yl) | 501 |

TABLE 9-continued
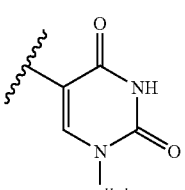
| Example | $R_P$ | $R_Q$ | $Ar_B$ | $[M + H]^+$ |
|---|---|---|---|---|
| 163 | t-Bu | H | 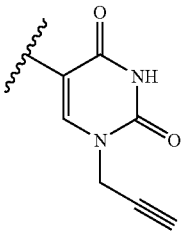 allyl | 499 |
| 164 | t-Bu | H | 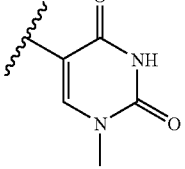 | 497 |
| 165 | t-Bu | H | 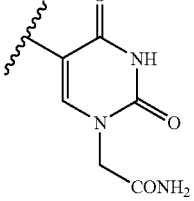 | 473 |
| 166 | t-Bu | H | 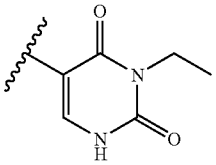 | 516 |
| 167 | t-Bu | {S}-Me | " | 530 |
| 168 | t-Bu | H | 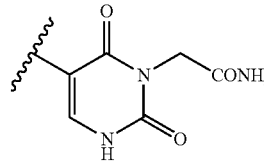 | 487 |
| 169 | t-Bu | H |  | 516 |

TABLE 9-continued

| Example | R_P | R_Q | Ar_B | [M + H]+ |
|---|---|---|---|---|
| 170 | t-Bu | H | (4-(2-methylthio)pyrimidinyl) | 473 |
| 171 | t-Bu | H | (4-(2-methylsulfonyl)pyrimidinyl) | 505 |
| 172 | t-Bu | H | (5-(2-methylthio)pyrimidinyl) | 473 |
| 173 | t-Bu | {S}-Me | " | 487 |
| 174 | Et_2N | H | " | 488 |
| 175 | t-Bu | H | (imidazo[1,2-a]pyrimidin-3-yl) | 466 |
| 176 | t-Bu | H | (2-pyridyl with methyl) | 426 |
| 177 | 3-HO-phenyl | H | " | 478 |
| 178 | MeSO_2 | H | " | 448 |
| 179 | 4-Et, 3-OH | H | " | 414 |
| 180 | t-Bu | H | (6-methyl-2-pyridyl) | 440 |
| 181 | t-Bu | H | (6-CO_2Me-2-pyridyl) | 484 |

TABLE 9-continued
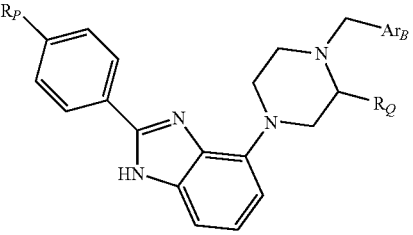
| Example | $R_P$ | $R_Q$ | $Ar_B$ | $[M + H]^+$ |
|---|---|---|---|---|
| 182 | t-Bu | H | 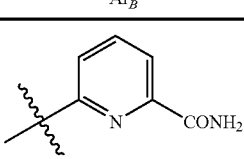 | 469 |
| 183 | t-Bu | H | 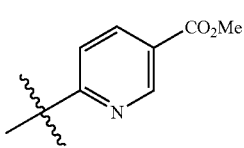 | 484 |
| 184 | t-Bu | H | 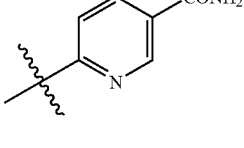 | 469 |
| 185 | t-Bu | H | 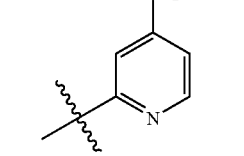 | 484 |
| 186 | t-Bu | H | 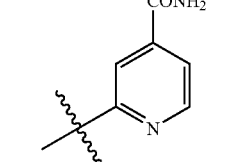 | 469 |
| 187 | t-Bu | H | 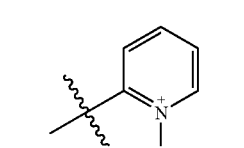 | 442 |
| 188 | t-Bu | H | 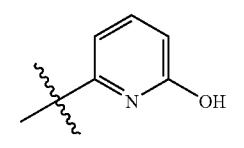 | 442 |
| 189 | t-Bu | H | 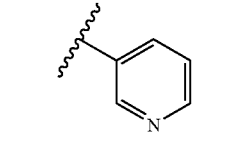 | 426 |

TABLE 9-continued
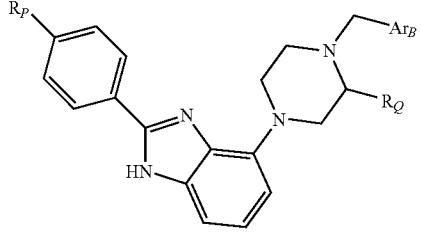
| Example | R_P | R_Q | Ar_B | [M + H]⁺ |
|---|---|---|---|---|
| 190 | t-Bu | H | 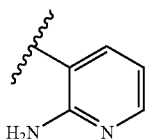 | 441 |
| 191 | t-Bu | H | 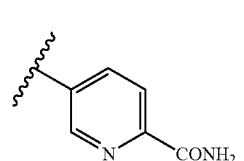 | 467 |
| 192 | t-Bu | H | 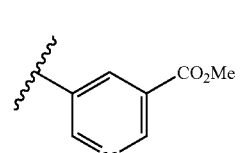 | 484 |
| 193 | t-Bu | H | 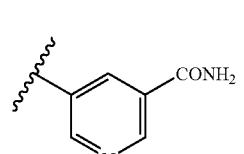 | 469 |
| 194 | t-Bu | H | 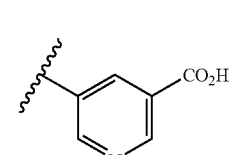 | 470 |
| 195 | t-Bu | H | 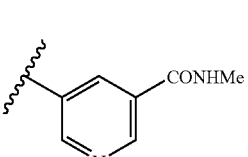 | 483 |
| 196 | t-Bu | H | 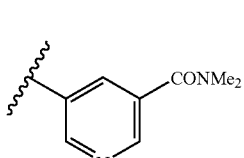 | 497 |
| 197 | t-Bu | H | 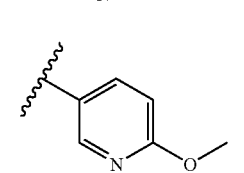 | 456 |

TABLE 9-continued

| Example | $R_P$ | $R_Q$ | $Ar_B$ | [M + H]+ |
|---|---|---|---|---|
| 198 | t-Bu | H | 4-pyridyl | 426 |
| 199 | t-Bu | H | pyridine N-oxide | 442 |
| 200 | t-Bu | H | 3-hydroxy-5-(hydroxymethyl)pyridinyl | 486 |
| 201 | t-Bu | H | pyrido-pyrazine-2,3-dione | 510 |
| 202 | t-Bu | {S}-Me | " | 524 |
| 203 | MeSO$_2$ | H | " | 532 |
| 204 | " | {S}-Me | " | 546 |
| 205 | t-Bu | H | pyrido[3,4-b]pyrazinyl | 478 |
| 206 | t-Bu | H | pyrido[2,3-b]pyrazinyl | 478 |
| 207 | t-Bu | H | quinoxalinyl | 477 |
| 208 | t-Bu | {S}-Me | " | 491 |
| 209 | Et$_2$N | H | " | 492 |
| 210 | t-Bu | {S}-Et | " | 505 |
| 211 | (CF$_3$)$_2$CH | H | " | 571 |

TABLE 9-continued
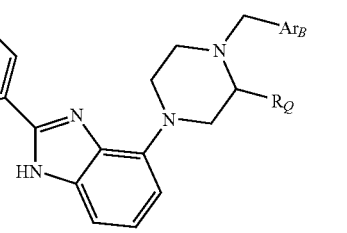
| Example | $R_P$ | $R_Q$ | $Ar_B$ | $[M + H]^+$ |
|---|---|---|---|---|
| 212 | t-Bu | H | 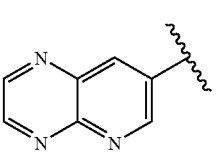 | 478 |
| 213 | t-Bu | {S}-Me | " | 492 |
| 214 | t-Bu | H | 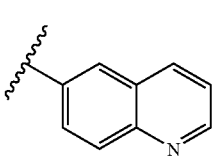 | 478 |
| 215 | SO$_2$Me | H | " | 500 |
| 216 | t-Bu | {S}-Me | " | 492 |
| 217 | (CF$_3$)$_2$COH | H | " | 588 |
| 218 | (CF$_3$)$_2$CH | H | " | 572 |
| 219 | t-Bu | H | 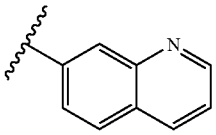 | 476 |
| 220 | t-Bu | H | 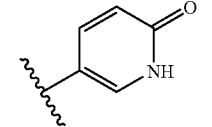 | 476 |
| 221 | t-Bu | H | 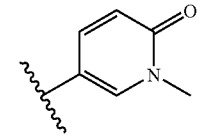 | 442 |
| 222 | t-Bu | H | 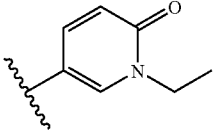 | 456 |
| 223 | t-Bu | H |  | 470 |

TABLE 9-continued
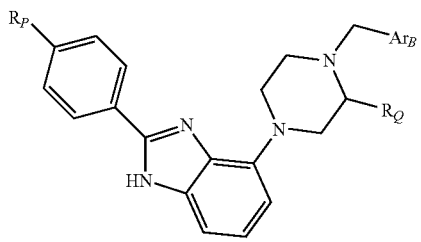
| Example | $R_P$ | $R_Q$ | $Ar_B$ | $[M + H]^+$ |
|---|---|---|---|---|
| 224 | t-Bu | H | 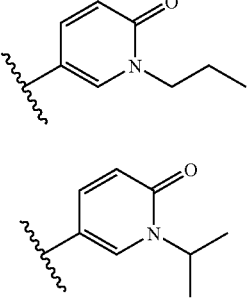 | 484 |
| 225 | t-Bu | H | 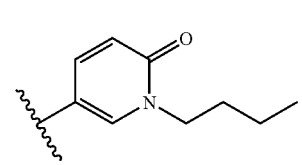 | 484 |
| 226 | t-Bu | H | 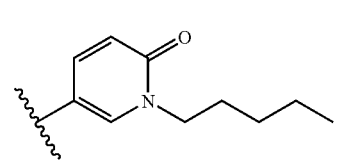 | 498 |
| 227 | t-Bu | H | 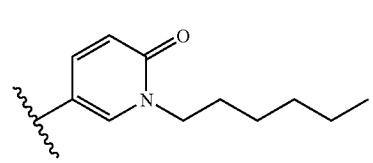 | 512 |
| 228 | t-Bu | H | 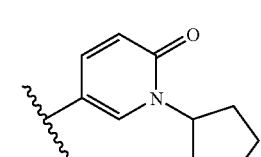 | 526 |
| 229 | t-Bu | H | 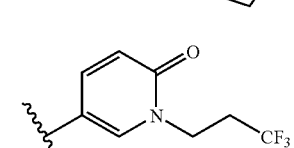 | 510 |
| 230 | t-Bu | H | 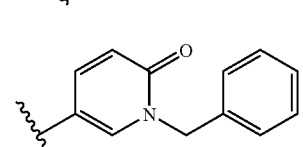 | 538 |
| 231 | t-Bu | H | | 532 |

TABLE 9-continued

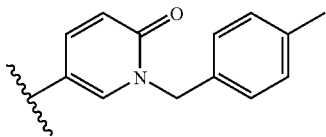

| Example | $R_P$ | $R_Q$ | $Ar_B$ | $[M + H]^+$ |
|---|---|---|---|---|
| 232 | t-Bu | H | 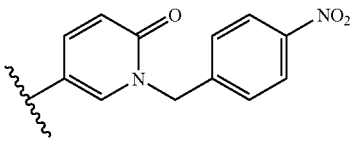 | 546 |
| 233 | t-Bu | H | 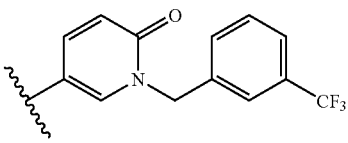 | 577 |
| 234 | t-Bu | H | 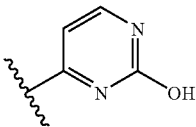 | 600 |

Examples 235-241

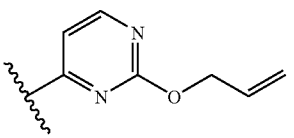

A solution of the sulfone (8 mg, 15.9 μmol) in dioxane (0.5 mL) was added to methanol (9.6 μL, 0.238 mmol) at room temperature. Cesium carbonate (6.7 mg, 0.207 mmol) was added and the reaction mixture was heated to 60° C. for 72 hr then purified directly using reversed-phase HPLC (method E) to yield the pure product (2.7 mg, 3.9 μmol, 8%). $^1$H NMR (methanol-$d_4$): δ 8.58 (d, J=2Hz, 1H), 7.98 (d, J=9 Hz, 2H), 7.64 (d, J=9 Hz, 2H), 7.40 (m, 2H), 7.13 (m, 3H), 4.57 (s, 2H), 3.99 (s, 3H), 3.53 (bm, 8H), 1.33 (s, 9H). Calculated mass=456.3, $[M+H]^-$=455.

Table 10 indicates other compounds prepared using the same method as example 235:

TABLE 10

| Example | $R_R$ | $[M + H]^+$ |
|---|---|---|
| 236 | pyrimidine-OH | 443 |
| 237 | pyrimidine-O-allyl | 483 |

TABLE 10-continued

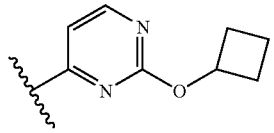

Examples 242-259

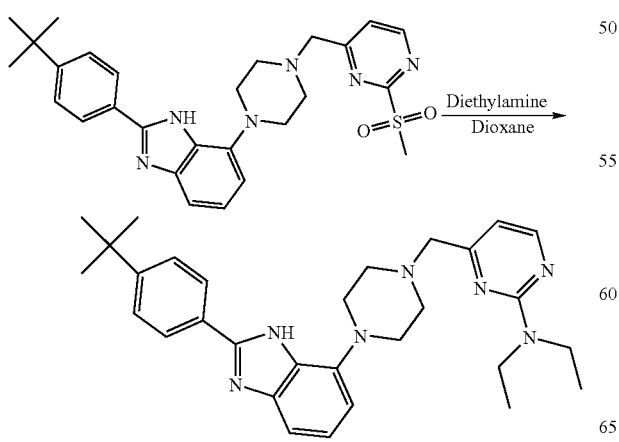

A solution of sulfone (7.5 mg, 14.9 9 µmol) in dioxane (0.6 mL) was added to diethylamine (21.8 mg, 0.298 mmol). The reaction was heated at 85° C. for 16 hr then purified directly using reversed-phase HPLC (method E) to yield pure product (2.0 mg, 4.0 µmol, 8%). $^1$H NMR (methanol-$d_4$): δ=8.16 (d, J=5 Hz, 1H), 7.95 (d, J=9 Hz, 2H), 7.49 (d, J=9 Hz, 2H), 7.08 (m, 2H), 6.63 (m, 2H), 3.3-3.8 (bm, 8H), 2.8 (bm, 4H), 1.30 (s, 9H), 1.28 (t, J=8 Hz, 6H). Calculated mass=497.7, M+H]$^-$=496.

Table 11 indicates other compounds prepared using the same method as example 242:

TABLE 11

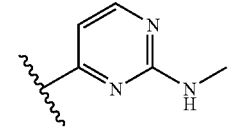

| Example | $R_S$ | [M + H]$^+$ |
|---|---|---|
| 243 | 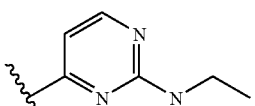 | 456 |
| 244 | 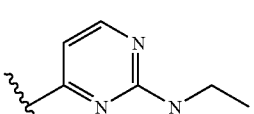 | 470 |
| 245 | 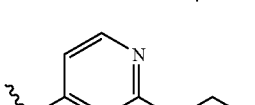 | 484 |
| 246 | 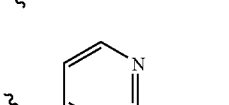 | 496 |
| 247 | 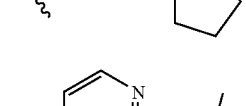 | 496 |
| 248 | | 498 |

| Example | $R_R$ | [M + H]$^+$ |
|---|---|---|
| 238 | 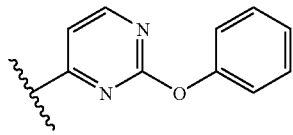 | 497 |
| 239 | 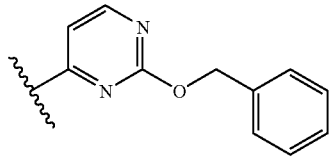 | 519 |
| 240 | 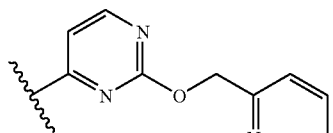 | 533 |
| 241 | | 534 |

TABLE 11-continued

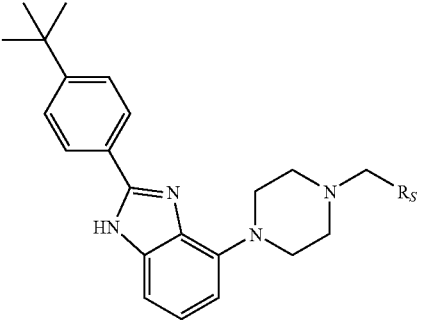

| Example | Rs | [M + H]+ |
|---|---|---|
| 249 | 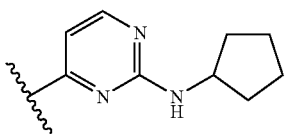 | 498 |
| 250 | 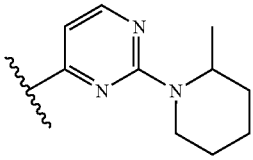 | 510 |
| 251 | 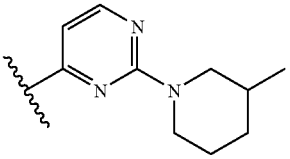 | 524 |
| 252 | 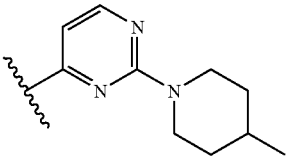 | 524 |
| 253 | 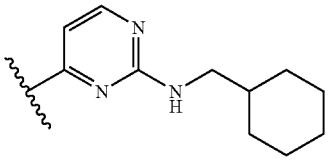 | 524 |
| 254 | 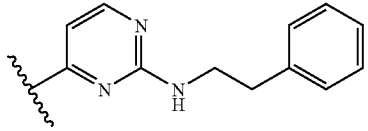 | 538 |
| 255 | 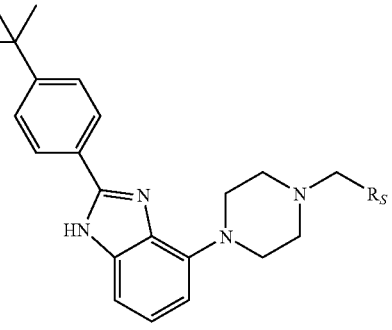 | 546 |

TABLE 11-continued

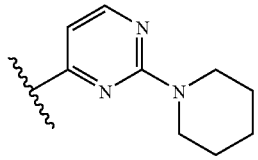

| Example | Rs | [M + H]+ |
|---|---|---|
| 256 | 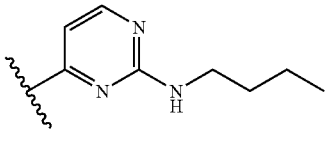 | 546 |
| 257 | | 510 |
| 258 | | 498 |
| 259 | | 526 |

Example 260

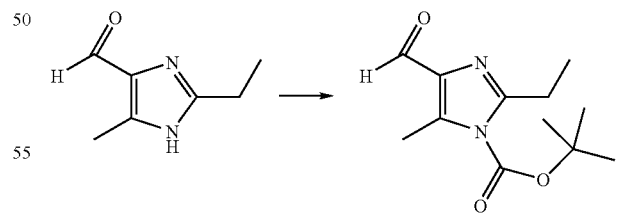

2-Ethyl-4-formyl-5-methyl-imidazole-1-carboxylic acid tert-butyl ester To a suspension of NaH (60% dispersion in oil, 0.33 g, 8.3 mmol) in THF (10 mL) and DMF (5 mL) cooled in an ice bath was added dropwise a solution of 2-ethyl-5-methyl-1H-imidazole-4-carbaldehyde (1.0 g, 7.2 mmol) in THF (10 mL). The reaction was stirred at rt for 15 mins. A solution of di-tert-butyl dicarbonate (1.89 g, 8.3 mmol) in THF (10 mL) was added and the reaction was heated in a 55° C. bath overnight. The orange solution was cooled to rt and quenched in an ice bath with the addition of H₂O (5 mL). The reaction was concentrated under reduced pressure. The residue was partitioned between EtOAc (200 mL) and H₂O (40 mL). The organic layer was washed with H₂O (3×30 mL) and brine (30 mL). The EtOAc layer was dried (Na₂SO₄), filtered, and concentrated. The crude material was purified using silica gel chromatography, eluting with a gradient of 2% MeOH/CH₂Cl₂ to 5% MeOH/CH₂Cl₂ to afford the product (1.69 g, 98%) as a golden powder. ¹H NMR 300 MHz (CDCl₃): δ=9.97 (s, 1H), 2.97 (q, J=7.4 Hz, 2H), 2.69 (s, 3H), 1.65 (s, 9H), 1.33 (t, J=7.4 Hz, 3H). MS (ESI-POS) [M+H]⁺=239.

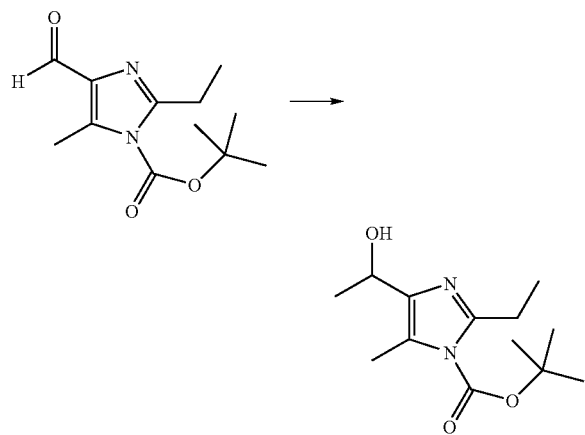

tert-Butyl 2-ethyl-4-(1-hydroxyethyl)-5-methyl-1H-imidazole-carboxylate To a solution of 2-ethyl-4-formyl-5-methyl-imidazole-1-carboxylic acid tert-butyl ester (1.07 g, 4.49 mmol) in THF (25 mL) cooled in a dry ice acetone bath was added dropwise a MeMgBr solution (1.0 M, 3.3 mL, 9.89 mmol). The reaction was stirred in the bath for another 15 mins., then transferred to an ice bath. After 1 h, the reaction was quenched by the addition of 1 M citric acid solution (5 mL), then sat. NH₄Cl solution (5 mL). The reaction pH was neutral. The solution was concentrated. To the residue was added EtOAc (200 mL) and H₂O (50 mL). The resulting slurry was filtered to collect a gummy precipitate. The layers of the filtrate were separated. The organic layer was washed with sat. NaHCO₃ (50 mL) and brine (50 mL). The EtOAc solution was dried (Na₂SO₄), filtered, and concentrated. The crude material was purified using silica gel chromatography, eluting with a gradient of 3% MeOH/CH₂Cl₂ to 4% MeOH/CH₂Cl₂ to afford the product (0.95 g, 83%) as a colorless oil. ¹H NMR 300 MHz (CDCl₃): δ=4.77 (q, J=6.6 Hz, 1H), 3.69 (bs, 1H), 2.94 (q, J=7.4 Hz, 2H), 2.32 (s, 3H), 1.61 (s, 9H), 1.49 (d, J=6.5 Hz, 3H), 1.25 (t, J=7.4 Hz, 3H). MS (ESI-POS) [M+H]⁺=255. HPLC (column: Xterra RP18, 3.5 μm, 4.6×50 mm; 85/15-5/95, 10 mins., hold for 4 mins., A=ammonium formate buffer, pH 3.5, B=acetonitrile/MeOH) rt=6.26 mins. (99.9% @ 210-370 mn; 96.0% @ 246 nm).

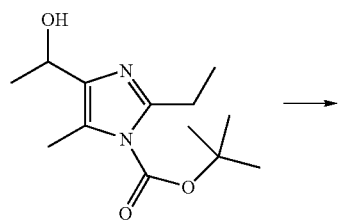

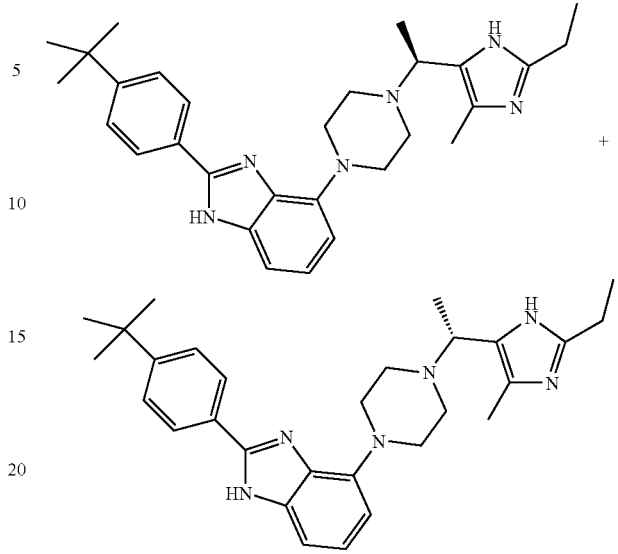

2-(4-tert-butylphenyl)-4-{4-[(1S)-1-(2-ethyl-5-methyl-1H-imidazol-4-yl)ethyl]piperazin-1-yl}-1H-benzimidazole: To a solution of tert-butyl 2-ethyl-4-(1-hydroxyethyl)-5-methyl-1H-imidazole-1-carboxylate (0.95 g, 3.74 mmol) in dioxane (10 mL) was added a solution of HCl in dioxane (4.0 M, 3 mL) with intermittent cooling in an ice bath. The solution was stirred at rt for 1 h. The reaction was monitored for disappearance of starting material hourly, and additional HCl in dioxane (9 mL total) was added over the course of 8 h. The reaction was stirred at rt overnight. The solution was concentrated to remove the solvent. To the residual oil cooled in an ice bath was added thionyl chloride (1.64 mL, 22.4 mmol). The reaction was stirred at rt for 1 h, and heated in a 55° C. bath for 0.5 h. The reaction was concentrated and azeotroped with benzene (2×15 mL) then EtOH (2 mL) and benzene (10 mL). To the residual semi-solid was added acetonitrile (130 mL), the piperazinylbenzimidazole (0.63 g, 1.86 mmol), and Et₃N (1.0 mL, 7.5 mmol). The mixture was heated in a 55° C. bath overnight. The solution was cooled to rt and concentrated under reduced pressure. The crude material was purified using silica gel chromatography, eluting with a gradient of 7% MeOH/CH₂Cl₂ to 9% MeOH/CH₂Cl₂ to afford crude product as an oil (0.55 g). The oil was purified using reversed-phase HPLC with a gradient of 10% to 40% of 0.1% TFA/acetonitrile/H₂O with UV detection at 254 and 310 nm. The pure fractions were combined and concentrated. To the residue was added sat. K₂CO₃ solution (15 mL). The mixture was extracted with EtOAc (3×30 mL). The EtOAc layers were washed with brine (10 mL). The EtOAc solution was dried (Na₂SO₄), filtered, and concentrated to afford a racemic mixture of alkylated product (0.17 g, 20%) as an ivory solid. The enantiomers were separated in 99% e.e. by chiral prep HPLC on an OD-H 20×250 mm column with 95% acetonitrile/5% MeOH/0.1% DEA with UV detection at 302 nm. The first peak which eluted (rt=5.03 mins.) showed a positive CD deflection. The second peak which eluted (rt=5.81 mins.) showed a negative CD deflection. The isomer from the first peak was collected to afford the title compound (45 mg) as an ivory solid. ¹H NMR 400 MHz (MeOH-d₄): δ=7.98 (d, J=8.4 Hz, 2H), 7.54 (d, J=8.4 Hz, 2H), 7.10 (bm, 2H), 6.64 (bm, 1H), 3.87 (q, J=7.1 Hz, 1H) 3.48-3.42 (m, 4H), 2.84-2.79 (m, Example 261

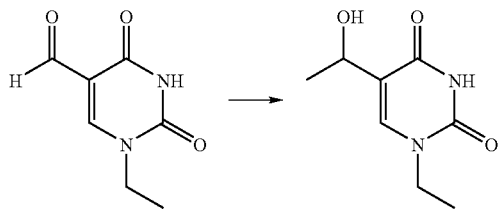

1-Ethyl-5-(1-hydroxy-ethyl)-1H-pyrimidine-2,4-dione To a solution of aldehyde (0.20 g, 1.21 mmol) in THF (15 mL) cooled in a dry ice acetone bath was added dropwise a solution of MeMgBr in Et$_2$O (3.0 M, 1.1 mL, 3.3 mmol). The mixture was stirred in the bath for 0.5 h, then transferred to an ice bath and stirred for 45 mins. The reaction was quenched in the ice bath with the addition of MeOH (2 mL) followed by 1 M citric acid solution (2 mL). The reaction was concentrated under reduced pressure. The crude material was purified using silica gel chromatography, eluting with 5% MeOH/CH$_2$Cl$_2$ to afford the product (0.12 g, 52%) as a white solid. $^1$H NMR 300 MHz (CDCl$_3$): δ=7.52 (s, 1H), 4.79 (q, J=6.5 Hz, 1H), 3.81 (q, J=7.2 Hz, 2H), 1.46 (d, J=6.5 Hz, 3H), 1.32 (t, J=7.2 Hz, 3H). MS (ESI-POS) [M−H$_2$O+H]$^+$=167.

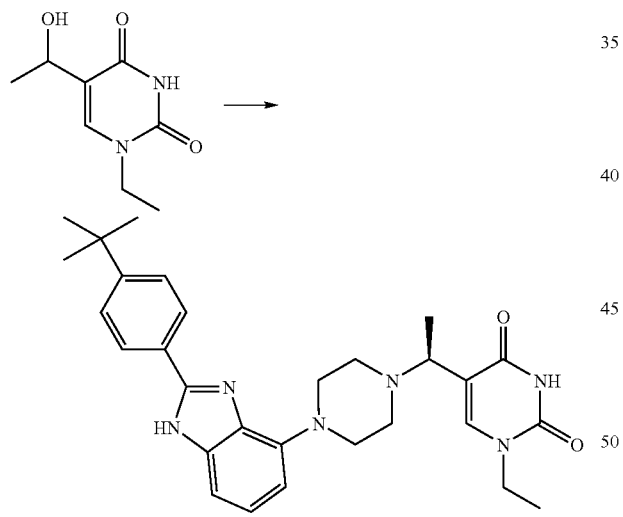

5-((1S)-1-{4-[2-(4-tert-Butylphenyl)-1H-benzimidazol-4-yl]piperazin-1-yl}ethyl)-1-ethylpyrimidine-2,4(1H,3H)-dione To a solution of CBr$_4$ (0.13 g, 0.39 mmol) in CH$_2$Cl$_2$ (15 mL) was added PPh$_3$ (0.10 g, 0.39 mmol). The reaction was stirred at rt for 5 mins. A solution of 1-ethyl-5-(1-hydroxy-ethyl)-1H-pyrimidine-2,4-dione (61 mg, 0.33 mmol) in CH$_2$Cl$_2$ (15 mL) was added to the reaction and the solution was stirred at rt overnight. A solution of CBr$_4$ (0.13 g, 0.39 mmol) and PPh$_3$ (0.10 g, 0.39 mmol) in CH$_2$Cl$_2$ (15 mL) was added to the alcohol reaction and the solution was stirred at rt for 3h. The solution was concentrated under reduced pressure. The residue was dissolved in acetonitrile (15 mL). To the solution was added the piperazinylbenzimidazole (44 mg, 0.13 mmol) and DIEA (57 μL, 0.33 mmol) and the mixture was heated in a 55° C. bath overnight. The solution was cooled to rt and concentrated under reduced pressure. The crude material was purified using silica gel chromatography, eluting with a gradient of 3% MeOH/CH$_2$Cl$_2$ to 5% MeOH/CH$_2$Cl$_2$ to afford crude product which was purified using reversed-phase HPLC (method E). The pure fractions were combined and concentrated to afford the racemic material as its trifluoroacetate salt (20 mg, 21%). The enantiomers were separated from the racemic mixture (6.5 mg) in 99% e.e. by chiral prep HPLC on an AD-H column with 60% hexane/40% EtOH/0.1% DEA with UV detection at 310 and 260 nm. The first peak which eluted (rt=5.61 mins.) showed a negative CD deflection. The second peak which eluted (rt=11.91 mins.) showed a positive CD deflection. The second peak was collected to afford the title compound (3.2 mg) as an ivory solid. $^1$H NMR 400 MHz (DMSO-d$_6$): δ=11.64 (s, 1H), 9.52 (bs, 1H), 8.06 (d, J=8.5 Hz, 2H), 8.01 (s, 1H), 7.58 (d, J=8.5 Hz, 2H), 7.15-7.11 (m, 2H), 6.63 (bs, 1H), 4.49 (q, J=6.6 Hz, 1H), 3.77 (q, J=7.1 Hz, 2H) 3.70-3.67 (m, 2H), 3.55-3.51 (m, 2H), 3.32-3.17, m, 4H), 1.64 (d, J=7.1 Hz, 3H), 1.34 (s, 9H), 1.24 (t, J=7.1 Hz, 3H). MS (ESI-POS) [M+H]$^+$=501.

Example 262

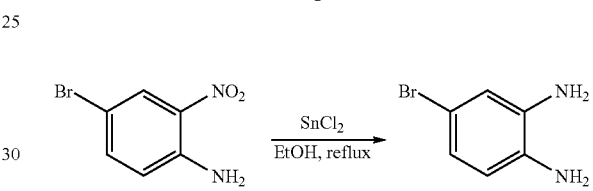

In a round bottom flask were combined 4-Bromo-2-nitroaniline (4.03 g, 18.6 mMol), ethanol (190 proof, 93 mL), and tin chloride dihydrate (8.38 g, 37.1 mMol) and a water-cooled condenser attached. The reaction was heated to reflux in an oil bath and stirred for three days. The mixture was then cooled to room temperature and diluted with ethyl acetate (250 mL). Saturated sodium bicarbonate solution was added until the pH was basic. The slurry was then filtered thru Celite and the filtrate transferred to a separatory funnel. The aqueous layer was discarded and the organics washed with saturated sodium bicarbonate (2×50 mL), brine (50 mL), and then dried with magnesium sulfate, filtered, and concentrated to dryness to yield 3.07 g (88% yield) of 4-Bromo-1,2-phenylenediamine as an orange-brown solid. $^1$H NMR (DMSO-d$_6$): δ=6.63 (d,1H,J=2.3Hz), 6.5-6.3 (m,2H), 4.71 (br s,2H), 4.56 (br s,2H).

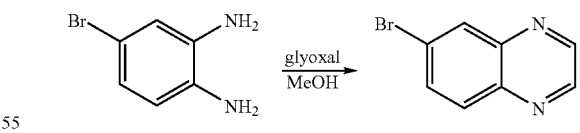

In a round bottom flask under nitrogen was combined 4-Bromo-benzene-1,2-diamine (2.01 g, 10.7 mMol), methanol (50 mL), and glyoxal (40% by wt. 3.1 mL, 26.9 mMol) and the resulting solution stirred overnight. Upon arrival the reaction was concentrated to dryness on a rotary evaporator and purified by flash column chromatography on silica gel using 5-10% ethyl acetate in dichloromethane as eluant to yield 1.14 g (50% yield) of 6-Bromo-quinoxaline as a yellow-orange solid. $^1$H NMR (DMSO-d$_6$): δ=9.00 (d, 2H, J=2.8 Hz), 8.36 (d, 1H, J=2.2 Hz), 8.07 (d, 1H, J=9.0 Hz), 8.02 (dd, 1H, J=8.8, 2.1 Hz). CHN for C$_8$H$_5$BrN$_2$: calc. C, 45.97; H, 2.41; N, 13.4. found C, 45.99; H 2.09; N 13.09. LC/MS (Method A), rt=1.10 mins., purity=99%, calculated mass=208, [M+H]⁺=209/21. HPLC (Method C): rt=7.4 mins., purity=98.52% @ 210-370 nm and 98.8% @ 322 nm.

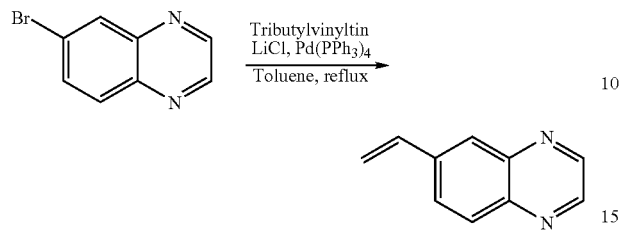

A mixture of 6-Bromoquinoxaline (1.05 g, 5.02 mMol), tetrakis(triphenylphosphine)palladium (0.232 g, 0.2 mMol), and lithium chloride (0.639 g, 15.1 mMol) in dry toluene (50 mL) under nitrogen was treated with tributylvinyl tin (4.4 mL, 15.1 mMol) and heated to one hundred degrees for three hours. After cooling to room temperature the mixture was partitioned between ethyl acetate (200 mL) and water (100 mL). The aqueous layer was discarded and the organics washed with brine (2×100 mL), dried with magnesium sulfate, filtered, and concentrated to dryness on a rotary evaporator. Purification by flash column chromatography on silica gel using 10% ethyl acetate in dichloromethane as eluant yielded 680 mg (87% yield) of 6-vinylquinoxaline as a light orange solid. ¹H NMR (DMSO-d₆): δ=8.92 (dd, 2H, J=14.1, 1.9 Hz), 8.10 (m, 3H), 7.03 (dd, 1H, J=17.7, 10.9 Hz), 6.15 (dd, 1H, J=17.7, 0.4Hz), 5.52 (d, 1H, J=11.1 Hz). LC/MS (Method A), rt=1.14 mins., purity=99%, calculated mass=156, [M+H]⁺=157.

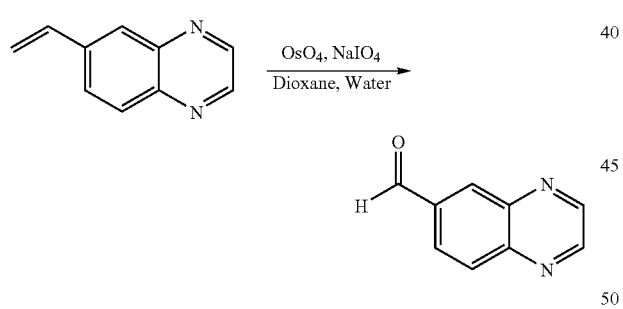

To a mixture of 6-vinylquinoxaline (0.68 g,4.35 mMol) in dioxane (44 mL) and water (35 mL) was added osmium tetraoxide (2.5% wt in t-BuOH, 2.18 mL, 0.17 mMol) followed by sodium periodate (2.79 g, 13.1 mMol) and the reaction stirred for three hours. The solution was diluted with ethyl acetate (150 mL) and then washed with water (3×75 mL) followed by brine (75 mL). The organics were dried with magnesium sulfate, filtered, and concentrated to dryness on a rotary evaporator. Purification by flash column chromatography on silica gel using 10-20% ethyl acetate in dichloromethane as eluant yielded 470 mg (68% yield) of quinoxaline-6-carboxaldehyde as a white solid. ¹H NMR (DMSO-d₆): δ=10.30 (s, 1H), 9.11 (d, 2H, J=1.9 Hz), 8.74 (d, 1H, J=1.4 Hz), 8.26 (m, 2H). LC/MS (Method A), rt=0.69 mins., purity=94.8%, calculated mass=158, [M+H]⁺=159.

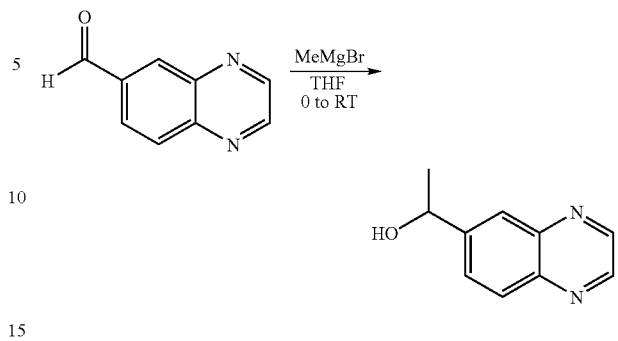

To a mixture of quinoxaline-6-carboxaldehyde (0.10 g, 0.63 mMol) in dry tetrahydrofuran (3 mL) at zero degrees was added methyl magnesium bromide (3M in Et₂O, 0.253 mL, 0.76 mMol) drop wise. Upon complete addition the ice bath was removed and the solution allowed to warm to room temperature. The reaction was quenched with methanol and 1N hydrochloric acid added until the pH was approximately seven. The neutral solution was partitioned between ethyl acetate and water, the aqueous layer discarded and the organics washed with brine. The organics were dried (MgSO₄), filtered, and concentrated to dryness on a rotary evaporator. Purification by flash column chromatography on silica gel using 10-100% methanol in dichloromethane yielded 62 mg (56% yield) of 6-(1-hydroxyethyl)quinoxaline as a clear oil. ¹H NMR (DMSO-d₆): δ=8.92 (dd, 2H, J=9.1, 1.9 Hz), 8.06 (d, 1H, J=8.6 Hz), 8.02 (d, 1H, J=1.7 Hz), 7.87 (dd, 1H, J=8.7, 1.9 Hz), 5.51 (br s, 1H), 4.99 (q, 1H, J=6.4 Hz), 1.43 (d, 3H, J=6.4 Hz). LC/MS (Method A), rt=0.56 mins., purity=99%, calculated mass=174, [M+H]⁺=175.

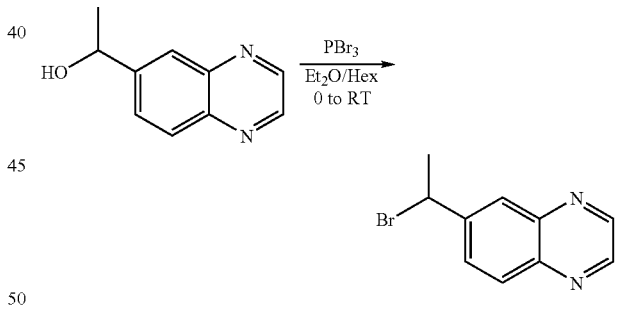

To a solution of 6-(1-hydroxyethyl)quinoxaline (0.4 g, 0.23 mMol) in ether (4 mL) and hexanes (2 mL) at zero degrees was added phosphorus tribromide (0.196 mL, 2.07 mMol) and the mixture stirred at zero degrees for one hour and then allowed to warm to room temperature. After two hours at room temperature the reaction mixture was poured over ice and then partitioned between ethyl acetate (100 mL) and water (100 mL). The aqueous layer was discarded and the organics washed with saturated sodium bicarbonate, then dried (MgSO₄), and concentrated to dryness to yield 20 mg (37% yield) of 6-(1-bromo-ethyl)-quinoxaline as a light yellow oil. ¹H NMR (CDCl₃): δ=8.79 (m, 2H), 8.06 (d, 1H, J=9.0 Hz), 8.04 (d, 1H, J=2.2 Hz), 7.85 (dd, 1H, J=9.0, 2.2 Hz), 5.34 (q, 1H, J=6.9 Hz), 2.10 (d, 3H, J=6.9 Hz).

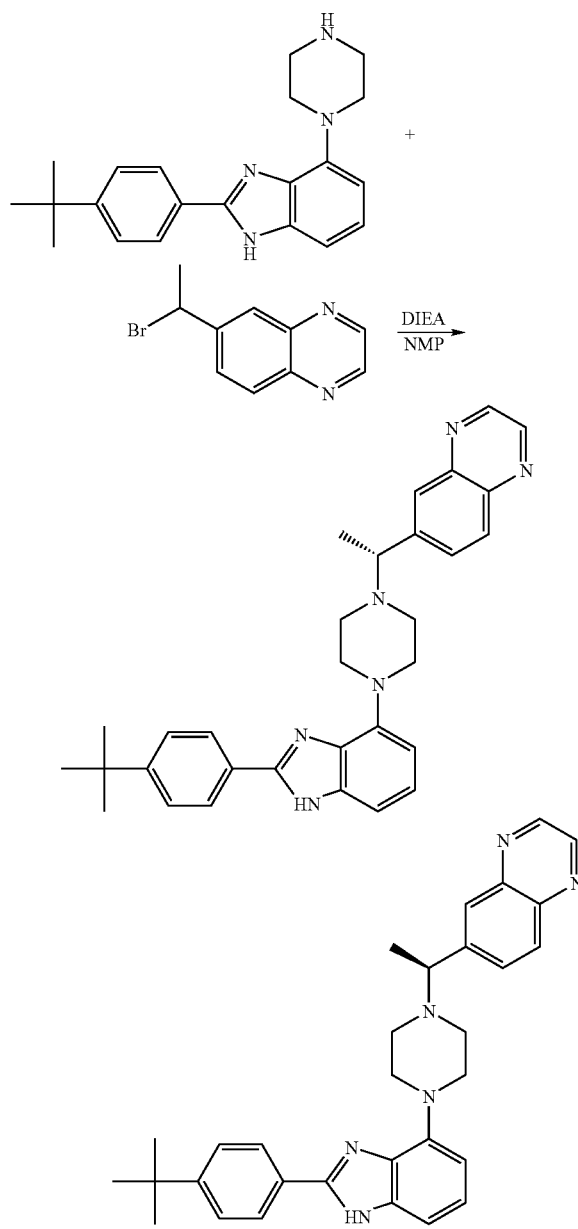

To a solution of 6-(1-Bromo-ethyl)-quinoxaline (0.2 g, 0.084 mMol) in N-methyl-pyrrolidinone (3 mL) and diisopropylethylamine (0.029 mL, 0.1 7 mMol) was added 2-(4-tert-Butyl-phenyl)-4-piperazin-1-yl-1H-benzoimidazole (0.028 g, 0.084 mMol) and the mixture stirred overnight. Upon arrival the solution was diluted with ethyl acetate (200 mL) and washed with water (4×75mL) and brine (75 mL). The organic layer was dried (MgSO$_4$), filtered, and concentrated to dryness on a rotary evaporator. Purification by flash column chromatography on silica gel using 5% methanol in dichloromethane yielded 38 mg (92% yield) of 6-(1-{4-[2-(4-tert-Butyl-phenyl)-1H-benzoimidazol-4-yl]-piperazin-1-yl}-ethyl)-quinoxaline as a racemate. This material was separated into the (R) and (S) enantiomers by chiral HPLC using a Chiralcel-OD 250×4.6 mmcolumn with an isocratic 90:10 acetonitrile:ethanol eluant. The first peak had a (+) chirality by CD and a retention time of 5.86 and the second peak a (−) chirality by CD and a retention time of 6.941. The fractions were concentrated and freeze dried to obtain 10 mg of each enantiomers. NMR,MS,and analytical HPLC were identical. $^1$H NMR (DMSO-d$_6$): δ=12.67 (s, 1H), 8.94 (dd, 2H, J=8.8, 1.8 Hz), 8.11 (d, 1H, J=8.7 Hz), 8.05 (s, 1H), 8.02 (d, 2H, J=8.5 Hz), 7.95 (dd, 1H, J=8.7, 1.7 Hz), 7.53 (d, 2H, J=8.6 Hz), 7.02 (m, 2H), 6.47 (dd, 1H, J=7, 1.4 Hz), 3.81 (q, 1H, J=6.8 Hz), 3.58 (br s, 4H), 2.75 (br s, 2H), 2.61 (br s, 2H), 1.49 (d, 3H, J=6.8 Hz), 1.32 (s, 9H). LC/MS (Method A), rt=1.07 mins., purity=99%, calculated mass=490, [M+H]$^+$=491,[M−H]$^-$=489. HPLC (Method C): rt=9.2mins., purity=94% @ 210-370 nm and 95.3% @ 304 nm.

Example 263

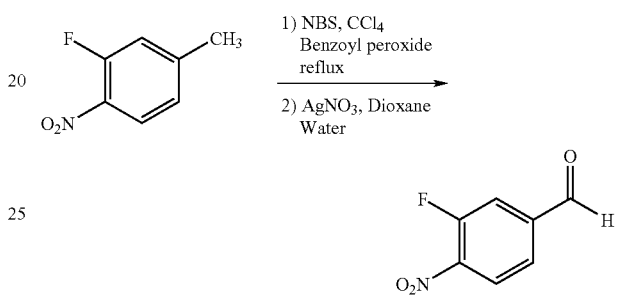

In a round bottom flask under nitrogen was combined 3-Fluoro-4-nitrotoluene (15 g, 96.7 mMol), N-bromosuccinimide (37.9 g, 212.7 mMol), and carbon tetrachloride (300 mL). The mixture was stirred at room temperature and benzoyl peroxide added (2.34 g, 9.67 mMol). A water-cooled reflux condenser was attached and the solution heated to reflux and stirred overnight. Upon arrival the solution was cooled to room temperature, diluted with dichloromethane (300 mL) and washed with 1N sodium hydroxide solution (2×200mL). The organic layer was then washed with water (200 mL) and concentrated to dryness on a rotary evaporator. The crude material was then redissolved in dioxane (450 mL) and water (50 mL) and stirred at room temperature. Silver nitrate (65.7 g, 387 mMol) was added and the material allowed to stir overnight. Upon arrival the reaction mixture was filtered and the solids washed with ethyl acetate. The filtrate was extracted with ethyl acetate (3×200 mL). The organics were dried with magnesium sulfate, filtered, and concentrated on a rotary evaporator. Purification by flash column silica gel chromatography 30% ethyl acetate in hexane as the eluant yielded a still impure product that was recolumned using 50% dichloromethane in hexane to give 5.7 g (35% yield) of 3-Fluoro-4-nitro-benzaldehyde. $^1$H NMR (DMSO-d$_6$): δ=10.09 (s, 1H), 8.36 (m, 1H), 8.07 (dd, 1H, J=11, 1.5 Hz), 7.96 (dd, 1H, J=8.3, 1.5 Hz).

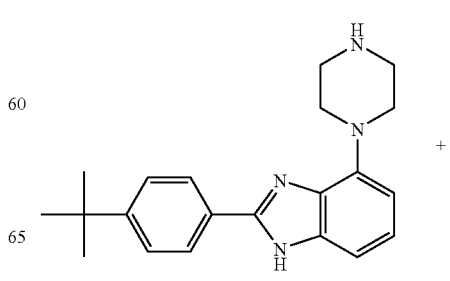

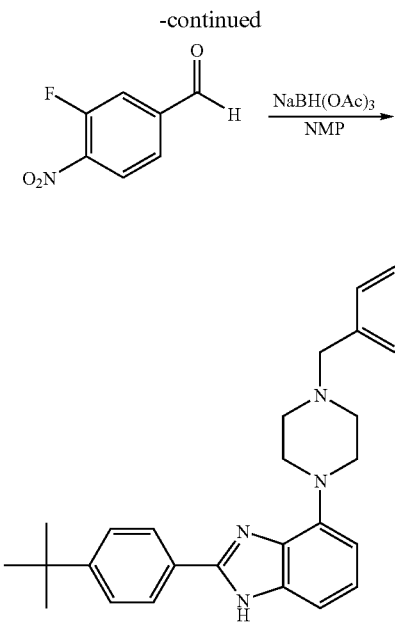

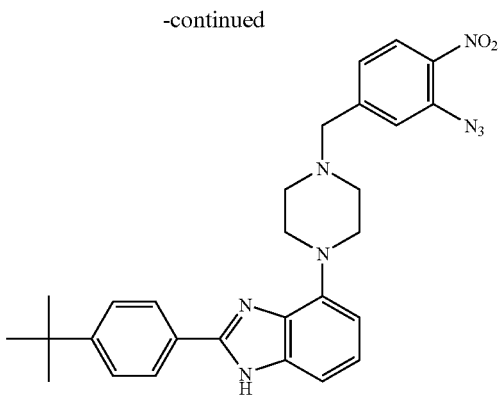

To a stirring solution of 2-(4-tert-Butyl-phenyl)-4-piperazin-1-yl-1H-benzoimidazole (0.857 g, 2.56 mMol) and 3-Fluoro-4-nitro-benzaldehyde (0.52 g, 3.07 mMol) in N-methylpyrrolidinone (20 mL) was added sodium triacetoxyborohydride (1.36 g, 6.40 mMol) and the solution stirred overnight. Upon arrival the solution was diluted with ethyl acetate (200 mL). The mixture was washed with saturated sodium bicarbonate solution (75 mL), water (75 mL), and brine (75 mL). The organic layer was then dried with magnesium sulfate, filtered, concentrated, and purified by flash column chromatography on silica gel using 40% ethyl acetate in hexane as the eluant to yield 850 mg (68% yield) of 2-(4-tert-Butyl-phenyl)-4-[4-(3-fluoro-4-nitro-benzyl)-piperazin-1-yl]-1H-benzoimidazole as a light yellow solid. $^1$H NMR (DMSO-d$_6$): δ=12.69 (s, 1H), 8.16 (t, 1H, J=8.2 Hz), 8.04 (d, 2H, J=8.5 Hz), 7.59 (m, 1H), 7.55 (d, 2H, J=8.5 Hz), 7.47 (d, 1H, J=8.6 Hz), 7.03 (m, 2H), 6.50 (dd, 1H, J=7.0, 1.8 Hz), 3.71 (s, 2H), 3.60 (br s, 4H), 2.66 (br s, 4H), 1.33 (s, 9H). LC/MS (Method A), rt=1.24 mins., purity=100%, calculated mass=487, [M+H]$^+$=488, [M−H]$^-$=486.

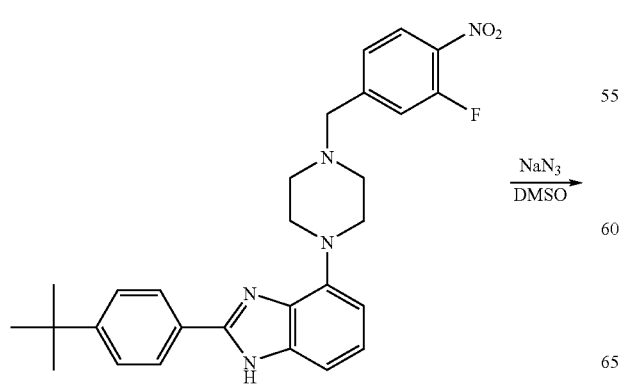

In a round bottom flask was combined 2-(4-tert-Butyl-phenyl)-4-[4-(3-fluoro-4-nitro-benzyl)-piperazin-1-yl]-1H-benzoimidazole (0.197 g, 0.40 mMol), dimethyl sulfoxide (3 mL), and sodium azide (0.029 g, 0.44 mMol) and the mixture stirred overnight. Upon arrival the mixture was diluted with ethyl acetate (100 mL), washed with water (2×50 mL), washed with brine (50 mL), and the organics dried with magnesium sulfate and filtered. The organics were concentrated on a rotary evaporator to yield 190 mg (92% yield) of 4-[4-(3-Azido-4-nitro-benzyl)-piperazin-1-yl]-2-(4-tert-butyl-phenyl)-1H-benzoimidazole as a light yellow solid. $^1$H NMR (DMSO-d$_6$): δ=12.69 (s, 1H), 8.04 (d, 2H, J=8.7 Hz), 8.01 (d, 1H, J=8.3 Hz), 7.57 (m, 1H), 7.54 (d, 2H, J=8.6 Hz), 7.39 (dd, 1H, J=8.5, 1.2 Hz), 7.03 (m, 2H), 6.50 (dd, 1H, J=5.5, 1.4 Hz), 3.70 (s, 2H), 3.60 (br s, 4H), 2.68 (br s, 4H), 1.33 (s, 9H). LC/MS (Method A), rt=1.41 mins., purity=89.8%, calculated mass=510, [M+H]$^+$=511, [M−H]$^-$=509.

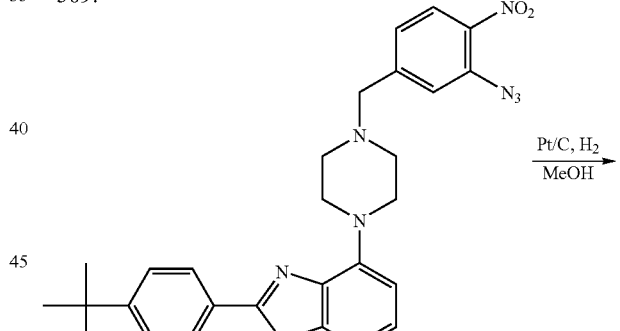

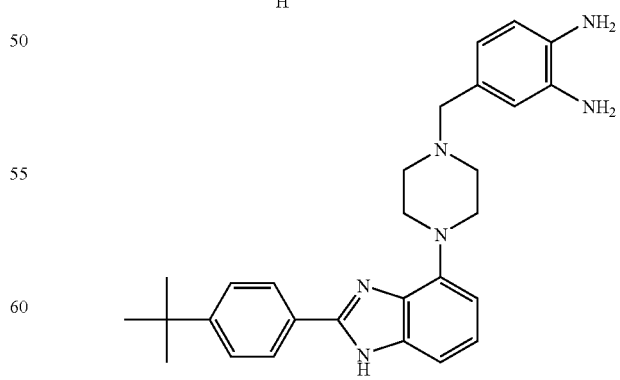

In a round bottom flask under nitrogen was combined 4-[4-(3-Azido-4-nitro-benzyl)-piperazin-1-yl]-2-(4-tert-butyl-phenyl)-1H-benzoimidazole (0.19 g, 0.37 mMol), methanol (20 mL), and 5% platinum on carbon (0.145 g, 0.037 mMol). A hydrogen balloon was attached, the flask evacuated, and a hydrogen atmosphere established. After stirring for four hours, the balloon was removed, the flask purged with nitrogen, and the reaction mixture filtered thru Celite with a large excess of methanol. The solution was concentrated to dryness on a rotary evaporator to yield 170 mg (100% yield) of 4-{4-[2-(4-tert-Butyl-phenyl)-1H-benzoimidazol-4-yl]-piperazin-1-ylmethyl}-benzene-1,2-diamine as a brown oil. LC/MS (Method A), rt=0.90 mins., purity=85.9%, calculated mass=454, [M+H]$^+$=455, [M−H]$^−$=453.

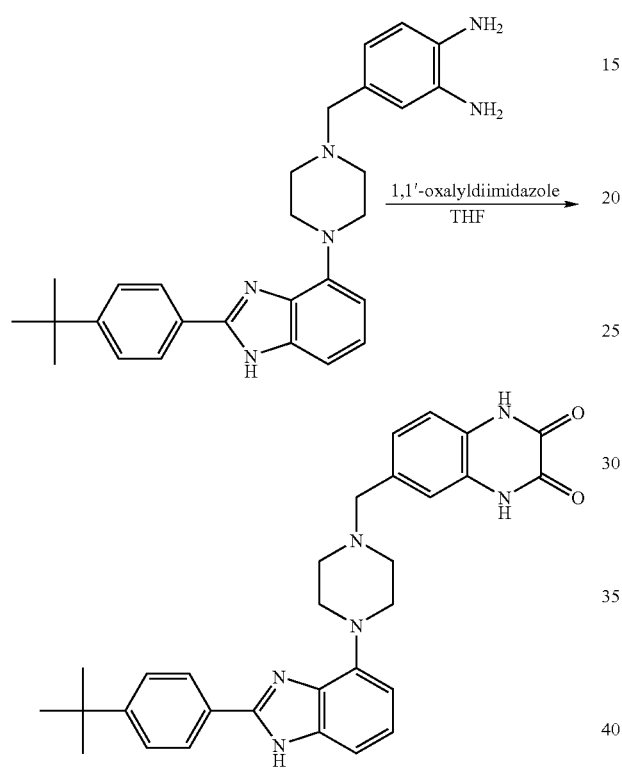

In a round bottom flask under nitrogen was combined 4-{4-[2-(4-tert-Butyl-phenyl)-1H-benzoimidazol-4-yl]-piperazin-1-ylmethyl}-benzene-1,2-diamine (0.17 g, 0.37 mMol), tetrahydrofuran (20 mL), and 1,1'-oxalyldiimidazole (0.284 g, 1.5 mMol) and the solution stirred overnight. Upon arrival the solution was diluted with ethyl acetate (100 mL) and washed with water (100 mL). A precipitate forms and was collected by filtration. The organic layer was concentrated to dryness on a rotary evaporator and combined with the precipitate. Purification by RP-HPLC (Method E) yielded 46 mg (24% yield) of 6-{4-[2-(4-tert-Butyl-phenyl)-1H-benzoimidazol-4-yl]-piperazin-1-ylmethyl}-1,4-dihydro-quinoxaline-2,3-dione as an off-white solid. $^1$H NMR (DMSO-d$_6$): δ=12.19 (s, 1H), 12.09 (s, 1H), 9.82 (br s, 1H), 8.07 (d, 2H, J=8.6 Hz), 7.58 (d, 2H, J=8.6 Hz), 7.27 (m, 2H), 7.22 (d ,1H, J=8.6 Hz), 7.13 (m, 2H), 6.64 (m, 1H), 4.48 (br s, 2H), 4.44 (s, 2H), 3.50 (br s, 2H), 3.38 (br s, 2H), 3.09 (m, 2H), 1.34 (s, 9H). HPLC: Xterra MS C18, 3.5 μm, 4.6×50 mm, flow=0.8 m/min, 5-95% ACN/PICB6 over 10 mins., rt=5.840 mins., 79% pure @ 210 nm, 77% pure @ 300 nm. LC/MS (Method A), rt=1.05 mins., purity=79.19%, calculated mass=508, [M+H]$^+$=509, [M−H]$^−$=507.

Examples 264-291

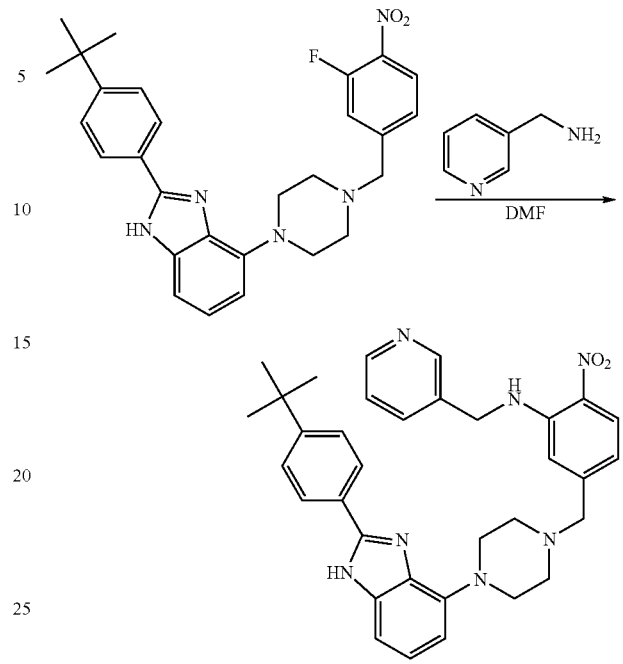

To a mixture of 2-(4-tert-Butyl-phenyl)-4-[4-(3-fluoro-4-nitro-benzyl)-piperazin-1-yl]-1H-benzoimidazole (75 mg, 0.15 mMol) in dimethylformamide (2 mL) under nitrogen was added 3-(Aminomethyl) pyridine (0.078 mL, 0.77 mMol) and the resulting solution stirred overnight at room temperature. Upon arrival the reaction mixture was diluted with ethyl acetate (50 mL) and washed three times with water (50 mL) followed by brine (50 mL). The organics were dried with magnesium sulfate, filtered, and evaporated to dryness. Purification by flash column chromatography on silica gel and 5% methanol in dichloromethane as eluant yielded 50 mg of (5-{4-[2-(4-tert-Butyl-phenyl)-1H-benzoimidazol -4-yl]-piperazin-1-ylmethyl}-2-nitro-phenyl)-pyridin-3-ylmethyl-amine as a yellow-orange solid (56% yield). $^1$H NMR (CDCl$_3$): δ=9.24 (s, 1H), 8.66 (s, 1H), 8.55 (m, 1H), 8.43 (m, 1H), 8.16 (d, 1H, J=7.5 Hz), 8.03 (m, 1H), 7.93 (d, 2H, J=7.5 Hz), 7.69 (d, 1H, J=6.0 Hz), 7.49 (d, 2H, J=7.5 Hz), 7.14 (m, 1H), 7.04 (d, 1H, J=6.0 Hz), 6.87 (s, 1H), 6.73 (m, 1H), 6.59 (d, 1H, J=6.0 Hz), 4.60 (m, 2H), 3.55 (m, 6H), 2.68 (m, 4H), 1.34 (s, 9H). LC/MS (Method A), rt=1.05 mins., purity=98.5%, calculated mass=575, [M+H]$^+$=576, [M−H]$^−$=574.

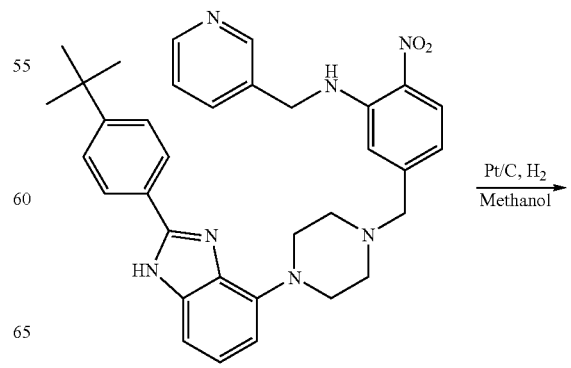

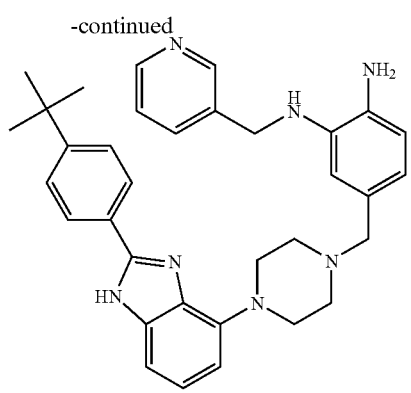

To a solution of (5-{4-[2-(4-tert-Butyl-phenyl)-1H-benzoimidazol-4-yl]-piperazin-1-ylmethyl}-2-nitro-phenyl)-pyridin-3-ylmethyl-amine (0.05 g, 0.087 mMol) in methanol (10 mL) under nitrogen was added platinum on carbon (0.034g, 0.0087 mMol) and the reaction mixture evacuated. A hydrogen filled balloon was attached and the mixture stirred under a hydrogen atmosphere for two hours. The balloon was removed, the flask purged with nitrogen, and the mixture filtered thru Celite with a large excess of methanol. The resulting solution was concentrated to dryness on a rotory evaporator to yield 4-{4-[2-(4-tert-Butyl-phenyl)-1H-benzoimidazol-4-yl]-piperazin-1-ylmethyl}-N2-pyridin-3-ylmethyl-benzene-1,2-diamine as a crude oil (0.047 g, 100% yield). LC/MS (Method A), rt=0.86 mins., purity=68%, calculated mass=545, [M+H]$^+$=546, [M−H]$^−$=544.

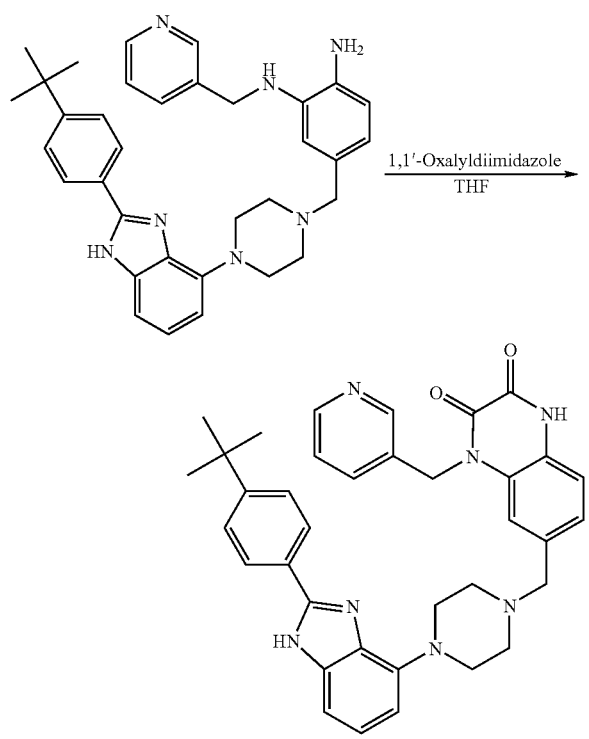

To a solution of 4-{4-[2-(4-tert-Butyl-phenyl)-1H-benzoimidazol-4-yl]-piperazin-1-ylmethyl}-N2-pyridin-3-ylmethyl-benzene-1,2-diamine (0.047g, 0.086 mMol) in dry tetrahydrofuran (10 mL) was added 1,1'-oxalyldiimidazole (0.082g, 0.43 mMol) and the solution stirred at room temperature for sixteen hours. The solution was diluted with ethyl acetate (100 mL), washed with water (2×50 mL), brine (50 mL), and the organic layer dried (MgSO$_4$). After filtration the solution was concentrated and purified by RP-HPLC (Method E). $^1$H NMR (DMSO-d$_6$): δ=12.29 (s, 1H), 9.86 (br s, 1H), 8.74 (s, 1H), 8.52 (d, 1H, J=4.3 Hz), 8.10 (d, 2H, J=8.4 Hz), 7.87 (d, 1H, J=8.0 Hz), 7.59 (d, 2H, J=8.5 Hz), 7.45 (dd, 1H, J=7.9, 4.9 Hz), 7.38 (s, 1H), 7.35 (d, 1H, J=8.6 Hz), 7.29 (d, 1H, J=8.1 Hz), 7.15 (m, 2H), 6.63 (dd, 1H, J=6.8, 1.6 Hz), 5.45 (s, 2H), 4.38 (m, 4H), 3.36-3.02 (m, 6H), 1.34 (s, 9H). LC/MS (Method A), rt=0.94 mins., purity=100%, calculated mass=599, [M+H]$^+$=600, [M−H]$^−$=598.

Table 12 indicates other examples prepared using the above method for example 264:

TABLE 12

| Example | $R_T$ | $R_U$ | $R_V$ | [M + H]$^+$ |
|---|---|---|---|---|
| 265 | Et | H | H | 481 |
| 266 | t-Bu | H | H | 509 |
| 267 | " | {R}-Me | H | 523 |
| 268 | " | {S}-Me | H | 523 |
| 269 | " | {S}-Et | H | 559 |
| 270 | i-Pr | H | H | 495 |
| 271 | MeSO$_2$ | H | H | 531 |
| 272 | EtSO$_2$ | H | H | 545 |
| 273 | Et | H | Me | 495 |
| 274 | Et | H | Et | 509 |
| 275 | Et | H | i-Pr | 523 |
| 276 | Et | H | cyclobutyl | 535 |
| 277 | Et | H | cyclopropylmethyl | 535 |
| 278 | Et | H | isobutyl | 537 |
| 279 | Et | H | cyclopentyl | 549 |
| 280 | Et | H | cyclohexyl | 563 |
| 281 | Et | H | benzyl | 571 |

TABLE 12-continued

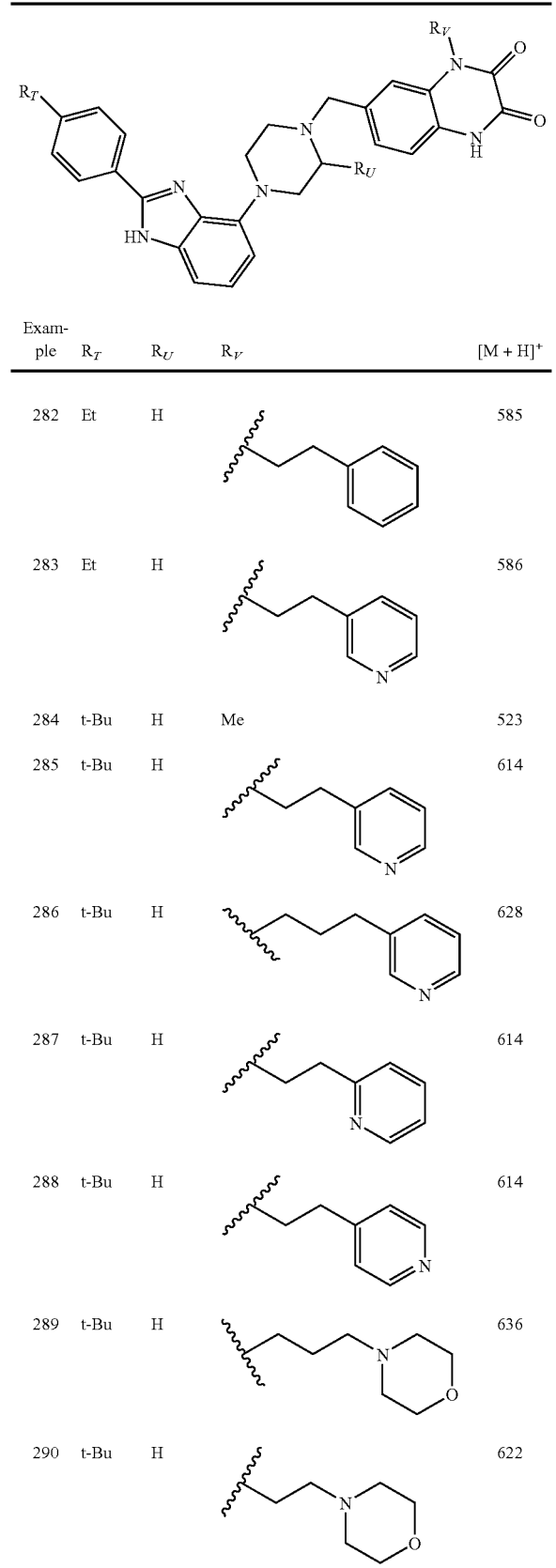

| Example | $R_T$ | $R_U$ | $R_V$ | $[M + H]^+$ |
|---|---|---|---|---|
| 282 | Et | H | | 585 |
| 283 | Et | H | | 586 |
| 284 | t-Bu | H | Me | 523 |
| 285 | t-Bu | H | | 614 |
| 286 | t-Bu | H | | 628 |
| 287 | t-Bu | H | | 614 |
| 288 | t-Bu | H | | 614 |
| 289 | t-Bu | H | | 636 |
| 290 | t-Bu | H | | 622 |

TABLE 12-continued

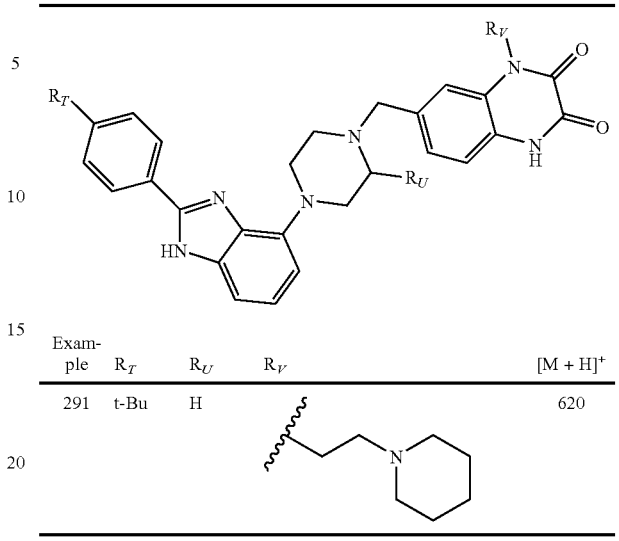

| Example | $R_T$ | $R_U$ | $R_V$ | $[M + H]^+$ |
|---|---|---|---|---|
| 291 | t-Bu | H | | 620 |

Example 292-303

(4-Fluoro-3-nitro-phenyl)-methanol

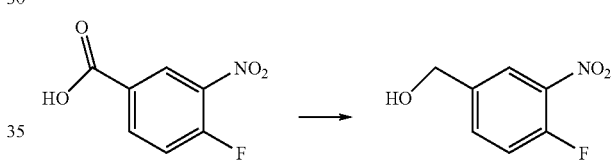

4-Fluoro-3-nitro-benzoic acid (185 mg, 1 mmol) was dissolved in THF (2 ml) and cooled to 0° C. under a nitrogen atmosphere. A Borane/THF solution (2 ml of a 1M solution, 2 mmol) was added dropwise, and the reaction mixture was heated to reflux for 1 h. The reaction was judged complete and quenched with 3N HCl (0.5 ml) and the solvent was removed under vacuum. The reaction mixture was partitioned between ethyl acetate and a sodium carbonate solution. The organic layer was washed with carbonate two additional times, and then it was washed with brine. It was dried over MgSO$_4$, and the solvent was removed to yield the title product (160 mg (95%), 0.94 mmol). $^1$H NMR (DMSO-d$_6$): δ=8.10 (s, 1H), 7.62 (d, J=7.3 Hz, 1H), 7.32 (d, J=7.3 Hz, 1H), 4.82 (d, J=4.5 Hz, 2H).

4-Bromomethyl-1-fluoro-2-nitro-benzene

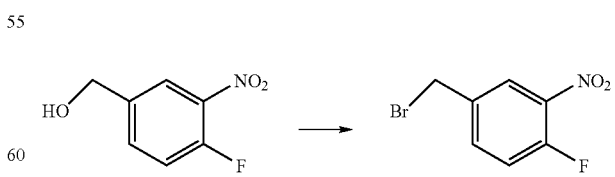

(4-Fluoro-3-nitro-phenyl)-methanol (100 mg, 0.58 mmol) was dissolved in toluene (1 ml) under nitrogen. PBr$_3$ (225 mg, 0.83 mmol) was added and the reaction was allowed to stir at room temperature. The solvent was removed under vacuum. The reaction mixture was partitioned between ethyl acetate and brine. The organic layer was washed with brine two additional times, dried over MgSO₄, and the solvent removed to yield the title product as a yellow oil (110 mg (81%), 0.47 mmol). ¹H NMR (DMSO-d₆): δ=8.04 (s, 1H), 7.68 (d, J=7.5 Hz, 1H), 7.38 (d, J=7.5 Hz, 1H), 3.85 (d, J=4.5 Hz, 2H).

2-(4-Ethyl-phenyl)-7-[4-(4-fluoro-3-nitro-benzyl)-piperazin-1-yl]-1H-benzoimidazole

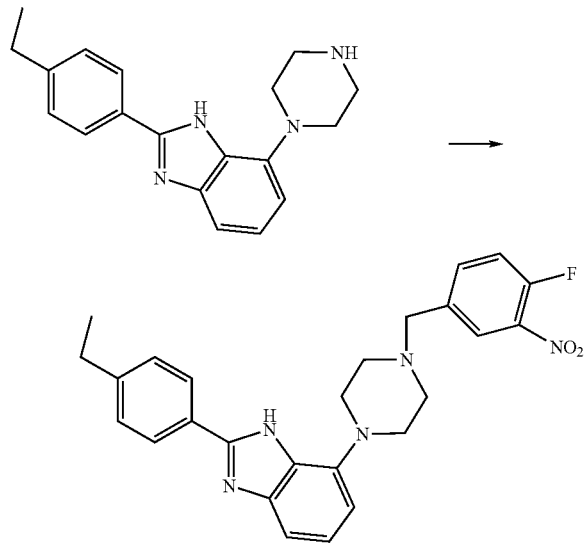

2-(4-Ethyl-phenyl)-7-piperazin-1-yl-1H-benzoimidazole (200 mg, 0.65 mmol) and 4-bromomethyl-1-fluoro-2-nitro-benzene (152 mg, 0.65 mmol) were stirred together with DIEA (83 mg, 0.6.5 mmol) in DMF (4 ml) at room temperature. After 1 h, the reaction is complete and it was purified by HPLC Method E to yield the title product (100 mg (34%), 0.22 mmol). ¹H NMR (DMSO-d₆): δ=12.71 (s, 1H), 8.15 (m, 1H), 8.04 (d, J=8.2 Hz, 2H), 7.83 (m, 1H), 7.59 (m, 1H), 7.34 (d, J=8.2 Hz, 2H), 7.08 (m, 2H), 6.52 (dd, J=6.64, 1.94 Hz, 1H), 3.69 (s, 2H), 3.65 (bs, 4H), 2.75 (bs, 6H), 1.32 (t, J=7.6 Hz, 3H). Calculated mass=457.43, [M+H]⁺=458.

6-{4-[2-(4-Ethyl-phenyl)-3H-benzoimidazol-4-yl]-piperazin-1-ylmethyl}-1-methyl-1,4-dihydro-quinoxaline-2,3-dione

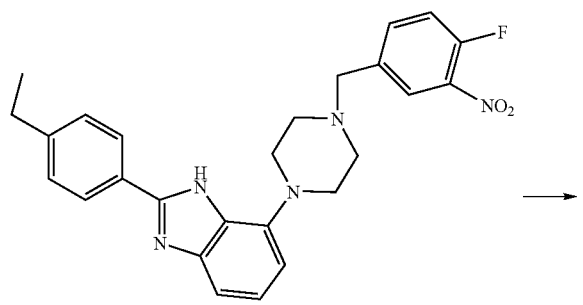

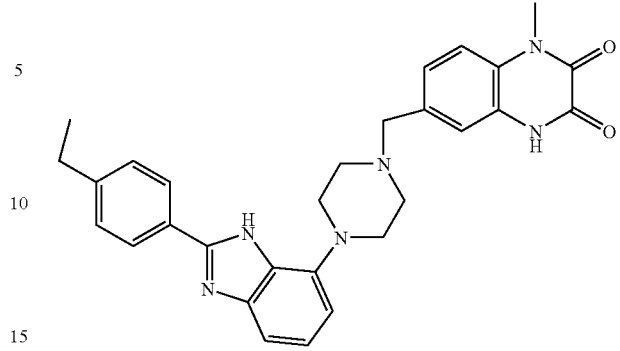

2-(4-Ethyl-phenyl)-7-[4-(4-fluoro-3-nitro-benzyl)-piperazin-1-yl]-1H-benzoimidazole (100 mg, 0.2 mmol) was dissolved in DMF (2 ml) with methylamine (0.15 ml of a 2.0 M solution) in a sealed tube. The reaction mixture was heated to 50° C. for 12 h. The reaction mixture was partitioned between ethyl acetate and brine. The organic layer was washed with brine two additional times, dried over MgSO₄, and the solvent removed to yield the crude nitro-amine. This crude was dissolved in MeOH (2 ml). The flask was purged of all oxygen, placed under a nitrogen atmosphere, and charged with Pd/C (20 mg of 10% palladium on carbon). The reaction mixture was purged, and placed under a hydrogen atmosphere, maintained with a balloon. It was allowed to stir for 18 h until the reduction was judged complete. The reaction mixture was filtered through Celite™ and the MeOH was removed under vacuum. The crude was taken up in THF (1 ml) and treated with oxalyl di-imidazole (44 mg, 0.23 mmol). This reaction mixture was purified by Method E to yield the title product (16 mg (16%), 0.03 mmol). ¹H NMR (DMSO-d₆): δ=12.29 (s, 1H), 9.90 (s, 1H), 8.06 (d, J=8Hz, 2H), 7.52 (d, J=8 Hz, 1H), 7.40 (m, 3H), 7.32 (d, J=2Hz, 1H), 7.18 (m, 2H), 6.64 (m, 1H), 4.53 (s, 2H), 3.72-3.92 (m, 8H), 3.56 (s, 3H), 2.70 (q, J=8 Hz, 2H), 1.21 (t, J=6 Hz, 3H). Calculated mass=494.62, [M+H]+495.

Table 13 indicates other examples prepared using the above method for example 292:

TABLE 13

| Example | R_W | [M + H]⁺ |
|---|---|---|
| 293 | cyclobutyl | 535 |
| 294 | cyclopropylmethyl | 535 |

TABLE 13-continued

| Example | R_W | [M + H]⁺ |
|---|---|---|
| 295 | isobutyl | 537 |
| 296 | cyclopentylmethyl | 549 |
| 297 | cyclohexylmethyl | 563 |
| 298 | benzyl | 571 |
| 299 | (4-pyridyl)methyl | 572 |
| 300 | (3-pyridyl)methyl | 572 |
| 301 | phenethyl | 585 |
| 302 | 2-(3-pyridyl)ethyl | 586 |
| 303 | Et | 509 |

Examples 304-323

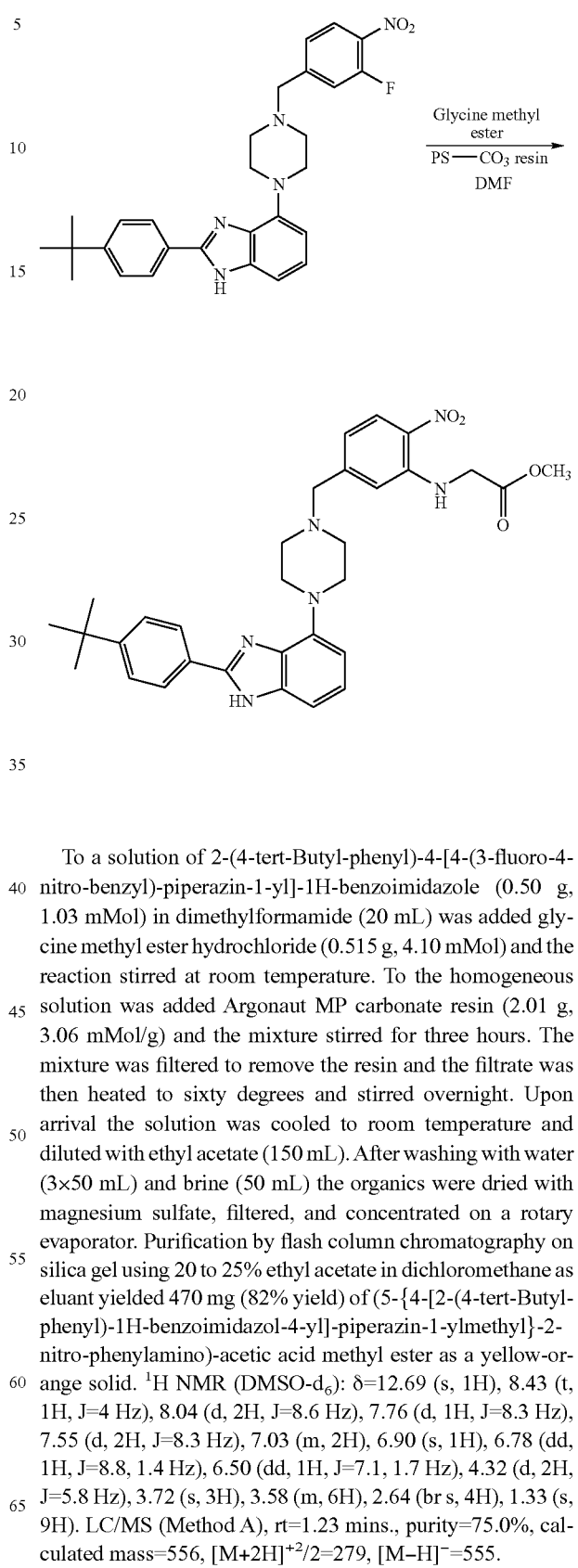

To a solution of 2-(4-tert-Butyl-phenyl)-4-[4-(3-fluoro-4-nitro-benzyl)-piperazin-1-yl]-1H-benzoimidazole (0.50 g, 1.03 mMol) in dimethylformamide (20 mL) was added glycine methyl ester hydrochloride (0.515 g, 4.10 mMol) and the reaction stirred at room temperature. To the homogeneous solution was added Argonaut MP carbonate resin (2.01 g, 3.06 mMol/g) and the mixture stirred for three hours. The mixture was filtered to remove the resin and the filtrate was then heated to sixty degrees and stirred overnight. Upon arrival the solution was cooled to room temperature and diluted with ethyl acetate (150 mL). After washing with water (3×50 mL) and brine (50 mL) the organics were dried with magnesium sulfate, filtered, and concentrated on a rotary evaporator. Purification by flash column chromatography on silica gel using 20 to 25% ethyl acetate in dichloromethane as eluant yielded 470 mg (82% yield) of (5-{4-[2-(4-tert-Butyl-phenyl)-1H-benzoimidazol-4-yl]-piperazin-1-ylmethyl}-2-nitro-phenylamino)-acetic acid methyl ester as a yellow-orange solid. $^1$H NMR (DMSO-$d_6$): δ=12.69 (s, 1H), 8.43 (t, 1H, J=4 Hz), 8.04 (d, 2H, J=8.6 Hz), 7.76 (d, 1H, J=8.3 Hz), 7.55 (d, 2H, J=8.3 Hz), 7.03 (m, 2H), 6.90 (s, 1H), 6.78 (dd, 1H, J=8.8, 1.4 Hz), 6.50 (dd, 1H, J=7.1, 1.7 Hz), 4.32 (d, 2H, J=5.8 Hz), 3.72 (s, 3H), 3.58 (m, 6H), 2.64 (br s, 4H), 1.33 (s, 9H). LC/MS (Method A), rt=1.23 mins., purity=75.0%, calculated mass=556, [M+2H]⁺²/2=279, [M−H]⁻=555.

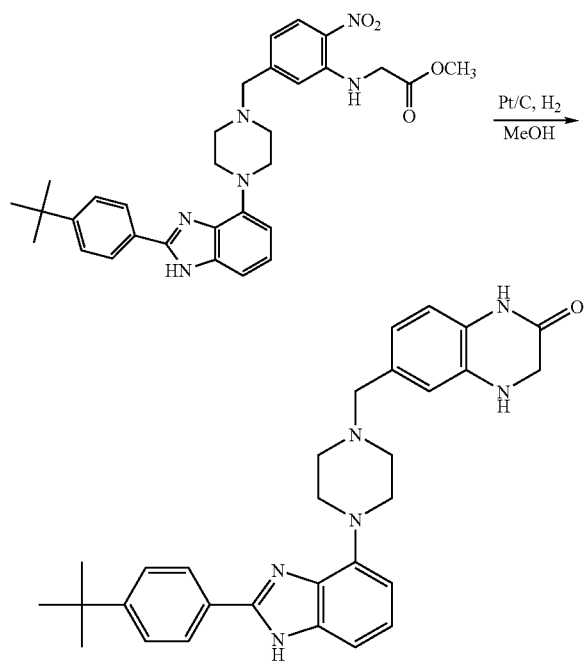

In a round bottom flask under nitrogen was combined (5-{4-[2-(4-tert-Butyl-phenyl)-1H-piperazin-1-ylmethyl}-2-nitro-phenylamino)-acetic acid methyl ester (0.47 g, 0.84 mMol), methanol (40 mL), and 10% platinum on carbon (0.165 g, 0.08 mMol). A hydrogen balloon was attached, the flask evacuated, and a hydrogen atmosphere established. After stirring for three hours, the balloon was removed, the flask purged with nitrogen, and the reaction mixture filtered thru Celite with a large excess of methanol. The solution was concentrated to dryness on a rotary evaporator and purified by RP-HPLC (Method E) to yield 49 mg (12% yield) of 6-{4-[2-(4-tert-Butyl-phenyl)-1H-benzoimidazol-4-yl]-piperazin-1-ylmethyl}-3,4-dihydro-1H-quinoxalin-2-one as a white solid. $^1$H NMR (DMSO-d$_6$): δ=12.61 (br s, 1H), 10.42 (s, 1H), 9.62 (br s, 1H), 8.07 (d, 2H, J=8.6 Hz), 7.58 (d, 2H, J=8.5 Hz), 7.15 (m, 2H), 6.80 (m, 3H), 6.64 (br s, 1H), 4.43 (br s, 2H), 4.28 (s, 2H), 3.78 (s, 2H), 3.50 (m, 2H), 3.33 (m, 2H), 3.10 (t, 2H, J=12 Hz), 1.34 (s, 9H). LC/MS (Method A), rt=0.99 mins., purity=99.0%, calculated mass=494, [M+H]$^+$=495, [M−H]$^-$=493.

Table 14 indicates other examples prepared using the above method for example 304:

TABLE 14

| Example | R$_X$ | [M + H]$^+$ |
|---|---|---|
| 306 | H | 467 |
| 307 | {S}-Me | 481 |
| 308 | {S}-CH$_2$OH | 497 |

TABLE 14-continued

| Example | R$_X$ | [M + H]$^+$ |
|---|---|---|
| 309 | {S}-i-Pr | 509 |
| 310 | {S}-i-Bu | 523 |
| 311 | benzyl | 557 |
| 312 | imidazolylmethyl | 547 |
| 313 | N-methylimidazolylmethyl | 561 |
| 314 | indolylmethyl | 596 |
| 315 | {R}-Me | 481 |
| 316 | {R}-CH$_2$OH | 497 |
| 317 | {R}-i-Pr | 509 |
| 318 | {R}-i-Bu | 523 |
| 319 | {R}-CH$_2$CONH$_2$ | 524 |
| 320 | benzyl | 557 |
| 321 | imidazolylmethyl | 547 |
| 322 | indolylmethyl | 596 |
| 323 | 4-hydroxybenzyl | 573 |

Examples 324-340

4-Ethylsulfonyl)Benzoic Acid

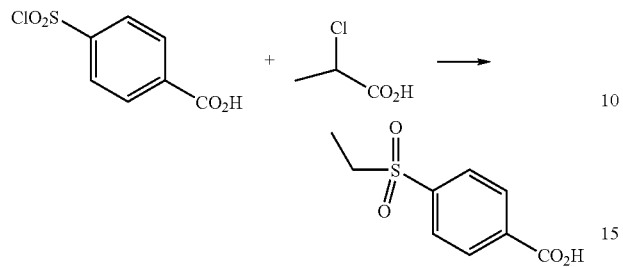

Prepared according to the method of *J. Org. Chem.* 1991, 4974. To a suspension of Na$_2$SO$_3$ (5.71 g, 45.3 mmol) and NaHCO$_3$ (11.42 g, 136 mmol) in H$_2$O (35 mL) heated in a 75° C. bath was added 4-(chlorosulfonyl)benzoic acid (10 g, 45.3 mmol) over 20 min. The resulting solution was heated in the bath for 1 h. To the reaction was added 2-chloropropionic acid (6.2 mL, 68 mmol), followed by a solution of NaOH (2.7 g) in H$_2$O (2.7 mL). The reaction was heated in a 105° C. bath for 72 h. The reaction was cooled to rt and brought to pH 1 by the addition of 3 N HCl. The white precipitate was collected by filtration and allowed to air dry. To complete the decarboxylation, the solid was heated in a flask in a 165° C. bath overnight. The resulting solid was heated in a 2:1 ethanol: H$_2$O solution (500 mL) and filtered hot. The filtrate was concentrated to half its volume and was cooled in an ice bath. The resulting slightly beige powder was collected by filtration to afford the title compound (5.3 g, 55%). $^1$H NMR (DMSO-d$_6$): δ 8.17 (d, J=8 Hz, 2H), 8.00 (d, J=8 Hz, 2H), 3.35 (q, J=7 Hz, 2H), 1.11 (t, J=7 Hz, 3H). MS (APCI) (M−H)$^-$ 213.

4-(Isopropylsulfonyl)benzoic acid

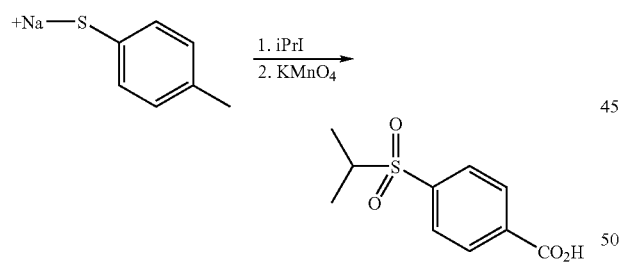

Prepared according to *J. Med. Chem.* 1968, 11, 1023. To a slurry of the sodium salt of 4-methyl benzenethiol (10.24 g, 70 mmol), 20% sodium ethoxide solution (1 mL) and ethanol (anhydrous, 60 mL) cooled in an ice bath was added 2-iodo propane (7 mL, 70 mmol) dropwise. The reaction was removed from the bath and was heated in a 75° C. bath for 5 h, then stirred at rt overnight. The reaction was concentrated to dryness. To the residue was added H$_2$O (40 mL) and Et$_2$O (70 mL) and the layers were separated. The aqueous layer was extracted with Et$_2$O (2×70 mL). The combined Et$_2$O layers were washed with H$_2$O (40 mL), 1 N NaOH solution (40 mL), H$_2$O (40 mL), 10% H$_2$SO$_4$ solution (40 mL) and H$_2$O (40 mL). The organic layer was dried (Na$_2$SO$_4$), filtered and concentrated to afford an orange oil (8.25 g). The oil was suspended in a solution of 10% NaOH (5 mL) and H$_2$O (250 mL) and KMnO$_4$ (31.4 g, 198 mmol) was added. The mixture was heated to reflux for 7 h, then cooled to rt. The solution was "decolorized" by adding 40% NaHSO$_3$ solution (250 mL), and filtering the mixture through diatomaceous earth. The filtrate was acidified with conc. HCl solution and the white precipitate was collected by filtration to afford the title compound (4.19 g, 26%) as a white powder. $^1$H NMR (DMSO-d$_6$): δ 8.18 (d, J=8 Hz, 2H), 7.97 (d, J=8 Hz, 2H), 1.16 (d, J=7 Hz, 6H). Note: methine is obscured by H$_2$O peak. MS (ESI) (M−H)$^-$ 227.

4-Benzenesulfonyl-benzoic acid

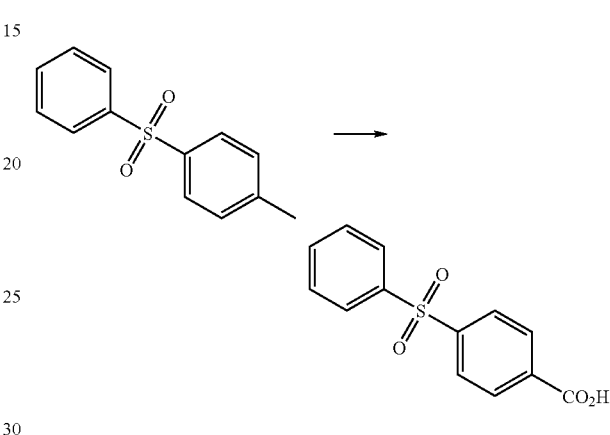

To a suspension of 1-benzenesulfonyl-4-methylbenzene (5.05 g, 21.7 mmol) in H$_2$O (100 mL) were added NaOH (2 pellets) and KMnO$_4$ (6.87 g, 43.5 mmol). The mixture was heated to reflux overnight. The reaction was cooled and additional NaOH (1 pellet) and KMnO$_4$ (4 g, 25 mmol) were added. The reaction was heated to reflux for 20 h. The reaction was cooled to rt and filtered to collect the solids. The filtrate was acidified with conc. HCl. The aqueous suspension was extracted with EtOAc (4×60 mL). The combined organic layers were washed with brine (60 mL), dried (Na$_2$SO$_4$), filtered and concentrated to provide the title compound (1.49 g, 26%) as an ivory powder. $^1$H NMR (DMSO-d$_6$): δ 8.11 (dd, J=7, 7 Hz, 4H), 7.97 (d, J=7 Hz, 2H), 7.71-7.65 (m, 3H). MS (M−H)$^-$ 261.

1-[(3-bromophenyl)thio]-2-methylpropan-2-ol

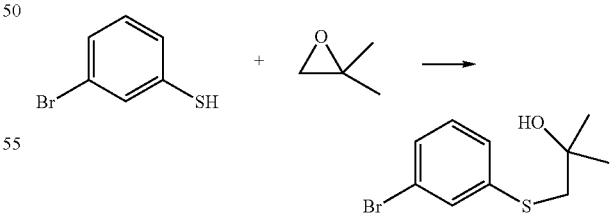

To a suspension of NaH (60% dispersion, 0.32 g, 8 mmol) in THF (30 mL) cooled in an ice bath was added dropwise 3-bromothiophenol (1.32 g, 7 mmol) in THF (5 mL). The solution was removed from the bath and stirred at rt for 1 h. The solution was returned to the ice bath and ethylene oxide (0.50 g, 7 mmol) in THF (2 mL) was added. The reaction was stirred at rt overnight. The solution was cooled in an ice bath, and NH$_4$Cl (aq.) solution was added to quench the reaction.

The solution was concentrated to remove the THF. The residue was dissolved in CH$_2$Cl$_2$ (75 mL) and washed with H$_2$O (35 mL) and brine (35 mL), dried (Na$_2$SO$_4$), filtered, and concentrated. The crude material was adsorbed onto silica and purified by column chromatography, eluting with a gradient of 15% EtOAc/hexane to 20% EtOAc/hexane to afford the title compound (1.34 g, 74%) as a colorless oil. $^1$H NMR (CDCl$_3$): δ 7.53 (t, J=2 Hz, 1H), 7.31 (dd, J=8, 2 Hz, 2H), 7.13 (t, J=8 Hz, 1H), 3.11 (s, 2H), 2.07 (s, 1H), 1.32 (s, 6H). MS (ESI) (M–OH)$^+$ 243.

4-Bromo-3,3-dimethyl-2,3-dihydro-1-benzothiophene and 6-bromo-3,3-dimethyl-2,3-dihydro-1-benzothiophene

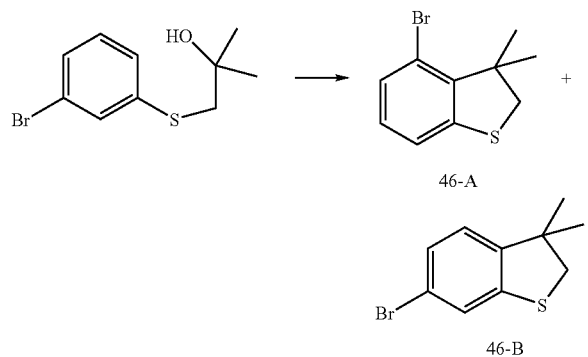

Prepared according to the method of EP (1993) 568898. To a suspension of aluminum chloride (2.30 g, 17.3 mmol) in carbon disulfide (20 mL) cooled in an ice bath was added dropwise a solution of 1-[(3-bromophenyl)thio]-2-methylpropan-2-ol (1.29 g, 4.9 mmol) in carbon disulfide (10 mL). The reaction was stirred at rt for 1 h, then heated in a 40° C. bath for 3 h. The reaction was cooled to rt, then poured onto conc. HCl (15 mL) on ice. The suspension was extracted with CH$_2$Cl$_2$ (2×50 mL). The combined organic layers were washed with sat. NaHCO$_3$ solution (30 mL), brine (30 mL), dried (Na$_2$SO$_4$), filtered, and concentrated. The mixture was purified by column chromatography, eluting with 1% EtOAc/hexane to afford the undesired isomer (46-A) and the bulk of the material (0.985 g, 82%) as a 60%:40% mixture of A:B isomers, which were carried on. $^1$H NMR (CDCl$_3$): 46-A δ 7.19 (dd, J=8, 1 Hz, 1H), 7.09 (dd, J=8, 1 Hz, 1H), 6.92 (t, J=8 Hz, 1H), 3.16 (s, 2H), 1.54 (s, 6H). $^1$H NMR (CDCl$_3$): 46-B δ 7.30 (d, J=2 Hz, 1H), 7.16 (dd, J=8, 2Hz, 1H), 6.88 (d, J=8 Hz, 1H), 3.17 (s, 2H), 1.35 (s, 6H). Anal. Calcd for C$_{10}$H$_{11}$BrS (mixture): C, 49.39; H, 4.56; N, 0.00. Found: C, 49.35; H, 4.74; N, 0.00.

3,3-dimethyl-2,3-dihydro-1-benzothiophene-4-carboxylic acid and 3,3-dimethyl-2,3-dihydro-1-benzothiophene-6-carboxylic acid

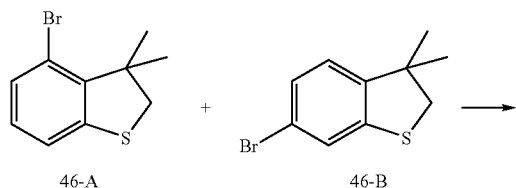

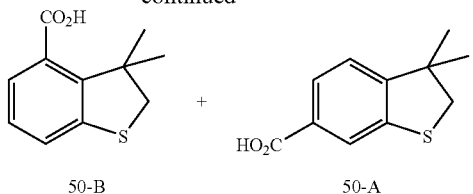

To a solution of the bromide isomers (0.98 g, 4.0 mmol) in THF (20 mL) cooled in a dry ice/acetone bath was added dropwise a solution of BuLi (2.5 M in hexane, 2 mL, 5.0 mmol). The reaction was stirred in the dry ice bath for 1.5 h, then was moved to an ice bath for 15 min. The reaction was returned to the dry ice/acetone bath and crushed solid dry ice (5 g) was added in portions. The reaction was poured onto crushed dry ice in a beaker, and allowed to come to rt. To the residue was added EtOAc (100 mL) and 1 N HCl solution (40 mL). The layers were separated and the aqueous layer was extracted with EtOAc (40 mL). The combined EtOAc layers were extracted with sat. NaHCO$_3$ solution (3×30 mL). The combined basic layers were cooled in an ice bath and acidified with conc. HCl. The aqueous mixture was extracted with EtOAc (3×40 mL). The combined EtOAc layers were washed with brine (30 mL), dried (Na$_2$SO$_4$), filtered and concentrated. The residue was purified by column chromatography, eluting with a gradient of 2% MeOH/CH$_2$Cl$_2$ to 4% MeOH/CH$_2$Cl$_2$ to afford a mixture of acid isomers (0.50 g, 60%) and a small portion of the slower eluting undesired isomer 50-B. $^1$H NMR (CDCl$_3$) mixture: only 3 peaks used for assignment of isomer ratio are reported: δ 7.90 (d, J=2 Hz, 1H, 50-A), 7.81 (dd, J=8, 2 Hz, 1H, 50-B), 3.23 (s, 2H), 3.17 (s, 2H), 1.55 (s, 6H, 50-B), 1.40 (s, 6H, 50-A). MS (ESI) (M–H)$^-$ 207.

3,3-Dimethyl-1,1-dioxo-2,3-dihydro-1H-1λ$^6$-benzo[b]thiophene-4-carboxylic acid and 3,3-dimethyl-1,1-dioxo-2,3-dihydro-1H-1λ$^6$-benzo[b]thiophene-6-carboxylic acid

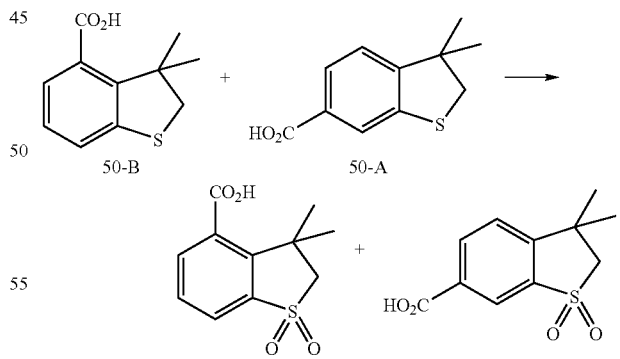

To a solution of the mixture of acid isomers (0.50 g, 2.4 mmol) in HOAc (10 mL) was added dropwise a solution of 30% H$_2$O$_2$ (2 mL). After the addition was complete, the reaction was heated in a 90° C. bath for 0.75 h. The reaction was cooled to rt and poured into H$_2$O (20 mL). EtOAc (50 mL) and NaCl were added and the layers were separated. The aqueous layer was extracted with EtOAc (2×40 mL) and the combined organic layers were washed with brine, dried (Na$_2$SO$_4$), filtered and concentrated to afford a mixture of the title compounds (0.48 g, 84%) as a white solid. MS (M–H)$^-$ 239.

-[2-(3,3-Dimethyl-1,1-dioxo-2,3-dihydro-1H-1λ$^6$-benzo[b]thiophen-6-yl)-1H-benzo-imidazol-4-yl]-piperazine-1-carboxylic acid tert-butyl ester

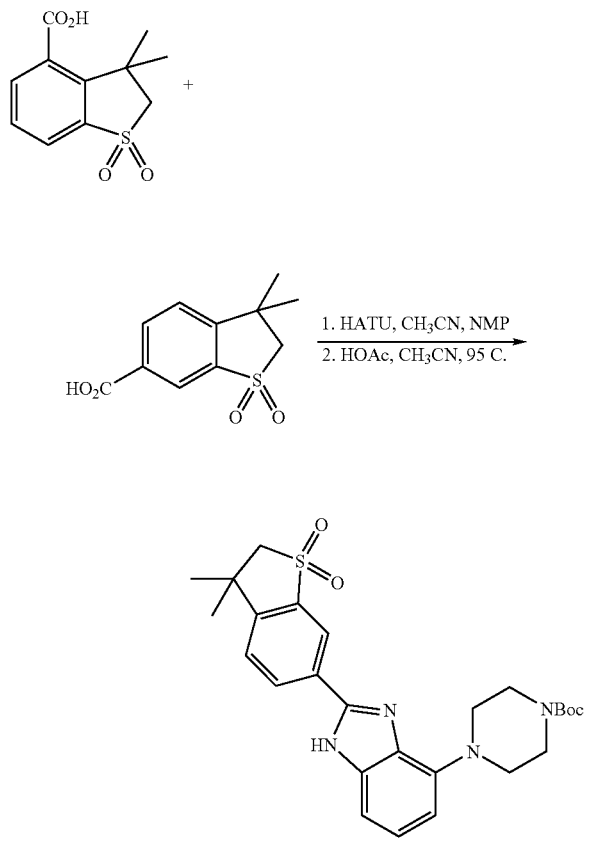

To a solution of the acid mixture (1.07 g, 4.45 mmol) and 4-(2,3-diamino-phenyl)-piperazine-1-carboxylic acid tert-butyl ester (1.3 g, 4.45 mmol) in CH$_3$CN (anh., 35 mL) was added HATU (2.03 g, 5.34 mmol) and the reaction was stirred at rt for 8 h. An additional portion of HATU (0.2 g) and NMP (4 mL) were added and the reaction was stirred overnight. The reaction was concentrated under reduced pressure to remove the CH$_3$CN. To the residue was added EtOAc (150 mL) and sat. NaHCO$_3$ (50 mL) and the layers were separated. The organic layer was washed with sat. NaHCO$_3$ (50 mL), H$_2$O (4×50 mL), and brine (50 mL). The organic layer was dried (Na$_2$SO$_4$), filtered and concentrated to afford a dark brown solid. The solid was dissolved in CH$_3$CN (50 mL) and glacial HOAc (10 mL) was added. The reaction was heated in a 95 C bath for 3.5 h. The reaction was cooled to rt and concentrated under reduced pressure. The remaining HOAc was neutralized by slow, careful addition of sat. NaHCO$_3$ solution. To the crude reaction was added EtOAc (75 mL) and H$_2$O (40 mL) and the layers were separated. The aqueous layer was extracted with EtOAc (2×40 mL). The combined organic layers were washed with H$_2$O (50 mL) and brine (40 mL), dried (Na$_2$SO$_4$), filtered, and concentrated. The residue was purified by column chromatography, eluting with a gradient of 40% EtOAc/hexane to 50% EtOAc/hexane to afford the title compound (0.37 g, 17%) as an orange foam. $^1$H NMR (CDCl$_3$): δ 8.50 (dd, J=8, 2 Hz, 1H), 8.34 (d, J=2 Hz, 1H), 7.51 (d, J=8 Hz, 1H), 7.22-7.16 (m, 2H), 6.67 (d, J=8 Hz, 1H), 3.72 (brs, 4H), 3.45 (brs, 4H), 3.43 (s, 2H), 1.57 (s, 6H), 1.51 (s, 9H); MS (M+H)$^+$ 497.

2-(4-tert-butylphenyl)-4-{4-[(2,4-dimethyl-1,3-oxazol-5-yl)carbonyl]piperazin-1-yl}-1H-benzimidazole

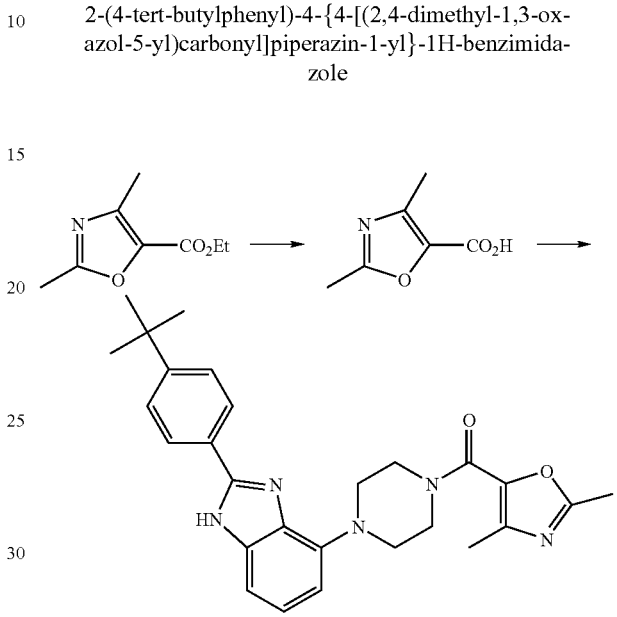

To a solution of 2,4-dimethyl-oxazole-5-carboxylic acid ethyl ester (1.8 g, 10.6 mmol) in THF (20 mL) cooled in an ice bath was added a solution of LiOH.H$_2$O (0.98 g, 23 mmol) in H$_2$O (20 mL), followed by MeOH (10 mL). The reaction was stirred in the ice bath and allowed to come to rt overnight. The solution was concentrated in vacuuo. The aqueous solution was cooled in an ice bath and brought to pH 3 with the addition of 2 N HCl. The white precipitate was collected by filtration and dried in vacuuo to afford the acid as a white powder (0.67 g, 45%). MS (ESI-POS): [M+H]$^+$=142. The crude acid (49 mg, 0.35 mmol) was combined with the piperazinylbenzimidazole (101 mg, 0.30 mmol), HATU (133 mg, 0.35 mmol), and DIEA (60 µL, 0.36 mmol) in NMP (6 mL) and the solution was stirred at rt for 48 h. To the solution was added EtOAc (50 mL) and H$_2$O (15 mL) and the layers were separated. The organic layer was washed with H$_2$O (8×15 mL) and brine (20 mL), dried (Na$_2$SO$_4$), filtered, and concentrated. The residue was purified using silica gel chromatography, eluting with a gradient of 2% MeOH/CH$_2$Cl$_2$ to 3% MeOH/CH$_2$Cl$_2$ to afford the amide (90 mg, 65%) as a white powder. $^1$H NMR 300 MHz (CDCl$_3$): δ=9.38 (s, 1 H), 7.97 (d, J=8.4 Hz, 2H), 7.52 (d, J=8.4 Hz, 2H), 7.17 (t, J=7.8 Hz, 1H), 7.11 (d, J=7.9 Hz, 1H), 6.65 (d, J=7.8 Hz, 1H), 4.01 (bs, 4H), 3.67 (bs, 4H), 2.49 (s, 3H), 2.39 (s, 3H), 1.37 (s, 9H). MS (ESI-POS): [M+H]$^+$=459. Anal. Calc. for C$_{27}$H$_{31}$N$_5$O$_2$ 0.2 CH$_2$Cl$_2$: C, 68.84; H, 6.67; N, 14.67. Found: C, 68.99; H, 6.87; N, 14.56.

2-(4-tert-butylphenyl)-4-{4-[(2,4-dimethyl-1,3-oxazol-5-yl)methyl]piperazin-1-'yl}-1H-benzimidazole

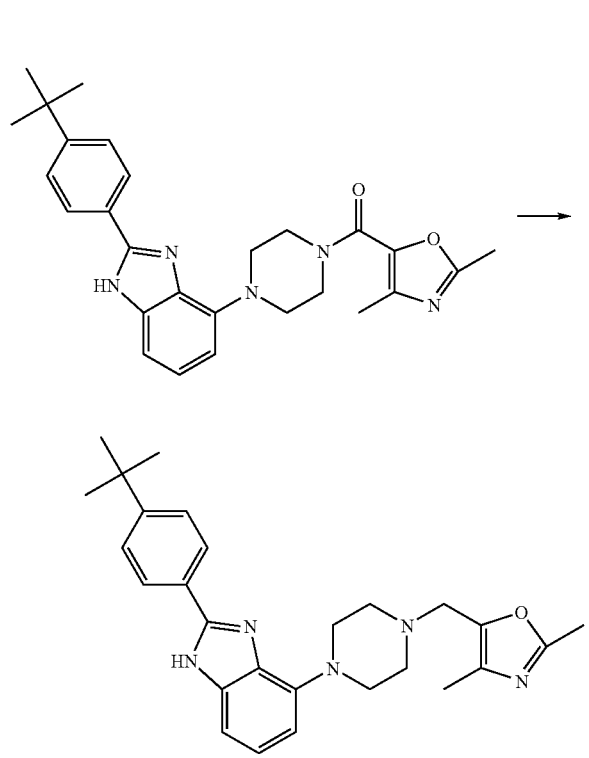

To a solution of 2-(4-tert-butylphenyl)-4-{4-[(2,4-dimethyl-1,3-oxazol-5-yl)carbonyl]piperazin-1-yl}-1H-benzimidazole (69 mg, 0.15 mmol) in THF (8 mL) cooled in an ice bath was added dropwise a 1.0 M solution of LiAlH₄ in THF (0.63 mL, 0.63 mmol). The reaction was warmed to rt, then heated in a 65° C. bath for 45 min. The reaction was cooled to rt, then cooled in an ice bath. The hydride was quenched by adding 1 N NaOH solution (2 mL) dropwise. The mixture was concentrated under reduced pressure. To the residue was added EtOAc (50 mL) and H₂O (15 mL) and the layers were separated. The organic layer was washed with H₂O (15 mL) and brine (15 mL). The organic layer was dried (Na₂SO₄), filtered, and concentrated under reduced pressure. The crude oil was purified by silica gel chromatography, eluting with 3% MeOH/CH₂Cl₂, then by reversed-phase HPLC (method E) to provide the product (28 mg, 28%) as its trifluoroacetate salt. $^1$H NMR 400 MHz (DMSO-$d_6$): δ 10.13 (s, 1H), 8.08 (d, J=8.5 Hz, 2H), 7.59 (d, J=8.6 Hz, 2H), 7.16-7.14 (m, 2H), 6.68-6.64 (m, 1H), 4.58 (s, 2H), 4.45 (bs, 2H), 3.61 (bs, 2H), 3.40 (bs, 2H), 3.11 (bs, 2H), 2.42 (s, 3H), 2.18 (s, 3H), 1.34 (s, 9H). MS (ESI-POS) [M+H]⁺=444. Anal. Calc. for $C_{27}H_{33}N_5O$ 2 $C_2HO_2F_3$ 2.5 $H_2O$: C, 51.95; H, 5.63; N, 9.77. Found: C, 52.01; H, 5.24; N, 9.65. HPLC (column: Xterra MS C18, 3.5 mm, 4.6×50 mm; 5/95-95/5, 10 mins., hold for 2.5 mins., A=acetonitrile, B=PIC-B-5) rt=6.4 mins. (99.4% @ 210 nm; 99.2% @ 254 nm).

Table 15 indicates other examples prepared using the above method for example 324:

TABLE 15

| Example | $R_Y$ | $R_Z$ | [M + H]⁺ |
|---|---|---|---|
| 325 | 4-methyl-2-ethyl-1,3-oxazol-5-yl | H | 458 |
| 326 | 4-methyl-2-(methoxymethyl)-1,3-oxazol-5-yl | H | 474 |
| 327 | 1,3-thiazol-2-yl | H | 432 |
| 328 | 2,4-dimethyl-1,3-thiazol-5-yl | H | 460 |
| 329 | " | {S}-Me | 474 |
| 330 | 2-(ethoxycarbonyl)-1,3-thiazol-4-yl | H | 504 |
| 331 | 2-(methylamino)-1,3-thiazol-4-yl | H | 461 |
| 332 | 2,4-dimethyl-1,3-thiazol-5-yl | H | 460 |
| 333 | 2-methyl-4-ethyl-1,3-thiazol-5-yl | H | 474 |

TABLE 15-continued

| Example | R_Y | R_Z | [M + H]⁺ |
|---|---|---|---|
| 334 | (2-ethyl-4-methyl-thiazol-5-yl) | H | 474 |
| 335 | (2-(3-butenyl)-4-methyl-thiazol-5-yl) | H | 500 |
| 336 | (2-propyl-4-methyl-thiazol-5-yl) | H | 502 |
| 337 | (2-(2-hydroxypropyl)-4-methyl-thiazol-5-yl) | H | 504 |
| 338 | (2-(methoxymethyl)-4-methyl-thiazol-5-yl) | H | 490 |
| 339 | (2-ethyl-4-methyl-oxazol-5-yl) | H | 458 |
| 340 | (2-(methoxymethyl)-4-methyl-oxazol-5-yl) | H | 474 |

Example 341

250 mg (1.62 mmol) of N-methyl-3(5)-ethyl-5(3)-carboxylic acid (Maybridge), 596 mg (1.79 mmol) piperazinyl-benzimidazole, and 814 mg (2.14 mmol) O-(7-azabenzotriazol-1-yl)-N,N,N',N'-tetramethyluronium hexafluorophosphate were combined in NMP (10 mL) and stirred at room temperature overnight. The mixture was diluted with water and ethyl acetate and the organic phase washed with saturated aqueous brine solution, producing a copious precipitate. The solid was collected on a Buchner funnel and combined with the concentrated ethyl acetate extracts to give 750 mg of crude products. Chromatography (40 wt. eq, silica gel), elution with DCM/EtOAc (5%), MeOH gradient (1-2%) gave 93 mg of the least polar isomer, as a pale yellow powder, determined (NOESY) to be the $N_1$-Me-3-Et pyrazole isomer, and 169 mg mixture of both isomers. $^1$H-NMR (DMSO-$d_6$), δ=12.75 (s, 1H), 8.07 (d, 2H, J=8.5 Hz), 7.56 (d, 2H, J=8.5 Hz), 7.07 m, 2H), 6.54 (m, 1H), 6.34 (s, 1H), 3.85-3.75 (s, bd, overlapping, 5H), 3.6 (bd, 3H), 2.56 (q, 2H, J=7.6 Hz), 1.33 (s, 9H) 1.19 (t, 3H, J=7.6 Hz). HPLC (column; Xterra RP18, 3.5 μm, 4.6×150 mm; 95/5-20/80, 8 min, hold for 2 min (phosphate buffer pH 2.1/ACN, rt=8.3 min. (97.8% @ 250 nm, 97.5% @ 303 nm), m/z=470 (±).

153

2-(4-tert-Butyl-phenyl)-4-[4-(5-ethyl-2-methyl-2H-pyrazol-3-ylmethyl)-piperazin-1-yl]-1H-benzoimidazole

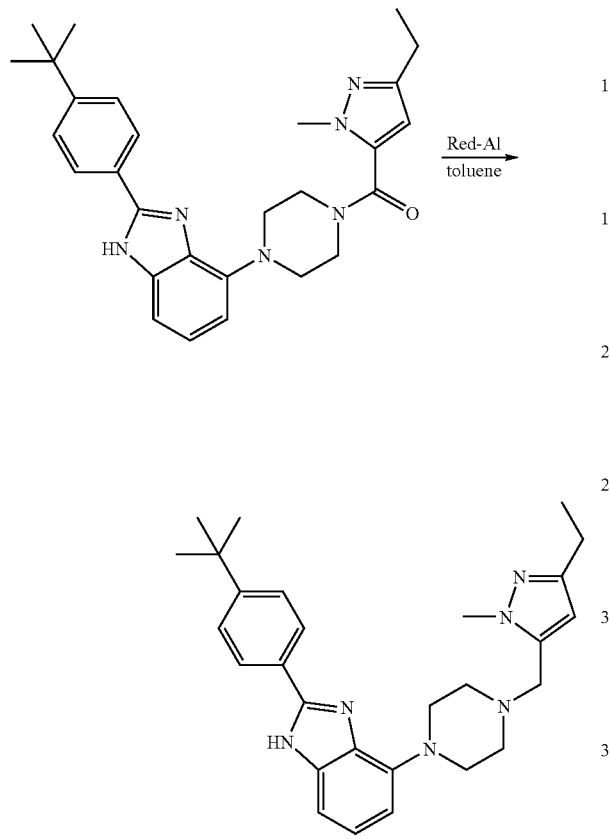

90 mg (0.19 mmol) of the above amide in toluene (1.5 mL) were treated with sodium bis(2-methoxyethoxy)aluminum hydride (65 wt % in toluene), added dropwise by syringe until ther was no further gas evolution (~0.2 mL), the an additional 0.1 mL (0.29 mmol). The mixture was then heated to 95° C. (oil bath) for 2 h. The reaction mixture was cooled to room temperature, quenched with 1N aqueous NaOH, and extracted with EtOAc. The organics were washed with water, dried (MgSO$_4$), filtered and concentrated to an oily solid. This material was treated with ACN and stirred overnight at room temperature. The white powder was collected on a Buchner funnel and dried under vacuum at 78° C. to give 40 mg 46%) of the title compound, as a ¼ hydrate. $^1$H-NMR (DMSO-d$_6$), δ=12.69 (s, 1H), 8.05 (d, 2H, J=8.5 Hz), 7.55 (d, 2H, J=8.5 Hz), 7.03 m, 2H), 6.50(dd, 1H), 6.00 (s, 1H), 3.76 (s, 3H), 3.6 (bd, 5H), 2.50 (q, 2H, overlapping with solvent), 1.33 (s, 9H) 1.16 (t, 3H, J=7.6 Hz). HPLC (column; Xterra RP18, 3.5 μm, 4.6×150 mm; 95/5-20/80, 8 min, hold for 2 min (phosphate buffer pH 2.1/ACN, rt=10.0, min.(99% @ 250 nm, 302 nm), m/z=457, [M+H]$^+$.

154

Examples 342-353

2-(4-tert-Butyl-phenyl)-4-[4-(5-ethyl-1-methyl-1H-pyrazol-3-ylmethyl)-piperazin-1-yl]-1H-benzoimidazole

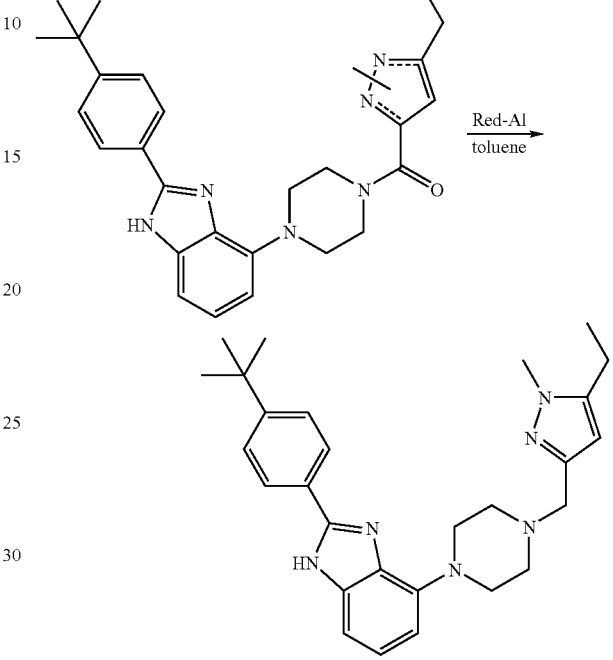

In like manner to example 343, 125 mg (0.27 mmol) of the unseparated mixture of isomeric N-methyl-3(5)-ethyl pyrazole amides were reduced with Red-Al. The crude products were chromatographed on silica gel, elution with DCM, then DCM/MeOH gradient (1-5%) to give the title compound as a brown powder. m/z=457 (±).

Table 16 indicates other examples prepared using the above method for example 342:

TABLE 16

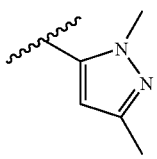

| Example | Y | Pyrazole | m/z |
|---|---|---|---|
| 343 | H | | 442 |

TABLE 16-continued

| Example | Y | Pyrazole | m/z |
|---|---|---|---|
| 344 | {S}-Me | 3,5-dimethyl-1H-pyrazol-4-yl | 456 |
| 345 | H | 1,5-dimethyl-1H-pyrazol-4-yl | 456 |
| 346 | H | 5-ethyl-1-methyl-1H-pyrazol-4-yl | 461 |
| 347 | H | 1,3-dimethyl-1H-pyrazol-4-yl | 456 |
| 348 | H | 3,5-dimethyl-1H-pyrazol-4-yl | 442 |
| 349 | H | 2,5-dimethyl-1H-pyrazol-3-yl | 442 |
| 350 | H | 5-methyl-1H-pyrazol-3-yl | 464 |
| 351 | H | 3-methyl-1H-pyrazol-4-yl | 442 |
| 352 | H | 5-methyl-1H-pyrazol-3-yl | 456 |
| 353 | H | 1-methyl-1H-pyrazol-5-yl | 428 |

Example 354

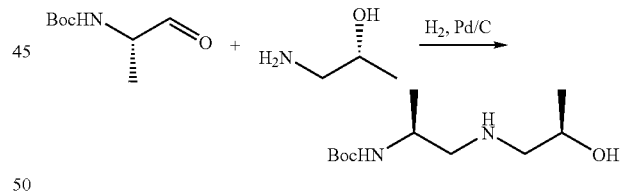

A mixture of (2S)-N-t-(butyloxycarbonyl)alaninal (0.41 g, 2.4 mMol) and (2R)-1-amino-2-propanol (0.29 g, 3.9 mMol) was hydrogenated in methanol (12 mL) over 10% Pd/C (50 mg) at 1 atmosphere hydrogen pressure for 18 h. The catalyst was filtered with the aid of diatomaceous earth, washed with methanol (2×20 mL) and the filtrate was evaporated under reduced pressure. The residue was dissolved in 1M sodium carbonate solution (25 mL) and extrated with dichloromethane (3×25 mL). The combined organic layers were dried (MgSO$_4$) and evaporated to leave the product as a white solid (0.54 g, 97%). $^1$H-NMR (CDCl$_3$), δ=4.50 (bs, 1H), 3.76 (m, 2H), 2.74 (dd, 1H, J=12.6 Hz, J=3.0 Hz), 2.68 (dd, 1H, J=11.8 Hz, J=4.9 Hz), 2.58 (dd, 1H, J=14.1 Hz, J=7.2 Hz), 2.39 (dd, 1H, J=12.1 Hz, J=9.4 Hz), 1.45 (s, 9H), 1.15 (d, 3H, J=6.3Hz), 1.14 (d, 3H, J=6.7Hz).

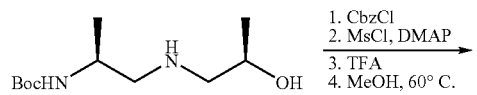

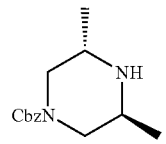

A solution of the amine (0.80 g, 3.4 mMol) and diisopropylethylamine (0.53 g, 4.1 mMol, 0.73 mL) in dichloromethane (35 mL) was stirred and cooled in an ice bath and treated with benzylchloroformate (0.70 g, 4.1 mMol, 0.58 mL). After 1 h the mixture was washed with 1N HCl (40 mL), water (40 mL), dried (MgSO$_4$) and evaporated under reduced pressure to leave the product as a colorless oil (1.3 g, 100%). The product was redissolved in dichloromethane (40 mL) under a nitrogen atmosphere and cooled in an ice bath. To the solution was added diisopropylamine (0.65 g, 5.0 mMol, 0.90 mL), 4-(N,N-dimethyl)pyridine (88 mg, 0.72 mMol) and methanesulfonylchloride (0.50 g, 4.3 mMol, 0.33 mL). The reaction mixture stirred for 1 h and the ice bath was removed. Stirring continued for 18 h at 20° C. then the mixture was washed with 1 N HCl (30 mL), water (30 mL) and brine (30 mL). The organic phase was dried (MgSO$_4$) and evaporated to leave the product as a colorless gum (1.5 g, 94%) that was stirred in a solution of trifluoroacetic acid (15 mL) and dichloromethane (15 mL) for 1 h. The solvents were evaporated, the residue was dissolved in dichloromethane (50 mL) and washed with 1 M sodium carbonate solution (30 mL). The aqueous layer was extracted with dichloromethane (2×20 mL), organic layers combined, dried (MgSO$_4$) and evaporated. The residue was dissolved in methanol (20 mL) and heated to 60° C. for 4 h. The solvent was evaporated, the product was dissolved in 1N HCl (30 mL), washed with ethyl acetate (20 mL) and neutralized with solid sodium carbonate. The product was extracted with dichloromethane (5×20 mL), combined, dried (MgSO$_4$) and evaporated to leave the product piperazine as a light brown oil (0.48 g, 57%). $^1$H-NMR (CDCl$_3$), δ=7.35 (m, 5H), 5.15 (dd, 2H, J=18.8, J=12.8 Hz), 3.05-3.81 (m, 6H), 1.12 (d, 6H, J=6.4 Hz).

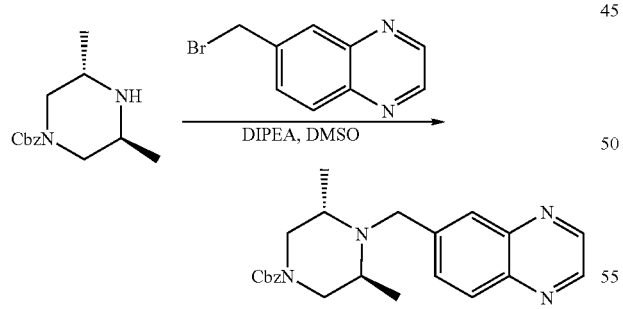

A solution of the dimethylpiperazine (0.15 g, 0.60 mMol) and diisopropylethylamine (0.11 g, 0.85 mMol, 0.15 mL) in DMSO (2 mL) was treated with 6-(bromomethyl)quinoxaline (based on 70% purity, 0.27 g, 0.85 mMol) and stirred 18 h at 20° C. The reaction mixture was diluted with water (0.3 mL) and purified by reversed phase HPLC (method E) to leave the product as a colorless gum (0.15 g, 64%). $^1$H-NMR (CDCl$_3$), δ=8.83 (d, 1H, J=1.9 Hz), 8.81 (d, 1H, J=1.9 Hz), 8.06 (d, 1H, J=8.5 Hz), 8.05 (d, 1H, J=1.8 Hz), 7.86 (dd, 1H, J=8.5 Hz, J=1.8 Hz), 7.37 (m, 5H), 5.14 (ABq, 2H, J=12.5 Hz), 4.13 (d, 1H, J=14.3 Hz), 3.65 (d, 1H, J=14.3 Hz), 3.60 (m, 2H), 3.27 (m, 2H), 2.92 (m, 2H), 1.03 (unresolved s, 6H). HPLC (method A), rt=1.05 mins., purity=99.0%, [M+H]$^+$=391.

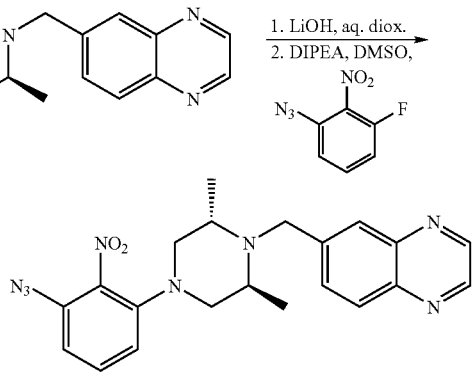

A solution of the piperazine (80 mg, 0.21 mMol) and lithium hydroxide monohydrate (86 mg, 2.1 mMol) was stirred under reflux in water (3 mL) and dioxane (3 mL) for 72 h. The reaction mixture was cooled to 20° C, diluted with 1 M sodium carbonate solution (20 mL) and extracted with ethyl acetate (3×20 mL). The combined organic layers were dried (MgSO$_4$) and evaporated to leave 54 mg of product which was dissolved in DMSO (1 mL) and treated with diisopropylethylamine (27 mg, 0.21 mMol, 38 mL) and 2-azido-6-fluoronitrobenzene (38 mg, 0.21 mMol). The reaction mixture was stirred and heated to 60° C. for 10 h. After cooling to room temperature the mixture was diluted with ethyl acetate (25 mL), washed with 1 M sodium carbonate solution (25 mL) and water (2×25 mL). The organic layer was dried (MgSO$_4$) and evaporated. The crude product was purified by silica gel chromatography eluting with a gradient of 20% ethyl acetate in dichloromethan to 25% ethyl acetate in dichloromethane to leave the purified product as a yellow foamy solid (29 mg, 33%). $^1$H-NMR (CDCl$_3$), δ=8.83 (s, 1H), 8.82 (s, 1H), 8.09 (s, 1H), 8.06 (d, 1H, J=8.6 Hz), 7.86 (d, 1H, J=8.6 Hz), 7.42 (dd, 1H, J=8.2 Hz, J=8.2 Hz), 6.98 (d, 1H, J=8.2 Hz), 6.96 (d, 1H, J=8.2 Hz), 4.17 (d, 1H, J=15.0 Hz), 3.70 (d, 1H, J=15.0 Hz), 3.03 (m, 4H), 2.78 (m, 2H), 1.09 (d, 6H, J=7.3 Hz).

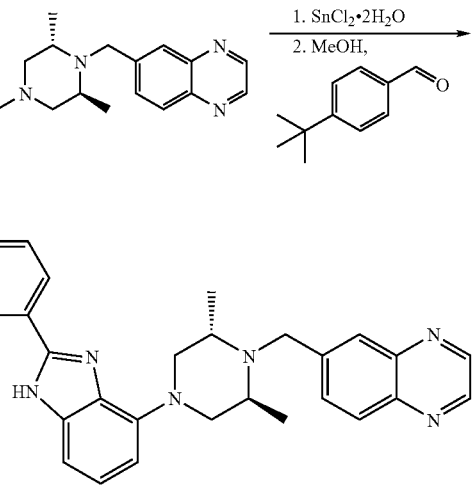

A mixture of the nitroazide (26 mg, 62 mMol) and tin(II) chloride dihydrate (141 mg, 0.62 mMol) was stirred in ethyl acetate (2 mL) at 20° C. for 15 mins. then at reflux for 45 mins. After cooling to room temperature it was diluted with ethyl acetate (25 mL) and 1N NaOH and stirred for 30 mins. The aqueous layer was washed with ethyl acetate (20 mL) and the organic layers combined, washed (brine), dried ($MgSO_4$) and evaporated to leave a tan gum (19 mg, 85%). The product was dissolved in methanol (0.25 mL), treated with 4-t-butylbenzaldehyde (7.7 mg, 47 mMol, 7.9 mL) and stirred at 25° C. for 18 h. Diluted with DMSO (1 mL) and water (0.25 mL) and purified by reversed phase HPLC (method E) to leave the product as a dark brown gum (ditrifluoroacetate salt, 22 mg, 48%). $^1$H-NMR ($CD_3OD$), δ=8.98 (s, 2H), 8.41 (d, 1H, J=2.0 Hz), 8.27 (d, 1H, J=8.6 Hz), 8.08 (d, 1H, J=2.0 Hz), 8.07 (d, 2H, J=8.7 Hz), 7.69 (d, 2H, J=8.7 Hz), 7.38 (m, 2H), 7.00 (dd, 1H, J=8.7 Hz, J=8.3 Hz), 5.11 (d, 1H, J=13.6 Hz), 4.63 (d, 1H, J=13.6 Hz), 3.71 (m, 2H), 3.21 (q, 2H, J=7.4 Hz), 1.67 (d, 6H, J=6.1 Hz), 1.39 (s, 9H). ). HRMS calculated for [M−H]$^-$=503.2923, found 503.2921. HPLC (method C), rt=9.83 mins., purity>99.9% @ 290 nm and 304 nm.

Example 355

2-Amino-3-nitro benzoic acid

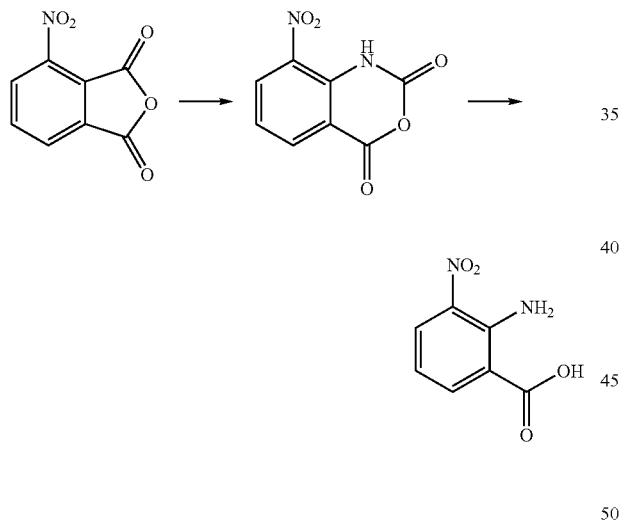

Prepared by the method of *J. Org. Chem.* 1998, 63, 6797. To a suspension of 3-nitrophthallic anhydride (5.0 g, 26 mmol) in benzene (anhydrous, 70 mL) was added trimethylsilyl azide and the resulting suspension was heated in an 80° C. bath for 2.5 h. The solution was cooled to rt and concentrated under reduced pressure to one-fourth its original volume. The concentrated solution was heated in a 100° C. bath overnight. The yellow solution was cooled and concentrated to afford a yellow solid. To the crude material was added EtOH (20 mL) and the solution was concentrated to dryness to provide 8-nitro isatoic anhydride (5.4 g, 99%). $^1$H NMR 300 MHz (DMSO-$d_6$): δ=11.2 (bs, 1H), 8.51 (dd, 1 H, J=8.5, 1.5 Hz), 8.35 (dd, 1H, J=7.7, 1.5 Hz), 7.42 (t, 1H, J=8.0 Hz). A suspension of 8-nitro isatoic anhydride (3.0 g, 14.4 mmol) in conc. HCl (100 mL) was heated in a 95° C. bath for 3 h. The solution was cooled to rt. The precipitate which formed was collected to provide the product as a yellow powder (1.50 g, 57%). LC/MS (Method A), rt=1.05 mins, purity=95%. MS (ESI-NEG): [M−H]$^-$=181.

(2-amino-3-nitrophenyl)methanol

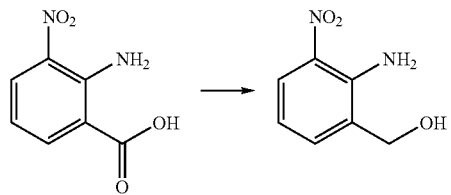

To a suspension of 2-amino-3-nitro benzoic acid (2.12 g, 10 mmol) in benzene (75 mL) was added dropwise thionyl chloride (1.8 mL, 25 mmol). The suspension was heated to reflux overnight. The mixture was cooled to room temperature and concentrated under reduced pressure to afford a golden solid. The crude material was dissolved in THF (40 mL) and cooled in an ice bath. Sodium borohydride (0.83 g, 22 mmol) was added in portions, and the reaction was allowed to come to room temperature with stirring. The ice bath was replaced and $H_2O$ (15 mL) was slowly added to the reaction. Once gas evolution had subsided, the solution was concentrated under reduced pressure. The residue was dissolved in EtOAc (200 mL) and washed with $NaHCO_3$ (2×50 mL) and brine (50 mL). The organic layer was dried ($Na_2SO_4$), filtered, and concentrated under reduced pressure. The reside was adsorbed onto silica gel and purified by column chromatography, eluting with a gradient of 25% EtOAc/hexane to 50% EtOAc/hexane to afford the alcohol (0.89 g, 46%) as an orange solid. mp: 100° C. $^1$H NMR 300 MHz (DMSO-$d_6$): δ=7.92 (dd, 1H, J=8.7, 1.4 Hz), 7.49 (d, 1H, J=6.8 Hz), 7.12 (bs, 2H), 6.66 (dd, 1H, J=8.7, 7.1 Hz), 5.45 (t, 1H, J=5.4 Hz), 4.52 (d, 2H, J=5.4 Hz). MS (ESI-POS): [M+H]$^+$=169.

2-Chloromethyl-6-nitroaniline

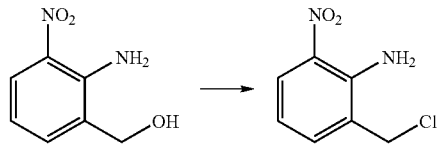

To a solution of (2-amino-3-nitrophenyl)methanol (5.83 g, 35 mmol) in $CH_2Cl_2$ (250 mL) cooled in an ice bath was added triethyl amine (6.3 mL, 45 mmol), followed by dropwise addition of thionyl chloride (3.16 mL, 43 mmol). The solution was stirred at room temperature overnight. The ice bath was replaced, and ice was added to quench the reaction. The reaction mixture was washed with 0.1 N HCl (30 mL), $H_2O$ (2×30 mL), and brine (30 mL). The organic layer was dried ($Na_2SO_4$), filtered, and concentrated under reduced pressure. The crude material was adsorbed onto silica gel and purified by column chromatography, eluting with a gradient of 20% EtOAc/hexane to 30% EtOAc/hexane to afford the chloromethyl compound (5.3 g) as a yellow powder. $^1$H NMR 300 MHz (DMSO-$d_6$): δ=7.89 (dd, 1H, J=8 Hz, 2 Hz), 7.44 (d, 1H, J=7 Hz), 7.12 (brs, 2H), 6.69-6.66 (m, 1H), 4.61 (s, 2H).

161

2-{4-[2-(4-tert-Butyl-phenyl)-1H-benzoimidazol-4-yl]piperazin-1-ylmethyl}-6-nitro-phenylamine

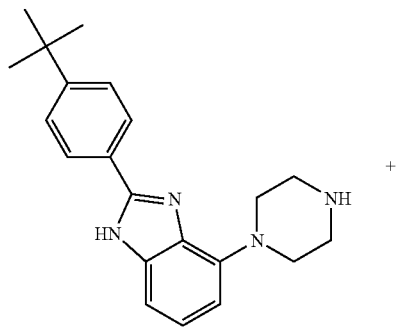

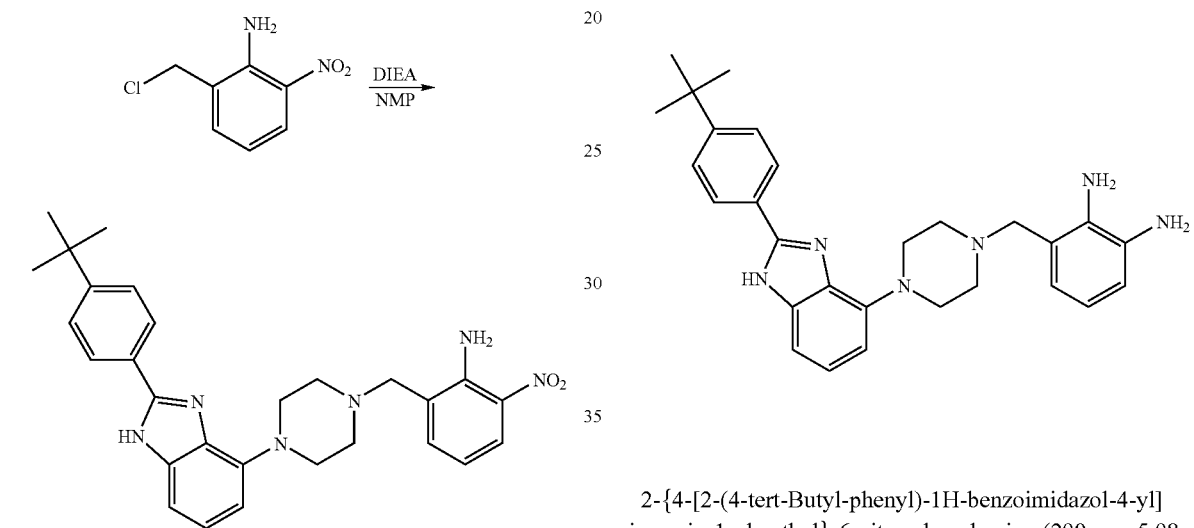

To a solution of 2-(4-tert-Butyl-phenyl)-4-piperazin-1-yl-1H-benzoimidazole (1.30 g, 3.89 mmol) and 2-chloromethyl-6-nitro-phenylamine (660 mg, 3.53 mmol) in anhydrous NMP (40 mL) was added diisopropylethylamine (1.0 mL, 4.24 mmol) and the solution stirred at room temperature, under nitrogen, for 18 h. The solution was diluted with Ethyl acetate (150 mL) and washed with distilled water (10×50 mL). The aqueous washings were combined and extracted with Ethyl acetate (2×100 mL). The organic extracts were combined and washed with brine (2×100 mL), dried ($Na_2SO_4$), filtered and the solvent removed to give a tan solid with some amber colored oil (1.84 g) This material was adsorbed onto silica gel and purified by column chromatography, eluting with a solution of 20% ethyl acetate in hexane to afford the nitro amino product (610 mg, 36% Yield) as a yellow solid. $^1$H NMR 300 MHz ($CDCl_3$): δ=8.25 (d, 1H, J=7.5 Hz), 8.00 (d, 2H, J=8.2 Hz), 7.50 (d, 1H, J=6.9 Hz), 7.35 (d, 2H, J=8.4 Hz), 7.00 (m, 1H), 6.95 (m, 1H), 6.75 (m, 1H), 6.65 (d, 1 H, J=6.7 Hz), 4.15 (s, 2H), 3.33 (bs, 4H), 3.15 (bs, 4H), 1.25 (s, 9H). HPLC (column: Luna, C18, 10 μM, 4.6×50 mm), Flow=1 mL/min., 5/95-95/5, 20 min., (acetonitrile/0.1% TFA), No impurities detected @ 254 nM and 300 nM, retention time=12.5 min., Mass Spec: Calculated mass=484.26, [M+H]$^-$=483, [M+H]$^+$=485.

162

3-{4-[2-(4-tert-Butyl-phenyl)-1H-benzoimidazol-4-yl]-piperazin-1-ylmethyl}-benzene-1,2-diamine 2-{4-[2-(4-tert-Butyl-phenyl)-1H-benzoimidazol-4-yl]piperazin-1-ylmethyl}-6-nitro-phenylamine (290 mg, 5.98× $10^{-1}$ mmol) and tin (II) chloride (681 mg, 3.59 mmol) were stirred in anhydrous NMP (40 mL) at 70° C., under nitrogen, for 18 h. The reaction was quenched with 1N HCl (100 mL) and extracted with methylene chloride (2×50 mL). The organic extracts were combined and extracted with 1N HCl (2×50 mL). The aqueous extracts were combined and neutralized with 2N NaOH solution. This neutral aqueous phase was extracted with ethyl acetate (4×100 mL). The organic extracts were combined and washed with distilled water (10× 50 mL). The aqueous washings were combined and extracted with ethyl acetate (100 mL). The ethyl acetate extracts were combined, dried ($Na_2SO_4$), filtered and the solvent removed to give a brown oil. This material was dissolved in aqueous DMSO and purified by Gilson RP-HPLC. The fractions were collected and the acetonitrile removed, in vacuo, and the aqueous residue lyophilized to give a white solid (55 mg, 20% Yield). $^1$H NMR 300 MHz (DMSO): δ=8.08 (d, 2H, J=8.2 Hz), 7.57 (d, 2H, J=8.5 Hz), 7.15 (m, 2H), 6.90 (m, 2H), 6.65 (m, 2H), 4.35 (s, 2H), 3.50 (bs, 8H), 1.35 (s, 9H). HPLC (Column; Xterra MS, C18, 3.5 μM, 4.6×50 mm), 5/95-95/5, 10 min., 95/5, 2.5 min., (acetonitrile/0.1% TFA in $H_2O$), 99% purity @ 254 nM and 300 nM, retention time=4.9 min. Calculated mass=454.28, [M+H]$^+$=453, [M+H]$^+$=455.

4-{4-[2-(4-tert-Butyl-phenyl)-1H-benzoimidazol-4-yl]-piperazin-1-ylmethyl}-1,3-dihydro-benzoimidazole-2-thione

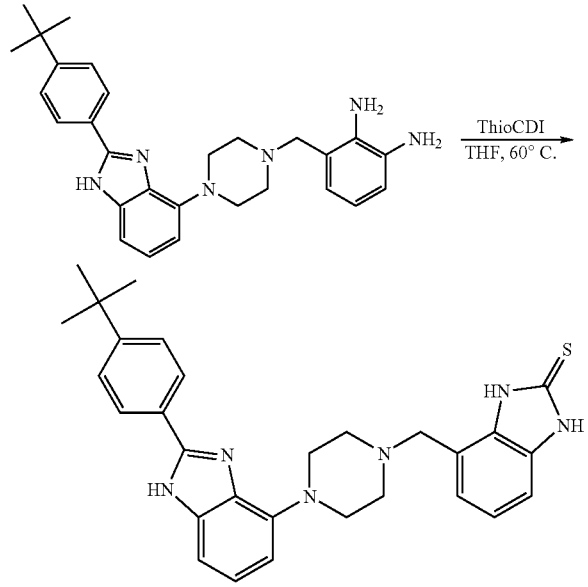

3-{4-[2-(4-tert-Butyl-phenyl)-1H-benzoimidazol-4-yl]-piperazin-1-ylmethyl}-benzene-1,2-diamine (140 mg, 3.08× $10^{-1}$ mmol) and 1,1'-thiocarbonyldiimidazole (67 mg, 3.39× $10^{-1}$ mmol) were stirred in anhydrous THF (10 mL) at 60° C. for 2 h. The solvent was removed, in vacuo, to give a reddish brown oil (220 mg). This material was adsorbed onto silica and purified by column chromatography, eluting with a 1:1 solution of hexane:ethyl acetate to give an off white solid (30 mg, 20% Yield). $^1$H NMR 300 MHz (DMSO): δ=8.05 (d, 2H, J=8.4 Hz), 7.55 (d, 2H, J=8.5 Hz), 7.05 (m, 5H), 6.48 (m, 1H), 3.75 (s, 2H), 3.55 (bs, 4H), 2.65 (bs, 4H), 1.30 (s, 9H). HPLC (Column; Xterra MS, C18, 5 μM, 4.6×150 mm), Flow=1 mL/min., 30/70-95/5, 10 min., (acetonitrile/50 mM NH$_4$OAc, pH=6.8), 20 min., 82% purity @ 254 nM, 79% @ 254 nM, retention time=11.9 min. Calculated mass=496.24, [M+H]$^-$=495, [M+H]$^+$=497.

Example 356

4-{4-[2-(4-tert-Butyl-phenyl)-1H-benzoimidazol-4-yl]-piperazin-1-ylmethyl}-1,3-dihydro-benzoimidazol-2-one

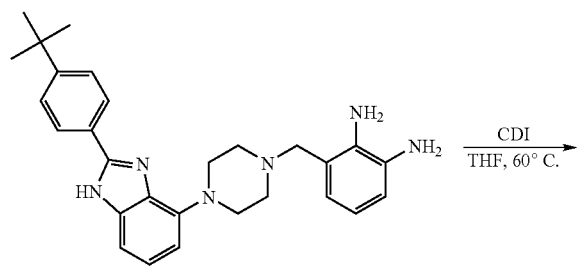

-continued

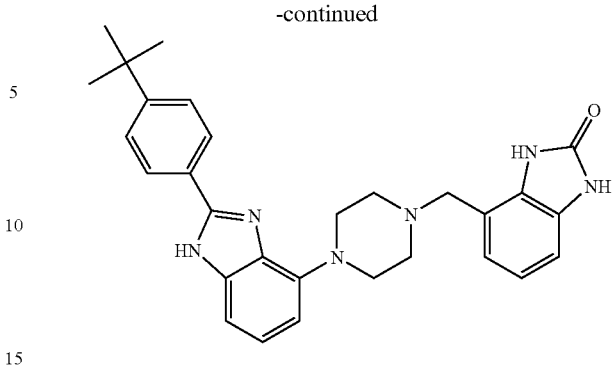

3-{4-[2-(4-tert-Butyl-phenyl)-1H-benzoimidazol-4-yl]-piperazin-1-ylmethyl}-benzene-1,2-diamine (150 mg, 3.30× $10^{-1}$ mmol) and 1,1'-carbonyldiimidazole (59 mg, 3.63×$10^{-1}$ mmol) were stirred in anhydrous THF at 60° C. for 2 h. The solvent was removed, in vacuo, dissolved in aqueous DMSO and purified by Gilson RP-HPLC. The fractions were combined, the acetonitrile was removed and the aqueous residue lyophilized to give a white solid (45 mg, 28% Yield). $^1$H NMR 300 MHz (DMSO): δ=11.10 (s, 1H), 10.90 (s, 1H) 8.08 (d, 2H, J=8.5 Hz), 7.60 (d, 2H, J=8.5 Hz), 7.10 (m, 3H), 7.05 (m, 2H), 6.65 (m, 1H), 4.45 (s, 2H), 3.55 (bs, 8H), 1.33 (s, 9H). HPLC (Column; Xterra MS, C18, 3.5 μM, 4.6×50 mm), Flow=0.8 mL/min., 5/95-80/20, 10 min., 80/20, 2.5 min., (acetonitrile/50 mM NH$_4$OAc), 87% purity @ 254 nM, 88% @ 300 nM, retention time=8.9 min. Calculated mass=480.26, [M+H]$^-$=479, [M+H]$^+$=481.

Example 357

5-{4-[2-(4-tert-Butyl-phenyl)-1H-benzoimidazol-4-yl]-piperazin-1-ylmethyl}-quinoxaline

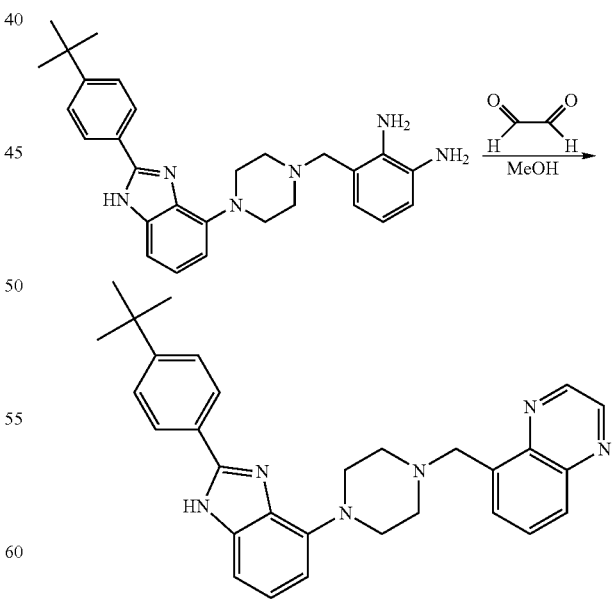

3-{4-[2-(4-tert-Butyl-phenyl)-1H-benzoimidazol-4-yl]-piperazin-1-ylmethyl}-benzene-1,2-diamine (50 mg, 1.10× $10^{-1}$ mmol) and glyoxal (40 wt %, 10 μL, 2.21×$10^{-1}$ mmol) were stirred in methanol (5 mL), under nitrogen for 18 h. The solvent was removed, in vacuo, to give an amber colored solid (150 mg). This material was adsorbed onto silica gel and purified by column chromatography, eluting with a 95:5 solution of chloroform:methanol to give a tan colored solid (20 mg, 38% Yield). $^1$H NMR 300 MHz (DMSO): δ=8.99 (m, 2H), 8.05 (m, 1H), 8.02 (d, 2H, J=8.1 Hz), 7.98 (m, 2H), 7.55 (d, 2H, J=8.5 Hz) 7.05 (m, 2H), 6.52 (dd, 1H, J=6.7 Hz, J=2.0 Hz), 4.25 (s, 2H), 3.60 (s, 8H), 1.32 (s, 9H). HPLC (Column; Xterra MS, C18, 3.5 μM, 4.6×50 mm), Flow=0.8 mL/min., 5/95-95/5, 10 min., 95/5, 2.5 min., (acetonitrile/0.1% TFA), 97.3% purity @ 210 nM, 96.7% @ 300 nM, retention time=5.5 min. Calculated mass=476.62, [M+H]$^-$=475, [M+H]$^+$=477.

Example 358

4-{4-[2-(4-tert-Butyl-phenyl)-1H-benzoimidazol-4-yl]-piperazin-1-ylmethyl}-1,3-dihydro-benzoimidazol-2-ylidene-cyanamide

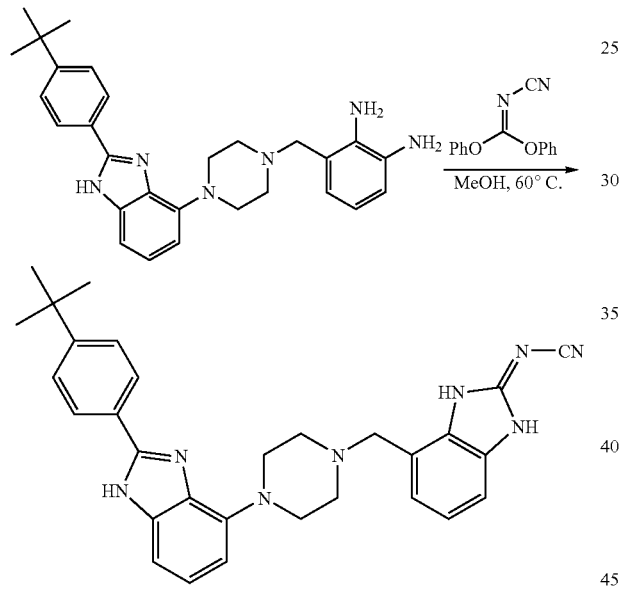

3-{4-[2-(4-tert-Butyl-phenyl)-1H-benzoimidazol-4-yl]-piperazin-1-ylmethyl}-benzene-1,2-diamine 50 mg, 1.10×10$^{-1}$ mmol) and diphenyl cyanocarboimidate (27 mg, 1.10×10$^{-1}$ mmol) were stirred in anhydrous methanol (3 mL) at 60° C., under nitrogen for 6 h. The solvent was removed to give a brown oil (80 mg). This material was adsorbed onto silica gel and purified by column chromatography, eluting with a 95:5 solution of chloroform:methanol to give a tan solid (24 mg, 43% Yield). $^1$H NMR 300 MHz (DMSO): δ=12.68 (s, 1H), 12.40 (s, 1H), 8.30 (d, 2H, J=8.4 Hz), 7.55 (d, 2H J=8.5 Hz), 7.12 (s, 4H), 7.01 (m, 1H), 6.50 (m, 1H), 3.72 (s, 2H), 3.55 (bs, 4H), 3.32 (s, 9H). HPLC (Column; Xterra MS, C18, 3.5 μM, 4.6×50 mm), Flow=0.8 mL/min., 5/95-95/5, 10 min., 95/5, 2.5 min., (acetonitrile/0.1% TFA), 94.5% purity @ 210 nM, 98.3% @ 300 nM, retention time =5.3 min. Calculated mass=504.28, [M+H]$^-$=503, [M+H]$^+$=505.

Various modifications of the invention, in addition to those described herein, will be apparent to those skilled in the art from the foregoing description. Such modifications are also intended to fall within the scope of the appended claims.

What is claimed:

1. A compound of the formula I:

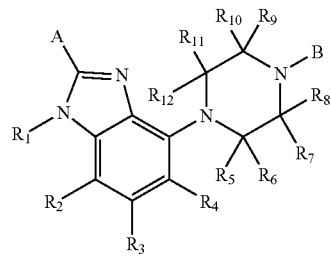

or a pharmaceutically acceptable salt thereof, wherein:

A is optionally substituted phenyl;

B is $(CR_{13}R_{14})_k$-D;

D is:

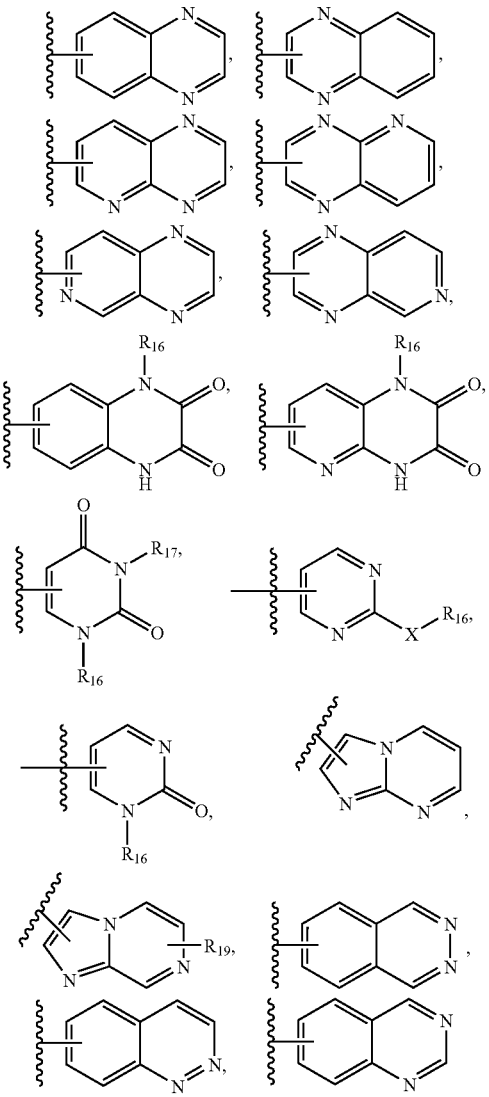

-continued

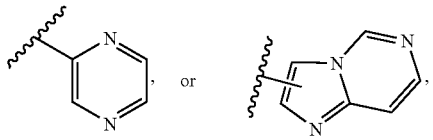

each D also having up to three $R_{19}$ substituents attached to the ring of D containing at least one N;

$R_{16}$ is hydrogen, $C_1$-$C_{10}$ alkyl, $C_2$-$C_{10}$ alkenyl, $C_2$-$C_{10}$ alkynyl, $R_{20}$-E-$R_{21}$, C(=O)E$R_{20}$, E$R_{20}$, N$R_{20}R_{21}$, or $(CH_2)_n$G, optionally substituted alkyl, optionally substituted aryl, aryl substituted with optionally substituted alkyl, alkyl substituted with optionally substituted aryl, alkyl substituted with imidazole, alkyl substituted with optionally substituted imidazole, or alkyl substituted with indole;

$R_{17}$ is hydrogen, $C_1$-$C_6$ alkyl, $C_2$-$C_{10}$ alkenyl, $C_2$-$C_{10}$ alkynyl, $(CH_2)_m CO_2 R_{20}$, $(CH_2)_m C(=O)NR_{20}R_{21}$;

$R_{19}$ is H, $C_1$-$C_3$ alkyl, alkenyl, or alkynyl; or alternatively, $R_{16}$ and $R_{19}$, taken together with the atoms to which they are attached, form a cyclic or heterocyclic group;

$R_{20}$ and $R_{21}$ are, independently, H, $C_1$-$C_3$ alkyl, or heteroalkyl, or alternatively, $R_{20}$ and $R_{21}$, taken together with the atoms to which they are attached, form a cyclic or heterocyclic group;

m is 0, 1, or 2;
n is 0, 1, 2, 3, or 4;
X is O, N$R_{21}$, or SO$_m$;
E is O, N, N$R_{21}$, or SO$_m$;
G is phenyl, 2-pyridyl, 3-pyridyl or 4-pyridyl;
k is 0, 1, 2, or 3;
$R_1$ is H or optionally substituted alkyl;
$R_2$, $R_3$, and $R_4$ are H;
$R_5$, $R_6$, $R_7$, $R_8$, $R_9$, $R_{10}$, $R_{11}$, and $R_{12}$, are, independently, H or optionally substituted alkyl;
$R_{13}$ and $R_{14}$ are, independently at each occurrence, H or optionally substituted alkyl.

2. The compound of claim 1, wherein $R_1$ is H or $C_1$-$C_3$ alkyl.

3. The compound of claim 1, wherein $R_5$, $R_6$, $R_7$, $R_8$, $R_9$, $R_{10}$, $R_{11}$, and $R_{12}$, are, independently, H or $C_1$-$C_4$ alkyl.

4. The compound of claim 1, wherein $R_1$, $R_2$, $R_3$, $R_4$, $R_5$, $R_6$, $R_7$, $R_{10}$, $R_{11}$, and $R_{12}$ are H.

5. The compound of claim 1, wherein $R_9$ is H.

6. The compound of claim 1, wherein $R_9$ is methyl or ethyl.

7. The compound of claim 1, wherein $R_{13}$ and $R_{14}$ are, independently at each occurrence, H or $C_1$-$C_3$ alkyl.

8. The compound of claim 1, wherein A is phenyl substituted with $C_1$-$C_6$ alkyl, alkenyl, alkynyl, N$R_{22}R_{23}$, C$R_{24}$(CF$_3$)$_2$, J$R_{22}$, or C(=O)$R_{22}$, wherein J is O or SO$_m$, wherein m is 0, 1, or 2; $R_{22}$ and $R_{23}$ are, independently, H, $C_1$-$C_7$ alkyl, alkenyl, alkynyl, aryl, or heteroalkyl, each alkyl, alkenyl, alkynyl, aryl, or heteroalkyl being optionally substituted; alternatively, $R_{22}$ and $R_{23}$, taken together with the atoms to which they are attached, form an optionally substituted cyclic or optionally substituted heterocyclic group; and $R_{24}$ is H, or OH.

9. The compound of claim 8, wherein when $R_{22}$ and $R_{23}$ form a cyclic or heterocyclic group, and said cyclic or heterocyclic group is substituted with $R_{20}$E$R_{21}$, wherein $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, and E is O, N, N$R_{21}$, or SO$_m$, wherein m is 0, 1, or 2.

10. The compound of claim 8, wherein $R_{22}$ and $R_{23}$ are ethyl.

11. The compound of claim 8, wherein $R_{22}$ and $R_{23}$ taken together with the atoms to which they are attached form pyrrolidine, piperidine, hexamethyleneimine, piperazine, homopiperazine, aziridine, or azetidine, each optionally substituted.

12. The compound of claim 11, wherein said pyrrolidine, piperidine, hexamethyleneimine, piperazine, homopiperazine, aziridine, or azetidine is substituted with $R_{20}$E$R_{21}$, wherein $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, and E is O, N, N$R_{21}$, or SO$_m$, wherein m is 0, 1, or 2.

13. The compound of claim 8, wherein $R_{22}$ is aryl, and is substituted with halogen, $R_{25}$, O$R_{25}$, or N$R_{26}R_{27}$, wherein $R_{25}$ is H, $C_1$-$C_3$ alkyl, or heteroalkyl; $R_{26}$ and $R_{27}$ are, independently, H, $C_1$-$C_3$ alkyl, or heteroalkyl, alternatively, $R_{26}$ and $R_{27}$, taken together with the atoms to which they are attached, form a cyclic or heterocyclic group.

14. The compound of claim 13, wherein $R_{26}$ and $R_{27}$ form pyrrolidine, piperidine, hexamethyleneimine, piperazine, homopiperazine, aziridine, or azetidine.

15. The compound of claim 8, wherein A is phenyl substituted with $C_1$-$C_4$ alkyl.

16. The compound of claim 15, wherein A is phenyl substituted with an ethyl or t-butyl group.

17. The compound of claim 16, wherein A is phenyl substituted with a t-butyl group.

18. The compound of claim 1, wherein D is quinoxalin-6-yl or pyridopyrazin-2-yl.

19. The compound of claim 1, wherein k is 1, $R_{13}$ is H, and $R_{14}$ is H or methyl.

20. The compound of claim 1, wherein $R_{13}$ and $R_{14}$ are H.

21. The compound of claim 1, wherein the compound is 6-({(2S)-4-[2-(4-tert-butylphenyl)-1H-benzimidazol-4-yl]-2-methylpiperazin-1-yl}methyl)quinoxaline; 6-({4-[2-(4-ethylphenyl)-1H-benzimidazol-4-yl]piperazin-1-yl}methyl) quinoxaline; 3-(4-{4-[4-(quinoxalin-6-ylmethyl)piperazin-1-yl]-1H-benzimidazol-2-yl}phenoxy)phenol; 6-({4-[2-(4-tert-butylphenyl)-1H-benzimidazol-4-yl]piperazin-1-yl}methyl)quinoxaline; phenyl(4-{4-[4-(quinoxalin-6-ylmethyl)piperazin-1-yl]-1H-benzimidazol-2-yl}phenyl) methanone; 6-({4-[2-(4-tert-butylphenyl)-1H-benzimidazol-4-yl]-2-methylpiperazin-1-yl}methyl)quinoxaline; 6-[(4-{2-[4-(methylsulfonyl)phenyl]-1H-benzimidazol-4-yl}piperazin-1-yl)methyl]quinoxaline; 6-[(4-{2-[4-(ethylsulfonyl)phenyl]-1H-benzimidazol-4-yl}piperazin-1-yl)methyl]quinoxaline; 6-({4-[2-(4-isopropylphenyl)-1H-benzimidazol-4-yl]piperazin-1-yl}methyl)quinoxaline; 6-({(2R)-4-[2-(4-tert-butylphenyl)-1H-benzimidazol-4-yl]-2-methylpiperazin-1-yl}methyl)quinoxaline; 6-({(2S)-4-[2-(4-tert-butylphenyl)-1H-benzimidazol-4-yl]-2-methylpiperazin-1-yl}methyl)quinoxaline; N,N-diethyl-N-(4-{4-[4-(quinoxalin-6-ylmethyl)piperazin-1-yl]-1H-benzimidazol-2-yl}phenyl)amine; 6-({(2S)-4-[2-(4-tert-butylphenyl)-1H-benzimidazol-7-yl]-2-ethylpiperazin-1-yl}methyl)quinoxaline; 6-[(4-{2-[4-(methylthio)phenyl]-1H-benzimidazol-4-yl}piperazin-1-yl)methyl]quinoxaline; 6-({4-[2-(4-methoxyphenyl)-1H-benzimidazol-4-yl]piperazin-1-yl}methyl)quinoxaline; 4-{4-[4-(quinoxalin-6-ylmethyl)piperazin-1-yl]-1H-benzimidazol-2-yl}benzenesulfonamide; 2-methoxy-5-{4-[4-(quinoxalin-6-ylmethyl)piperazin -1-yl]-1H-benzimidazol-2-yl}phenol; 6-[(4-{2-[4-(1H-pyrrol-1-yl)phenyl]-1H-benzimidazol-4-yl}piperazin-1-yl)methyl]quinoxaline; 6-({(2R,6S)-4-[2-(4- tert-butylphenyl)-1H-benzimidazol -4-yl]-2,6-dimethylpiperazin-1-yl}methyl)quinoxaline; 6-[(4-{2-[4-(phenylsulfonyl)phenyl]-1H -benzimidazol-4-yl}piperazin-1-yl)methyl]quinoxaline; N,N-diethyl-N-(4-{7-[(3 S)-3-ethyl-4-(quinoxalin-6-ylmethyl)piperazin-1-yl]-1H-benzimidazol-2-yl}phenyl)amine; 6-({4-[2-(4-pyrrolidin-1-ylphenyl)-1H-benzimidazol-4-yl]piperazin-1-yl}methyl)quinoxaline; 1(4-{4-[4-(quinoxalin-6-ylmethyl)piperazin-1-yl]-1H-benzimidazol-2-yl}phenyl)ethanone; 2,2,2-trifluoro-1(4-{4-[4-(quinoxalin-6-ylmethy)piperazin-1-yl]-1H-benzimidazol-2-yl}phenyl)ethane-1,1 -diol; 1,1,1,3,3,3-hexafluoro-2-(4-{7-[4-(quinoxalin-6-ylmethyl)piperazin-1yl]-1H -benzimidazol-2-yl}phenyl)propan-2-ol; 6-{[4-(2-{4-[2,2,2-trifluoro-1-(trifluoromethyl)ethyl]phenyl}-1H-benzimidazol-7-yl)piperazin-1yl]methyl}quinoxaline; 2-({4-[2-(4-tert-butylphenyl)-1H-benzimidazol-7-yl]piperazin-1-yl}methyl)imidazo[1,2-a]pyrimidine; 2-({(2 S)-4-[2-(4-tert-butylphenyl)-1H-benzimidazol-7-yl]-2-methylpiperazin-1-yl}methyl)imidazo[1,2-a]pyrimidine; 2-({4-[2-(4-tert-butylphenyl)-1H-benzimidazol-7-yl]piperazin-1-yl}methyl)-3-nitroimidazo[1,2-a]pyrimidine; 2-(4-tert-butylphenyl)-4-[4-(imidazo[1,2-a]1pyridin-2-ylmethyl)piperazin-1-yl]-1H-benzimidazole; 2-(4-tert-butylphenyl)-7-{4-[(5,7-dimethylimidazo[1,2-a]pyridin-2-y1)methyl]piperazin-1-yl}-1H-benzimidazole; 2-(4-tert-butylphenyl)-7-{(3S)-4-[(5,7-dimethylimidazo[1,2-a]pyridin-2-yl)methyl]-3-methylpiperazin-1-yl}-1H-benzimidazole; 2-(4-tert-butylphenyl)-7-{4-[(7-methylimidazo[1,2-a]pyridin-2-yl)methyl]piperazin-1-yl}-1H-benzimidazole; 2-(4-tert-butylphenyl)-7-{(3S)-3-methyl-4-[(7-methylimidazo [1,2-a]pyridin-2-yl)methyl]piperazin-1-yl}-1H-benzimidazole; 2-({4-[2-(4-tert-butylphenyl)-1H-benzimidazol-7-yl]piperazin-1-yl}methyl)imidazo[1,2-a]pyridine-6-carboxamide; 2-(4-tert-butylphenyl)-7-{4-[(5-methylimidazo[1,2-a]pyridin-2-yl)methyl]piperazin-1-yl}-1H-benzimidazole; 2-({4-[2-(4-tert-butylphenyl)-1H-benzimidazol-7-yl]piperazin-1-yl}methyl)-5,7-dimethylimidazo[1,2-c]pyrimidine; 2-({4-[2-(4-tert-butylphenyl) -1H-benzimidazol-7-yl]piperazin-1-yl}methyl)imidazo[1,2-a]pyrazine; 5-](4-{2-[4-(diethylamino)phenyl]-1H-benzimidazol-4-yl}piperazin-1yl)methyl]-1-ethylpyrimidine -2,4(1H,3H)-dione; 5-({4-[2-(4-tert-butylphenyl)-1H-benzimidazol-4-yl]piperazin-1-yl}methyl) -1hexylpyrimidine-2,4(1H,3H)-dione; 1butyl-5-({4-[2-(4-tert-butylphenyl)-1H-benzimidazol-4-yl]piperazin-1-yl}methyl)pyrimidine-2,4(1H,3H)-dione; 5-({4-[2-(4-tert-butylphenyl)-1H -benzimidazol-4-yl]piperazin-1-yl}methyl)-1-(2,6-difluorobenzyl)pyrimidine-2,4 (1H,3H)-dione;

1benzyl-5-({4-[2-(4-tert-butylphenyl)-1H-benzimidazol-4-yl]piperazin-1-yl}methyl)pyrimidine-2,4(1H,3H)-dione; 5-({4-[2-(4-tert-butylphenyl)-1H-benzimidazol-4-yl]piperazin-1-yl}methyl)-1(2-fluorobenzyl)pyrimidine-2,4(1H,3H)-dione; 5-({4-[2-(4-tert-butylpheny)-1H-benzimidazol-4-yl]piperazin-1-yl}methyl)-1pentylpyrimidine-2,4(1H,3H)-dione; 5-({4-[2-(4-tert-butylphenyl)-1H-benzimidazol-4yl]piperazin-1-yl}methyl)-1[(2-methoxyethoxy)methyl]pyrimidine-2,4(1H,3H)-dione; 5-({4-[2-(4-tert-butylphenyl)-1H -benzimidazol-4-yl]piperazin-1-yl}methyl)pyrimidine-2,4(1H,3H)-dione; 5-({(2S)-4-[2-(4-tert -butylphenyl)-1H-benzimidazol-4-yl]-2-methylpiperazin-1-yl}methyl)pyrimidine-2,4(1H,3H) -dione; 5-({(2 S)-4-[2-(4-tert-butylphenyl)-1H-benzimidazol-7-yl]-2-ethylpiperazin-1-yl}methyl)pyrimidine-2,4(1H,3H)-dione; 5-[(4-{2-[4-(methylsulfonyl)phenyl]-1H -benzimidazol-4-yl}piperazin-1yl)methyl]pyrimidine-2,4(1H,3H)-dione; 5-[((2S)-2-methyl-4-{2-[4-(methylsulfonyl)phenyl]-1H-benzimidazol-4-yl}piperazin-1yl)methyl]pyrimidine -2,4(1H,3H)-dione; 5-[(4-{2-[4-(ethylsulfonyl)phenyl]-1H-benzimidazol-4-yl}piperazin-1-yl)methyl]pyrimidine-2,4(1H,3H)-dione; 5-[(4-{2-[4-(isopropylsulfonyl)phenyl]-1H -benzimidazol-4-yl}piperazin-1-yl)methyl]pyrimidine-2,4(1H,3H)-dione; 5-[(4-{2-[4-(diethylamino)phenyl]-1H-benzimidazol-4-yl}piperazin-1yl)methyl]pyrimidine-2,4(1H,3H)-dione; 5-({4-[2-(4-tert-butylphenyl)-1H-benzimidazol-4-yl]piperazin-1-yl}methyl)-1,3-dimethylpyrimidine-2,4(1H,3H)-dione; 5-({4-[2-(4-tert-butylphenyl)-1H-benzimidazol-4-yl]piperazin-1-yl}methyl)-1,3-diethylpyrimidine-2,4(1H,3H)-dione; 5-({4-[2-(4-tert -butylphenyl)-1H-benzimidazol-4-yl1]piperazin-1-yl}methyl)-1ethylpyrimidine-2,4(1H,3H) -dione; 5-({(2S)-4-[2-(4-tert-butylphenyl)-1H-benzimidazol-4-yl]-2-methylpiperazin-1-yl}methyl)-1ethylpyrimidine-2,4(1H,3H)-dione; 5-({(2S)-4-[2-(4-tert-butylphenyl)-1H-benzimidazol-7-yl]-2-ethylpiperazin-1-yl}methyl)-1ethylpyrimidine-2,4(1H,3H)-dione; 1-ethyl-5-[(4-{2-[4-(methylsulfonyl)phenyl]-1H-benzimidazol-4-yl}piperazin-1-yl)methyl]pyrimidine-2,4(1H,3H)-dione; 5-[((2S)-4-{2-[4-(diethylamino)phenyl]-1H -benzimidazol-7-yl}-2-ethylpiperazin-1-yl)methyl]-1ethylpyrimidine-2,4(1H,3H)-dione; 1-ethyl-5-{[4-(2-{4-[2,2,2-trifluoro-1-hydroxy-1-(trifluoromethy1)ethy]phenyl}-1H -benzimidazol-7-yl)piperazin-1yl]methyl}pyrimidine-2,4(1H,3H)-dione; 1ethyl-5-[(4-{2-[4-(2,2,2-trifluoro-1hydroxyethyl)phenyl]-1H-benzimidazol-4-yl}piperazin-1-yl)methyl]pyrimidine-2,4(1H,3H)-dione; 5-({4-[2-(4-tert-butylphenyl)-1H-benzimidazol-4-yl]piperazin-1-yl}methyl)-1propylpyrimidine-2,4(1H,3H)-dione; 5-({4-[2-(4-tert-butylphenyl)-1H-benzimidazol-4-yl]piperazin-1-yl}methyl)-1-isopropylpyrimidine-2,4(1H,3H)-dione; 1-allyl-5-({4-[2-(4-tert-butylphenyl)-1H-benzimidazol-4-yl]piperazin-1-yl}methyl)pyrimidine -2,4(1H,3H)-dione; 5-({4-[2-(4-tert-butylphenyl)-1H-benzimidazol-4-yl]piperazin-1-yl}methyl) -1prop-2-ynylpyrimidine-2,4(1H,3H)-dione; 5-({4-[2-(4-tert-butylphenyl)-1H-benzimidazol-4-yl]piperazin-1-yl}methyl)-1-methylpyrimidine-2,4(1H,3H)-dione; 2-[5-({4-[2-(4-tert -butylphenyl)-1H-benzimidazol-4-yl]piperazin-1-yl}methyl)-2,4-dioxo-3,4-dihydropyrimidin -1(2H)-yl]acetamide; 2-[5-({(2S)-4-[2-(4-tert-butylphenyl)-1H-benzimidazol-4-yl]-2-methylpiperazin-1-yl}methyl)-2,4-dioxo-3,4-dihydropyrimidin-1(2H)-yl]acetamide; 5-({4-[2-(4-tert-butylphenyl)-1H-benzimidazol-4-yl]piperazin-1-yl}methyl)-3-ethylpyrimidine-2,4(1H,3H) -dione; 2-[5-({4-[2-(4-tert-butylphenyl)-1H-benzimidazol-4-yl]piperazin-1-yl}methyl)-2,6-dioxo-3,6-dihydropyrimidin-1(2H)-yl]acetamide; 2-(4-tert-butylphenyl)-7-(4-{[2-(methylthio)pyrimidin-4-yl]methyl}piperazin-1-yl)-H-benzimidazole; 2-(4-tert-butylphenyl)-7-(4-{[2-(methylsulfonyl)pyrimidin-4-yl]methyl}piperazin-1-yl)-1H-benzimidazole; 2-(4-tert -butylphenyl)-4-(4-{[2-(methylthio)pyrimidin-5-yl]methyl}piperazin-1-yl)-1H-benzimidazole; 2-(4-tert-butylphenyl)-4-((3 S)-3-methyl-4-{[2-(methylthio)pyrimidin-5-yl]methyl}piperazin-1-yl) -1H-benzimidazole; N,N-diethyl-N-{4-[4-(4-{[2-(methylthio)pyrimidin-5-yl]methyl}piperazin -1-yl)-1H-benzimidazol-2-yl]phenyl}amine; 3-({4-[2-(4-tert-butylphenyl)-1H-benzimidazol-7-yl]piperazin-1-yl}methyl)imidazo [1,2-a]pyrimidine; 7-({4-[2-(4-tertbutylphenyl)-1H-benzimidazol-4-yl]piperazin-1-yl}methyl)-1,4-dihydropyrido[2,3-b]pyrazine-2,3-dione; 7-({(2S)-4-[2-(4-tert-butylphenyl)-1H-benzimidazol-4-yl]-2-methylpiperazin-1-yl}methyl)-1,4-dihydropyrido [2,3-b]pyrazine-2,3-dione; 7-[(4-{2-[4-(methylsulfonyl)phenyl]-1H-benzimidazol-4-yl}piperazin-1yl)methyl]-1,4-dihydropyrido[2,3-b]pyrazine-2,3-dione; 7-[((2S)-2-methyl-4-{2-[4-(methylsulfonyl)phenyl]-1H-benzimidazol-4-yl}piperazin-1-yl)methyl]-1,4-dihydropyrido[2,3-b]pyrazine-2,3-dione; 3-({4-[2-(4-tert-butylphenyl)-1H-benzimidazol-4-yl]piperazin-1-yl}methyl)pyrido[3,4-b]pyrazine; 3-({4-[2-(4-tert-butylphenyl)-1H-benzimidazol-4-yl]piperazin-1yl}methyl)pyrido [2,3-b]pyrazine; 2-({4-[2-(4-tert-butylphenyl)-1H-benzimidazol-4-yl]piperazin-1-yl}methyl)quinoxaline; 2-({(2S)-4-[2-(4-tert-butylphenyl)-1H-benzimidazol-4-yl]-2-methylpiperazin-1-yl}methyl)quinoxaline; N,N-diethyl-N-(4-{4-[4-(quinoxalin-2-ylmethyl)piperazin-1-yl]-1H-benzimidazol-2-yl}phenyl)amine; 2-({(2S)-4-[2-(4-tert-butylphenyl)-1H-benzimidazol-4-yl]-2-ethylpiperazin-1-yl}methyl)quinoxaline; 2-{[4-(2-{4-[2,2,2-trifluoro-1(trifluoromethyl)ethyl]phenyl}-1H-benzimidazol-7-yl)piperazin-1yl]methyl}quinoxaline; 6-({4-[2-(4-tert-butylphenyl)-1H-benzimidazol-4-yl]piperazin-1-yl}methyl)pyrido[2,3-b]pyrazine; 6-({(2S)-4-[2-(4-tert-butylphenyl)-1H-benzimidazol-4-yl]-2-methylpiperazin-1-yl}methyl)pyrido [2,3-b]pyrazine; 7-({4-[2-(4-tert-butylphenyl)-1H-benzimidazol-4-yl]piperazin-1-yl}methyl)pyrido [2,3-b]pyrazine; 7-[(4-{2-[4-(methylsulfonyl)phenyl]-1H-benzimidazol-4-yl}piperazin-1-yl)methyl]pyrido[2,3-b]pyrazine; 7-({4-[2-(4-tert-butylphenyl)-H-benzimidazol-7-yl]-2-methylpiperazin-1-yl}methyl)pyrido[2,3-b]pyrazine; 1,1,1,3,3,3-hexafluoro-2-(4-{7-[4-(pyrido [2,3-b]pyrazin-7-ylmethyl)piperazin-1-yl]-1H-benzimidazol-2-yl}phenyl)propan-2-ol; 7-{[4-(2-{4-[2,2,2-trifluoro-1(trifluoromethyl)ethyl]phenyl}-1H-benzimidazol-7-yl)piperazin-1-yl]methyl}pyrido[2,3-b]pyrazine; 2-(4-tert-Butyl-phenyl)-7-[4-(2-methoxy-pyrimidin-4-ylmethyl)-piperazin-1-yl]-1H-benzoimidazole; 4-{4-[2-(4-tert-Butyl-phenyl)-3H-benzoimidazol-4-yl]-piperazin-1-ylmethyl}-pyrimidin-2-ol; 7-[4-(2-Allyloxy-pyrimidin-4-ylmethyl)-piperazin-1-yl]-2-(4-tert-butyl-phenyl)-1H-benzoimidazole; 2-(4-tert-Butyl-phenyl)-7-[4-(2-cyclobutoxy-pyrimidin-4-ylmethyl)-piperazin-1-yl]-1H-benzoimidazole; 2-(4-tert-Butyl-phenyl)-7-[4-(2-phenoxy-pyrimidin-4-ylmethyl)-piperazin-1-yl]-1H-benzoimidazole; 7-[4-(2-Benzyloxy-pyrimidin-4-ylmethyl)-piperazin-1-yl]-2-(4-tert-butyl-phenyl)-1H-benzoimidazole;

2-(4-tert-Butyl-phenyl)-7-{4-[2-(pyridin-2-ylmethoxy)-pyrimidin-4-ylmethyl]-piperazin-1-yl}-1H-benzoimidazole; (4-{4-[2-(4-tert-Butyl-phenyl)-3H-benzoimidazol-4-yl]-piperazin-1-ylmethyl}-pyrimidin-2-yl)-diethyl-amine; (4-{4-[2-(4-tert-Butyl-phenyl)-3H-benzoimidazol-4-yl]-piperazin-1-ylmethyl}-pyrimidin-2-yl)-ethyl-amine; (4-{4-[2-(4-tert-Butyl-phenyl)-3H-benzoimidazol-4-yl]-piperazin-1-ylmethyl}-pyrimidin-2-yl)-methyl-amine; (4-{4-[2-(4-tert-Butyl-phenyl)-3H-benzoimidazol-4-yl]-piperazin-1-ylmethyl}-pyrimidin-2-yl)-ethyl-methyl-amine; (4-{4-[2-(4-tert-Butyl-phenyl)-3H-benzoimidazol-4-yl]-piperazin-1-ylmethyl}-pyrimidin-2-yl)-cyclopropylmethy-amine; 2-(4-tert-Butyl-phenyl)-7-[4-(2-pyrrolidin-yl-pyrimidin-4-ylmethyl)-piperazin-1-yl]-1H-benzoimidazole; (4-{4-[2-(4-tert-Butyl-phenyl)-3H-benzoimidazol-4-yl]-piperazin-1-ylmethyl}-pyrimidin-2-yl)-isopropyl--methyl-amine; (4-{4-[2-(4-tert-Butyl-phenyl)-3H-benzoimidazol-4-yl]-piperazin-1-ylmethyl}-pyrimidin-2-yl)-isobutyl -amine; (4-{4-[2-(4-tert-Butyl-phenyl)-3H-benzoimidazol-4yl]-piperazin-1-ylmethyl}-pyrimidin-2-yl)-cyclopentyl-amine; 2-(4-tert-Butyl-phenyl)-7-{4-[2-(2-methyl-piperidin-1-yl)-pyrimidin-4-ylmethyl]-piperazin-1-yl}-1H-benzoimidazole; 2-(4-tert-Butyl-phenyl)-7-{4-[2-(3-methyl-piperidin-1yl)-pyrimidin-4-ylmethyl]-piperazin-1-yl}-1H-benzoimidazole; 2-(4-tert-Butyl-phenyl)-7-{4-[2-(4-methyl-piperidin-1-yl)-pyrimidin-4-ylmethyl]-piperazin-1-yl}-1H-benzoimidazole; (4-{4-[2-(4-tert-Butyl-phenyl)-3H-benzoimidazol-4-yl]-piperazin-1-ylmethyl}-pyrimidin-2-yl)-cyclohexyl-methyl-amine; (4-{4-[2-(4-tert-Butyl-phenyl)-3H-benzoimidazol-4-yl]-piperazin-1-ylmethyl}-pyrimidin-2-yl)-phenethyl-amine; (4-{4-[2-(4-tert-Butyl-phenyl)-3H-benzoimidazol-4-yl]-piperazin-1-ylmethyl}-pyrimidin-2-yl)-(4-methyl-benzyl)-amine; 2-(4-tert-butylphenyl)-7-{4-[(2-piperidin-1-ylpyrimidin-4-yl)methyl]piperazin-1-yl}-1H-benzimidazole; N-butyl-4-({4-[2-(4-tert-butylphenyl)-1H-benzimidazol-7-yl]piperazin-1-yl}methyl)pyrimidin-2-amine; 4-({4-[2-(4-tert-butylphenyl)-1H-benzimidazol-7-yl]piperazin-1-yl}methyl)-N,N-dipropylpyrimidin-2-amine; 5-((1S)-1-{4-[2-(4-tert-butylphenyl)-1H-benzimidazol-4-yl]piperazin-1-yl}ethyl)-1-ethylpyrimidine-2,4(1H,3H)-dione; 6-((1S)-1-{4-[2-(4-tert-butylphenyl)-1H-benzimidazol-4-yl]piperazin-1-yl}ethyl)quinoxaline; 6-({4-[2-(4-tert-butylphenyl)-1H-benzimidazol-4-yl]piperazin-1-yl}methyl)-1,4-dihydroquinoxaline-2,3-dione; 7-({4-[2-(4-tert-butylphenyl)-1H-benzimidazol-4-yl]piperazin-1-yl}methyl)-1-(pyridin-3-ylmethyl)-1,4-dihydroquinoxaline-2,3-dione; 6-({4-[2-(4-ethylphenyl)-1H-benzimidazol-4-yl]piperazin-1-yl}methyl)-1,4-dihydroquinoxaline-2,3-dione; 6-({4-[2-(4-tert-butylphenyl)-1H-benzimidazol-4-yl]piperazin-1-yl}methyl)-1,4-dihydroquinoxaline-2,3-dione; 6-({(2R)-4-[2-(4-tert-butylphenyl)-1H-benzimidazol-4-yl]-2-methylpiperazin-1-yl}methyl)-1,4-dihydroquinoxaline-2,3-dione; 6-({(2S)-4-[2-(4-tert-butylphenyl)-1H-benzimidazol-4-yl]-2-methylpiperazin-1-yl}methyl)-1,4-dihydroquinoxaline-2,3-dione; 6-({(2S)-4-[2-(4-tert-butylphenyl)-1H-benzimidazol-7-yl]-2-ethylpiperazin-1-yl}methyl)-1,4-dihydroquinoxaline-2,3-dione; 6-({4-[2-(4-isopropylphenyl)-1H-benzimidazol-4-yl]piperazin-1-yl}methyl)-1,4-dihydroquinoxaline-2,3-dione; 6-[(4-{2-[4-(methylsulfonyl)phenyl]-1H-benzimidazol-4-yl}piperazin-1-yl)methyl]-1,4-dihydroquinoxaline-2,3-dione; 6-[(4-{2-[4-(ethylsulfonyl)phenyl]-1H-benzimidazol-4-yl}piperazin-1yl)methyl]-1,4-dihydroquinoxaline-2,3-dione; 7-({4-[2-(4-ethylphenyl)-1H-benzimidazol-4-yl]piperazin-1-yl}methyl)-1-methyl-1,4-dihydroquinoxaline-2,3-dione; 1-Ethyl-7-{4-[2-(4-ethyl-phenyl)-1H-benzimidazol-4-yl]-piperazin-1-ylmethyl}-1,4-dihydro-quinoxaline-2,3-dione; 7-{4-[2-(4-Ethyl-phenyl)-1H-benzimidazol-4-yl]-piperazin-1-ylmethyl}-1-isopropyl-1,4-dihydro-quinoxaline-2,3-dione; 1-Cyclobutyl-7-{4-[2-(4-ethyl-phenyl)-1H-benzoimidazol-4-yl]-piperazin-1-ylmethyl}-1,4-dihydro-quinoxaline-2,3-dione; 1Cyclopropylmethyl-7-{4-[2-(4-ethyl-phenyl)-1H-benzoimidazol-4-yl]-piperazin-1-ylmethyl}-1,4-dihydro-quinoxaline-2,3- dione; 7-{4-[2-(4-Ethyl-phenyl)-1H-benzoimidazol-4-yl]-piperazin-1-ylmethyl}-1isobutyl-1,4-dihydro-quinoxaline-2,3-dione; 1Cyclopentyl-7-{4-[2-(4-ethyl-phenyl)-1H-benzoimidazol-4-yl]-piperazin-1-ylmethyl}-1,4-dihydro-quinoxaline-2,3-dione; 1Cyclohexyl-7-{4-[2-(4-ethyl-phenyl)-1H-benzoimidazol-4-yl]-piperazin-1-ylmethyl}-1,4-dihydro-quinoxaline-2,3-dione; 1-Benzyl-7-{4-[2-(4-ethyl-phenyl)-1H-benzoimidazol-4-yl]-piperazin-1-ylmethyl}-1,4-dihydro-quinoxaline-2,3-dione; 7-{4-[2-(4-Ethyl-phenyl)-1H-benzoimidazol-4-yl]-piperazin-1-ylmethyl}-1pyridin-3-ylmethyl-1,4-dihydro-quinoxaline-2,3-dione; 7-{4-[2-(4-Ethyl-phenyl)-1H-benzoimidazol-4-yl]-piperazin-1-ylmethyl}-1phenethyl-1,4-dihydro-quinoxaline-2,3-dione; 7-{4-[2-(4-Ethyl-phenyl)-1H-benzoimidazol-4-yl]-piperazin-1-ylmethyl}-1(2-pyridin-3-yl-ethyl)-1,4-dihydro-quinoxaline-2,3-dione; 7-({4-[2-(4-tert-butylphenyl)-1H-benzimidazol-4-yl]piperazin-1-yl}methyl)-1-methyl-1,4-dihydroquinoxaline-2,3-dione; 7-({4-[2-(4-tert-butylphenyl)-1H-benzimidazol-4-yl]piperazin-1-yl}methyl)-1-(2-pyridin-3-ylethyl)-1,4-dihydroquinoxaline-2,3-dione; 7-({4-[2-(4-tert-butylphenyl)-1H-benzimidazol-4-yl]piperazin-1-yl}methyl)-1-(3-pyridin-3-ylpropyl)-1,4-dihydroquinoxaline-2,3-dione; 7-({4-[2-(4-tert-butylphenyl)-1H-benzimidazol-4-yl]piperazin-1-yl}methyl)-1-(2-pyridin-2-ylethyl)-1,4-dihydroquinoxaline-2,3-dione; 7-({4-[2-(4-tert-butylphenyl)-1H-benzimidazol-4-yl]piperazin-1-yl}methyl)-1-(2-pyridin-4-ylethyl)-1,4-dihydroquinoxaline-2,3-dione; 7-{4-[2-(4-tert-Butyl-phenyl)-1H-benzoimidazol-4-yl]-piperazin-1-ylmethyl}-1(3-morpholin-4-yl-propyl)-1,4-dihydro-quinoxaline-2,3-dione; 7-{4-[2-(4-tert-Butyl-phenyl)-1H-benzoimidazol-4-yl]-piperazin-1-ylmethyl}-1(2-morpholin-4-yl-ethyl)-1,4-dihydro-quinoxaline-2,3-dione; 7-{4-[2-(4-tert-Butyl-phenyl)-1H-benzoimidazol-4-yl]-piperazin-1-ylmethyl}-1(2-piperidin-1yl-ethyl)-1,4-dihydro-quinoxaline-2,3-dione; 6-({4-[2-(4-ethylphenyl)-1H-benzimidazol-4-yl]piperazin-1-yl}methyl)-1-methyl-1,4-dihydroquinoxaline-2,3-dione; 1Cyclobutyl-6-{4-[2-(4-ethyl-phenyl)-3H-benzoimidazol-4-yl]-piperazin-1-ylmethyl}-1,4-dihydro-quinoxaline-2,3-dione; 1-Cyclopropylmethyl-6-{4-[2-(4-ethyl-phenyl)-3H-benzoimidazol-4-yl]-piperazin-1-ylmethyl}-1,4-dihydro-quinoxaline-2,3-dione; 6-{4-[2-(4-Ethyl-phenyl)-3H-benzoimidazol-4-yl]-piperazin-1-ylmethyl}-1-isobutyl-1,4-dihydro-quinoxaline-2,3-dione; 1Cyclopentyl-6-{4-[2-(4-ethyl-phenyl)-3H-benzoimidazol-4-yl]-piperazin-1-ylmethyl}-1,4-dihydro-quinoxaline-2,3-dione; 1Cyclohexyl-6-{4-[2-(4-ethyl-phenyl)-3H-benzoimidazol-4-yl]-piperazin-1-ylmethyl}-1,4-dihydro-quinoxaline-2,3-dione; 1Benzyl-6-{4-[2-(4-ethyl-phenyl)-3H-benzoimidazol-4-yl]-piperazin-1-ylmethyl}-1,4-dihydro-quinoxaline-2,3-dione; 6-{4-[2-(4-Ethyl-phenyl)-3H-benzoimidazol-4-yl]-piperazin-1-ylmethyl}-1-pyridin-4-ylmethyl-1,4-dihydro-quinoxaline-2,3-dione; 6-{4-[2-(4-Ethyl-phenyl)-3H-benzoimidazol-4-yl]-piperazin-1-ylmethyl}-1pyridin-3-ylmethyl-1,4-dihydro-quinoxaline-2,3-dione; 6-{4-[2-(4-Ethyl-phenyl)-3H-benzoimidazol-4-yl]-piperazin-1-ylmethyl}-1phenethyl-1,4-dihydro-quinoxaline-2,3-dione; 6-{4[2-(4-Ethyl-phenyl)-3H-benzoimidazol-4-yl]-piperazin-1-ylmethyl}-1(2-pyridin-3-yl-ethyl)-1,4-dihydro-quinoxaline-2,3-dione; 1ethyl-6-({4-[2-(4-ethylphenyl)-1H-benzimidazol-4-yl]piperazin-1-yl}methyl)-1,4-dihydroquinoxaline-2,3-dione; ;6-({(2S,6S)-4-[2-(4-tert-butylphenyl)-1H-benzimidazol-4-yl]-2,6-dimethylpiperazin-1-yl}methyl)quinoxaline; or 5-({4-[2-(4-tert-butylphenyl)-1H-benzimidazol-4-yl]piperazin-1-yl}methyl)quinoxaline(, or a pharmaceutically acceptable salt thereof.

22. A pharmaceutical composition, comprising a compound according to claim 1; or a pharmaceutically acceptable salt thereof and a pharmaceutically acceptable carrier.

23. A pharmaceutical composition, comprising a compound of claim 21 or a pharmaceutically acceptable salt thereof, and a pharmaceutically acceptable carrier.

\* \* \* \* \*